US011273319B2

(12) United States Patent
De Taboada et al.

(10) Patent No.: US 11,273,319 B2
(45) Date of Patent: *Mar. 15, 2022

(54) METHOD AND APPARATUS FOR IRRADIATING A SURFACE WITH PULSED LIGHT

(71) Applicant: Pthera LLC, Newark, DE (US)

(72) Inventors: Luis De Taboada, Carlsbad, CA (US); Jackson Streeter, Newberry, FL (US)

(73) Assignee: Pthera LLC, Newark, DE (US)

( * ) Notice: Subject to any disclaimer, the term of this patent is extended or adjusted under 35 U.S.C. 154(b) by 251 days.

This patent is subject to a terminal disclaimer.

(21) Appl. No.: 16/147,293

(22) Filed: Sep. 28, 2018

(65) Prior Publication Data

US 2019/0232077 A1 Aug. 1, 2019

Related U.S. Application Data

(63) Continuation of application No. 12/403,824, filed on Mar. 13, 2009, now abandoned, which is a
(Continued)

(51) Int. Cl.
*A61N 5/06* (2006.01)
*A61N 5/00* (2006.01)

(52) U.S. Cl.
CPC ...... *A61N 5/0613* (2013.01); *A61N 2005/007* (2013.01); *A61N 2005/0644* (2013.01);
(Continued)

(58) Field of Classification Search
CPC ...... A61N 5/06; A61N 5/0613; A61N 5/0618; A61N 5/0622; A61N 2005/0626;
(Continued)

(56) References Cited

U.S. PATENT DOCUMENTS

| 3,735,755 A | 5/1973 | Eggleton et al. |
| 3,810,367 A | 5/1974 | Peterson |

(Continued)

FOREIGN PATENT DOCUMENTS

| DE | 3200584 | 7/1983 |
| DE | 4108328 | 9/1992 |

(Continued)

OTHER PUBLICATIONS

U.S. Appl. No. 10/488,262, filed May 29, 2003, Oron et al.
(Continued)

*Primary Examiner* — Ahmed M Farah
(74) *Attorney, Agent, or Firm* — Fish & Richardson P.C.

(57) ABSTRACT

A method and apparatus irradiates a surface with at least one pulsed light beam emitted from an emission surface of an optical element. The at least one pulsed light beam comprises a plurality of pulses having a temporal pulsewidth in a range between about 0.1 millisecond and about 150 seconds. The at least one pulsed light beam has a beam cross-sectional area at the emission surface greater than about 2 $cm^2$ and a time-averaged irradiance in a range between about 1 $mW/cm^2$ and about 100 $W/cm^2$.

23 Claims, 57 Drawing Sheets

Related U.S. Application Data continuation-in-part of application No. 12/389,294, filed on Feb. 19, 2009, now Pat. No. 10,357,662.

(60) Provisional application No. 61/037,668, filed on Mar. 18, 2008.

(52) U.S. Cl.
CPC ............... *A61N 2005/0647* (2013.01); *A61N 2005/0659* (2013.01)

(58) Field of Classification Search
CPC .... A61N 2005/0627; A61N 2005/0628; A61N 2005/063; A61N 2005/0631; A61N 2005/0635; A61N 2005/0643; A61N 2005/0647; A61N 2005/065; A61N 2005/0651; A61N 2005/0658; A61N 2005/0659; A61N 2005/0662; A61N 2005/0665; A61N 2005/0666; A61N 2005/067; A61N 2005/002; A61N 2005/005; A61N 2005/007
USPC ...................................... 607/88–91; 128/898
See application file for complete search history.

(56) References Cited

U.S. PATENT DOCUMENTS

| | | |
|---|---|---|
| 4,315,514 A | 2/1982 | Drewes et al. |
| 4,343,301 A | 8/1982 | Indech |
| 4,630,273 A | 12/1986 | Inous et al. |
| 4,633,872 A | 1/1987 | Chaffee et al. |
| 4,669,466 A | 6/1987 | L'Esperance |
| 4,671,285 A | 6/1987 | Walker |
| 4,798,215 A | 1/1989 | Turner |
| 4,846,196 A | 7/1989 | Wiksell et al. |
| 4,850,351 A | 7/1989 | Herman et al. |
| 4,930,504 A | 6/1990 | Diamantopoulos et al. |
| 4,951,482 A | 8/1990 | Gilbert |
| 4,951,653 A | 8/1990 | Fry et al. |
| 4,966,144 A | 10/1990 | Rochkind et al. |
| 5,029,581 A | 7/1991 | Kaga et al. |
| 5,037,374 A | 8/1991 | Carol |
| 5,047,006 A | 9/1991 | Brandston et al. |
| 5,054,470 A | 10/1991 | Fry et al. |
| 5,150,704 A | 9/1992 | Tatebayashi et al. |
| 5,259,380 A | 11/1993 | Mendes et al. |
| 5,267,294 A | 11/1993 | Kuroda et al. |
| 5,282,797 A | 2/1994 | Chess |
| 5,358,503 A | 10/1994 | Bertwell et al. |
| 5,368,555 A | 11/1994 | Sussman et al. |
| 5,401,270 A | 3/1995 | Muller et al. |
| 5,441,495 A | 8/1995 | Liboff et al. |
| 5,445,146 A | 8/1995 | Bellinger |
| 5,445,608 A | 8/1995 | Chen et al. |
| 5,464,436 A | 11/1995 | Smith |
| 5,474,528 A | 12/1995 | Meserol |
| 5,501,655 A | 3/1996 | Rolt et al. |
| 5,580,555 A | 3/1996 | Schwartz |
| 5,580,550 A | 4/1996 | Gough et al. |
| 5,511,563 A | 6/1996 | Diamond |
| 5,540,737 A | 7/1996 | Fenn |
| 5,601,526 A | 2/1997 | Chapelon et al. |
| 5,616,140 A | 4/1997 | Prescott |
| 5,617,258 A | 4/1997 | Negus et al. |
| 5,621,091 A | 4/1997 | Kunkel et al. |
| 5,622,168 A | 4/1997 | Keusch et al. |
| 5,627,870 A | 5/1997 | Kopecky |
| 5,640,978 A | 6/1997 | Wong |
| 5,643,334 A | 7/1997 | Eckhouse et al. |
| 5,728,090 A | 3/1998 | Martin et al. |
| 5,755,752 A | 5/1998 | Segal |
| 5,762,867 A | 6/1998 | D'Silva |
| 5,817,008 A | 10/1998 | Rafert et al. |
| 5,842,477 A | 12/1998 | Naughton et al. |
| 5,843,073 A | 12/1998 | Sinofsky |
| 5,849,585 A | 12/1998 | Mather et al. |
| 5,871,521 A | 2/1999 | Kaneda et al. |
| 5,879,376 A | 3/1999 | Miller |
| 5,902,741 A | 5/1999 | Purchio et al. |
| 5,928,207 A | 7/1999 | Pisano et al. |
| 5,928,945 A | 7/1999 | Sliktar et al. |
| 5,954,762 A | 9/1999 | Di Mino et al. |
| 5,958,761 A | 9/1999 | Yogev et al. |
| 5,983,141 A | 11/1999 | Sluijter et al. |
| 5,989,245 A | 11/1999 | Prescott |
| 6,030,767 A | 2/2000 | Wagner et al. |
| 6,033,431 A | 3/2000 | Segal |
| 6,042,531 A | 3/2000 | Holcomb |
| 6,045,575 A | 4/2000 | Rosen et al. |
| 6,046,046 A | 4/2000 | Hassanein |
| 6,060,306 A | 5/2000 | Flatt et al. |
| 6,063,108 A | 5/2000 | Salansky et al. |
| 6,100,290 A | 8/2000 | Levy et al. |
| 6,107,325 A | 8/2000 | Chan et al. |
| 6,107,608 A | 8/2000 | Hayes |
| 6,112,110 A | 8/2000 | Wilk |
| 6,117,128 A | 9/2000 | Gregory |
| 6,129,748 A | 10/2000 | Kamei |
| 6,143,878 A | 11/2000 | Koopman et al. |
| 6,146,410 A | 11/2000 | Nagypal et al. |
| 6,149,679 A | 11/2000 | Mino et al. |
| 6,156,028 A | 12/2000 | Prescott |
| 6,162,211 A | 12/2000 | Tankovich et al. |
| 6,179,771 B1 | 1/2001 | Mueller |
| 6,179,830 B1 | 1/2001 | Kokubu |
| 6,187,210 B1 | 2/2001 | Lebouitz et al. |
| 6,198,958 B1 | 3/2001 | Ives et al. |
| 6,210,317 B1 | 4/2001 | Bonlie |
| 6,210,425 B1 | 4/2001 | Chen |
| 6,214,035 B1 | 4/2001 | Streeter |
| 6,221,095 B1 | 4/2001 | Van Zuylen et al. |
| 6,235,015 B1 | 5/2001 | Mead, III et al. |
| 6,267,780 B1 | 7/2001 | Streeter |
| 6,273,885 B1 | 8/2001 | Kopp et al. |
| 6,273,905 B1 | 8/2001 | Streeter |
| 6,277,974 B1 | 8/2001 | Lo et al. |
| 6,290,713 B1 | 9/2001 | Russell |
| 6,290,714 B1 | 9/2001 | Streeter |
| 6,306,130 B1 | 10/2001 | Anderson et al. |
| 6,312,451 B1 | 11/2001 | Streeter |
| 6,344,050 B1 | 2/2002 | Chen |
| 6,358,272 B1 | 3/2002 | Wilden |
| 6,363,285 B1 | 3/2002 | Wey |
| 6,364,907 B1 | 4/2002 | Obochi et al. |
| 6,379,295 B1 | 4/2002 | Woo |
| 6,395,016 B1 | 5/2002 | Oron et al. |
| 6,397,107 B1 | 5/2002 | Lee et al. |
| 6,402,678 B1 | 6/2002 | Fischell et al. |
| 6,421,562 B1 | 7/2002 | Ross |
| 6,443,974 B1 | 9/2002 | Oron et al. |
| 6,443,978 B1 | 9/2002 | Zharov |
| 6,447,537 B1 | 9/2002 | Hartman |
| 6,471,716 B1 | 10/2002 | Pecukonis |
| 6,494,900 B1 | 12/2002 | Salansky et al. |
| 6,514,220 B2 | 2/2003 | Melton et al. |
| 6,537,301 B1 | 3/2003 | Kamei |
| 6,537,304 B1 | 3/2003 | Oron |
| 6,551,308 B1 | 4/2003 | Muller et al. |
| 6,571,735 B1 | 6/2003 | Wilkinson |
| 6,602,274 B1 | 8/2003 | Chen |
| 6,663,659 B2 | 12/2003 | McDaniel |
| 6,689,062 B1 | 2/2004 | Mesallum |
| 6,743,222 B2 | 6/2004 | Durkin et al. |
| 6,899,723 B2 | 5/2005 | Chen |
| 6,918,922 B2 | 7/2005 | Oron |
| 6,974,224 B2 | 12/2005 | Thomas-Benedict |
| 7,041,094 B2 | 5/2006 | Connors et al. |
| 7,118,563 B2 | 10/2006 | Weckwerth et al. |
| 7,303,578 B2 * | 12/2007 | De Taboada ......... A61N 5/0622 607/88 |
| 7,309,348 B2 * | 12/2007 | Streeter ............... A61N 5/0622 607/88 |
| 7,344,555 B2 | 3/2008 | Anders et al. |

(56) References Cited

U.S. PATENT DOCUMENTS

| | | | |
|---|---|---|---|
| 7,351,253 B2 | 4/2008 | DiMauro et al. | |
| 7,534,255 B1 | 5/2009 | Streeter et al. | |
| 7,559,945 B2 | 7/2009 | Breden et al. | |
| 7,848,035 B2 | 12/2010 | Delapp et al. | |
| 8,308,784 B2* | 11/2012 | Streeter | A61N 5/0618 607/88 |
| 10,315,042 B2* | 6/2019 | De Taboada | A61N 5/04 |
| 10,695,579 B2* | 6/2020 | De Taboada | A61N 5/0613 |
| 2001/0044623 A1 | 11/2001 | Chen | |
| 2002/0029071 A1 | 3/2002 | Whitehurst | |
| 2002/0068927 A1 | 6/2002 | Prescott | |
| 2002/0087205 A1 | 7/2002 | Chen | |
| 2002/0123781 A1 | 9/2002 | Shanks et al. | |
| 2002/0156371 A1 | 10/2002 | Hedlune et al. | |
| 2002/0161418 A1 | 10/2002 | Wilkens et al. | |
| 2002/0188334 A1 | 12/2002 | Carlgren | |
| 2002/0198575 A1 | 12/2002 | Sulivan | |
| 2003/0004556 A1 | 1/2003 | McDaniel | |
| 2003/0021124 A1 | 1/2003 | Elbrech et al. | |
| 2003/0109906 A1 | 6/2003 | Streeter | |
| 2003/0125782 A1 | 7/2003 | Streeter | |
| 2003/0125783 A1 | 7/2003 | Moran | |
| 2003/0144712 A1 | 7/2003 | Streeter | |
| 2003/0167080 A1 | 9/2003 | Hart et al. | |
| 2003/0212442 A1 | 11/2003 | Streeter | |
| 2003/0216797 A1 | 11/2003 | Oron | |
| 2004/0014199 A1 | 1/2004 | Streeter | |
| 2004/0015214 A1 | 1/2004 | Simkin et al. | |
| 2004/0030325 A1 | 2/2004 | Cahir et al. | |
| 2004/0044384 A1 | 3/2004 | Leber et al. | |
| 2004/0073278 A1 | 4/2004 | Pachys | |
| 2004/0093042 A1 | 5/2004 | Altshuler et al. | |
| 2004/0132002 A1 | 7/2004 | Streeter | |
| 2004/0138727 A1* | 7/2004 | Taboada | A61N 5/0622 607/88 |
| 2004/0153130 A1 | 7/2004 | Taboada et al. | |
| 2004/0016750 A1 | 8/2004 | Island | |
| 2004/0153131 A1 | 8/2004 | Oron et al. | |
| 2004/0167501 A1 | 8/2004 | Island et al. | |
| 2004/0220513 A1 | 11/2004 | Streeter | |
| 2004/0260367 A1 | 12/2004 | Taboada et al. | |
| 2005/0009161 A1 | 1/2005 | Streeter | |
| 2005/0024853 A1 | 2/2005 | Thomas-Benedict | |
| 2005/0107851 A1 | 5/2005 | Taboada et al. | |
| 2005/0159793 A1 | 7/2005 | Streeter | |
| 2005/0187595 A1 | 8/2005 | Streeter | |
| 2005/0203595 A1 | 9/2005 | Oron | |
| 2006/0253177 A1 | 11/2006 | Taboada | |
| 2007/0179570 A1 | 8/2007 | Taboada et al. | |
| 2007/0179571 A1 | 8/2007 | De Taboada et al. | |
| 2009/0254154 A1 | 10/2009 | De Taboada et al. | |
| 2010/0211136 A1 | 8/2010 | De Taboada et al. | |

FOREIGN PATENT DOCUMENTS

| | | |
|---|---|---|
| DE | 29515096 | 1/1993 |
| DE | 4213053 | 10/1993 |
| EP | 0130950 | 4/1990 |
| EP | 0763371 | 3/1997 |
| EP | 0783904 | 7/1997 |
| EP | 0827716 | 3/1998 |
| EP | 1074275 | 2/2001 |
| EP | 1226787 | 7/2002 |
| EP | 2082696 | 7/2009 |
| JP | 04023634 | 2/1992 |
| WO | WO 92/03964 | 3/1992 |
| WO | WO 96/36397 | 11/1996 |
| WO | WO 96/36396 | 1/1997 |
| WO | WO98/04321 | 2/1998 |
| WO | WO98/22573 | 5/1998 |
| WO | WO 1998/33556 | 8/1998 |
| WO | WO99/42178 | 8/1999 |
| WO | WO99/46005 | 9/1999 |
| WO | WO99/62599 | 12/1999 |
| WO | WO 22/25684 | 5/2000 |
| WO | WO00/35534 | 6/2000 |
| WO | WO02/055149 | 7/2002 |
| WO | WO02/092509 | 11/2002 |
| WO | WO02/098509 | 12/2002 |
| WO | WO05/025672 | 3/2005 |
| WO | WO 2006/115761 | 11/2006 |
| WO | WO 2006/138659 | 12/2006 |
| WO | WO 2008/049905 | 5/2008 |

OTHER PUBLICATIONS

U.S. Appl. No. 10/723,171, filed Nov. 26, 2003, Streeter.

Agov, B. S., et al., "On the mechanism of therapeutic action of helium-neon laser in ischemic heart disease", KUN MED (Mose), pp. 102-105, 1985.

Arvidsson, Andreas, et al., "Neuronal replacement from endogenous precursors in the adult rat brain after stroke", Nature Medicine, vol. 8, No. 9, Sep. 2002, pp. 963-970.

Asahi, Minoru, et al., Expression of Interleukin B Converting Enzyme Gene Family and bcl-2 Gene Family in the Rat Brain Following Permanent Occlusion of the Middle Cerebral Artery, Journal of Cerebral Blood Flow & Metabolism, vol. 17, No. 1, Jan. 1997.

Assia, E. et al., "Temporal Parameters of Low Energy Laser Irradiation for Optimal Delay of Post-Traumatic Degeneration of Rat Optic Nerve", Brain Research, vol. 476, 1989, pp. 205-212.

Basford, Jeffrey R., M.D., Ph.D., "Lasers In Orthopedic Surgery—Laser Therapy: Scientific Basis and Clinical Role", May 1993, vol. 16, No. 5, pp. 541-547.

Belevich et al., "Exploring the proton pump mechanism of cytochrome c oxidase in real time," Proc. Nat'l Acad. Sci., Feb. 20, 2007, 104:2685-2690.

Belevich et al., "Proton-coupled electron transfer drives the proton pump of cytochrome c oxidase," Nature, Apr. 2006, 440:829-832.

Belkin, M. et al., "A Critical Review of Low Energy Laser Bioeffects", Lasers and Light in Ophthalmology, vol. 2, No. 1, pp. 63-71, 1988.

Bevilacqua et al.; "In Vivo Local Determiniation of Tissue Optical Properties: Applications to the Human Brain"; Agglied Ogtics; vol. 28, No. 22; Aug. 1, 1999; pp. 4939-4950.

Bibikova, A. et al., "Enhancement of Angiogenesis in Regenerating Gastroenemius Muscle of the Toad (*Bufo viridis*) by Low-Energy Laser Irradiation", Anatomy and Embryology (1994), vol. 190, pp. 597-602.

Bibikova, A. et al., "Enhancement of Muscle Regeneration in the Toad (*Bufo viridis*) Gastrocnemius Muscle by Low-Energy Laser Irradiation", The Anatomical Reocrd, vol. 235, 1993, pp. 374-380.

Brazzle, John, et al., Active Microneedles with Integrated Functionality, Technical Digest of the 2000 Solid-State Sensor and Actuator Workshog, Department of Bioengineering, University of Utah, Salt Lake Citv, Utah 84112 (five pages) (2000).

Brill, G.E., et al., Modifying influence of low level laser irradiation on the relationships in endothelial cell—blood platelet system, 10th Congress of the Eurogean Society: for Photobiology:, Vienna, Austria (one paqe). Jun. 8, 2004.

Burton et al., "Relation Between Blood Pressure and Flow in the Human Forearm," J. Appl. Physiology, Nov. 1, 1951 4(5):329-339.

Byrnes, K.R., et al., Light Therapy Promotes Axonal Regeneration After Acute Spinal Cord Injury in Adult Rats, Program No. 275.2, Society: for Neuroscience, 2003, Abstract.

Catanzaro et al., "Managing Tissue Heating in Laser Therapy to Enable Double-Blind Clinical Study," Mechanisms for Low-Light Therapy, Proc. of the SPIE, Feb. 28, 2006, 6140:199-208.

Chance et al.: "Comparison of Time-Resolved and -Unresolved Measurements of Oeoxyhemoglobin in Brain"; Proc. Natl Acad. Sc.i USA; vol. 85; ul. 1988; pp. 4971-4975.

Cohen, Michael A., Method of Forming Microneedles and other Micron-Scale Transdermal Probes, Office of Technology Licensing, University of California, Berkeley, http://otl.berkeley.edu!technology/inventiondetai/. Php/1000335, Abstract (two pages) Dec. 5, 2003.

(56) References Cited

OTHER PUBLICATIONS

Conlan, M.J. et al., Biostimulation of Wound Healing by Low-Energy Laser Irradiation:, Journal of Clin. Periodontology, vol. 23, 1996, pp. 492-496.

De Taboada et al., "Transcranial application of low-energy laser irradiation improves neurological deficits in rats following acute stroke," Lasers Surg. Med., Jan. 1, 2006, 38(1):70-73.

Dirnagl, Ulrich, et al., Pathobiology of ischaemic stroke: an integrated view, TINS, vol. 22, No. 9, 1999, pp. 391-397.

Dobson, J., et al., Theory and Applications of a Magnetic Force Bioreactor, European Cells and Materials, vol. 4, Suppl. 2, 2002 (pp. 42-44).

Eells, J.T., et al., Therapeutic photobiomodulation for methanol-induced retinal toxicity, Proceedings National Academy: of Science (PNAS}, vol. 100, No. 6, Mar. 18, 2003, pp. 3439-3444.

Elimadi, Aziz, et al., Trimetazidine Counteracts the Hepatic Injury Associated with Ischemia-Reperfusion by Michondrial Function, Journal of Phamacoloqy: and Experimental Therapeutics, vol. 286, No. 1, 1998, pp. 23-28.

EPO Extended Search Reported in EP Application No. 09170679.6, dated Jan. 4, 2010, 6 pages.

Fisher, M., "Characterizing the Target of Acute Stroke Therapy", Stroke, 1997, vol. 28, pp. 866-872.

Fl Rbank et al.; "A Theoretical Study of the Signal Contributions of Regions of the Adult Head to Near-Infrared Spectroscopy Studies of Visual Evoked Responses"; Neuroimage; No. 8; 1998; pp. 69-78.

Gage, Fred H., Brain, Repair Yourself, Scientific American, Sep. 2003, pp. 47-53.

Gasparyan, Levon V., Biochemical and Biophysical Effects of Low Level Laser Irradiation, MAL 2000, Helsinki, Finland (three pages), Sep. 28-30, 2000.

Gasparyan, Levon V., et al., Low Level Laser Therapy of Male Genital Tract Chronic Inflammations, WALT 2-nd Congress (Kansas City, USA), 1998 (two pages).

Gasparyan, Levon V., et al., The influence of LED irradiation at different wavelengths on functional activity of blood platelets, 1 oth Congress of the European Societ'.)! of Photobiolog:x:, Vienna, Austria, 2003 (one page).

Gasparyan, Levon V., et al., The influence of LED irradiation at different wavelengths with antioxidants on functional activity of blood platelets, Laser, Florence, 2003 (one page).

Gasparyan, Levon V., Experience of Russian (former USSR) Scientists in LLLT and UV Blood Irradiation, MAL 2000, Helsinki, Finland (four pages), Sep. 28-30, 2000.

Gasparyan, Levon V., Investigation of Sensations, Associated with Laser Blood Irradiation, WALT 2-nd Congress (Kansas City, USA), 1998 (two pages).

Gasparyan, Levon V., Millimeter Wave Therapy, MAL 2000, Helsinki, Finland (three pages). Sep. 28-30, 2000.

Gordon, G. A., "The Use of low power lasers in sports medicine", Clinical Sports Medicine 2, 53-61 (1990).

Gross, Garrett J., et al., Mechanisms of Postischemic Contractile Dysfunction, Myocardial Protection From Surgical Ischemic-Reperfusion Injury, An International Symposium, Asheville, North Carolina, Sep. 21-24, 1997, pp. 1898-1904.

Hamblin et al., "Mechanisms of Low Level Light Therapy," Proc. of SPIE, Feb. 10, 2006, 6140:614001, 12 pages.

Iadecola, Costantino, et al., Inhibition of inducible nitric oxide synthase ameliorates ischemic damage, Am. J. Physiol., vol. 268, 1995, pp. R286-R292.

Ilic et al., "Effects of power densities, continuous and pulse frequencies, and number of sessions of low-level laser therapy on intact rat brain," Photomed. Laser Surg. Aug. 1, 2006, 24(1):458-466.

International Preliminary Report on Patentability for PCT/US04/029724 (ACULSR.5CP1 HPC), dated Mar. 23, 2006.

International Preliminary Report on Patentability for PCT/US2005/004873 (ACULSR.008QPC), dated Sep. 14, 2006.

International Preliminary Report on Patentability for PCT/US2007/002219 (ACULSR.052VPC), dated May 2, 1998.

International Preliminary Report on Patentability for PCT/US2007/002474 ACULSR.051VPC), dated Apr. 16, 2008.

International Search Report and Written Opinion dated Oct. 28, 2009, for PCT/US2009/037121, 20 pages.

International Search Report and Written Opinion for PCT/US2005/004873 (ACULSR.008QPC), dated Sep. 5, 2005.

International Search Report and Written Opinion for PCT/US2007/002219 (ACULSR.052VPC), dated Jul. 5, 2007.

International Search Report and Written Opinion for PCT/US2007/002474 (ACULSR.051VPC), dated Sep. 27, 2007.

International Search Report for PCT/CA99/00156, dated Jun. 11, 1999.

International Search Report for PCT/US02/36808 (ACULSR.009VPC), dated Apr. 2, 2003.

International Search Report for PCT/US03/00747 (ACULSR.007VPC), dated May 14, 2003.

Janssen et al., "Modeling of temperature and perfusion during scalp cooling," Phys. Med. Biol., Aug. 18, 2005, 50(17):4065-4073.

Kara et al., "Cell Attachment to Extracellular Matrices is Modulated by Pulsed Radiation at 820 nm and Chemicals that Modify the Activity of Enzymes in the Plasma Membrane," Lasers in Surgery and Medicine, Sep. 1, 2001, 29:274-281.

Karu, et al., Biostimulation of HeLa Cells by Low-Intensity Visible Light. II. Stimulation of DNA and RNA Synthesis in a Wide Spectral Range. IL Nuovo Cimento, (1984) p. 309-318.

Karu, T.I., Low power laser therapy, in Biomedical Photonics Handbook, Ch. 48, Editor-in-Chief Tuan Vo-Dinh, Boca Raton, CRC Press, 2003.

Karu, Tiina, Mechanisms of interaction of monochromatic visible light with cells, Proc. SPIE, vol. 2630, pp. 2-9, 1996.

Karu, Tiina, Mechanisms of Low-Power Laser Light Action on Cellular Level, Effects of Low-Power Light on Biological Systems V, Proceedings of SPIE, Jul. 7, 2000, vol. 4159 pp. 1-17.

Karu, Tiina, Photobiological Fundamentals of Low Power Laser Therapy, IEEE Journal of Quantum Electronics, vol. QE-23, No. 10, Oct. 1987, pp. 1703-1717.

Lampl et al., "Infrared laser therapy for ischemic stroke: a new treatment strategy: results of the NeuroThera Effectiveness and Safety Trial-I (NEST-I)," Stroke, Jun. 1, 2007, 38(6):1843-1849.

Lapchak et al., "Neuroprotective effects of the spin trap agent disodium-[(tert-butylimino)methyl]benzene-1,3-disulfonate N-oxide (generic NXY-059) in a rabbit small clot embolic stroke model: combination studies with the thrombolytic tissue plasminogen activator," Stroke, May 1, 2002, 33(5):1411-1415.

Lapchak et al., "Transcranial infrared laser therapy improves clinical rating scores after embolic strokes in rabbits," Stroke Aug. 1, 2004, 35(8):1985-1988.

Laser Exchange: Delivering the medicine of the future, http:llwww.laserexchanqe.eo.uk//asertherap'tfu/trasound.htm; 42 pages, Oct. 13, 2004.

Lepselter et al., "Biological and clinical aspects in laser hair removal, J. Dermatological Treatment," Apr. 1, 2004, 15(2):72-83.

Leung, Mason C.P., et al., Treatment of Experimentally Induced Transient Cerebral Ischemia with Low Energy Laser Inhibits Nitric Oxide Synthase Activity and Up-Regulates the Expression of Transforminq Growth Factor-Beta 1, Laser in Suraerv and Medicine, 31 :283-288 (2002).

Lisman et al., "Two Light-Induced Processes in the Photoreceptor Cells of Limulus Ventral Eye," J. Gen, Physiology, Nov. 1, 1971, 58(5):544-561.

Lychagov, Vladislav V., et al. Experimental study of NIRtransmittance of the human skull, Proc. of SPIE, vol. 6085, 2006 (five pages).

Matas et al., "Eliminating the Issue of Skin Color in Assessment of the Blanch Response," Adv. in Skin & Wound Care, Jul. 2001, 14(4, part 1of2):180-188.

Mester, E., et al., Effect of Laser Rays on Wound Healing, The American Journal of Surgerv, vol. 122, Oct. 1971, pp. 532-535.

Mochizuki-Oda, Noriko, et al., Effects of near-infra-red laser irradiation on adenosine triphosphate and adenosine diphosphate contents of rat brain tissue, Neuroscience Letters 323, May 3, 2002, pp. 207-210.

(56) References Cited

OTHER PUBLICATIONS

Niitsuma et al., "Experimental study of decubitus ulcer formation in the rabbit ear lobe," J. of Rehab. Res. and Dev., Jan. 2003, 40(1):67-72.

Nishioka, Norman S., et al., Reflection and Transmission of Laser Light From the Esophagus: The Influence of Incident Angle, Gastroenterology, vol. 94, 1988, pp. 1180-1185.

Nissan, M. et al., "HeNe Laser Irradiation Delivered Transcutaneously: Its Effect on the Sciatic Nerve of Rats", Lasers in Surgery and Medicine, vol. 6, pp. 435-438, 1986.

Olesin, Al, et al., Laser irradiation of venous blood for production of reperfusion syndrome in myocardial infarction, Patologisheskaia fiziologiia, Sep.-Dec. 1992 (5-6) p. 20-3, ISSN 0031-2991 Journal Code: 0376421, EnQlish abstract of Russian article).

Oron et al., "Low-Level Laser Therapy Applied Transcranially to Mice following Traumatic Brain Injury Significantly Reduces Long-Term Neurological Deficits," Journal of Neurotrauma, Apr. 1, 2007, 24:(4)651-6.

Oron et al., "Low-level laser therapy applied transcranially to rats after induction of stroke significantly reduces long-term neurological deficits," Stroke, Oct. 1, 2006, 37:2620-2624.

Oron, et al., Attenuation of Infarct Size in Rats and Dogs after Myocardial Infarction by Low-Energy Laser Irradiation, Lasers in Surge!)'. and Medicine, vol. 28, 2001, pp. 204-211.

Oron, et al., Low-Energy Laser Irradiation Reduces Formation of Scar Tissue After Myocardial Infarction in Rats and Dogs, Circulation, vol. 103, Jan. 16, 2001, pp. 296-301.

Park, James L., Ph.D., et al., Mechanisms of Myocardial Reperfusion Injury, The Annals of Thoracic.

Physical Therapy, The Efficacy of Laser Therapy for Musculoskeletal and Skin Disorders: A Criteria-Based Metanalysis of Randomized Clinical Trials, vol. 72, No. 7, Jul. 1992, pp. 483/12-491/21.

Pogue et al.: "Comparison of Image Geometries for Diffuse Optical Tomography of Tissue"; Optics Express; vol. 4, No. 8; Apr. 12, 1999; pp. 270-286.

Semenza, Gregg L., et al., Regulation of Mammalian 02 Homeostatis by Hypoxia-Inducible Factor 1, Ann. Rev. Cell Dev. Biol., vol. 15, 1999, pp. 551-578.

Smith. Kendric C., "The Photobiological Basis of Low Level Laser Radiation Therapy", Photoblological Basis ofLLLT, pp. 1-7, 1991.

Sommer et al., "Stressed cells survive better with light," J. Proteome. Res. Oct. 1, 2002. 1:475.

Stys, Peter K., Anoxis and Ischemic Injury of Myelinated Axons in CNS White Matter: From Mechanistic Concepts to Therapeutics, J. Cereb. Blood Flow Metab., vol. 18, No. 1, Jan. 1998, 42 pages (037C1 lists DD. 2-25).

Surgery, Official Journal of Thoracic Surgeons and the Southern Thoracic Surgical Association, vol. 68, No. 5, Nov. 1999, pp. 1905-1912.

THOR Laser, Specifications, THOR: Specifications, Thor, lilt, LLLT, Low Level Laser Therapy, low level laser therapy, http.f!www.thorlaser.com! specs, Oct. 6, 1999, pp. 1-2.

THOR Laser. 100mW, Thor, lilt, LLLT, Low Level Laser Therapy, low level laser therapy, Lazer, Thor httQ:ilwww.thorlaser.com/specs/ 100m Whtml, Oct. 6, 1999, p. 1.

THOR, Specification, 200mW/650nm Laser probe, http:llwww.thorlaser.com!specs/200mW650nm.html, web page (1 page), Oct. 6, 1999.

THOR, Specification, 200mW/81 Onm Laser probe, http:l/www.thorlaser.com/sQecs/ 200mWhtml, web page (1 page), Oct. 6, 2009.

THOR, Specification, 30mW Red Laser probe, www.thorlaser.com/specs/ 680.html, web page (1 page), Oct. 6, 1999.

THOR, Specification, 500mW/810nm Laser probe, http:!!www.thorlaser.com/specs! 500mWhtmf, web page (1 page), Oct. 6, 1999.

THOR: Is LL T Different from Ultrasound?, http://www.thorlaser.com/LLL Tlis-LLL T-diff-fromuftrasound. htm, 2 pages, Oct. 13, 2004.

THOR: Product List, Thor, lilt, LLL T, Low Level Laser Therapy, Laz., httQ.flwww.thorlaser.comlerodlist!index.html, Oct. 6, 1999, pp. 1-4.

Toon, John, Taking the "Ouch" Out of Needles: Arrays of Micron-Scale "Microneedles" Offer New Technique for Drug Delivery, Georgia Tech Research News, Jun. 22, 1998 (three pages).

Tori Celli, P., et al., Laser Biostimulation of cartilage: in vitro evaluation, Biomed. Pharmacother., 2001, vol. 55, pp. 117-120.

Tuchin, Valery, Tissue Optics: Light Scattering Methods and Instruments for Medical Diagnosis, SPIE Press, Tutorial Texts in Optical Engineering, vol. TI38, 2000, pp. 3-11, 2000.

Tuner, Jan, et al., Low Level Laser Therapy, Clinical Practice and Scientific Background, Prima 261 Books in Sweden AB, 1999, pp. 1-9, 45-58, 62-114, 113-116, 118, 132-134, 134-135, 149-151, 151-156, 185, 334-364.

Van Breugel et al. "He—Ne laser irradiation affects proliferation of cultured rat-Schwann cells in a dose-dependent manner," Journal of Neurocytology 22, 185-190 (1993).

Van Breugel, Hans H.F.I., et al., Power Density and Exposure Time of He—Ne Laser Irradiation are More Important than Total Energy Dose in Photo-Biomoducation of Human Fibroblasts InVitro, Lasers in Suraerv and Medicine, Jan. 1, 1992, 12(5):528-537.

Weiss, N. et al., "Enhancement of Muscle Regeneration in the Rat Gastrocnemius Muscle by Low Energy Laser Irradiation", Anat. Embroyl. (1992), vol. 186, pp. 497-503.

Wells et al., "Biophysical mechanisms responsible for pulsed low-level laser excitation of neural tissue," Proc. SPIE, Mar. 1, 2006, 6084:60840X.

Wong-Riley, Margaret T.T., et al., Light-emitting diode treatment reverse the effect ofTTX on cytochrome oxidase in neurons, NeuroRegort, vol. 12, No. 14, Oct. 8, 2001, pp. 3033-3037.

Yaakobi, Tali, et al., Long-term effect of low energy laser irradiation on infarction and reperfusion injury in the rat heart, J. Aggi. Ph)'.siol., vol. 90, 2001, pp. 2411-2419.

\* cited by examiner

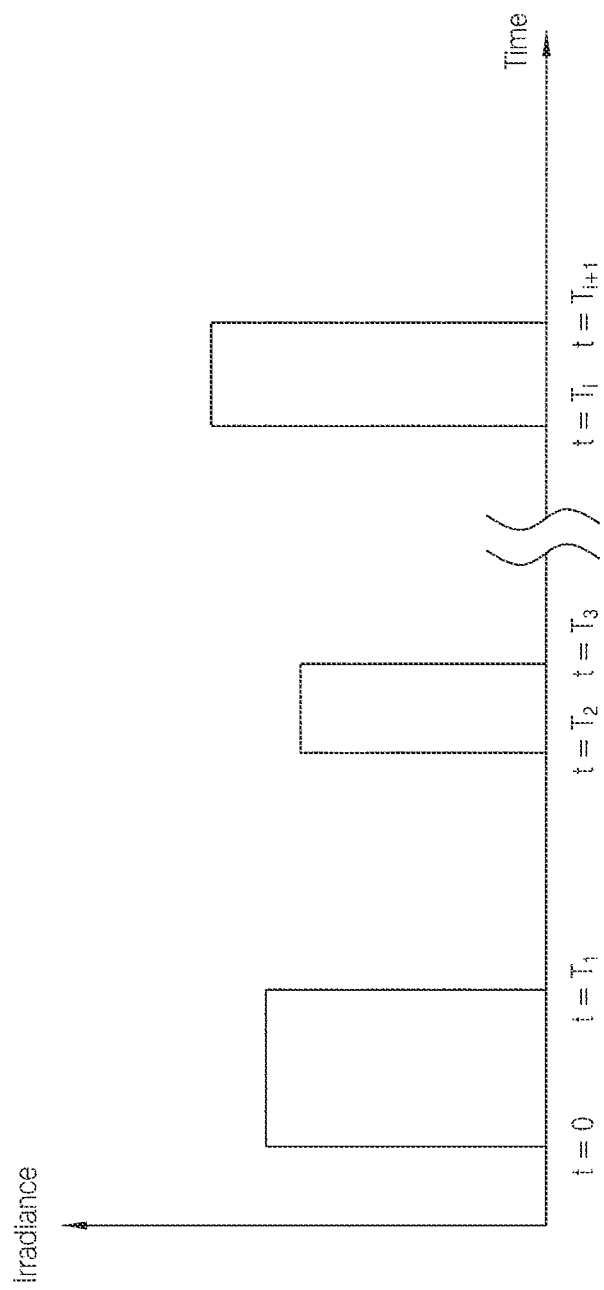

METHOD AND APPARATUS FOR IRRADIATING A SURFACE WITH PULSED LIGHT

CLAIM OF PRIORITY

This application is a continuation of U.S. patent application Ser. No. 12/403,824, filed Mar. 13, 2009, which is a continuation-in-part of U.S. patent application Ser. No. 12/389,294, filed Feb. 19, 2009, now U.S. Pat. No. 10,357, 662, which claims the benefit of priority to U.S. Provisional Application No. 61/037,668, filed Mar. 18, 2008. The entire contents of the foregoing are hereby incorporated by reference.

BACKGROUND OF THE INVENTION

Field of the Invention

The present invention relates in general to phototherapy, and more particularly, to novel apparatuses and methods for phototherapy of brain tissue.

Description of the Related Art

There are numerous neurologic conditions, such as neurodegenerative diseases (e.g., Alzheimer's disease, Parkinson's disease), Huntington's disease, demyelinating diseases (e.g., multiple sclerosis), cranial nerve palsies, traumatic brain injury, stroke, and spinal cord injury which could possibly benefit from application of phototherapy. Most of these conditions cause significant morbidity and mortality and involve tremendous burden to society, families and caregivers. Many neurologic conditions have no currently available effective therapies or the therapies that are available are not adequate to restore functional recovery, sustain quality of life, or halt disease progression.

One example of a neurologic condition that remains a major unmet medical need is stroke, also called cerebrovascular accident (CVA). Stroke is caused by a sudden disruption of blood flow to a discrete area of the brain that is brought on by the lodging of a clot in an artery supplying blood to an area of the brain (called an ischemic stroke), or by a cerebral hemorrhage due to a ruptured aneurysm or a burst artery (called a hemorrhagic stroke). There are over 750,000 stroke victims per year in the United States, and approximately 85% of all strokes are ischemic and 15% are hemorrhagic. The consequence of stroke is a loss of function in the affected brain region and concomitant loss of bodily function in areas of the body controlled by the affected brain region. Depending upon the extent and location of the primary insult in the brain, loss of function varies greatly from mild or severe, and may be temporary or permanent. Lifestyle factors such as smoking, diet, level of physical activity and high cholesterol increase the risk of stroke, and thus stroke is a major cause of human suffering in developed nations. Stroke is the third leading cause of death in most developed nations, including the United States.

Stroke treatment is often restricted to providing basic life support at the time of the stroke, followed by rehabilitation. Currently, the only FDA-cleared treatment of ischemic stroke involves thrombolytic therapy using tissue plasminogen activator (tPA). However, tPA can only be used within three hours of stroke onset and has several contraindications, therefore, only a small percentage of stroke victims receive this drug.

Traumatic brain injury (TBI) occurs when a sudden physical trauma (e.g., crush or compression injury in the central nervous system, including a crush or compression injury of the brain, spinal cord, nerves or retina, or any acute injury or insult producing cell death) causes damage to the head. For example, a sudden and/or violent blow to the head or an object piercing the skull and entering brain tissue can result in TBI. The extent of damage to the brain can be severe, however even mild and moderate TBI has been associated with neurological sequelae that can be long lasting. Development of neurodegenerative conditions has been associated with TBI. TBI can result in a sudden disruption of blood flow to a discrete area of the brain. The consequence of stroke or TBI can be a loss of function in the affected brain region and concomitant loss of bodily function in areas of the body controlled by the affected brain region. Depending upon the extent and location of the primary insult in the brain, loss of function varies greatly from mild or severe, and may be temporary or permanent.

A high level of interest and clinical need r finding new and improved therapeutic interventions for treatment of stroke and other neurologic conditions that continue to devastate millions of lives each year and where few effective therapies exist.

SUMMARY OF THE INVENTION

In certain embodiments, an apparatus for irradiating a portion of a patient's scalp or skull with light is provided. The apparatus comprises a source of light and an output optical element in optical communication with the source. The output optical element comprises an emission surface configured to emit a pulsed light beam comprising a plurality of pulses having a temporal pulsewidth in a range between 0.1 millisecond and 150 seconds. The pulsed light beam has a cross-sectional area greater than about 2 cm$^2$ at the emission surface of the output optical element, and has a time-averaged irradiance in a range of about 10 mW/cm$^2$ to about 10 W/cm$^2$ across the cross-sectional area.

In certain embodiments, a method of irradiating a surface with light is provided. The method comprises irradiating the surface with at least one pulsed light beam emitted from an emission surface of an optical element. The at least one pulsed light beam comprises a plurality of pulses having a temporal pulsewidth in a range between about 0.1 millisecond and about 150 seconds. The at least one pulsed light beam has a beam cross-sectional area at the emission surface greater than about 2 cm$^2$ and a time-averaged irradiance in a range between about 1 mW/cm$^2$ and about 100 W/cm$^2$.

In certain embodiments, a method of treating a patient's brain is provided. The method comprises irradiating at least a portion of the scalp or skull of the patient with at least one pulsed light beam comprising a plurality of pulses transmitted through the patient's skull to irradiate at least a portion of the brain. The at least one pulsed light beam has a temporal profile comprising a time-averaged irradiance at the scalp averaged over one second in a range between about 100 mW/cm$^2$ and about 10 W/cm$^2$ and a peak irradiance at the scalp in a range between about 12.5 mW/cm$^2$ and about 1000 W/cm$^2$.

In certain embodiments, a method of treating a patient who has experienced a traumatic brain injury is provided. The method comprises noninvasively irradiating at least a portion of the patient's scalp or skull with pulsed light penetrating the patient's skull to irradiate and stimulate brain cells of the patient. The pulsed light has a temporal profile comprising an average irradiance per pulse, a temporal pulse width, and a pulse duty cycle. The temporal profile is selected to modulate membrane potentials in order to enhance, restore, or promote cell survival, cell function, or both of the irradiated brain cells following the traumatic brain injury.

In certain embodiments, a method of treating a patient experiencing a neurodegenerative disease or depression is provided. The method comprises noninvasively irradiating at least a portion of the patient's scalp or skull with pulsed light penetrating the patient's skull to irradiate and stimulate brain cells of the patient. The pulsed light has a temporal profile comprising an average irradiance per pulse, a temporal pulse width, and a pulse duty cycle. The temporal profile is selected to modulate membrane potentials in order to enhance, restore, or promote cell survival, cell function, or both of the irradiated brain cells.

For purposes of summarizing the present invention, certain aspects, advantages, and novel features of the present invention have been described herein above. It is to be understood, however, that not necessarily all such advantages may be achieved in accordance with any particular embodiment of the present invention. Thus, the present invention may be embodied or carried out in a manner that achieves or optimizes one advantage or group of advantages as taught herein without necessarily achieving other advantages as may be taught or suggested herein.

BRIEF DESCRIPTION OF THE DRAWINGS

FIGS. 21A-21D schematically illustrate example pulses in accordance with certain embodiments described herein.

DETAILED DESCRIPTION OF THE PREFERRED EMBODIMENT

Figure 1:
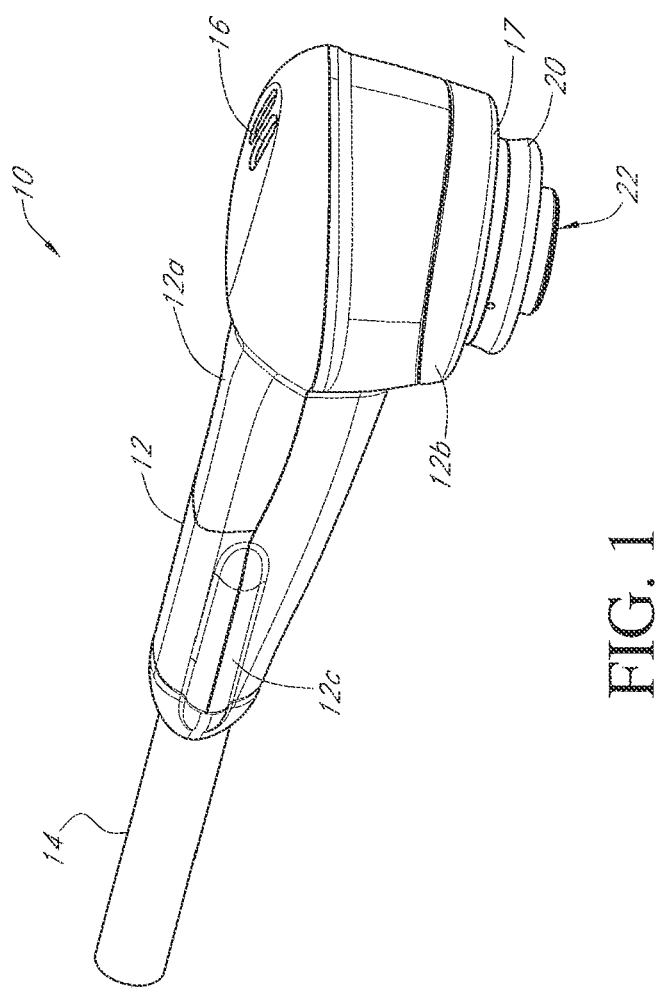
FIG. 1 schematically illustrates an example beam delivery apparatus in accordance with certain embodiments described herein.

Low level light therapy ("LLLT") or phototherapy involves therapeutic administration of light energy to a patient at lower irradiances than those used for cutting, cauterizing, or ablating biological tissue, resulting in desirable biostimulatory effects while leaving tissue undamaged. In non-invasive phototherapy, it is desirable to apply an efficacious amount of light energy to the internal tissue to be treated using light sources positioned outside the body. (See, e.g., U.S. Pat. Nos. 6,537,304 and 6,918,922, both of which are incorporated in their entireties by reference herein.)

Laser therapy has been shown to be effective in a variety of settings, including treating lymphoedema and muscular trauma, and carpal tunnel syndrome. Recent studies have shown that laser-generated infrared radiation is able to penetrate various tissues, including the brain, and to modify function. In addition, laser-generated infrared radiation can induce effects including, but not limited to, angiogenesis, modify growth factor (transforming growth factor-β) signaling pathways, and enhance protein synthesis.

However, absorption of the light energy by intervening tissue can limit the amount of light energy delivered to the target tissue site, while heating the intervening tissue. In addition, scattering of the light energy by intervening tissue can limit the irradiance (or power density) or energy density delivered to the target tissue site. Brute force attempts to circumvent these effects by increasing the power and/or irradiance applied to the outside surface of the body can result in damage (e.g., burning) of the intervening tissue. For example, a patient experiencing TBI can have a significant amount of bleeding within the skull (e.g., "blood in the field"), and this blood can absorb the applied light, thereby inhibiting propagation of light energy to brain tissue below the blood-filled region and heating up.

Non-invasive phototherapy methods are circumscribed by setting selected treatment parameters within specified limits so as to preferably avoid damaging the intervening tissue. A review of the existing scientific literature in this field would cast doubt on whether a set of undamaging, yet efficacious, parameters could be found for treating neurologic conditions. However, certain embodiments, as described herein, provide devices and methods which can achieve this goal.

Such embodiments may include selecting a wavelength of light at which the absorption by intervening tissue is below a damaging level. Such embodiments may also include setting the power output of the light source at low, yet efficacious, irradiances (e.g., between approximately 100 $\mu W/cm^2$ to approximately 10 $W/cm^2$ at the target tissue site, setting the temporal profile of the light applied to the head (e.g., temporal pulsewidths, temporal pulse shapes, duty cycles, pulse frequencies), and time periods of application of the light energy at hundreds of microseconds to minutes to achieve an efficacious energy density at the target tissue site being treated. Other parameters can also be varied in the use of phototherapy. These other parameters contribute to the light energy that is actually delivered to the treated tissue and may play key roles in the efficacy of phototherapy. In certain embodiments, the irradiated portion of the brain can comprise the entire brain.

In certain embodiments, the target area of the patient's brain includes the area of injury, e.g., to neurons within the "zone of danger." In other embodiments, the target area includes portions of the brain not within the zone of danger. Information regarding the biomedical mechanisms or reactions involved in phototherapy is provided by Tiina I. Karu in "Mechanisms of Low-Power Laser Light Action on Cellular Level", Proceedings of SPIE Vol. 4159 (2000), Effects of Low-Power Light on Biological Systems V, Ed. Rachel Lubart, pp. 1-17, and Michael R. Hamblin et al., "Mechanisms of Low Level Light Therapy," Proc. of SPIE, Vol. 6140, 614001 (2006), each of which is incorporated in its entirety by reference herein.

In certain embodiments, the apparatuses and methods of phototherapy described herein are used to treat physical trauma (e.g., TBI or ischemic stroke) or other sources of neurodegeneration. As used herein, the term "neurodegeneration" refers to the process of cell destruction resulting from primary destructive events such as stroke or CVA, as well as from secondary, delayed and progressive destructive mechanisms that are invoked by cells due to the occurrence of the primary destructive event. Primary destructive events include disease processes or physical injury or insult, including stroke, but also include other diseases and conditions such as multiple sclerosis, amylotrophic lateral sclerosis, heat stroke, epilepsy, Alzheimer's disease, dementia resulting from other causes such as AIDS, cerebral ischemia including focal cerebral ischemia, and physical trauma such as crush or compression injury in the CNS, including a crush or compression injury of the brain, spinal cord, nerves or retina, or any acute injury or insult producing neurodegeneration. Secondary destructive mechanisms include any mechanism that leads to the generation and release of neurotoxic molecules, including but not limited to, apoptosis, depletion of cellular energy stores because of changes in mitochondrial membrane permeability, release or failure in the reuptake of excessive glutamate, reperfusion injury, and activity of cytokines and inflammation. Both primary and secondary mechanisms contribute to forming a "zone of danger" for neurons, wherein the neurons in the zone have at least temporarily survived the primary destructive event, but are at risk of dying due to processes having delayed effect.

In certain embodiments, the apparatuses and methods described herein are used to provide neuroprotection. As used herein, the term "neuroprotection" refers to a therapeutic strategy for slowing or preventing the otherwise irreversible loss of neurons due to neurodegeneration after a primary destructive event, whether the neurodegeneration loss is due to disease mechanisms associated with the primary destructive event or secondary destructive mechanisms.

In certain embodiments, the apparatuses and methods described herein are used to improve neurologic function, to provide neurologic enhancement, or to regain previously lost neurologic function. The term "neurologic function" as used herein includes both cognitive function and motor function. The term "neurologic enhancement" as used herein includes both cognitive enhancement and motor enhancement. The terms "cognitive enhancement" and "motor enhancement" as used herein refer to the improving or heightening of cognitive function and motor function, respectively.

The term "cognitive function" as used herein refers to cognition and cognitive or mental processes or functions, including those relating to knowing, thinking, learning, perception, memory (including immediate, recent, or remote memory), and judging. Symptoms of loss of cognitive function can also include changes in personality, mood, and behavior of the patient. The term "motor function" as used herein refers to those bodily functions relating to muscular movements, primarily conscious muscular movements, including motor coordination, performance of simple and complex motor acts, and the like.

Diseases or conditions affecting neurologic function include, but are not limited to, Alzheimer's disease, dementia, AIDS or HIV infection, Cruetzfeldt-Jakob disease, head trauma (including single-event trauma and long-term trauma such as multiple concussions or other traumas which may result from athletic injury), Lewy body disease, Pick's disease, Parkinson's disease, Huntington's disease, drug or alcohol abuse, brain tumors, hydrocephalus, kidney or liver disease, stroke, depression, and other mental diseases which cause disruption in cognitive function, and neurodegeneration.

Beam Delivery Apparatus

The phototherapy methods for the treatment of neurologic conditions (e.g., ischemic stroke, Alzheimer's Disease, Parkinson's Disease, depression, or TBI) described herein may be practiced and described using various light delivery systems. Such light delivery systems may include a low level laser therapy apparatus such as that shown and described in U.S. Pat. Nos. 6,214,035, 6,267,780, 6,273,905, 6,290,714, and 7,303,578, U.S. patent application Ser. No. 12/389,294, and U.S. Pat. Appl. Publ. Nos. 2005/0107851 A1 and 2007/0179571 A1, each of which is incorporated in its entirety by reference herein. For example, in certain embodiments, the light delivery apparatus can irradiate a portion of the patient's scalp or skull while cooling the irradiated portion of the scalp or skull. In certain other embodiments, the irradiated portion of the patient's scalp or skull is not cooled while irradiating the portion of the scalp or skull.

These previously-disclosed light delivery apparatuses were described primarily in conjunction with phototherapy treatment of stroke, however in certain embodiments, such light delivery apparatuses can also be used for phototherapy treatment of other neurologic conditions (e.g., Alzheimer's Disease, Parkinson's Disease, depression, TBI). A patient who has experienced a TBI may have a portion of their scalp damaged, thereby exposing a portion of their cranium or skull. In certain such embodiments, the light delivery apparatus can irradiate an exposed portion of the cranium or skull without the light propagating through scalp tissue. Certain embodiments described herein are compatible with irradiation of the brain with light applied to at least a portion of the scalp or with light applied to at least a portion of the cranium or skull without propagating through the scalp.

FIG. 1 schematically illustrates an example beam delivery apparatus 10 in accordance with certain embodiments described herein. The apparatus 10 comprises a housing 12, a flexible conduit 14 operatively coupled to the housing 12, and at least one status indicator 16. In certain embodiments, the apparatus 10 comprises an output optical assembly 20 comprising an emission surface 22 through which a light beam 30 is emitted. The output optical assembly 20 is configured to be releasably mechanically coupled to other components of the apparatus 10.

In certain embodiments, the housing 12 is sized to be easily held in one hand (e.g., having a length of approximately 5½ inches). The housing 12 of certain embodiments further comprises one or more portions 12a, 12b comprising a biocompatible material since they may contact the operator, the patient, or both. For example, one or more low durometer elastomer materials (e.g., rubber, polymers, thermoplastic resins) can be used in certain embodiments. The portion 12a is configured to be grasped by a user's hand during operation of the apparatus 10. The housing 12 of certain embodiments is configured so that the emission surface 22 can be held in position and sequentially moved by hand to irradiate selected portions of the patient's skin. In certain embodiments, the housing 12 comprises one or more recesses or protrusions which facilitate the housing 12 being gripped by the user. In certain embodiments, the housing 12 is configured to be placed on a testing system to measure or monitor the operative parameters of the apparatus 10. The housing 12 of certain such embodiments comprises an alignment rib 12c configured to provide a registration protrusion which mates with a corresponding registration recess on the testing system to facilitate proper alignment of the emission surface 22 with the testing system. The housing 12 of certain embodiments comprises two or more portions (e.g., 2-piece cast urethane with 60 A overmolding or 3-piece Lustran® with thermoplastic elastomer overmolding) which fit together to form a shell in which other operative components are held. In certain embodiments, the light used by the apparatus 10 can cause eye damage if viewed by an individual. In such embodiments, the apparatus 10 can be configured to provide eye protection so as to avoid viewing of the light by individuals. For example, opaque materials can be used for the housing 12 and appropriately placed to block the light from being viewed directly. In addition, interlocks can be provided so that the light source is not activated unless the apparatus 10 is in place, or other appropriate safety measures are taken.

In certain embodiments, the housing 12 further comprises a flexible boot 17 generally surrounding the portion of the apparatus 10 which is releasably mounted to the output optical assembly 20. The boot 17 of certain embodiments provides a barrier to control, inhibit, prevent, minimize, or reduce contaminants from entering the housing 12. Thus, by virtue of the boot 17 providing a barrier, the contamination entering the housing 12 is lower than it would otherwise be if the boot 17 did not provide a barrier. Example materials for the flexible boot 17 include but are not limited to, rubber or another elastomer.

In certain embodiments, the conduit 14 is configured to operatively couple the apparatus 10 to various control, power, and cooling systems that are spaced from the housing 12. In certain embodiments, the conduit 14 comprises at least one optical fiber configured to transmit light from a light source to the apparatus 10 to be emitted from the emission surface 22. In certain embodiments, the conduit 14 further comprises one or more electrically conductive wires (e.g., one 20-conductor cable, four 6-conductor cables, ground braid) configured to transmit signals between the apparatus 10 (e.g., trigger switches or temperature sensors within the apparatus 10) and a control system spaced from the apparatus 10 and/or to provide electrical power to the apparatus 10 (e.g., for a thermoelectric cooler) from a power system. In still other embodiments, the apparatus 10 comprises a power source (e.g., a battery). In certain embodiments, the conduit 14 comprises one or more coolant tubes (e.g., 0.125-inch inner diameter) configured to have a coolant (e.g., liquid or gas) flow to the apparatus 10 from a cooling system. In certain embodiments, the conduit 14 comprises one or more connectors which are mechanically coupled to one or more corresponding connectors within the housing 12. For example, the conduit 14 can comprise an SMA connector at an end of the optical fiber which is mechanically coupled to a corresponding SMA mount within the housing 12.

In certain embodiments, the conduit 14 comprises a protective sheath around the one or more fibers, wires, and tubes of the conduit 14. The protective sheath of certain embodiments controls, inhibits, prevents, minimizes, or reduces light from exiting the conduit 14 in the event of a failure of the at least one optical fiber. Thus, by virtue of having the sheath, the light exiting the conduit 14 upon fiber failure is lower than it would otherwise be without the sheath. In certain embodiments, the protective sheath comprises a strain relief apparatus having a plurality of rigid segments (e.g., stainless steel), with each segment having a generally cylindrical tubular shape and a longitudinal axis. Each segment is articulately coupled to neighboring segments such that an angle between the longitudinal axes of neighboring segments is limited to be less than a predetermined angle. In certain embodiments, the protective sheath allows the conduit 14 to be moved and to bend, but advantageously limits the radius of curvature of the bend to be sufficiently large to avoid breaking the one or more fibers, wires, or tubes therein. In certain embodiments, the sheath comprises a flexible compression spring (e.g., 4 inches in length) to provide bend relief and/or a tension line to provide strain relief In certain embodiments, the at least one status indicator 16 comprises one, two, or more light-emitting diodes (LEDs) which are lit to visually provide the user with information regarding the status of the apparatus 10. For example, the at least one status indicator 16 can be used in certain embodiments to indicate when the laser source is ready to lase pending engagement of the trigger. In certain embodiments, the LEDs can be lit to show different colors depending on whether the optical power, electrical power, or coolant flow being provided to the apparatus 10 are sufficient for operation of the apparatus 10. In certain embodiments, the at least one status indicator 16 provides information regarding whether the output optical assembly 20 is properly mounted to the apparatus 10. Other types of status indicators (e.g., flags, sound alarms) are also compatible with certain embodiments described herein.

Figure 2A:
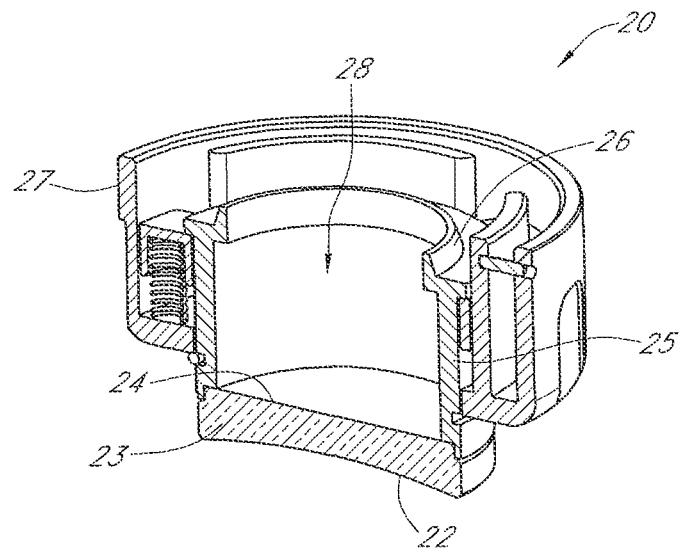
FIG. 2A schematically illustrates a cross-sectional view of an example output optical assembly in accordance with certain embodiments described herein.
Figure 2B:
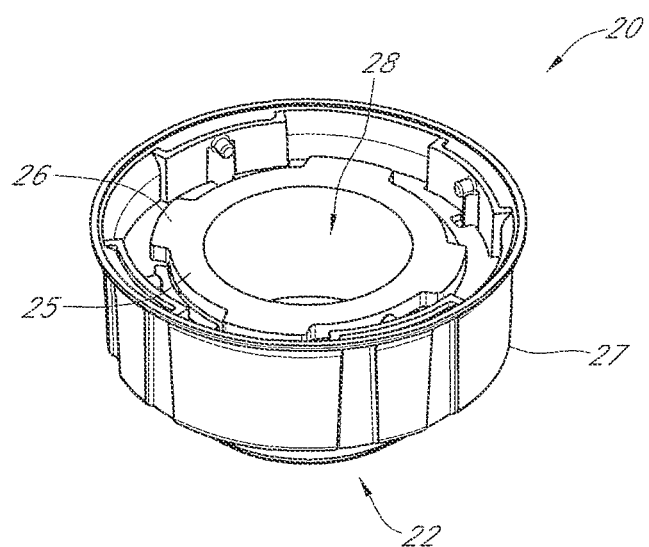
FIG. 2B schematically illustrates another example output optical assembly in accordance with certain embodiments described herein.

FIG. 2A schematically illustrates a cross-sectional view of an example output optical assembly 20 in accordance with certain embodiments described herein. FIG. 2B schematically illustrates another example output optical assembly 20 in accordance with certain embodiments described herein. The output optical assembly 20 comprises an optical element 23 comprising the emission surface 22 and a surface 24 facing generally away from the emission surface 22. As used herein, the term "element" is used in its broadest sense, including, but not limited to, as a reference to a constituent or distinct part of a composite device. The output optical assembly 20 further comprises a thermal conduit 25 in thermal communication with the optical element 23 (e.g., with a portion of the surface 24). The thermal conduit 25 comprises at least one surface 26 configured to be in thermal communication with at least one heat dissipating surface of the apparatus 10 (e.g., a surface of a cooling mechanism). The output optical assembly 20 further comprises a coupling portion 27 (e.g., spring-loaded 3-pin bayonet mount or 4-pin bayonet mount) configured to be releasably attached and detached from the housing 12. In certain embodiments, the output optical assembly 20 comprises one or more springs which provide a sufficient force on the at least one surface 26 towards the at least one heat dissipating surface of the apparatus 10 to have the desired thermal conductivity between the two. Various examples of output optical assemblies 20 compatible with certain embodiments described herein are described more fully in U.S. patent application Ser. No. 12/233,498, which is incorporated in its entirety by reference herein.

In certain embodiments, the output optical assembly 20 is configured to be placed in thermal communication with the patient's scalp or skull (e.g., the optical element 23 is configured to contact the patient's scalp or skull or is configured to be spaced from the patient's scalp or skull but to contact a thermally conductive material in contact with the patient's scalp or skull). In certain embodiments in which the output optical assembly 20 is cooled, the output optical assembly 20 cools at least a portion of the patient's scalp or skull (e.g., the portion of the scalp or skull being irradiated). Thus, in certain embodiments, the output optical assembly 20 is adapted to control, inhibit, prevent, minimize, or reduce temperature increases at the scalp or skull caused by the light. Thus, by virtue of the output optical assembly 20 cooling the portion of the patient's scalp or skull being irradiated, the temperature of the irradiated portion of the patient's scalp or skull is lower than it would otherwise be if the output optical assembly 20 did not cool the irradiated portion of the scalp or skull. For example, by cooling the irradiated portion of the patient's scalp or skull using the output optical assembly 20, the temperature of the irradiated portion of the patient's scalp or skull can be higher than the temperature of the portion of the patient's scalp or skull if it were not irradiated, but lower than the temperature of the portion of the patient's scalp or skull if it were irradiated but not cooled. In certain embodiments, the patient's scalp comprises hair and skin which cover the patient's skull. In other embodiments, at least a portion of the hair is removed prior to the phototherapy treatment, so that the output optical assembly 20 substantially contacts the skin of the scalp.

The optical element 23 of certain embodiments is thermally conductive, and optically transmissive at wavelengths which are transmitted by skin. For example, in certain embodiments, the thermal conductivity of the optical element 23 is sufficient to remove heat from the irradiated portion of the patient's scalp or skull, and the optical transmissivity of the optical element 23, at wavelengths selected to provide the desired irradiance at a target region of the brain, is sufficient to allow the desired irradiance of light to propagate through the optical element 23 to irradiate the patient's scalp or skull. In certain embodiments, the optical element 23 comprises a rigid material, while in certain other embodiments, the optical element 23 comprises a low durometer, thermally conductive, optically transmissive material (e.g., a flexible bag or container filled with a thermally conductive, optically transmissive liquid such as water). Example rigid materials for the optical element 23 include, but are not limited to, sapphire, diamond, calcium fluoride, and zinc selenide. In certain embodiments, the optical element 23 has an emission surface 22 configured to face generally towards the surface to be irradiated (e.g., the patient's scalp or skull). In certain embodiments, the emission surface 22 is adapted to be placed in contact with either the irradiated surface or with a substantially optically transmissive and substantially thermally conductive material which is in contact with the irradiated surface. The emission surface 22 of certain embodiments is configured to be in thermal communication with the surface to be irradiated by the light beam emitted from the emission surface 22. In certain such embodiments, the thermal conductivity of the optical element 23 is sufficiently high to allow heat to flow from the emission surface 22 to the thermal conduit 25 at a sufficient rate to control, inhibit, prevent, minimize, or reduce damage to the skin or discomfort to the patient from excessive heating of the skin due to the irradiation. Thus, by virtue of the thermal conductivity of the optical element 23, any damage to the skin or discomfort to the patient can be lower than it would otherwise be if the optical element 23 did not have a sufficiently high thermal conductivity. For example, the damage to the skin or discomfort to the patient can be higher than it would be if the portion of the patient's scalp were not irradiated, but the damage to the skin or discomfort to the patient would be lower than it would be if the optical element 23 did not have a sufficiently high thermal conductivity.

In certain embodiments, the optical element 23 has a thermal conductivity of at least approximately 10 watts/meter-K. In certain other embodiments, the thermal conductivity of the optical element 23 is at least approximately 15 watts/meter-K. Examples of materials for the optical element 23 in accordance with certain embodiments described herein include, but are not limited to, sapphire which has a thermal conductivity of approximately 23.1 watts/meter-K, and diamond which has a thermal conductivity between approximately 895 watts/meter-K and approximately 2300 watts/meter-K.

In certain embodiments, the emission surface 22 is adapted to conform to the curvature of the scalp or skull. The emission surface 22 of certain embodiments is concave (e.g., generally spherical with a radius of curvature of about 100 millimeters). By fitting to the curvature of the scalp or skull, the emission surface 22 advantageously controls, inhibits, prevents, minimizes, or reduces temperature increases at the scalp or skull that would otherwise result from air-filled gaps between the emission surface 22 and the scalp or skull. Thus, by virtue of the emission surface 22 fitting to the curvature of the portion of the patient's scalp or skull being irradiated, the temperature of the irradiated portion of the patient's scalp or skull is lower than it would otherwise be if the emission surface 22 did not fit to the curvature of the irradiated portion of the scalp or skull. For example, by fitting the emission surface 22 to the curvature of the irradiated portion of the patient's scalp or skull, the temperature of the irradiated portion of the patient's scalp or skull can be higher than the temperature of the portion of the patient's scalp or skull if it were not irradiated, but lower than the temperature of the portion of the patient's scalp or skull if it were irradiated but the emission surface 22 did not fit to the portion of the patient's scalp or skull. The existence of air gaps between the emission surface 22 and the scalp or skull can reduce the thermal conductivity between the emission surface 22 and the scalp or skull, thereby increasing the probability of heating the scalp or skull by the irradiation.

In addition, the refractive-index mismatches between such an air gap and the emission surface 22 and/or the scalp or skull can cause a portion of the light propagating toward the scalp or skull to be reflected away from the scalp or skull. In certain embodiments, the emission surface 22 is placed in contact with the skin of the scalp or skull so as to advantageously substantially reduce air gaps between the emission surface 22 and the scalp or skull in the optical path of the light. In certain other embodiments in which an intervening material (e.g., a substantially optically transmissive and substantially thermally conductive gel) is in contact with the scalp or skull and with the emission surface 22, the emission surface 22 is placed in contact with the intervening material so as to advantageously avoid creating air gaps between the emission surface 22 and the intervening material or between the intervening material and the scalp or skull. In certain embodiments, the intervening material has a refractive index at a wavelength of light impinging the scalp which substantially matches the refractive index of the scalp (e.g., about 1.3), thereby reducing any index-mismatch-generated back reflections between the emission surface 22 and the scalp. Examples of materials compatible with certain such embodiments described herein include, but are not limited to, glycerol, water, and silica gels. Example index-matching gels include, but are not limited to, those available from Nye Lubricants, Inc. of Fairhaven, Mass.

In certain embodiments, the emission surface 22 comprises one or more optical coatings, films, layers, membranes, etc. in the optical path of the transmitted light which are adapted to reduce back reflections. By reducing back reflections, the emission surface 22 increases the amount of light transmitted to the brain and reduces the need to use higher irradiances which may otherwise create temperature increases at the scalp or skull.

Figure 3A:
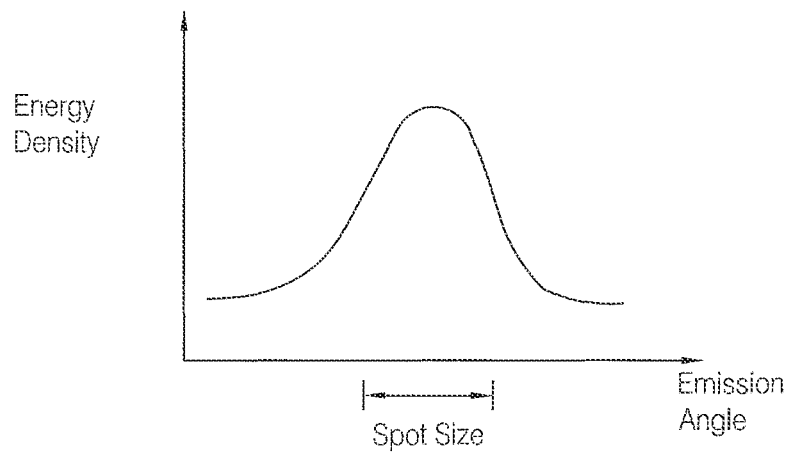
FIGS. 3A and 3B schematically illustrate the diffusive effect on the light by the output optical assembly.
Figure 3B:
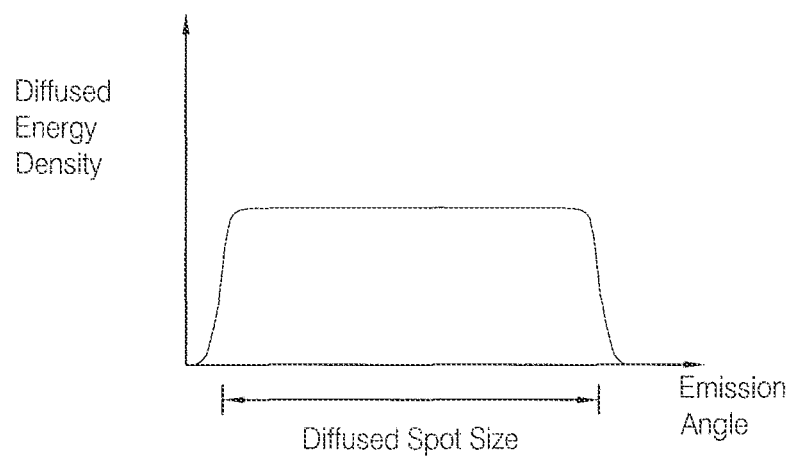

In certain embodiments, the output optical assembly 20 is adapted to diffuse the light prior to reaching the scalp or skull to advantageously homogenize the light beam prior to reaching the emission surface 22. Generally, intervening tissues of the scalp and skull are highly scattering, which can reduce the impact of non-uniform beam intensity distributions on the illumination of the patient's cerebral cortex. However, non-uniform beam intensity distributions with substantial inhomogeneities could result in some portions of the patient's scalp or skull being heated more than others (e.g., localized heating where a "hot spot" of the light beam impinges the patient's scalp or skull). In certain embodiments, the output optical assembly 20 advantageously homogenizes the light beam to have a non-uniformity less than approximately 3 millimeters. FIGS. 3A and 3B schematically illustrate the diffusive effect on the light by the output optical assembly 20. An example energy density profile of the light prior to being transmitted through the output optical assembly 20, as illustrated by FIG. 3A, is peaked at a particular emission angle. After being diffused by the output optical assembly 20, as illustrated by FIG. 3B, the energy density profile of the light does not have a substantial peak at any particular emission angle, but is substantially evenly distributed among a range of emission angles. By diffusing the light, the output optical assembly 20 distributes the light energy substantially evenly over the area to be illuminated, thereby controlling, inhibiting, preventing, minimizing, or reducing "hot spots" which would otherwise create temperature increases at the scalp or skull. Thus, by virtue of the output optical assembly 20 diffusing the light, the temperature of the irradiated portion of the patient's scalp or skull is lower than it would otherwise be if the output optical assembly 20 did not diffuse the light. For example, by diffusing the light using the output optical assembly 20, the temperature of the irradiated portion of the patient's scalp or skull can be higher than the temperature of the portion of the patient's scalp or skull if it were not irradiated, but lower than the temperature of the portion of the patient's scalp or skull if it were irradiated but the light were not diffused by the output optical assembly 20. In addition, by diffusing the light prior to reaching the scalp or skull, the output optical assembly 20 can effectively increase the spot size of the light impinging the scalp or skull, thereby advantageously lowering the irradiance at the scalp or skull, as described in U.S. Pat. No. 7,303,578, which is incorporated in its entirety by reference herein.

In certain embodiments, the output optical assembly 20 provides sufficient diffusion of the light such that the irradiance of the light is less than a maximum tolerable level of the scalp, skull, or brain. For example, the maximum tolerable level of certain embodiments is a level at which the patient experiences discomfort or pain, while in certain other embodiments, the maximum level is a level at which the patient's scalp or skull is damaged (e.g., burned). In certain other embodiments, the output optical assembly 20 provides sufficient diffusion of the light such that the irradiance of the light equals a therapeutic value at the subdermal target tissue. The output optical assembly 20 can comprise example diffusers including, but not limited to, holographic diffusers such as those available from Physical Optics Corp. of Torrance, Calif. and Display Optics P/N SN1333 from Reflexite Corp. of Avon, Conn.

In certain embodiments, the output optical assembly 20 provides a reusable interface between the apparatus 10 and the patient's scalp or skull. In such embodiments, the output optical assembly 20 can be cleaned or sterilized between uses of the apparatus 10, particularly between uses by different patients. In other embodiments, the output optical assembly 20 provides a disposable and replaceable interface between the apparatus 10 and the patient's scalp or skull. By using pre-sterilized and pre-packaged replaceable interfaces, certain embodiments can advantageously provide sterilized interfaces without undergoing cleaning or sterilization processing immediately before use.

In certain embodiments, the output optical assembly 20 is adapted to apply pressure to at least an irradiated portion of the scalp. For example, the output optical assembly 20 is capable of applying pressure to at least an irradiated portion of the scalp upon a force being applied to the apparatus 10 (e.g., by an operator of the apparatus 10 pressing the apparatus 10 against the patient's scalp by hand or by mechanical means to generate force, such as weights, springs, tension straps). By applying sufficient pressure, the output optical assembly 20 can blanch the portion of the scalp by forcing at least some blood out the optical path of the light energy. (For a general discussion of skin blanching, see, e.g., A C. Burton et al., "Relation Between Blood Pressure and Flow in the Human Forearm," J. Appl. Physiology, Vol. 4, No. 5, pp. 329-339 (1951); A. Matas et al., "Eliminating the Issue of Skin Color in Assessment of the Blanch Response," Adv. in Skin & Wound Care, Vol. 14 (4, part 1 of 2), pp. 180-188 (July/August 2001); J. Niitsuma et al., "Experimental study of decubitus ulcer formation in the rabbit ear lobe," J. of Rehab. Res. and Dev., Vol. 40, No. 1, pp. 67-72 (January/February 2003).) The blood removal resulting from the pressure applied by the output optical assembly 20 to the scalp decreases the corresponding absorption of the light energy by blood in the scalp. As a result, temperature increases due to absorption of the light energy by blood at the scalp are reduced. As a further result, the fraction of the light energy transmitted to the subdermal target tissue of the brain is increased. In certain embodiments, a pressure of at least 0.1 pound per square inch is used to blanch the irradiated portion of the scalp, while in certain other embodiments, a pressure of at least one pound per square inch is used to blanch the irradiated portion of the scalp. In certain embodiments, a pressure of at least about two pounds per square inch is used to blanch the irradiated portion of the scalp. Other values or ranges of pressures for blanching the irradiated portion of the scalp are also compatible with certain embodiments described herein. The maximum pressure used to blanch the irradiated portion of the scalp is limited in certain embodiments by patient comfort levels and tissue damage levels.

Figure 4A:
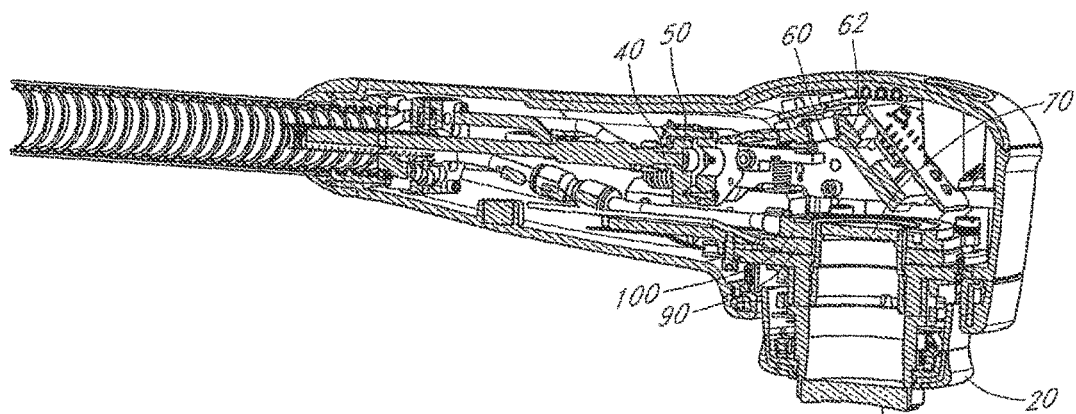
FIGS. 4A and 4B schematically illustrate cross-sectional views of two example beam delivery apparatuses in accordance with certain embodiments described herein.
Figure 4B:
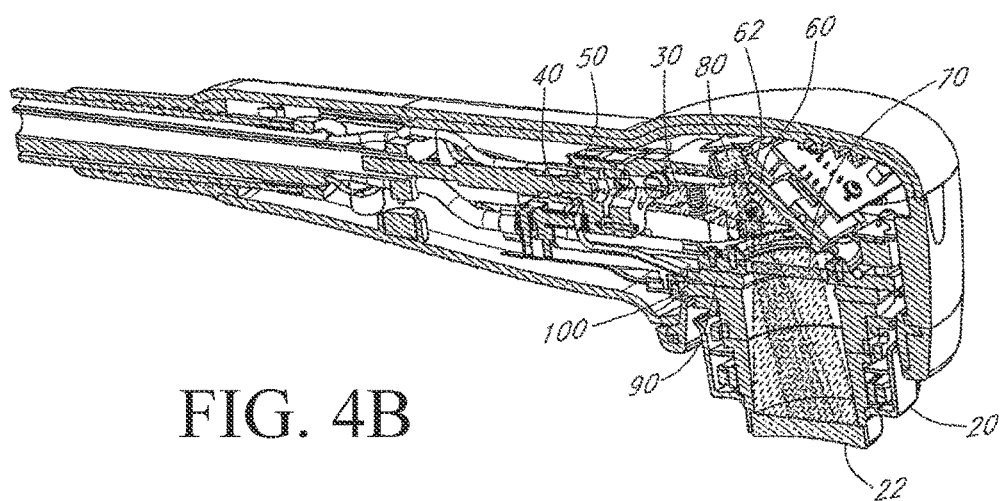

FIGS. 4A and 4B schematically illustrate cross-sectional views of two example beam delivery apparatuses 10 in accordance with certain embodiments described herein. In FIGS. 4A and 4B, the apparatus 10 comprises an output optical assembly 20 having an emission surface 22 and releasably operatively coupled to the other components of the apparatus 10. The apparatus 10 comprises an optical fiber 40, a fiber alignment mechanism 50 operatively coupled to the optical fiber 40, a mirror 60 in optical communication with the optical fiber 40, and a window 70 in optical communication with the mirror 60. During operation of the apparatus 10, light 30 from the optical fiber 40 propagates to the mirror 60 and is reflected by the mirror 60 to propagate through the window 70. The light 30 transmitted through the window 70 propagates through the output optical assembly 20 along a first optical path and is emitted from the emission surface 22. In certain embodiments, the apparatus 10 comprises additional optical elements (e.g., lenses, diffusers, and/or waveguides) which transmit at least a portion of the light received via the optical fiber 40 to the emission surface 22. In certain such embodiments, the additional optical elements of the apparatus 10 shape, format, or otherwise modify the light such that the light beam emitted from the emission surface 22 has the desired beam intensity profile.

In certain embodiments, the optical fiber 40 comprises a step-index or graded-index optical fiber. The optical fiber 40 of certain embodiments is single-mode, while in certain other embodiments, the optical fiber is multimode. An example optical fiber 40 compatible with certain embodiments described herein has a 1000-micron diameter and a numerical aperture of approximately 0.22.

Figure 5:
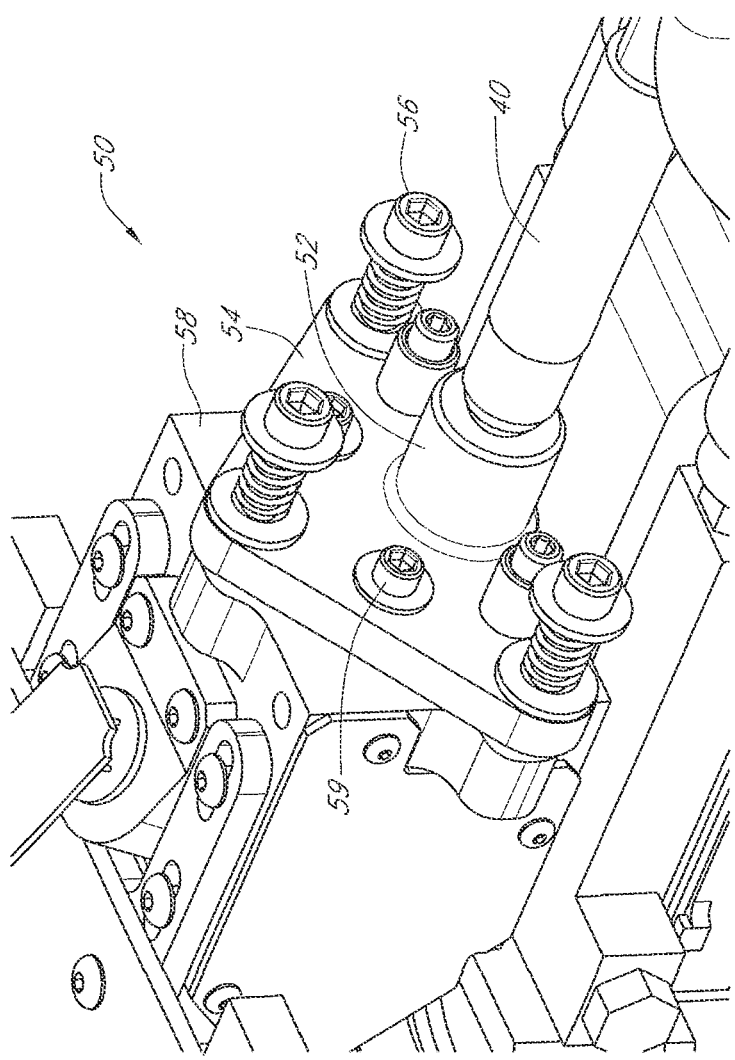
FIG. 5 schematically illustrates an example fiber alignment mechanism in accordance with certain embodiments described herein.

FIG. 5 schematically illustrates an example fiber alignment mechanism 50 in accordance with certain embodiments described herein. In certain embodiments, the fiber alignment mechanism 50 is mechanically coupled to a portion of the optical fiber 40 and is configured to allow adjustments of the position, tilt, or both of the end of the optical fiber 40 from which the light is emitted. In certain embodiments, the fiber alignment mechanism 50 provides an adjustment range of at least ±5 degrees. The fiber alignment mechanism 50 of FIG. 5 comprises a connector 52 (e.g., SMA connector) mechanically coupled to the optical fiber 40, a plate 54 (e.g., a kinematic tilt stage) mechanically coupled to the connector 52, and a plurality of adjustment screws 56 (e.g., 80 turns per inch or 100 turns per inch) adjustably coupled to the plate 54. By turning the adjustment screws 56, a distance between a portion of the plate 54 and a corresponding portion of a reference structure 58 can be adjusted. In certain embodiments, the fiber alignment mechanism 50 comprises one or more locking screws 59 configured to be tightened so as to fix the plate 54 at a position, orientation, or both relative to the reference structure 58. Other configurations of the fiber alignment mechanism 50 are also compatible with certain embodiments described herein.

Figure 6:
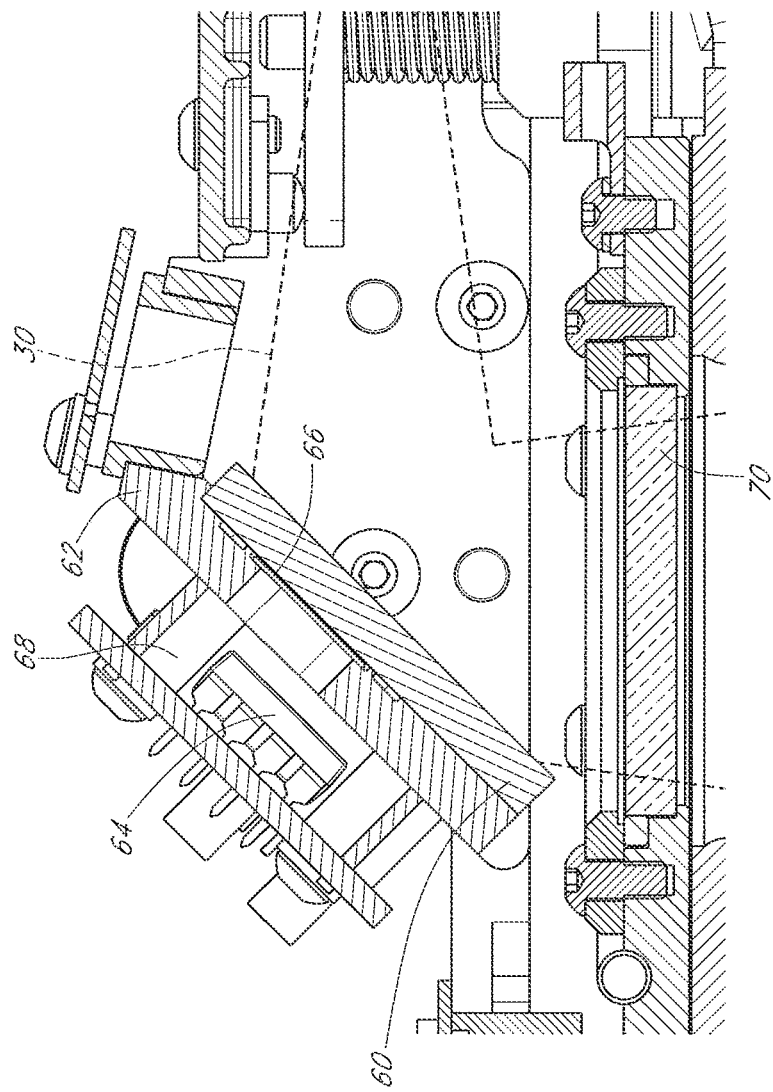
FIG. 6 schematically illustrates an example mirror compatible with certain embodiments described herein.

FIG. 6 schematically illustrates an example mirror 60 compatible with certain embodiments described herein. In certain embodiments, the mirror 60 is substantially reflective of light emitted from the optical fiber 40 to reflect the light through a non-zero angle (e.g., 90 degrees). The mirror 60 of certain embodiments comprises a glass substrate coated on at least one side by a metal (e.g., gold or aluminum). Examples of mirrors 60 compatible with certain embodiments described herein include, but are not limited to, a flat, generally planar glass mirror (e.g., NT43-886 available from Edmund Optics Inc. of Barrington, N.J.). The mirror 60 of certain embodiments can be configured to have an optical power (e.g., the mirror 60 can be concave) and be adapted to shape, format, or otherwise modify the light to produce a desired beam intensity profile. In certain embodiments, the mirror 60 is bonded around its perimeter by an adhesive (e.g., OP-29 adhesive available from Dymax Corp. of Torrington, Conn.) to a support structure 62.

In certain embodiments, the mirror 60 is partially transmissive of light emitted from the optical fiber 40. In certain such embodiments, the support structure 62 comprises an opening and the apparatus 10 comprises at least one light sensor 64 positioned to receive light transmitted through the mirror 60 and the opening of the support structure 62. The at least one light sensor 64 is configured to generate a signal indicative of the intensity of the received light, thereby providing a measure of the intensity of the light reaching the mirror 60. Examples of light sensors 64 compatible with certain embodiments described herein include, but are not limited to, OPT101 photodiode available from Texas Instruments of Dallas, Tex. In certain embodiments, a plurality of light sensors 64 are used to provide operational redundancy to confirm that light with a sufficient intensity for operation of the apparatus 10 is being provided by the optical fiber 40. In certain embodiments, a diffuser 66 is positioned to diffuse the light transmitted through the mirror 60 before the light impinges the light sensor 64. In certain embodiments, the light sensor 64 is protected from stray light by an opaque shroud 68 generally surrounding the light sensor 64.

In certain embodiments, the window 70 is substantially transmissive to infrared radiation. Example windows 70 compatible with certain embodiments described herein include, but are not limited to, a flat, generally planar $CaF_2$ window (e.g., TechSpec® calcium fluoride window available from Edmund Optics Inc. of Barrington, N.J.).

In certain embodiments, the window 70 at least partially bounds a region within the apparatus 10 which contains the mirror 60. The window 70 of certain such embodiments substantially seals the region against contaminants (e.g., dust, debris) from entering the region from outside the region. For example, when the output optical assembly 20 is decoupled from the apparatus 10, the window 70 controls, inhibits, prevents, minimizes, or reduces contaminants entering the region. Thus, by virtue of the window 70 substantially sealing the region, the contamination of the region is lower than it would otherwise be if the window 70 did not substantially seal the region.

Figure 7:
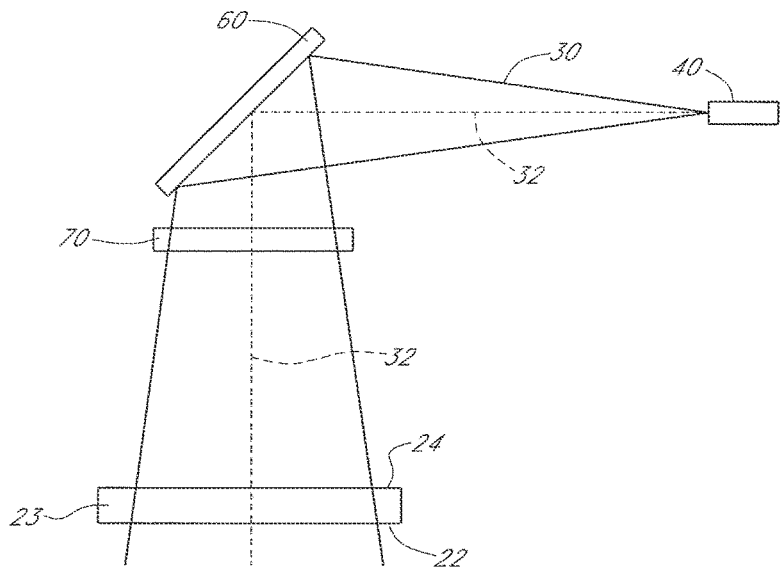
FIG. 7 schematically illustrates an example first optical path of light emitted from the optical fiber in accordance with certain embodiments described herein.

FIG. 7 schematically illustrates an example first optical path 32 of light 30 emitted from the optical fiber 40 in accordance with certain embodiments described herein. The diverging light 30 exiting the optical fiber 40 propagates along the first optical path 32 towards the mirror 60. The light 30 is reflected by the mirror 60 and propagates along the first optical path 32 through the window 70, impinges or is received by the surface 24 of the optical element 23, and is emitted from the emission surface 22 towards the surface to be irradiated. In certain embodiments, the mirror 60 reflects the light 30 through an angle of about 90 degrees. In certain embodiments, the mirror 60 is about 2.3 inches from the face of the optical fiber 40 and the first optical path 32 is about 4.55 inches in length from the fiber output face to the emission surface 22 of the optical element 23.

Figure 8:
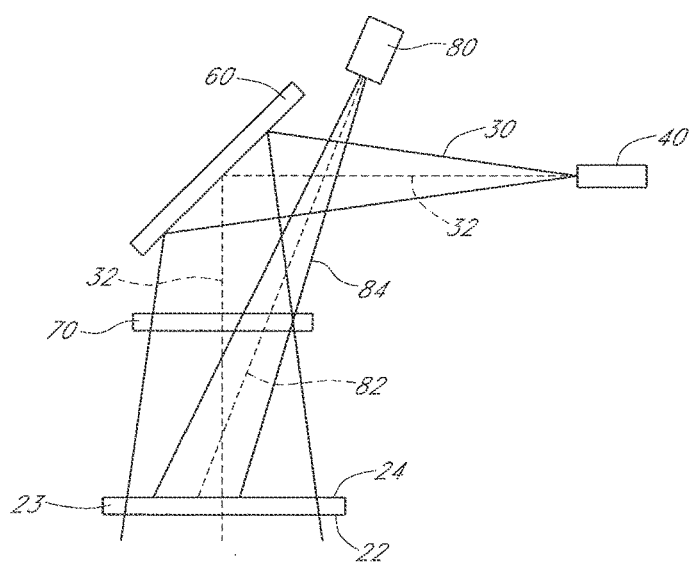
FIG. 8 schematically illustrates an example second optical path of radiation received by the sensor.

In certain embodiments, the apparatus 10 further comprises a sensor 80 spaced from the output optical assembly 20. FIG. 8 schematically illustrates an example second optical path 82 of radiation 84 received by the sensor 80. The sensor 80 is positioned to receive the radiation 84 from the output optical assembly 20 propagating through the output optical assembly 20 along the second optical path 82. The first optical path 32 and the second optical path 82 have a non-zero angle therebetween. In certain embodiments, the second optical path 82 is co-planar with the first optical path 32, while in certain other embodiments, the first optical path 32 and the second optical path 82 are non-co-planar with one another. The sensor 80 of certain embodiments receives radiation 84 propagating along the second optical path 82 from at least a portion of the surface 24 of the optical element 23 during operation of the apparatus 10.

The sensor 80 of certain embodiments comprises a temperature sensor (e.g., thermopile) configured to receive infrared radiation from a region and to generate a signal indicative of the temperature of the region. Examples of temperature sensors compatible with certain embodiments described herein include, but are not limited to, DX-0496 thermopile available from Dexter Research Center, Inc. of Dexter, Mich. In certain embodiments, the field-of-view of the sensor 80 comprises an area of about 0.26 square inches of the surface 24 spaced from the thermal conduit 25 (e.g., by a distance between 0.05 inch and 0.3 inch). In certain other embodiments, the field-of-view of the sensor 80 comprises an area of about 0.57 square inches of the surface 24.

In certain embodiments, the sensor 80 is responsive to the received radiation 84 by generating a signal indicative of a temperature of the skin or of a portion of the output optical assembly 20 (e.g., the optical element 23). In certain such embodiments, the apparatus 10 further comprises a controller configured to receive the signal from the sensor 80 and to cause a warning to be generated, to turn off a source of the light propagating along the first optical path 32, or both in response to the signal indicating that the temperature is above a predetermined threshold temperature (e.g., 42 degrees Celsius).

The sensor 80 of certain embodiments is not in thermal communication with the output optical assembly 20. As shown in FIG. 8, the infrared-transmissive window 70 is between the sensor 80 and the output optical assembly 20. The light 30 propagating along the first optical path 32 and the infrared radiation 84 propagating along the second optical path 82 both propagate through the window 70. In certain embodiments, the sensor 80 is wholly or at least partially within a region of the housing 12 at least partially bound, and substantially sealed by the window 70 against contaminants from entering the region from outside the region.

In certain embodiments, the apparatus 10 is adapted to cool the irradiated portion of the scalp or skull by removing heat from the scalp or skull so as to control, inhibit, prevent, minimize, or reduce temperature increases at the scalp or skull. Thus, by virtue of the apparatus 10 cooling the irradiated portion of the patient's scalp or skull, the temperature of the irradiated portion of the patient's scalp or skull is lower than it would otherwise be if the apparatus 10 did not cool the irradiated portion of the scalp or skull. For example, by cooling the irradiated portion of the patient's scalp or skull using the apparatus 10, the temperature of the irradiated portion of the patient's scalp or skull can be higher than the temperature of the portion of the patient's scalp or skull if it were not irradiated, but lower than the temperature of the portion of the patient's scalp or skull if it were irradiated but not cooled. Referring to FIGS. 4A and 4B, in certain embodiments, the apparatus 10 comprises a thermoelectric assembly 90 and a heat sink 100 in thermal communication with the thermoelectric assembly 90. In certain embodiments, the thermoelectric assembly 90 actively cools the patient's scalp or skull via the output optical assembly 20, thereby advantageously avoiding large temperature gradients at the patient's scalp or skull which would otherwise cause discomfort to the patient. In certain embodiments, the apparatus 10 further comprises one or more temperature sensors (e.g., thermocouples, thermistors) which generate electrical signals indicative of the temperature of the thermoelectric assembly 90.

In certain embodiments, the thermoelectric assembly 90 comprises at least one thermoelectric element 91 and a thermal conduit 92. The at least one thermoelectric element 91 of the thermoelectric assembly 90 is responsive to an electric current applied to the thermoelectric assembly 90 by cooling at least a first surface 93 of the thermoelectric assembly 90 and heating at least a second surface 94 of the thermoelectric assembly 90. The thermoelectric assembly 90 is configured to be releasably mechanically coupled to the output optical assembly 20 so as to have the first surface 93 in thermal communication with the output optical assembly 20. In certain embodiments, the first surface 93 comprises a surface of the thermal conduit 92 and the second surface 94 comprises a surface of the thermoelectric element 91.

Figure 9A:
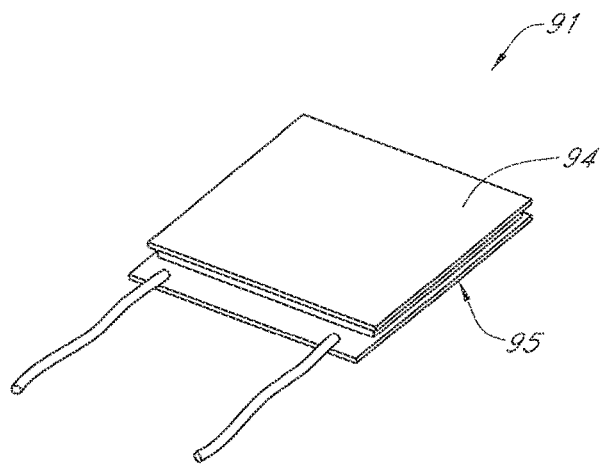
FIG. 9A schematically illustrates an example thermoelectric element and FIG. 9B schematically illustrates two views of an example thermal conduit in accordance with certain embodiments described herein.
Figure 9B:
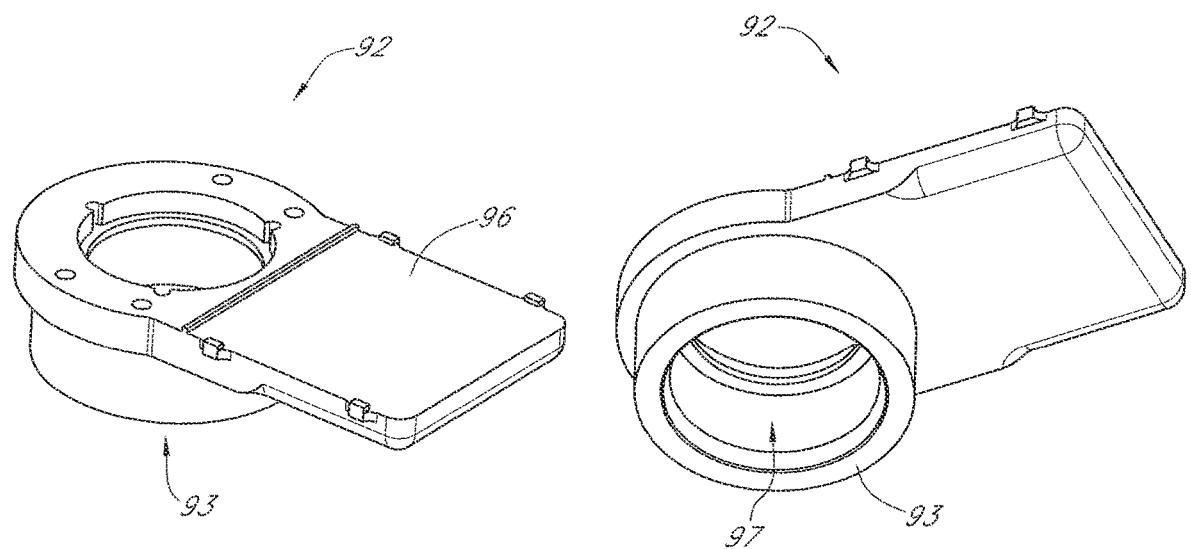
Figure 10A:
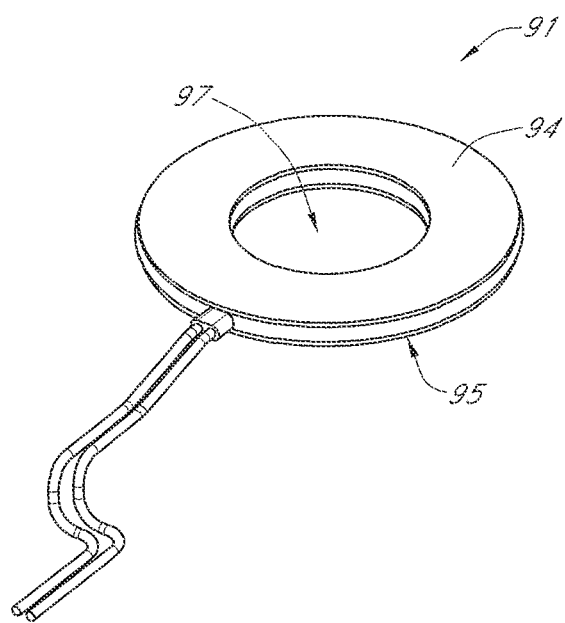
FIG. 10A schematically illustrates another example thermoelectric element and FIG. 10B schematically illustrates two views of another example thermal conduit in accordance with certain embodiments described herein.
Figure 10B:
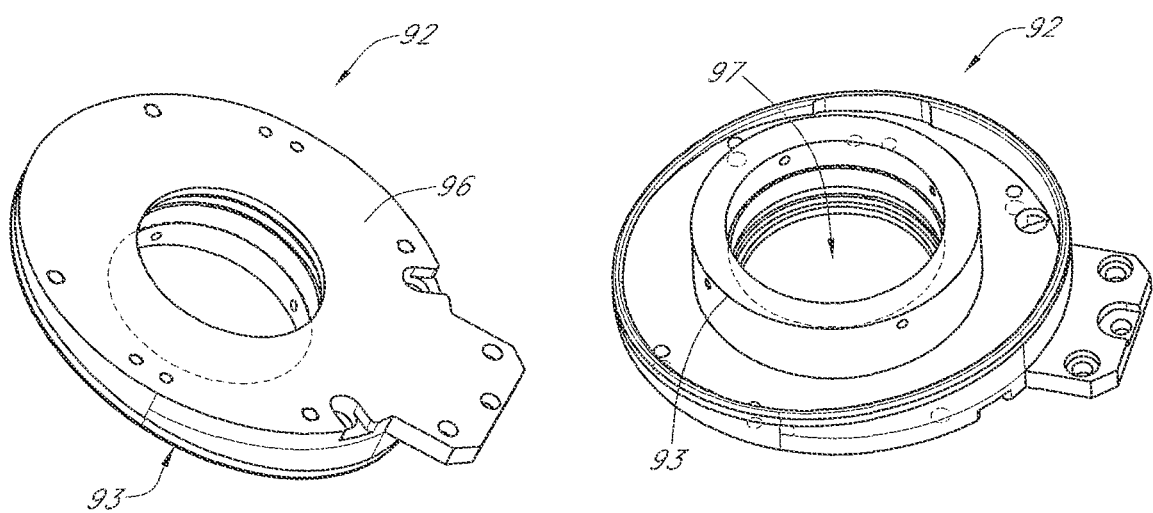

FIG. 9A schematically illustrates an example thermoelectric element 91 and FIG. 9B schematically illustrates two views of an example thermal conduit 92 in accordance with certain embodiments described herein. FIG. 10A schematically illustrates another example thermoelectric element 91 and FIG. 10B schematically illustrates two views of another example thermal conduit 92 in accordance with certain embodiments described herein. The thermoelectric element 91 has a surface 95 configured to be in thermal communication with a corresponding surface 96 of the thermal conduit 92 (e.g., by a thermally conductive adhesive). Upon application of an electric current to the thermoelectric element 91, the second surface 94 is heated and the surface 95 is cooled, thereby cooling the first surface 93. In certain such embodiments, the first surface 93 serves as at least one heat dissipating surface of the apparatus 10 configured to be in thermal communication with the at least one surface 26 of the thermal conduit 25 of the output optical assembly 20 (e.g., by contacting or mating so as to provide a thermally conductive connection between the thermoelectric assembly 26 and the output optical assembly 20). By having the thermally conductive output optical assembly 20 in thermal communication with the thermoelectric assembly 90, certain embodiments advantageously provide a conduit for heat conduction away from the treatment site (e.g., the skin). In certain embodiments, the output optical assembly 20 is pressed against the patient's skin and transfers heat away from the treatment site.

Examples of thermoelectric elements 91 compatible with certain embodiments described herein include, but are not limited to, DT12-6, $Q_{max}$=60 W, square thermoelectric element available from Marlow Industries of Dallas, Tex., and $Q_{MAX}$=45 W toroidal- or donut-shaped thermoelectric element from Ferrotec Corp. of Bedford, N.H. In certain embodiments, the thermoelectric element 91 removes heat from the output optical assembly 20 at a rate in a range of about 0.1 Watt to about 5 Watts or in a range of about 1 Watt to about 3 Watts. Example temperature controllers for operating the thermoelectric assembly 90 in accordance with certain embodiments described herein include, but are not limited to, MPT-5000 available from Wavelength Electronics, Inc. of Bozeman, Mont. Example materials for the thermal conduit 92 compatible with certain embodiments described herein include, but are not limited to, aluminum and copper. The thermal conduit 92 of certain embodiments has a thermal mass in a range of about 30 grams to about 70 grams, and has a thermal length between surface 93 and surface 96 in a range of about 0.5 inch to about 3.5 inches.

In certain embodiments, the thermoelectric assembly 90 generally surrounds a first region 97, wherein, during operation of the apparatus 10, light irradiating a portion of the patient's skin propagates through the first region 97. As shown in FIGS. 9B and 10B, in certain embodiments, the first region 97 comprises an aperture through the thermal conduit 92. As shown in FIG. 10B, the first region 97 in certain embodiments further comprises an aperture through the thermoelectric element 91. In certain embodiments, the thermoelectric assembly 90 comprises a plurality of thermoelectric elements 91 which are spaced from one another and are distributed to generally surround the first region 97. As used herein, the term "generally surrounds" has its broadest reasonable interpretation, including but not limited to, encircles or extends around at least one margin of the region, or being distributed around at least one margin of the region with one or more gaps along the at least one margin.

Figure 11A:
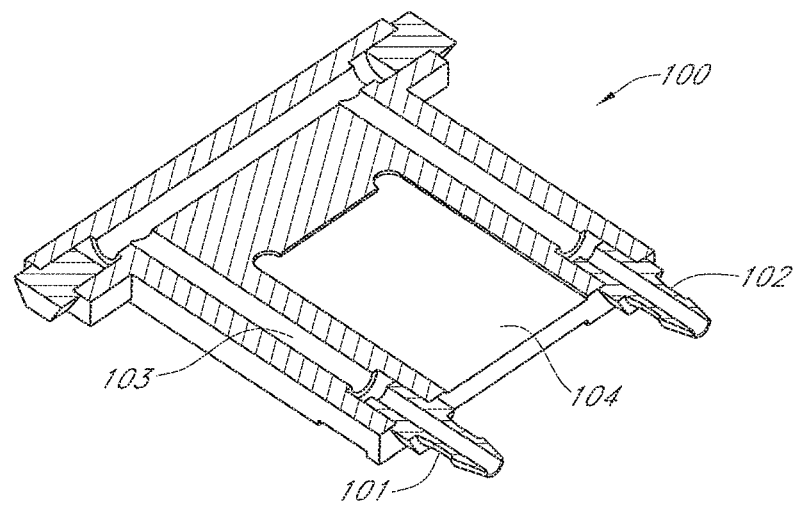
FIG. 11A schematically illustrates a cross-sectional view of an example heat sink and FIG. 11B schematically illustrates another example heat sink in accordance with certain embodiments described herein.
Figure 11B:
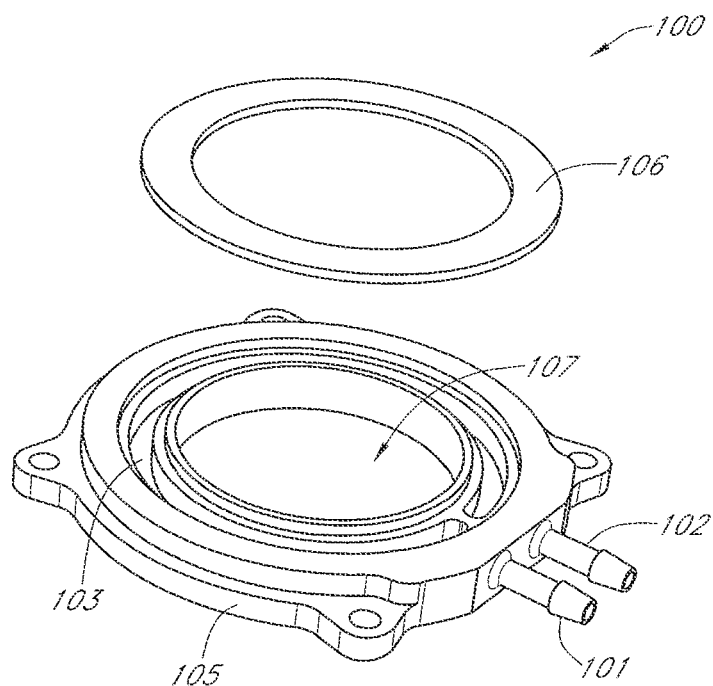

FIG. 11A schematically illustrates a cross-sectional view of an example heat sink 100 and FIG. 11B schematically illustrates another example heat sink 100 in accordance with certain embodiments described herein. The heat sink 100 comprises an inlet 101, an outlet 102, and a fluid conduit 103 in fluid communication with the inlet 101 and the outlet 102. The inlet 101 and the outlet 102 of certain embodiments comprise stainless steel barbs configured to be connected to tubes (e.g., using nylon or stainless steel hose barb locks, clamps, or crimps) which provide a coolant (e.g., water, air, glycerol) to flow through the fluid conduit 103 and to remove heat from the fluid conduit 103. In certain embodiments, the coolant is provided by a chiller or other heat transfer device which cools the coolant prior to its being supplied to the heat sink 100.

The example heat sink 100 of FIG. 11A is machined from an aluminum block and has a recess 104 in which the thermoelectric assembly 90 is placed to provide thermal communication between the heat sink 100 and the second surface 94 of the thermoelectric assembly 90. The example heat sink 100 of FIG. 11B comprises a first portion 105 and a second portion 106 which fit together to form the coolant conduit 103. In certain embodiments, a thermally conductive adhesive (e.g., EP1200 thermal adhesive available from Resinlab, LLC of Germantown, Wis., with a 0.005-inch stainless steel wire to set the bondline) is used to bond the thermoelectric assembly 90 and the heat sink 100 together in thermal communication with one another.

The output optical assembly 20 comprises a thermally conductive thermal conduit 25 having at least one surface 26 configured to be in thermal communication with the first surface of the thermoelectric assembly 90. As shown in FIGS. 2A and 2B, the thermal conduit 25 generally surrounds a second region 28. During operation of the apparatus 10, the light propagates through the first region 97, the second region 28, and the optical element 23. In certain embodiments, the heat sink 100 generally surrounds a third region 107, as schematically illustrated by FIG. 11B. During operation of the apparatus 10 in certain such embodiments, the light propagates through the third region 107, the first region 97, the second region 28, and the optical element 23.

Figure 12A:
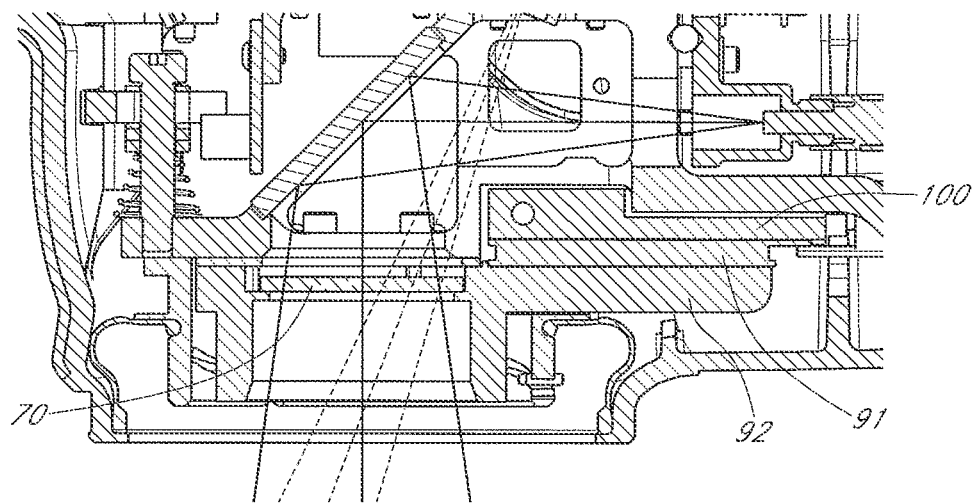
FIGS. 12A and 12B schematically illustrate two example configurations of the window with the thermoelectric assembly.
Figure 12B:
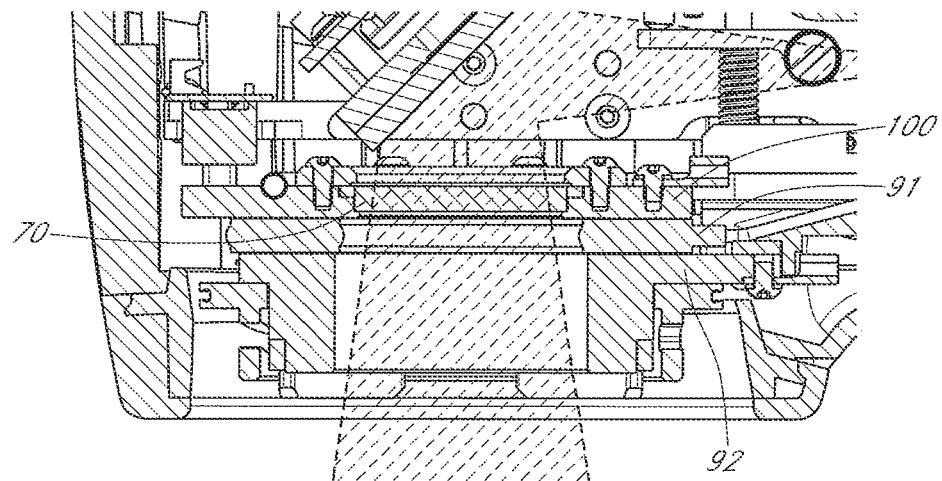

FIGS. 12A and 12B schematically illustrate two example configurations of the window 70 with the thermoelectric assembly 90. In certain embodiments, the window 70 is in thermal communication with at least a portion of the thermoelectric assembly 90 (e.g., bonded to a recess in the thermal conduit 92, as shown in FIG. 12A, using OP-29 adhesive available from Dymax Corp. of Torrington, Conn.). In certain embodiments, the window 70 is in thermal communication with at least a portion of the heat sink 100 (e.g., retained by an o-ring in the heat sink 100), as shown in FIG. 12B. In certain embodiments, the window 70 is not in thermal communication with either the thermoelectric assembly 90 or the heat sink 100.

Figure 13A:
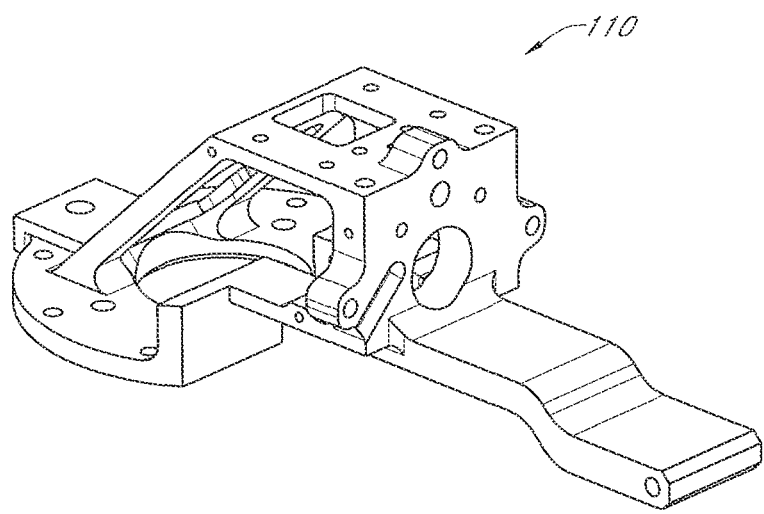
FIG. 13A schematically illustrates an example chassis for supporting the various components of the beam delivery apparatus within the housing in accordance with certain embodiments described herein.
Figure 13B:
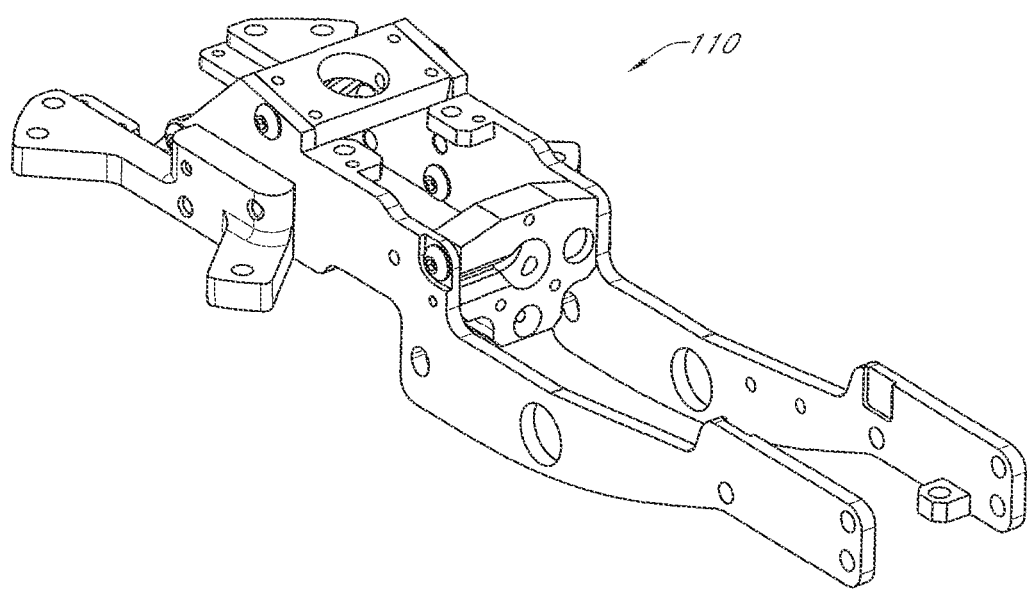
FIG. 13B schematically illustrates another example chassis in accordance with certain embodiments described herein.

FIG. 13A schematically illustrates an example chassis 110 for supporting the various components of the beam delivery apparatus 10 within the housing 12 in accordance with certain embodiments described herein. The chassis 110 of FIG. 13A comprises a single unitary or monolithic piece which is machined to provide various surfaces and holes used to mount the various components of the beam delivery apparatus 10. FIG. 13B schematically illustrates another example chassis 110 in accordance with certain embodiments described herein. The chassis 110 of FIG. 13B comprises a plurality of portions which are bolted or pinned together.

Figure 14A:
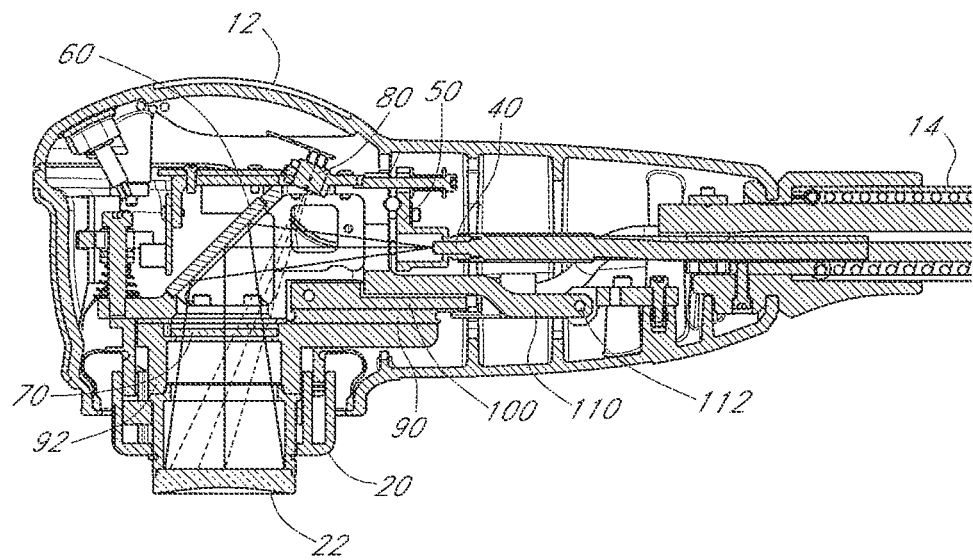
FIG. 14A schematically illustrates a cross-sectional view of an example configuration of the chassis and the housing in accordance with certain embodiments described herein.

FIG. 14A schematically illustrates a cross-sectional view of an example configuration of the chassis 110 and the housing 12 in accordance with certain embodiments described herein. The chassis 110 of certain embodiments is electrically connected to ground, while in certain other embodiments, the chassis 110 is electrically insulated from ground (e.g., floating). In certain embodiments, the chassis 110 is configured to move relative to the housing 12. For example, the chassis 110 and the housing 12 are mechanically coupled together by a pivot 112, as schematically illustrated by FIG. 14A. The optical fiber 40, fiber adjustment apparatus 50, mirror 60, window 70, sensor 80, and heat sink 100 are each mechanically coupled to the chassis 110. The output optical assembly 20 is also mechanically coupled to the chassis 110 via the thermoelectric assembly 90 and the heat sink 100.

For the configuration of FIG. 14A, the emission surface 22 of the output optical assembly 20 is placed in thermal communication (e.g., in contact) with the patient's scalp or skull by a user pressing the housing 12 towards the scalp or skull. The pivot 112 allows the chassis 110 to rotate about the pivot 112 relative to the housing 12 (e.g., by an angle between 1 and 2 degrees, or about 1.75 degrees) such that the emission surface 22 moves towards the housing 12 (e.g., by a distance of 0.05-0.3 inch, or about 0.1 inch). In certain such embodiments, this movement of the chassis 110, as well as of the fiber adjustment apparatus 50 and the optical fiber 40, results in a flexing of a portion of the optical fiber 40 (e.g., in proximity to the coupling between the housing 12 and the conduit 14).

Figure 14B:
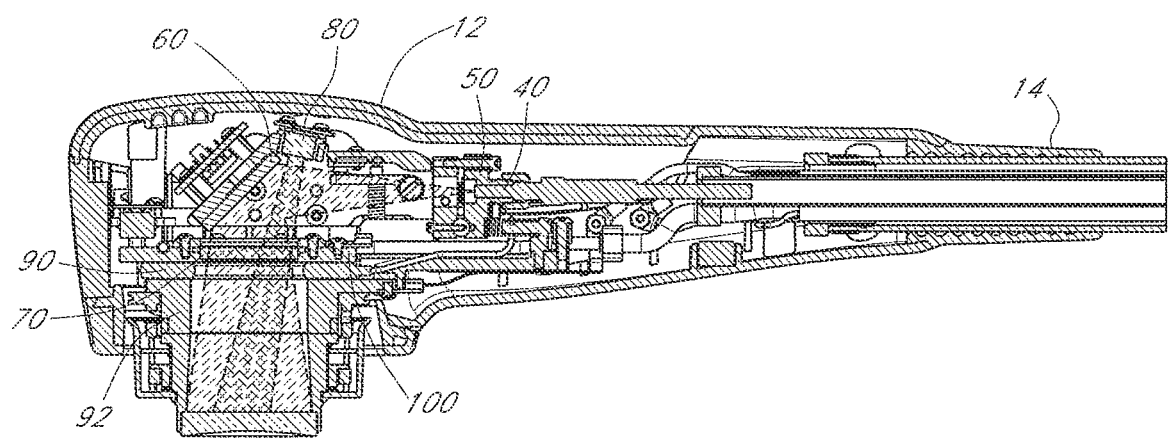
FIGS. 14B and 14C schematically illustrate another example configuration of the chassis and the housing in accordance with certain embodiments described herein.
Figure 14C:
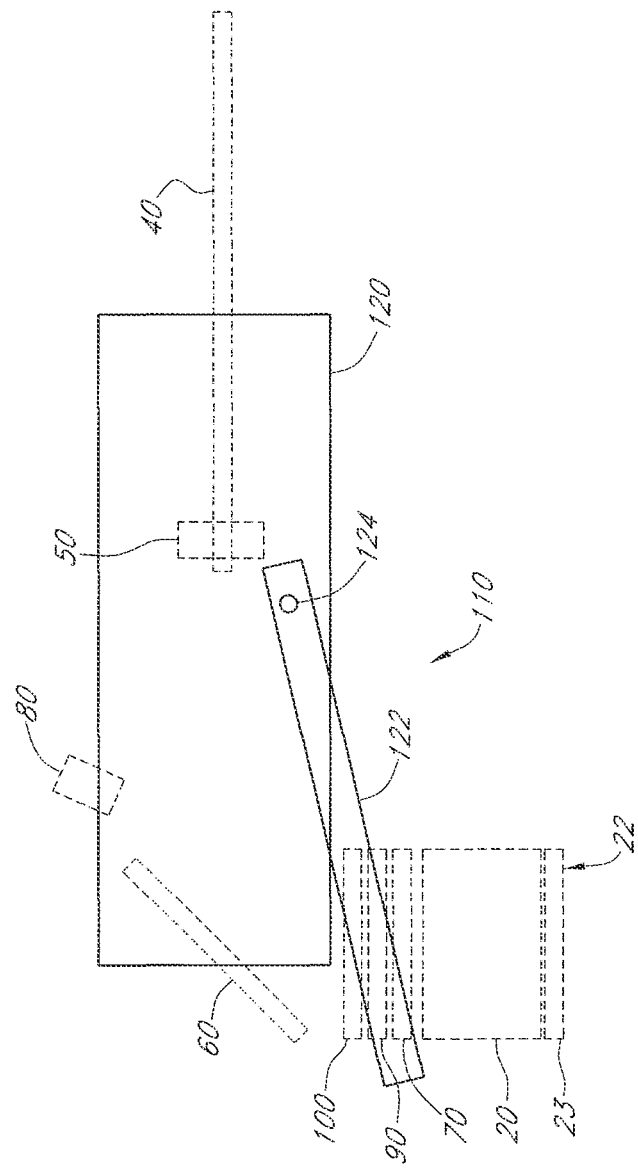

This flexing of the optical fiber 40 can be undesirable in certain circumstances, such as when the optical fiber 40 or its connection to the fiber adjustment apparatus 50 is fragile and prone to breakage or failure due to repeated flexing. FIGS. 14B and 14C schematically illustrate another example configuration of the chassis 110 and the housing 12 in accordance with certain embodiments described herein. The chassis 110 comprises a first chassis element 120 and a second chassis element 122 mechanically coupled to the first chassis element 120 such that the first chassis element 120 and the second chassis element 122 can move relative to one another. For example, in certain embodiments, the apparatus 10 further comprises a hinge 124 (e.g., a pivot or flexible portion) about which the first chassis element 120 and the second chassis element 122 are configured to deflect relative to one another.

In certain embodiments, the first chassis element 120 is mechanically coupled to the housing 12, and the optical fiber 40, fiber adjustment apparatus 50, mirror 60, and sensor 80 (each shown in dotted lines in FIG. 14C) are mechanically coupled to the first chassis element 120. The second chassis element 122 is mechanically coupled to the window 70, thermoelectric assembly 90, and the heat sink 100 (each shown in dotted lines in FIG. 14C). The output optical assembly 20 is also mechanically coupled to the second chassis element 122 via the thermoelectric assembly 90 and the heat sink 100. Thus, in certain such embodiments, a first portion of the apparatus 10 comprises the housing 12, first chassis element 120, optical fiber 40, fiber adjustment apparatus 50, mirror 60, and sensor 80, and a second portion of the apparatus 10 comprises the second chassis element 122, window 70, thermoelectric assembly 90, heat sink 100, and output optical assembly 20. The second portion is mechanically coupled to the first portion and is in optical communication with the first portion. The second portion is configured to be placed in thermal communication with the patient's skin such that the light from the first portion propagates through the second portion during operation of the apparatus 10. The first portion and the second portion are configured to move relative to one another in response to the second portion being placed in thermal communication with the patient's skin.

In certain embodiments, the second portion comprises the output optical assembly 20 and the first portion and the second portion are configured to deflect relative to one another by a non-zero angle. In certain embodiments, this deflection occurs upon the output optical assembly 20 applying a pressure to a portion of the patient's scalp sufficient to at least partially blanch the portion of the patient's scalp. In certain embodiments, this deflection occurs upon the output optical assembly 20 being placed in thermal communication with the patient's scalp or skull. In certain embodiments, the apparatus 10 further comprises a spring mechanically coupled to the first portion and the second portion. The spring provides a restoring force in response to movement of the first portion and the second portion relative to one another.

For the configuration of FIGS. 14B and 14C, the emission surface 22 of the output optical assembly 20 is placed in thermal communication (e.g., in contact) with the patient's scalp or skull by a user pressing the housing 12 towards the scalp or skull. The hinge 124 allows the second portion (e.g., including the second chassis element 122) to rotate about the hinge 124 relative to the first portion (e.g., including the first chassis element 120). This rotation can be by an angle between 1 and 3 degrees, or about 2.3 degrees) such that the emission surface 22 moves towards the housing 12 (e.g., by a distance of 0.05-0.3 inch, or about 0.08 inch). In certain such embodiments in which the first portion comprises the optical fiber 40, deflection of the first portion and the second portion relative to one another controls, inhibits, prevents, minimizes, or reduces flexing or movement of the optical fiber 40 (e.g., to control, inhibit, prevent, minimize, or reduce damage to the optical fiber 40). Thus, by virtue of the movement of the first and second portions relative to one another, the flexing, movement, or damage of the optical fiber 40 is lower than it would otherwise be if the first and second portions did not move relative to one another.

In certain embodiments, the relative movement of the output optical assembly 20 and the mirror 60 can result in the light beam 30 being at least partially occluded or "clipped" by the thermal conduit 25 of the output optical assembly 20. For example, for a light beam diameter of 30 millimeters, the light beam 30 is not clipped by the thermal conduit 25. For larger light beam diameters, the light beam 30 is partially occluded by the thermal conduit 25. For a light beam diameter of 31 millimeters, about 0.02% of the light beam area is occluded, and for 32 millimeters, about 1.56% of the light beam area is occluded, resulting in an estimated power loss of less than about 0.08%.

In certain embodiments, the apparatus 10 further comprises a sensor 130 configured to detect movement of the first portion and the second portion relative to one another (e.g., movement of the first chassis element 120 and the second chassis element 122 relative to one another). The sensor 130 is configured to transmit a signal to a controller configured to receive the signal and to control a light source in response to the signal, where the light source is configured to generate the light used by the apparatus 10 irradiate the patient's scalp or skull. In certain embodiments, the sensor 130 transmits the signal to the controller upon detecting that the movement between the first portion and the second portion is larger than a predetermined threshold value. In this way, the sensor 130 serves as a trigger switch which is used to trigger the apparatus 10 (e.g., providing the apparatus 10 with light upon the sensor 130 detecting the predetermined amount of movement between the first portion and the second portion indicative of the apparatus 10 being in a condition for use). The trigger switch of certain embodiments is actuated by pressing the output optical assembly 20 against a surface. The light source providing light to the apparatus 10 is responsive to the trigger switch by emitting light only when the trigger switch is actuated. Therefore, in certain such embodiments, to utilize the apparatus 10, the output optical assembly 20 is pressed against the patient's skin, such as described above.

Figure 15A:
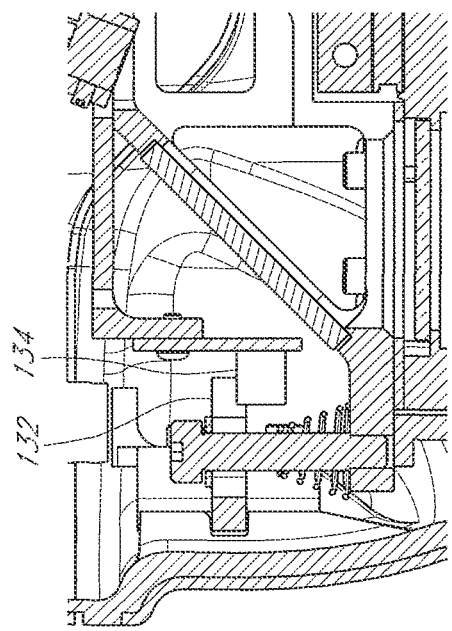
FIGS. 15A and 15B schematically illustrate two states of an example sensor in accordance with certain embodiments described herein.
Figure 15B:
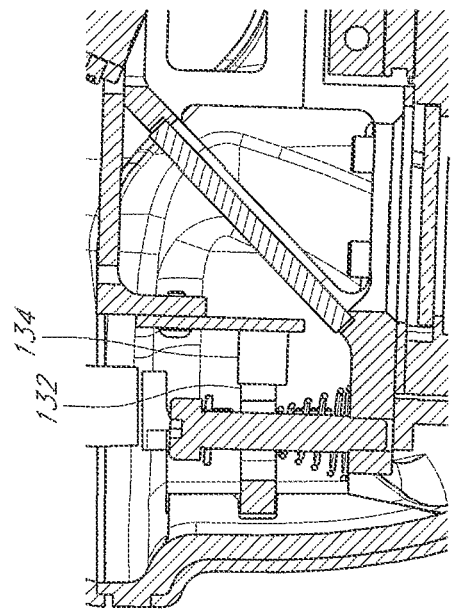

FIGS. 15A and 15B schematically illustrate two states of an example sensor 130 in accordance with certain embodiments described herein. The sensor 130 comprises at least one trigger flag 132 mechanically coupled to the first portion (e.g., the housing 12) and at least one optical switch 134 mechanically coupled to the second portion (e.g., the second chassis element 122). For example, the at least one optical switch 134 of certain embodiments comprises one, two, or more EE-SX-1035 optical switches available from Omron Electronics Components LLC of Schaumburg, Ill. In a first state, the trigger flag 132 is displaced away from a sensor light beam which is detected by the optical switch 134. Upon pressing the output optical assembly 20 in thermal communication with the patient's scalp or skull, the optical switch 134 moves relative to the trigger flag 132 (e.g., by a distance of about 0.07 inch) such that the trigger flag 132 intercepts the sensor light beam such that it is no longer detected by the optical switch 134. In response to this second state, the sensor 130 generates a corresponding signal. In certain other embodiments, the trigger flag 132 can be positioned to intercept the sensor light beam in the first state and to not intercept the sensor light beam in the second state.

Figure 15D:
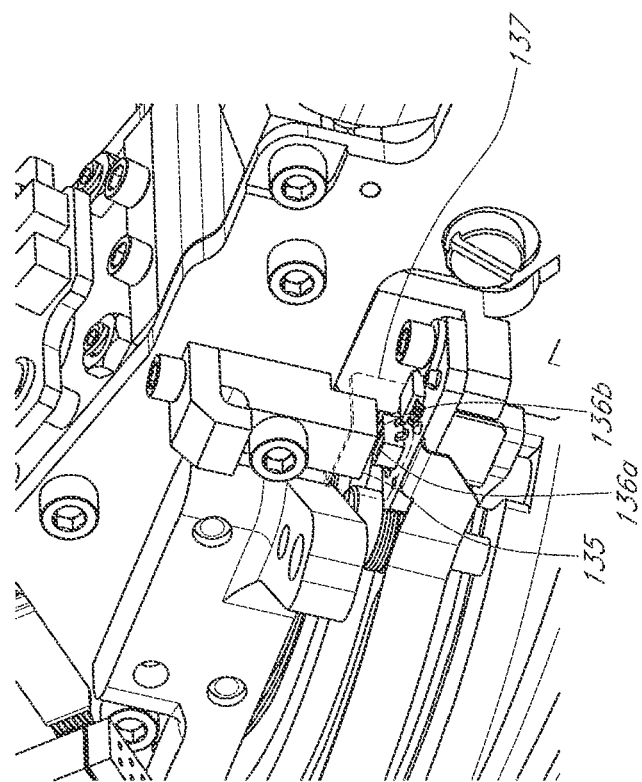
FIGS. 15C and 15D schematically illustrate two states of another example sensor in accordance with certain embodiments described herein.
Figure 15C:
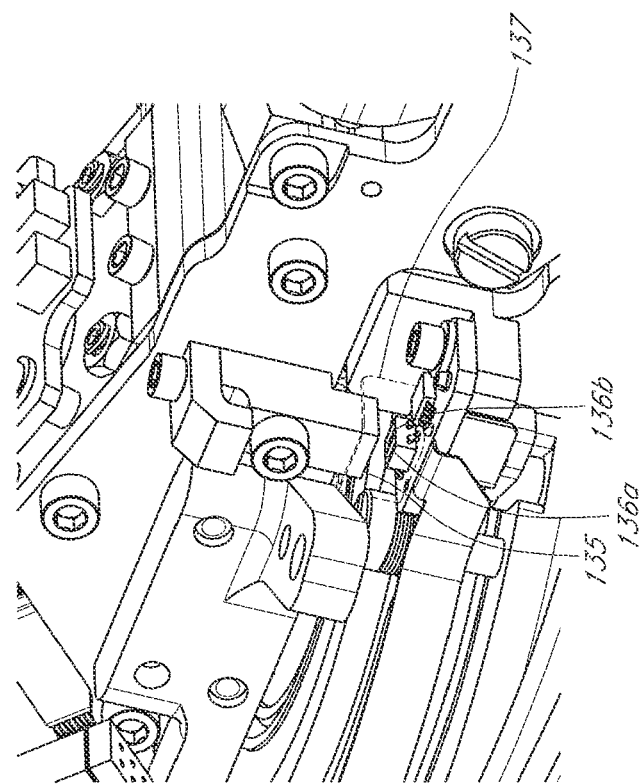

FIGS. 15C and 15D schematically illustrate two states of another example sensor 130 in accordance with certain embodiments described herein. The sensor 130 comprises a reflective element 135 mechanically coupled to the first portion (e.g., the first chassis element 120) and at least one light source/detector pair 136 mechanically coupled to the second portion (e.g., the second chassis element 122). For example, the at least one light source/detector pair 136a, 136b of certain embodiments comprises one, two, or more QRE1113GR reflective sensors available from Fairchild Semiconductor Corp. of San Jose, Calif. In a first state, the reflective surface 135 is a first distance away from the light source/detector pair 136a, 136b such that a sensor light beam from the source 136a is reflected from the surface 135 but is not detected by the detector 136b. Upon pressing the output optical assembly 20 in thermal communication with the patient's scalp or skull, the reflective surface 135 moves (e.g., by a distance of about 0.04 inch) to be a second distance away from the light source/detector pair 136a, 136b such that the sensor light beam from the source 136a is reflected from the surface 135 and is detected by the detector 136b. In response to this second state, the sensor 130 generates a corresponding signal. In certain embodiments, the sensor 130 further comprises a shroud 137 configured to protect the detector 136b from stray light. In certain other embodiments, the reflective surface 135 can be positioned to reflect the sensor light beam to the detector 136b in the first state and to not reflect the sensor light beam to the detector 136b in the second state.

In certain embodiments, the apparatus 10 further comprises an adjustment mechanism configured to set the predetermined threshold value, to change the predetermined threshold value, or both. In certain such embodiments, the adjustment mechanism comprises a set screw which changes the relative positions of the two portions of the sensor 130 which move relative to one another. Certain embodiments further comprise a stop configured to limit a range of movement of the first portion and the second portion relative to one another.

Figure 16A:
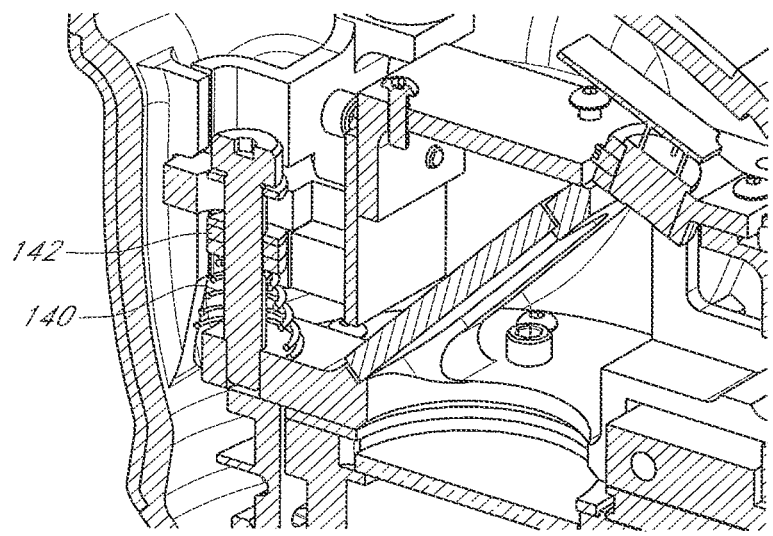
FIGS. 16A and 16B schematically illustrate two example configurations of the trigger force spring and trigger force adjustment mechanism in accordance with certain embodiments described herein.
Figure 16B:
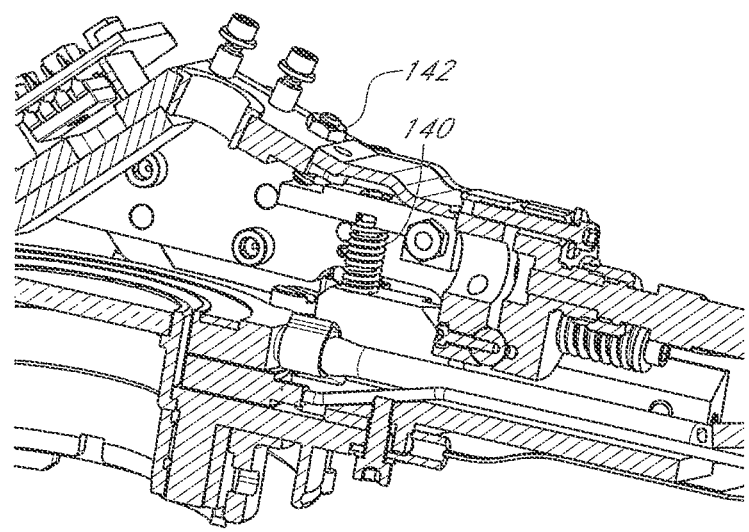

In certain embodiments, the apparatus 10 comprises a trigger force spring 140 and a trigger force adjustment mechanism 142. FIGS. 16A and 16B schematically illustrate two example configurations of the trigger force spring 140 and trigger force adjustment mechanism 142 in accordance with certain embodiments described herein. The trigger force spring 140 is mechanically coupled to the first portion (e.g., the first chassis element 120) and the second portion (e.g., the second chassis element 122) and provides a restoring force when the first portion and the second portion are moved relative to one another. The trigger force adjustment mechanism 142 of FIG. 16A comprises one or more shims (e.g., each shim providing about 100 grams of adjustment) placed between the spring 140 and at least one of the first portion and the second portion. The trigger force adjustment mechanism 142 of FIG. 16B comprises one, two, or more adjustment set screws. In either configuration, the trigger force adjustment mechanism 142 compresses the spring 140 to adjust the amount of force which will move the first and second portions relative to one another by a sufficient amount to trigger the apparatus 10. In certain embodiments, the trigger force adjustment mechanism 142 is set such that the apparatus 10 is triggered by a pressure applied to the emission surface 22 towards the housing 12 of at least 0.1 pound per square inch, at least one pound per square inch, or at least about two pounds per square inch.

Figure 17:
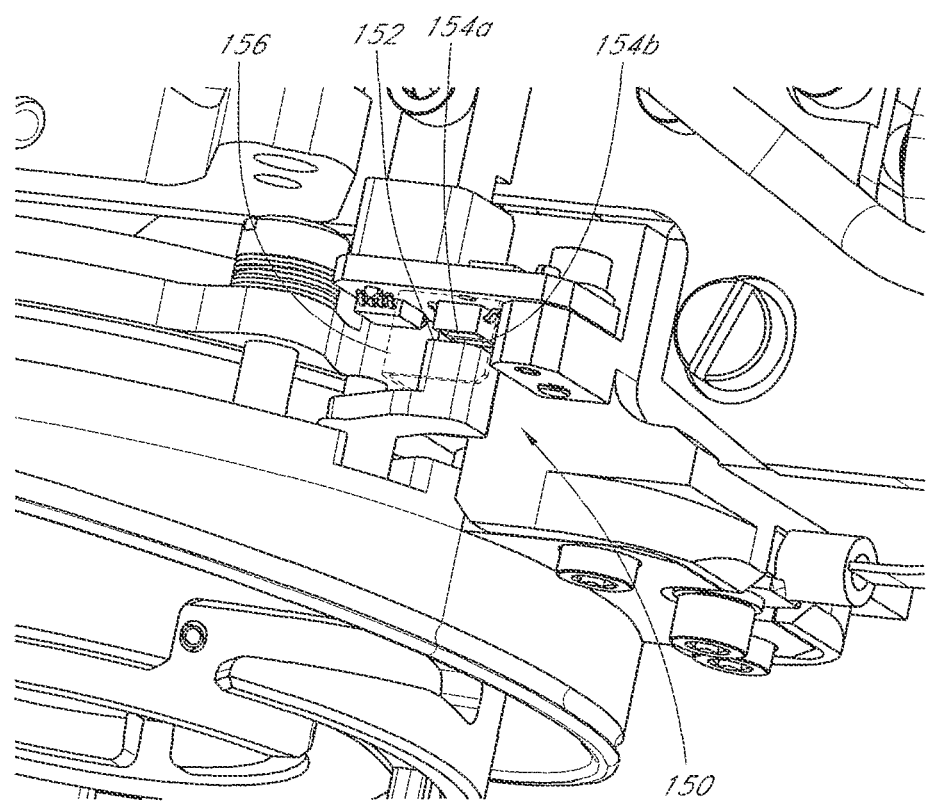
FIG. 17 schematically illustrates an example lens assembly sensor in accordance with certain embodiments described herein.

In certain embodiments, the apparatus 10 further comprises a lens assembly sensor 150 configured to detect the presence of the output optical assembly 20 mounted on the apparatus 10. FIG. 17 schematically illustrates an example lens assembly sensor 150 in accordance with certain embodiments described herein. For example, the lens assembly sensor 150 of certain embodiments comprises at least one reflective surface 152 and at least one light source/detector pair 154a, 154b (e.g., one, two, or more QRE1113GR reflective sensors available from Fairchild Semiconductor Corp. of San Jose, Calif.). The reflective surface 152 moves relative to the light source/detector pair 154a, 154b upon mounting the output optical assembly 20 to be in thermal communication with the thermal conduit 92. For example, when the output optical assembly 20 is mounted, the bayonet is pulled downward. In response to this movement, the sensor 150 generates a corresponding signal. In certain embodiments, the sensor 150 further comprises a shroud 156 configured to protect the detector 154b from stray light.

Control Circuit

Figure 18:
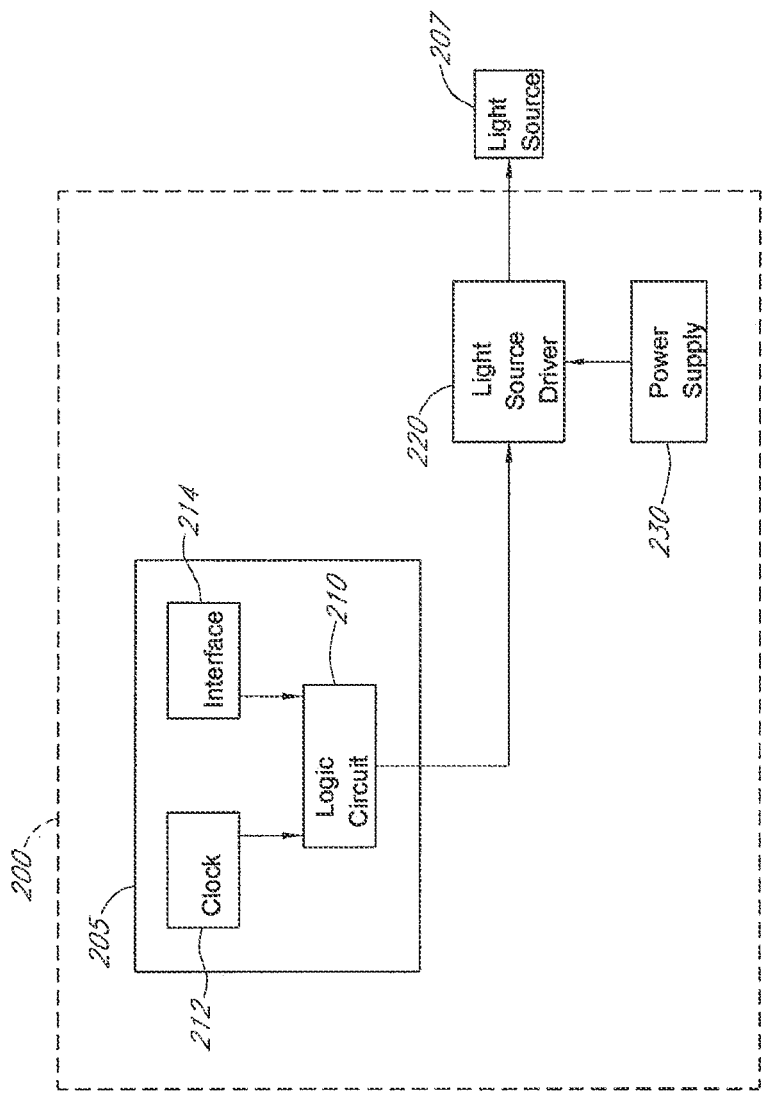
FIG. 18 is a block diagram of a control circuit comprising a programmable controller for controlling a light source according to embodiments described herein.

FIG. 18 is a block diagram of a control circuit 200 comprising a programmable controller 205 for controlling a light source 207 according to embodiments described herein. The control circuit 200 is configured to adjust the power of the light energy generated by the light source 207 such that the light emitted from the emission surface 22 generates a predetermined surface irradiance at the scalp or skull corresponding to a predetermined energy delivery profile, such as a predetermined subsurface irradiance, to the target area of the brain.

In certain embodiments, the programmable controller 205 comprises a logic circuit 210, a clock 212 coupled to the logic circuit 210, and an interface 214 coupled to the logic circuit 210. The clock 212 of certain embodiments provides a timing signal to the logic circuit 210 so that the logic circuit 210 can monitor and control timing intervals of the applied light. Examples of timing intervals include, but are not limited to, total treatment times, pulsewidth times for pulses of applied light, and time intervals between pulses of applied light. In certain embodiments, the light source 207 can be selectively turned on and off to reduce the thermal load on the scalp or skull and to deliver a selected irradiance to particular areas of the brain.

The interface 214 of certain embodiments provides signals to the logic circuit 210 which the logic circuit 210 uses to control the applied light. The interface 214 can comprise a user interface or an interface to a sensor monitoring at least one parameter of the treatment. In certain such embodiments, the programmable controller 126 is responsive to signals from the sensor to preferably adjust the treatment parameters to optimize the measured response. The programmable controller 126 can thus provide closed-loop monitoring and adjustment of various treatment parameters to optimize the phototherapy. The signals provided by the interface 214 from a user are indicative of parameters that may include, but are not limited to, patient characteristics (e.g., skin type, fat percentage), selected applied irradiances, target time intervals, and irradiance/timing profiles for the applied light.

In certain embodiments, the logic circuit 210 is coupled to a light source driver 220. The light source driver 220 is coupled to a power supply 230, which in certain embodiments comprises a battery and in other embodiments comprises an alternating current source. The light source driver 220 is also coupled to the light source 207. The logic circuit 210 is responsive to the signal from the clock 212 and to user input from the user interface 214 to transmit a control signal to the light source driver 220. In response to the control signal from the logic circuit 210, the light source driver 220 adjust and controls the power applied to the light source. Other control circuits besides the control circuit 200 of FIG. 18 are compatible with embodiments described herein.

In certain embodiments, the logic circuit 110 is responsive to signals from a sensor monitoring at least one parameter of the treatment to control the applied light. For example, certain embodiments comprise a temperature sensor in thermal communication with the scalp or skull to provide information regarding the temperature of the scalp or skull to the logic circuit 210. In such embodiments, the logic circuit 210 is responsive to the information from the temperature sensor to transmit a control signal to the light source driver 220 so as to adjust the parameters of the applied light to maintain the scalp or skull temperature below a predetermined level. Other embodiments include example biomedical sensors including, but not limited to, a blood flow sensor, a blood gas (e.g., oxygenation) sensor, an ATP production sensor, or a cellular activity sensor. Such biomedical sensors can provide real-time feedback information to the logic circuit 210. In certain such embodiments, the logic circuit 110 is responsive to signals from the sensors to preferably adjust the parameters of the applied light to optimize the measured response. The logic circuit 110 can thus provide closed-loop monitoring and adjustment of various parameters of the applied light to optimize the phototherapy.

Light Parameters

The various parameters of the light beam emitted from the emission surface 22 are advantageously selected to provide treatment while controlling, inhibiting, preventing, minimizing, or reducing injury or discomfort to the patient due to heating of the scalp or skull by the light. While discussed separately, these various parameters below can be combined with one another within the disclosed values in accordance with embodiments described herein.

Wavelength

In certain embodiments, light in the visible to near-infrared wavelength range is used to irradiate the patient's scalp or skull. In certain embodiments, the light is substantially monochromatic (i.e., light having one wavelength, or light having a narrow band of wavelengths). So that the amount of light transmitted to the brain is maximized, the wavelength of the light is selected in certain embodiments to be at or near a transmission peak (or at or near an absorption minimum) for the intervening tissue. In certain such embodiments, the wavelength corresponds to a peak in the transmission spectrum of tissue at about 820 nanometers. In certain other embodiments, the light comprises one or more wavelengths between about 630 nanometers and about 1064 nanometers, between about 600 nanometers and about 980 nanometers, between about 780 nanometers and about 840 nanometers, between about 805 nanometers and about 820 nanometers, or includes wavelengths of about 785, 790, 795, 800, 805, 810, 815, 820, 825, or 830 nanometers. An intermediate wavelength in a range between approximately 730 nanometers and approximately 750 nanometers (e.g., about 739 nanometers) appears to be suitable for penetrating the skull, although other wavelengths are also suitable and may be used. In other embodiments, a plurality of wavelengths is used (e.g. applied concurrently or sequentially). In certain embodiments, the light has a wavelength distribution peaked at a peak wavelength and has a linewidth less than ±10 nanometers from the peak wavelength. In certain such embodiments, the light has a linewidth less than 4 nanometers, full width at 90% of energy. In certain embodiments, the center wavelength is (808±10) nanometers with a spectral linewidth les than 4 nanometers, full width at 90% of energy.

In certain embodiments, the light is generated by a light source comprising one or more laser diodes, which each provide coherent light. In embodiments in which the light from the light source is coherent, the emitted light may produce "speckling" due to coherent interference of the light. This speckling comprises intensity spikes which are created by wavefront interference effects and can occur in proximity to the target tissue being treated. For example, while the average irradiance or power density may be approximately 10 mW/cm$^2$ the power density of one such intensity spike in proximity to the brain tissue to be treated may be approximately 300 mW/cm$^2$. In certain embodiments, this increased power density due to speckling can improve the efficacy of treatments using coherent light over those using incoherent light for illumination of deeper tissues. In addition, the speckling can provide the increased power density without overheating the tissue being irradiated. The light within the speckle fields or islands containing these intensity spikes is polarized, and in certain embodiments, this polarized light provides enhanced efficacy beyond that for unpolarized light of the same intensity or irradiance.

In certain embodiments, the light source includes at least one continuously emitting GaAlAs laser diode having a wavelength of about 830 nanometers. In another embodiment, the light source comprises a laser source having a wavelength of about 808 nanometers. In still other embodiments, the light source includes at least one vertical cavity surface-emitting laser (VCSEL) diode. Other light sources compatible with embodiments described herein include, but are not limited to, light-emitting diodes (LEDs) and filtered lamps.

In certain embodiments, the one or more wavelengths are selected so as to work with one or more chromophores within the target tissue. Without being bound by theory or by a specific mechanism, it is believed that irradiation of chromophores increases the production of ATP in the target tissue and/or controls, inhibits, prevents, minimizes, or reduces apoptosis of the injured tissues, thereby producing beneficial effects, as described more fully below.

Some chromophores, such as water or hemoglobin, are ubiquitous and absorb light to such a degree that little or no penetration of light energy into a tissue occurs. For example, water absorbs light above approximately 1300 nanometers. Thus energy in this range has little ability to penetrate tissue due to the water content. However, water is transparent or nearly transparent in wavelengths between 300 and 1300 nanometers. Another example is hemoglobin, which absorbs heavily in the region between 300 and 670 nanometers, but is reasonably transparent above 670 nanometers.

Based on these broad assumptions, one can define an "IR window" into the body. Within the window, there are certain wavelengths that are more or less likely to penetrate. This discussion does not include wavelength dependent scattering effects of intervening tissues.

Figure 19A:
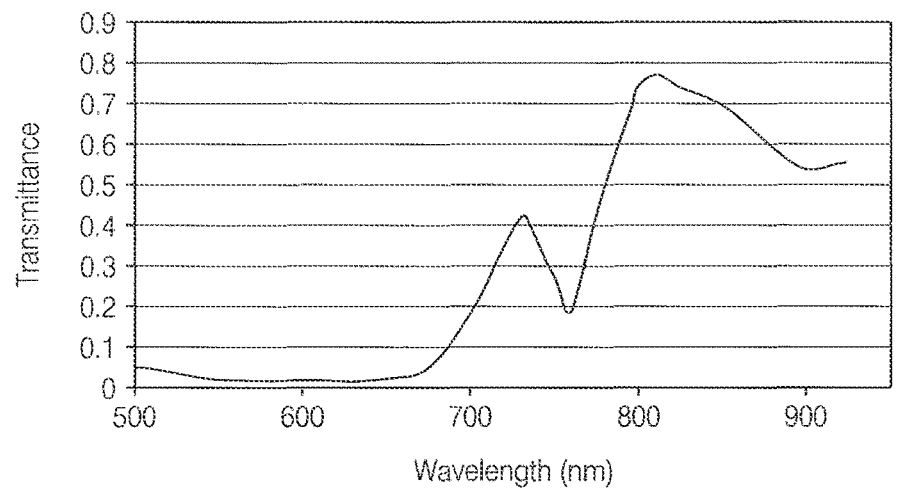
FIG. 19A is a graph of the transmittance of light through blood (in arbitrary units) as a function of wavelength.

The absorption/transmittance of various tissues have been directly measured to determine the utility of various wavelengths. FIG. 19A is a graph of the transmittance of light through blood (in arbitrary units) as a function of wavelength. Blood absorbs less in the region above 700 nanometers, and is particularly transparent at wavelengths above 780 nanometers. Wavelengths below 700 nanometers are heavily absorbed, and are not likely to be useful therapeutically (except for topical indications).

Figure 19B:
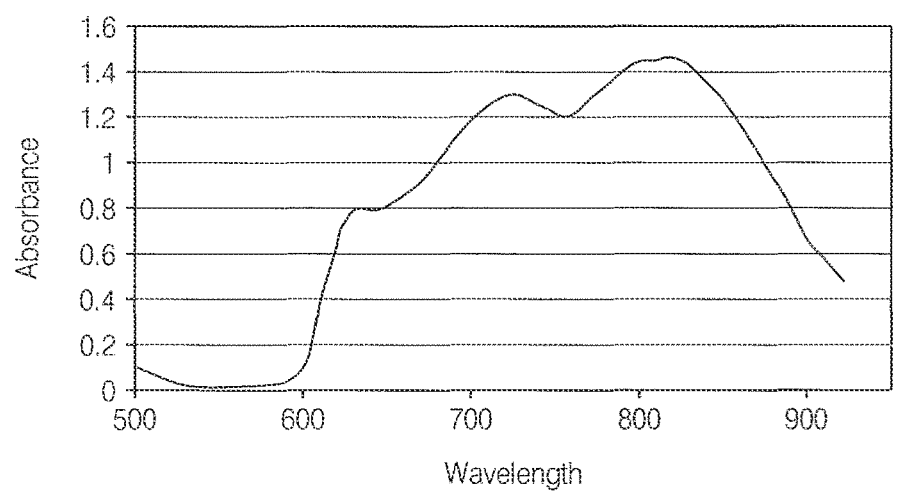
FIG. 19B is a graph of the absorption of light by brain tissue.

FIG. 19B is a graph of the absorption of light by brain tissue. Absorption in the brain is strong for wavelengths between 620 and 980 nanometers. This range is also where the copper centers in mitochondria absorb. The brain is particularly rich in mitochondria as it is a very active tissue metabolically (the brain accounts for 20% of blood flow and oxygen consumption). As such, the absorption of light in the 620 to 980 nanometer range is expected if a photostimulative effect is to take place.

Figure 19C:
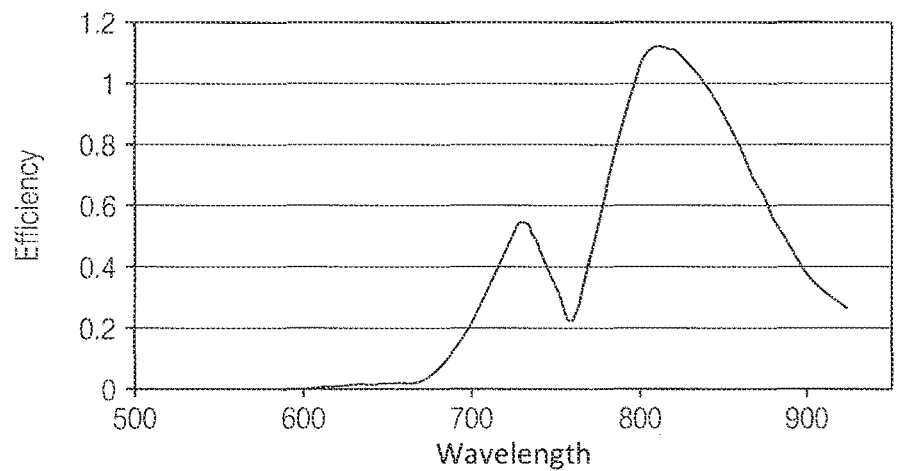
FIG. 19C shows the efficiency of energy delivery as a function of wavelength.

By combining FIGS. 19A and 19B, the efficiency of energy delivery as a function of wavelength can be calculated, as shown in FIG. 19C. Wavelengths between 780 and 880 nanometers are preferable (efficiency of 0.6 or greater) for targeting the brain. The peak efficiency is about 800 to 830 nanometers (efficiency of 1.0 or greater). These wavelengths are not absorbed by water or hemoglobin, and are likely to penetrate to the brain. Once these wavelengths reach the brain, they will be absorbed by the brain and converted to useful energy.

Figure 20:
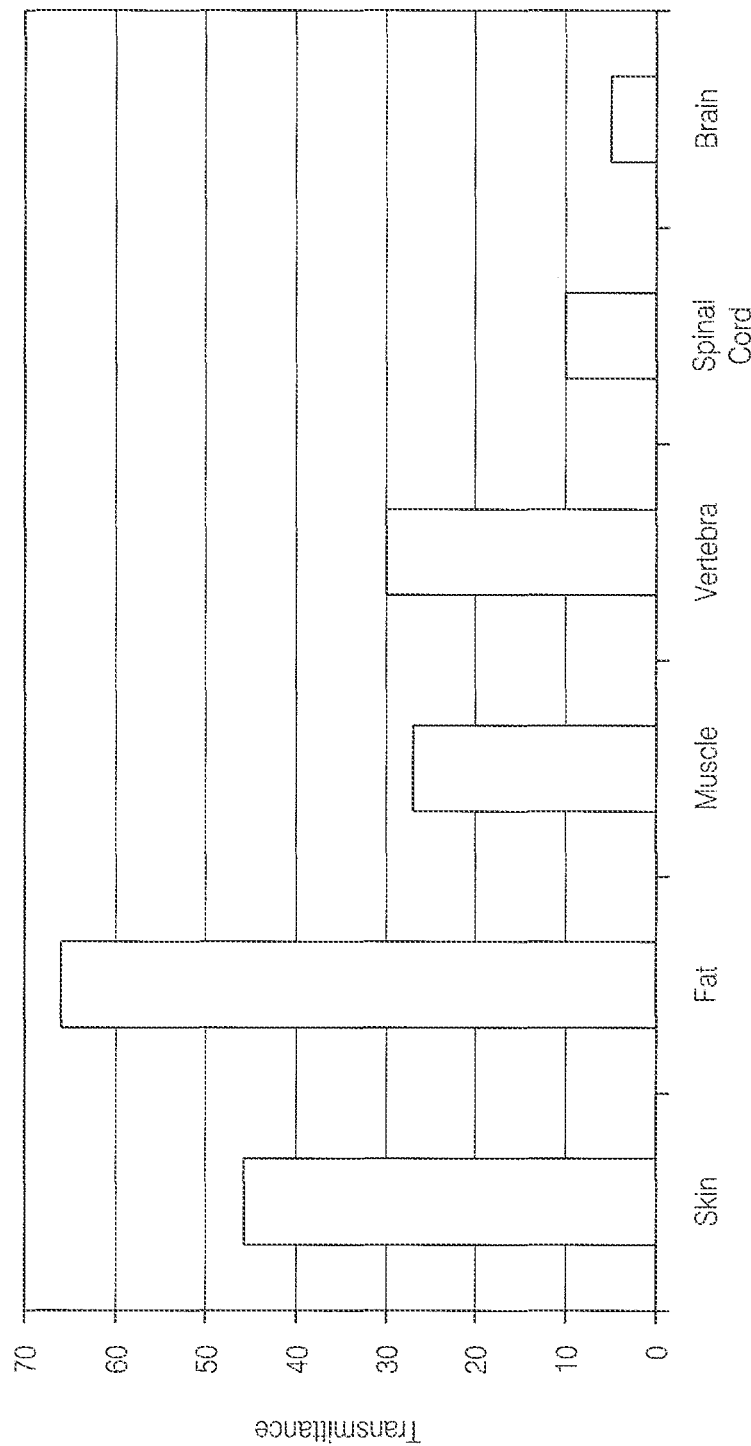
FIG. 20 shows measured absorption of 808 nanometer light through various rat tissues.

These effects have been directly demonstrated in rat tissues. The absorption of 808 nanometer light was measured through various rat tissues, as shown in FIG. 20. Soft tissues such as skin and fat absorb little light. Muscle, richer in mitochondria, absorbs more light. Even bone is fairly transparent. However, as noted above, brain tissue, as well as spinal cord tissue, absorb 808 nanometer light well.

Irradiance or Power Density

In certain embodiments, the light beam has a time-averaged irradiance or power density at the emission surface 22 of the output optical assembly 20 between about 10 mW/cm$^2$ to about 10 W/cm$^2$, between about 100 mW/cm$^2$ to about 1000 mW/cm$^2$, between about 500 mW/cm$^2$ to about 1 W/cm$^2$, or between about 650 mW/cm$^2$ to about 750 mW/cm$^2$ across the cross-sectional area of the light beam. For a pulsed light beam, the time-averaged irradiance is averaged over a time period long compared to the temporal pulse widths of the pulses (e.g., averaged over a fraction of a second longer than the temporal pulse width, over 1 second, or over multiple seconds). For a continuous-wave (CW) light beam with time-varying irradiance, the time-averaged irradiance can be an average of the instantaneous irradiance averaged over a time period longer than a characteristic time period of fluctuations of the light beam. In certain embodiments, a duty cycle in a range between 1% and 80%, between 10% and 30%, or about 20% can be used with a peak irradiance at the emission surface 22 of the output optical assembly 20 between about 12.5 mW/cm$^2$ to about 1000 W/cm$^2$ between about 50 mW/cm$^2$ to about 50 W/cm$^2$ between about 500 mW/cm$^2$ to about 5000 mW/cm$^2$ between about 2500 mW/cm$^2$ to about 5 W/cm$^2$ or between about 3.25 W/cm$^2$ to about 3.75 W/cm$^2$ across the cross-sectional area of the light beam. In certain embodiments, the pulsed light beam has an energy or fluence (e.g., peak irradiance multiplied by the temporal pulsewidth) at the emission surface 22 of the output optical assembly 20 between about 12.5 µJ/cm$^2$ to about 1 J/cm$^2$ between about 500 µJ/cm$^2$ to about 5 mJ/cm$^2$ between about 50 µJ/cm$^2$ to about 50 mJ/cm$^2$ between about 2.5 mJ/cm$^2$ to about 5 mJ/cm$^2$ or between about 3.25 mJ/cm$^2$ to about 3.75 mJ/cm$^2$.

The cross-sectional area of the light beam of certain embodiments (e.g., multimode beams) can be approximated using an approximation of the beam intensity distribution. For example, as described more fully below, measurements of the beam intensity distribution can be approximated by a Gaussian (1/e$^2$ measurements) or by a "top hat" distribution and a selected perimeter of the beam intensity distribution can be used to define a bound of the area of the light beam. In certain embodiments, the irradiance at the emission surface 22 is selected to provide the desired irradiances at the subdermal target tissue. The irradiance of the light beam is preferably controllably variable so that the emitted light energy can be adjusted to provide a selected irradiance at the subdermal tissue being treated. In certain embodiments, the light beam emitted from the emission surface 22 is continuous with a total radiant power in a range of about 4 Watts to about 6 Watts. In certain embodiments, the radiant power of the light beam is 5 Watts±20% (CW). In certain embodiments, the peak power for pulsed light is in a range of about 10 Watts to about 30 Watts (e.g., 20 Watts). In certain embodiments, the peak power for pulsed light multiplied by the duty cycle of the pulsed light yields an average radiant power in a range of about 4 Watts to about 6 Watts (e.g., 5 Watts).

In certain embodiments, the time-averaged irradiance at the subdermal target tissue (e.g., at a depth of approximately 2 centimeters below the dura) is at least about 0.01 mW/cm$^2$ and up to about 1 W/cm$^2$ at the level of the tissue. In various embodiments, the time-averaged subsurface irradiance at the target tissue is at least about 0.01, 0.05, 0.1, 0.5, 1, 5, 10, 15, 20, 30, 40, 50, 60, 70, 80, or 90 mW/cm$^2$ depending on the desired clinical performance. In certain embodiments, the time-averaged subsurface irradiance at the target tissue is about 0.01 mW/cm$^2$ to about 100 mW/cm$^2$ about 0.01 mW/cm$^2$ to about 50 mW/cm$^2$ about 2 mW/cm$^2$ to about 20 mW/cm$^2$ or about 5 mW/cm$^2$ to about 25 mW/cm$^2$. In certain embodiments, a duty cycle in a range between 1% and 80%, between 10% and 30%, or about 20% can be used with a peak irradiance at the target tissue of 0.05 mW/cm$^2$ to about 500 mW/cm$^2$ about 0.05 mW/cm$^2$ to about 250 mW/cm$^2$ about 10 mW/cm$^2$ to about 100 mW/cm$^2$ or about 25 mW/cm$^2$ to about 125 mW/cm$^2$.

In certain embodiments, the irradiance of the light beam is selected to provide a predetermined irradiance at the subdermal target tissue (e.g., at a depth of approximately 2 centimeters from the dura). The selection of the appropriate irradiance of the light beam emitted from the emission surface to use to achieve a desired subdermal irradiance preferably includes consideration of scattering by intervening tissue. Further information regarding the scattering of light by tissue is provided by U.S. Pat. No. 7,303,578, which is incorporated in its entirety by reference herein, and V. Tuchin in "Tissue Optics: Light Scattering Methods and Instruments for Medical Diagnosis," SPIE Press (2000), Bellingham, Wash., pp. 3-11, which is incorporated in its entirety by reference herein.

Phototherapy for the treatment of neurologic conditions (e.g., ischemic stroke, Alzheimer's Disease, Parkinson's Disease, depression, or TBI) is based in part on the discovery that irradiance or power density (i.e., power per unit area or number of photons per unit area per unit time) and energy density (i.e., energy per unit area or number of photons per unit area) of the light energy applied to tissue appear to be significant factors in determining the relative efficacy of low level phototherapy. This discovery is particularly applicable with respect to treating and saving surviving but endangered neurons in a zone of danger surrounding the primary injury. Certain embodiments described herein are based at least in part on the finding that, given a selected wavelength of light energy, it is the irradiance and/or the energy density of the light delivered to tissue (as opposed to the total power or total energy delivered to the tissue) that appears to be important factors in determining the relative efficacy of phototherapy.

Without being bound by theory or by a specific mechanism, it is believed that light energy delivered within a certain range of irradiances and energy densities provides the desired biostimulative effect on the intracellular environment, such that proper function is returned to previously nonfunctioning or poorly functioning mitochondria in at-risk neurons. The biostimulative effect may include interactions with chromophores within the target tissue, which facilitate production of ATP and/or controls, inhibits, prevents, minimizes, or reduces apoptosis of the injured cells which have experienced decreased blood flow (e.g., due to the stroke or TBI). Because strokes and TBI correspond to interruptions of blood flow to portions of the brain, it is thought that any effects of increasing blood flow by phototherapy are of less importance in the efficacy of phototherapy for stroke or TBI victims. Further information regarding the role of irradiance and exposure time is described by Hans H. F. I. van Breugel and P. R. Dop Bär in "Power Density and Exposure Time of He—Ne Laser Irradiation Are More Important Than Total Energy Dose in Photo-Biomodulation of Human Fibroblasts In Vitro," Lasers in Surgery and Medicine, Volume 12, pp. 528-537 (1992), which is incorporated in its entirety by reference herein. In addition, the significance of the irradiance used in phototherapy with regard to the devices and methods used in phototherapy of brain tissue, are described more fully in U.S. Pat. No. 7,303,578, U.S. Patent Appl. Publ. Nos. 2005/0107851 A1, 2007/0179570 A1, and 2007/0179571 A1, each of which is incorporated in its entirety by reference herein. While these previous discussions of irradiance were primarily in conjunction with phototherapy of stroke, they apply as well to phototherapy of TBI. For example, in certain embodiments, to obtain a desired average power density at the brain for treating TBI, higher total power at the scalp or skull can be used in conjunction with a larger spot size at the scalp or skull. Thus, by increasing the spot size at the scalp or skull, a desired average power density at the brain can be achieved with lower power densities at the scalp or skull which can reduce the possibility of overheating the scalp, skull, or brain.

In certain embodiments, delivering the neuroprotective amount of light energy includes selecting a surface irradiance of the light energy at the scalp or skull corresponding to the predetermined irradiance at the target area of the brain. As described above, light propagating through tissue is scattered and absorbed by the tissue. Calculations of the irradiance to be applied to the scalp or skull so as to deliver a predetermined irradiance to the selected target area of the brain preferably take into account the attenuation of the light energy as it propagates through the skin and other tissues, such as bone and brain tissue. Factors known to affect the attenuation of light propagating to the brain from the scalp or skull include, but are not limited to, skin pigmentation, the presence, type, and color of hair over the area to be treated, amount of fat tissue, the presence of bruised tissue, skull thickness, patient's age and gender, and the location of the target area of the brain, particularly the depth of the area relative to the surface of the scalp or skull. (For a general discussion of the absorption of light by melanins in the body, see, e.g., "Optical Absorption Spectra of Melanins—a Comparison of Theoretical and Experimental Results," accelrys.com/references/case-studies/melanins _partII.pdf.) The higher the level of skin pigmentation, the higher the irradiance applied to the scalp to deliver a predetermined irradiance of light energy to a subsurface site of the brain. The target area of the patient's brain can be previously identified such as by using standard medical imaging techniques.

The irradiance selected to be applied to the target area of the patient's brain depends on a number of factors, including, but not limited to, the wavelength of the applied light, the type of CVA (ischemic or hemorrhagic), and the patient's clinical condition, including the extent of the affected brain area. The irradiance or power density of light energy to be delivered to the target area of the patient's brain may also be adjusted to be combined with any other therapeutic agent or agents, especially pharmaceutical neuroprotective agents, to achieve the desired biological effect. In such embodiments, the selected irradiance can also depend on the additional therapeutic agent or agents chosen.

Figure 21A:
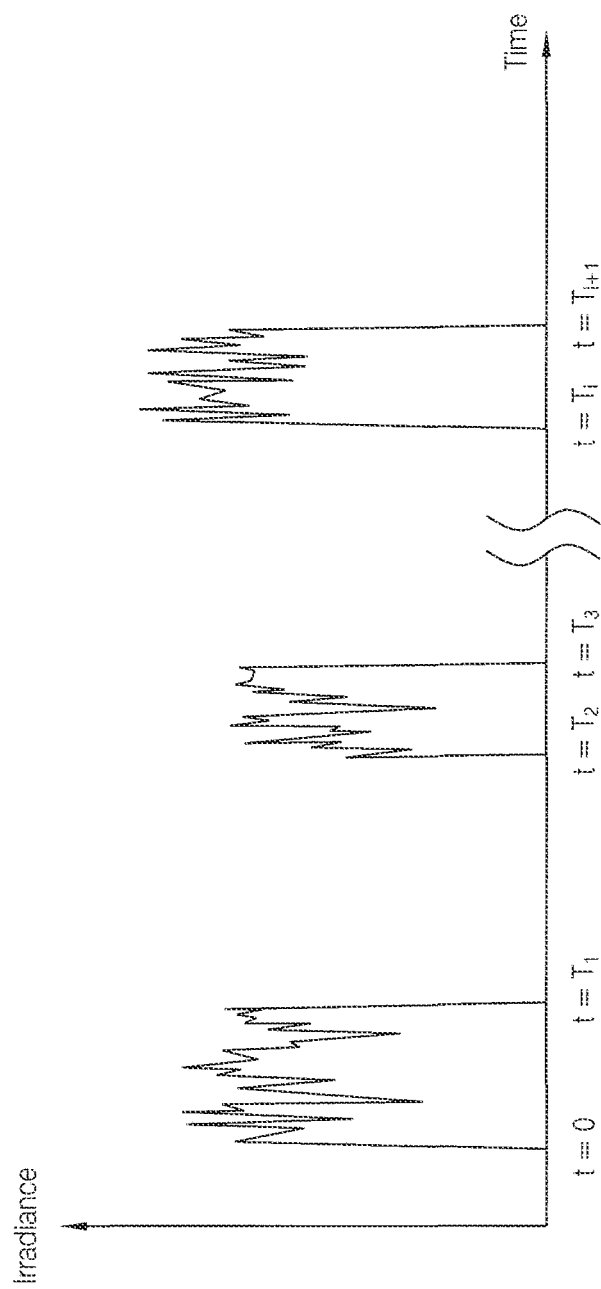

Temporal Pulsewidth, Temporal Pulseshape, Duty Cycle, Repetition Rate, and Irradiance Per Pulse FIG. 21A schematically illustrates a generalized temporal profile of a pulsed light beam in accordance with certain embodiments described herein. The temporal profile comprises a plurality of pulses ($P_1, P_2, \ldots, P_i$), each pulse having a temporal pulsewidth during which the instantaneous intensity or irradiance $I(t)$ of the pulse is substantially non-zero. For example, for the pulsed light beam of FIG. 21A, pulse $P_1$ has a temporal pulsewidth from time $t=0$ to time $t=T_1$, pulse $P_2$ has a temporal pulsewidth from time $t=T_2$ to time $t=T_3$, and pulse $P_i$ has a temporal pulsewidth from time $t=T_i$ to time $t=T_{i+1}$. The temporal pulsewidth can also be referred to as the "pulse ON time." The pulses are temporally spaced from one another by periods of time during which the intensity or irradiance of the beam is substantially zero. For example, pulse $P_1$ is spaced in time from pulse $P_2$ by a time $t=T_2-T_1$. The time between pulses can also be referred to as the "pulse OFF time." In certain embodiments, the pulse ON times of the pulses are substantially equal to one another, while in certain other embodiments, the pulse ON times differ from one another. In certain embodiments, the pulse OFF times between the pulses are substantially equal to one another, while in certain other embodiments, the pulse OFF times between the pulses differ from one another. As used herein, the term "duty cycle" has its broadest reasonable interpretation, including but not limited to, the pulse ON time divided by the sum of the pulse ON time and the pulse OFF time. For a pulsed light beam, the duty cycle is less than one. The values of the duty cycle and the temporal pulsewidth fully define the repetition rate of the pulsed light beam.

Figure 21C:
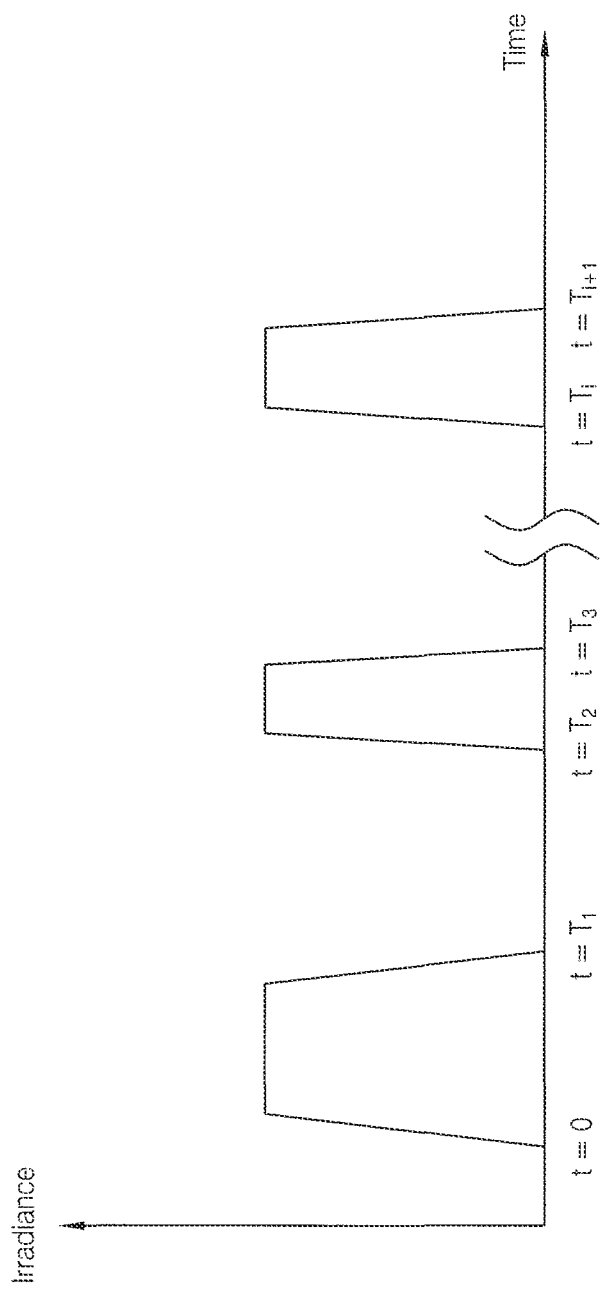

Each of the pulses can have a temporal pulseshape which describes the instantaneous intensity or irradiance of the pulse I(t) as a function of time. For example, as shown in FIG. 21A, the temporal pulseshapes of the pulsed light beam are irregular, and are not the same among the various pulses. In certain embodiments, the temporal pulseshapes of the pulsed light beam are substantially the same among the various pulses. For example, as schematically shown in FIG. 21B, the pulses can have a square temporal pulseshape, with each pulse having a substantially constant instantaneous irradiance over the pulse ON time. In certain embodiments, the peak irradiances of the pulses differ from one another (see, e.g., FIGS. 21A and 21B), while in certain other embodiments, the peak irradiances of the pulses are substantially equal to one another (see, e.g., FIGS. 21C and 21D). Various other temporal pulseshapes (e.g., triangular, trapezoidal) are also compatible with certain embodiments described herein. FIG. 21C schematically illustrates a plurality of trapezoidal pulses in which each pulse has a rise time (e.g., corresponding to the time between an instantaneous irradiance of zero and a peak irradiance of the pulse) and a fall time (e.g., corresponding to the time between the peak irradiance of the pulse and an instantaneous irradiance of zero). In certain embodiments, the rise time and the fall time can be expressed relative to a specified fraction of the peak irradiance of the pulse (e.g., time to rise/fall to 50% of the peak irradiance of the pulse).

As used herein, the term "peak irradiance" of a pulse Pi has its broadest reasonable interpretation, including but not limited to, the maximum value of the instantaneous irradiance I(t) during the temporal pulsewidth of the pulse. In certain embodiments, the instantaneous irradiance is changing during the temporal pulsewidth of the pulse (see, e.g., FIGS. 21A and 21C), while in certain other embodiments, the instantaneous irradiance is substantially constant during the temporal pulsewidth of the pulse (see, e.g., FIGS. 21B and 21D).

As used herein, the term "pulse irradiance" $I_{P_i}$ of a pulse $P_i$ has its broadest reasonable interpretation, including but not limited to, the integral of the instantaneous irradiance I(t) of the pulse $P_i$ over the temporal pulsewidth of the pulse:
$I_{P_i} = \int_{T_i}^{T_{i+1}} I(t) \cdot dt/(T_{i+1}-T)$ As used herein, the term "total irradiance" $I_{TOTAL}$ has its broadest reasonable interpretation, including, but not limited to, the sum of the pulse irradiances of the pulses: $I_{TOTAL} = \Sigma_{i=0}^{N} I_{P_i}$. As used herein, the term "time-averaged irradiance" $I_{AVE}$ has its broadest reasonable interpretation, including but not limited to, the integral of the instantaneous I(t) over a period of time T large compared to the temporal pulsewidths of the pulses: $I_{AVE} = \int_0^T I(t) \cdot dt/T$. The integral $\int_0^T I(t) \cdot dt$ provides the energy of the pulsed light beam.

For example, for a plurality of square pulses with different pulse irradiances $I_{P_i}$ and different temporal pulsewidths $\Delta T_i$, the time-averaged irradiance over a time T equals $$I_{AVE} = \frac{1}{T} \Sigma_i I_{P_i} \cdot \Delta T_i.$$

Figure 21D:
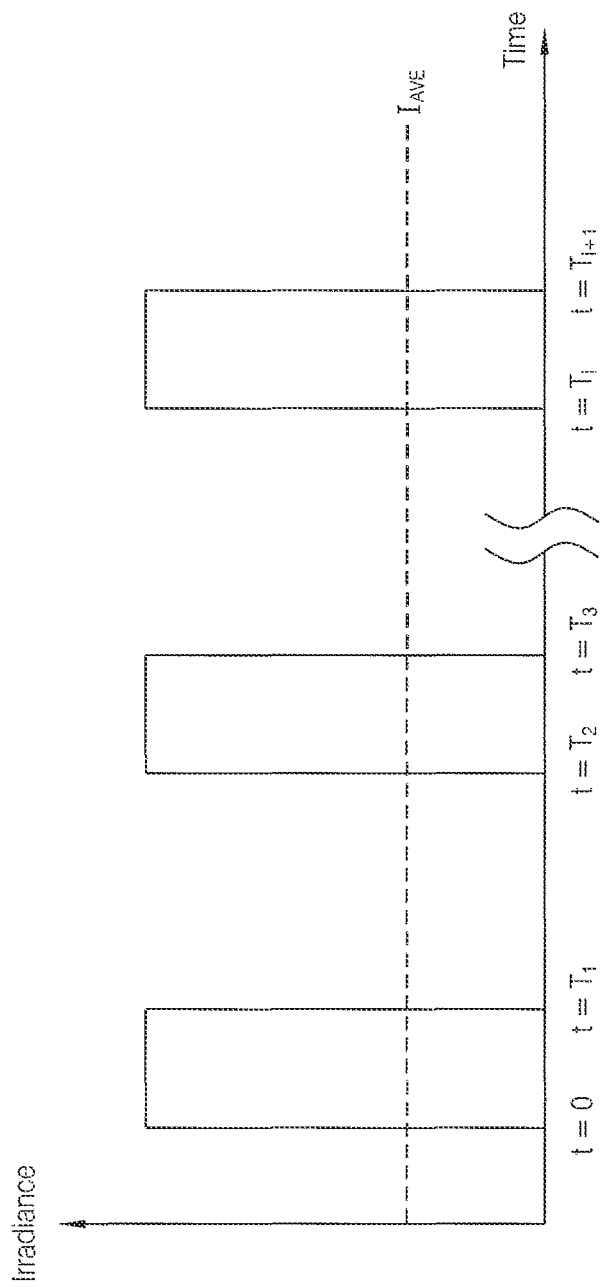

For another example, for a plurality of square pulses with equal pulse irradiances $I_P$, with equal temporal pulsewidths, and equal pulse OFF times (having a duty cycle D), the time-averaged irradiance equals $I_{AVE} = I_P \cdot D$. For example, as shown in FIG. 21D, the time-averaged irradiance (shown as a dashed line) is less than the pulse irradiance of the pulses.

The pulse irradiances and the duty cycle can be selected to provide a predetermined time-averaged irradiance. In certain embodiments in which the time-averaged irradiance is equal to the irradiance of a continuous-wave (CW) light beam, the pulsed light beam and the CW light beam have the same number of photons or flux as one another. For example, a pulsed light beam with a pulse irradiance of 5 mW/cm² and a duty cycle of 20% provides the same number of photons as a CW light beam having an irradiance of 1 mW/cm². However, in contrast to a CW light beam, the parameters of the pulsed light beam can be selected to deliver the photons in a manner which achieve results which are not obtainable using CW light beams.

For example, for hair removal, tattoo removal, or wrinkle smoothing, pulsed light beams have previously been used to achieve selective photothermolysis in which a selected portion of the skin is exposed to sufficiently high temperatures to damage the hair follicles (e.g., temperatures greater than 60 degrees Celsius), to ablate the tattoo ink (e.g., temperatures much greater than 60 degrees Celsius), or to shrink the collagen molecules (e.g., temperatures between 60-70 degrees Celsius), respectively, while keeping the other portions of skin at sufficiently low temperatures to avoid unwanted damage or discomfort. The parameters of these pulsed light beams are selected to achieve the desired elevated temperature at the selected portion of the skin by absorption of the light by the selected chromophore while allowing heat to dissipate (characterized by a thermal relaxation time) during the pulse OFF times to keep other areas of skin at lower temperatures. As described by J. Lepselter et al., "Biological and clinical aspects in laser hair removal," J. Dermatological Treatment, Vol. 15, pp. 72-83 (2004), the pulse ON time for hair removal is selected to be between the thermal relaxation time for the epidermis (about 3-10 milliseconds) and the thermal relaxation time for the hair follicle (about 40-100 milliseconds). In this way, the hair follicle can be heated to sufficiently high temperatures to damage the follicle without causing excessive damage to the surrounding skin.

In contrast to these treatments which are based on creating thermal damage to at least a portion of the skin, certain embodiments described herein utilize pulse parameters which do not create thermal damage to at least a portion of the skin. In certain embodiments, one or more of the temporal pulsewidth, temporal pulseshape, duty cycle, repetition rate, and pulse irradiance of the pulsed light beam are selected such that no portion of the skin is heated to a temperature greater than 60 degrees Celsius, greater than 55 degrees Celsius, greater than 50 degrees Celsius, or greater than 45 degrees Celsius. In certain embodiments, one or more of the temporal pulsewidth, temporal pulseshape, duty cycle, repetition rate, and pulse irradiance of the pulsed light beam are selected such that no portion of the skin is heated to a temperature greater than 30 degrees Celsius above its baseline temperature, greater than 20 degrees Celsius above its baseline temperature, or greater than 10 degrees Celsius above its baseline temperature. In certain embodiments, one or more of the temporal pulsewidth, temporal pulseshape, duty cycle, repetition rate, and pulse irradiance of the pulsed lightbeam are selected such that no portion of the brain is heated to a temperature greater than 5 degrees Celsius above its baseline temperature, greater than 3 degrees Celsius above its baseline temperature, or greater than 1 degree Celsius above its baseline temperature. As used herein, the term "baseline temperature" has its broadest reasonable interpretation, including but not limited to, the temperature at which the tissue would have if it were not irradiated by the light. In contrast to previous low-light level therapies, the pulsed light beam has an average radiant power in the range of about 1 Watt to about 6 Watts or in a range of about 4 Watt to about 6 Watts.

In certain embodiments, the pulse parameters are selected to achieve other effects beyond those which are achievable using CW light beams. For example, while CW irradiation of brain cells in vivo provides an efficacious treatment of stroke, the use of CW irradiation for the treatment of TBI is more difficult, owing in part to the excess blood within the region of the scalp, skull, or cranium to be irradiated (e.g., due to intercranial bleeding). This excess blood may be between the light source and the target brain tissue to be irradiated, resulting in higher absorption of the light applied to the scalp or skull before it can propagate to the target tissue. This absorption can reduce the amount of light reaching the target tissue and can unduly heat the intervening tissue to an undesirable level.

In certain embodiments described herein, pulsed irradiation may provide a more efficacious treatment. The pulsed irradiation can provide higher peak irradiances for shorter times, thereby providing more power to propagate to the target tissue while allowing thermal relaxation of the intervening tissue and blood between pulses to avoid unduly heating the intervening tissue. The time scale for the thermal relaxation is typically in the range of a few milliseconds. For example, the thermal relaxation time constant (e.g., the time for tissue to cool from an elevated temperature to one-half the elevated temperature) of human skin is about 3-10 milliseconds, while the thermal relaxation time constant of human hair follicles is about 40-100 milliseconds. Thus, previous applications of pulsed light to the body for hair removal have optimized temporal pulsewidths of greater than 40 milliseconds with time between pulses of hundreds of milliseconds.

However, while pulsed light of this time scale advantageously reduces the heating of intervening tissue and blood, it does not provide an optimum amount of efficaciousness as compared to other time scales. In certain embodiments described herein, the patient's scalp or skull is irradiated with pulsed light having parameters which are not optimized to reduce thermal effects, but instead are optimized to stimulate, to excite, to induce, or to otherwise support one or more intercellular or intracellular biological processes which are involved in the survival, regeneration, or restoration of performance or viability of brain cells. Thus, in certain such embodiments, the selected temporal profile can result in temperatures of the irradiated tissue which are higher than those resulting from other temporal profiles, but which are more efficacious than these other temporal profiles. In certain embodiments, the pulsing parameters are selected to utilize the kinetics of the biological processes rather than optimizing the thermal relaxation of the tissue. In certain embodiments, the pulsed light beam has a temporal profile (e.g., peak irradiance per pulse, a temporal pulse width, and a pulse duty cycle) selected to modulate membrane potentials in order to enhance, restore, or promote cell survival, cell function, or both of the irradiated brain cells following the traumatic brain injury. For example, in certain embodiments, the pulsed light has a temporal profile which supports one or more intercellular or intracellular biological processes involved in the survival or regeneration of brain cells, but does not optimize the thermal relaxation of the irradiated tissue. In certain embodiments, the brain cells survive longer after the irradiation as compared to their survival if the irradiation did not occur. For example, the light of certain embodiments can have a protective effect on the brain cells, or can cause a regeneration process in the brain cells.

In certain embodiments, the temporal profile (e.g., peak irradiance, temporal pulse width, and duty cycle) are selected to utilize the kinetics of the biological processes while maintaining the irradiated portion of the scalp or skull at or below a predetermined temperature. This predetermined temperature is higher than the optimized temperature which could be achieved for other temporal profiles (e.g., other values of the peak irradiance, temporal pulse width, and duty cycle) which are optimized to minimize the temperature increase of surrounding tissue due to the irradiation. For example, a temporal profile having a peak irradiance of 10 $W/cm^2$ and a duty cycle of 20% has a time-averaged irradiance of 2 $W/cm^2$. Such a pulsed light beam provides the same number of photons to the irradiated surface as does a continuous-wave (CW) light beam with an irradiance of 2 $W/cm^2$. However, because of the "dark time" between pulses, the pulsed light beam can result in a lower temperature increase than does the CW light beam. To minimize the temperature increase of the irradiated portion of the scalp or skull, the temporal pulse width and the duty cycle can be selected to allow a significant portion of the heat generated per pulse to dissipate before the next pulse reaches the irradiated portion. In certain embodiments described herein, rather than optimizing the beam temporal parameters to minimize the temperature increase, the temporal parameters are selected to effectively correspond to or to be sufficiently close to the timing of the biomolecular processes involved in the absorption of the photons to provide an increased efficacy. Rather than having a temporal pulse width on the order of hundreds of microseconds, certain embodiments described herein utilize a temporal pulse width which does not optimize the thermal relaxation of the irradiated tissue (e.g., milliseconds, tens of milliseconds, humdreds of milliseconds). Since these pulse widths are significantly longer than the thermal relaxation time scale, the resulting temperature increases are larger than those of smaller pulse widths, but still less than that of CW light beams due to the heat dissipation the time between the pulses.

A number of studies have investigated the effects of in vitro irradiation of cells using pulsed light on various aspects of the cells. A study of the action mechanisms of incoherent pulsed radiation at a wavelength of 820 nanometers (pulse repetition frequency of 10 Hz, pulse width of 20 milliseconds, dark period between pulses of 80 milliseconds, and duty factor (pulse duration to pulse period ratio) of 20%) on in vitro cellular adhesion has found that pulsed infrared radiation at 820 nanometers increases the cell-matrix attachment. (T. I. Karu et al., "*Cell Attachment to Extracellular Matrices is Modulated by Pulsed Radiation at* 820 *nm and Chemicals that Modify the Activity of Enzymes in the Plasma Membrane*," Lasers in Surgery and Medicine, Vol. 29, pp. 274-281 (2001) which is incorporated in its entirety by reference herein.) It was hypothesized in this study that the modulation of the monovalent ion fluxes through the plasma membrane, and not the release of arachidonic acid, is involved in the cellular signaling pathways activated by irradiation at 820 nanometers. A study of light-induced changes to the membrane conductance of ventral photoreceptor cells found behavior which was dependent on the pulse parameters, indicative of two light-induced membrane processes. (J. E. Lisman et al., "*Two Light-Induced Processes in the Photoreceptor Cells of Limulus Ventral Eye*," J. Gen. Physiology, Vol. 58, pp. 544-561 (1971), which is incorporated in its entirety by reference herein.) Studies of laser-activated electron injection into oxidized cytochrome c oxidase observed kinetics which establish the reaction sequence of the proton pump mechanism and some of its thermodynamic properties have time constants on the order of a few milliseconds. (I. Belevich et al., "*Exploring the proton pump mechanism of cytochrome c oxidase in real time*," Proc. Nat'l Acad. Sci., Vol. 104, pp. 2685-2690 (2007); I. Belevich et al., "*Proton-coupled electron transfer drives the proton pump of cytochrome c oxidase*," Nature, Vol. 440, pp. 829-832 (2006), both of which are incorporated in its entirety by reference herein.) An in vivo study of neural activation based on pulsed infrared light proposed a photothermal effect from transient tissue temperature changes resulting in direct or indirect activation of transmembrane ion channels causing propagation of the action potential. (J. Wells et al., "*Biophysical mechanisms responsible for pulsed low-level laser excitation of neural tissue*," Proc. SPIE, Vol. 6084, pp. 60840X (2006), which is incorporated in its entirety by reference herein.)

In certain embodiments, the temporal profile of the pulsed light beam comprises a peak irradiance, a temporal pulse width, a temporal pulse shape, a duty cycle, and a pulse repetition rate or frequency. In certain embodiments in which the pulsed light beam is transmitted through a region of the scalp or skull containing an excess amount of hemorrhagic blood due to the at least one physical trauma (e.g., due to intercranial bleeding), at least one of the peak irradiance, temporal pulse width, temporal pulse shape, duty cycle, and pulse repetition rate or frequency is selected to provide a time-averaged irradiance (averaged over a time period including a plurality of pulses) at the emission surface 22 of the output optical assembly 20 between about 10 mW/cm$^2$ to about 10 W/cm$^2$, between about 100 mW/cm$^2$ to about 1000 mW/cm$^2$, between about 500 mW/cm$^2$ to about 1 W/cm$^2$, or between about 650 mW/cm$^2$ to about 750 mW/cm$^2$ across the cross-sectional area of the light beam. In certain such embodiments, the time-averaged irradiance at the brain cells being treated (e.g., at a depth of approximately 2 centimeters below the dura) is greater than 0.01 mW/cm$^2$.

In certain embodiments, the peak irradiance per pulse across the cross-sectional area of the light beam at the emission surface 22 of the output optical assembly 20 is in a range between about 10 mW/cm$^2$ to about 10 W/cm$^2$, between about 100 mW/cm$^2$ to about 1000 mW/cm$^2$, between about 500 mW/cm$^2$ to about 1 W/cm$^2$, between about 650 mW/cm$^2$ to about 750 mW/cm$^2$, between about 20 mW/cm$^2$ to about 20 W/cm$^2$, between about 200 mW/cm$^2$ to about 2000 mW/cm$^2$, between about 1 W/cm$^2$ to about 2 W/cm$^2$, between about 1300 mW/cm$^2$ to about 1500 mW/cm$^2$, between about 1 W/cm$^2$ to about 1000 W/cm$^2$, between about 10 W/cm$^2$ to about 100 W/cm$^2$, between about 50 W/cm$^2$ to about 100 W/cm$^2$, or between about 65 W/cm$^2$ to about 75 W/cm$^2$. In certain embodiments, the temporal pulse shape is generally rectangular, generally triangular, or any other shape. In certain embodiments, the pulses have a rise time (e.g., from 10% of the peak irradiance to −52-90% of the peak irradiance) less than 1% of the pulse ON time, or a fall time (e.g., from 90% of the peak irradiance to 10% of the peak irradiance) less than 1% of the pulse ON time.

In certain embodiments, the pulses have a temporal pulsewidth (e.g., pulse ON time) in a range between about 0.001 millisecond and about 150 seconds, between about 0.01 millisecond and about 10 seconds, between about 0.1 millisecond and about 1 second, between about 0.5 millisecond and about 100 milliseconds, between about 2 milliseconds and about 20 milliseconds, or between about 1 millisecond and about 10 milliseconds. In certain embodiments, the pulse width is about 0.5, 1, 2, 4, 6, 8, 10, 15, 20, 30, 40, 50, 60, 70, 80, 90, 100, 120, 140, 160, 180, 200, 220, 240, 260, 280, or 300 milliseconds. In certain embodiments, the temporal pulsewidth is in a range between about 0.1 millisecond and 150 seconds.

In certain embodiments, the time between pulses (e.g., pulse OFF time) is in a range between about 0.01 millisecond and about 150 seconds, between about 0.1 millisecond and about 100 millisecond, between about 4 milliseconds and about 1 second, between about 8 milliseconds and about 500 milliseconds, between about 8 milliseconds and about 80 milliseconds, or between about 10 milliseconds and about 200 milliseconds. In certain embodiments, the time between pulses is about 4, 8, 10, 20, 50, 100, 200, 500, 700, or 1000 milliseconds.

In certain embodiments, the pulse duty cycle is in a range between about 1% and about 80% or in a range between about 10% and about 30%. In certain embodiments, the pulse duty cycle is about 10%, 20%, 30%, 40%, 50%, 60%, 70%, 80%, or 90%.

Beam Size and Beam Profile

In certain embodiments, the light beam emitted from the output optical assembly 20 has a nominal diameter in a range of about 10 millimeters to about 40 millimeters, in a range of about 20 millimeters to about 35 millimeters, or equal to about 30 millimeters. In certain embodiments, the cross-sectional area is generally circular with a radius in a range of about 1 centimeter to about 2 centimeters. In certain embodiments, the light beam emitted from the emission surface 22 has a cross-sectional area greater than about 2 cm$^2$ or in a range of about 2 cm$^2$ to about 20 cm$^2$ at the emission surface 22 of the optical element 23. In certain embodiments, the output optical element 23 has an aperture diameter of less than 33 millimeters.

As used herein, the beam diameter is defined to be the largest chord of the perimeter of the area of the scalp or skull irradiated by the light beam at an intensity of at least $1/e^2$ of the maximum intensity of the light beam. The perimeter of the light beam used to determine the diameter of the beam is defined in certain embodiments to be those points at which the intensity of the light beam is $1/e^2$ of the maximum intensity of the light beam. The maximum-useful diameter of certain embodiments is limited by the size of the patient's head and by the heating of the patient's head by the irradiation. The minimum-useful diameter of certain embodiments is limited by heating and by the total number of treatment sites that could be practically implemented. For example, to cover the patient's skull with a beam having a small beam diameter would correspondingly use a large number of treatment sites. In certain embodiments, the time of irradiation per treatment site can be adjusted accordingly to achieve a desired exposure dose.

Specifying the total flux inside a circular aperture with a specified radius centered on the exit aperture ("encircled energy") is a method of specifying the power (irradiance) distribution over the light beam emitted from the emission surface 22. The "encircled energy" can be used to ensure that the light beam is not too concentrated, too large, or too small. In certain embodiments, the light beam emitted from the emission surface has a total radiant power, and the light beam has a total flux inside a 20-millimeter diameter cross-sectional circle centered on the light beam at the emission surface 22 which is no more than 75% of the total radiant power. In certain such embodiments, the light beam has a total flux inside a 26-millimeter diameter cross-sectional circle centered on the light beam at the emission surface 22 which is no less than 50% of the total radiant power.

In certain embodiments, the beam intensity profile has a semi-Gaussian profile, while in certain other embodiments, the beam intensity profile has a "top hat" profile. In certain embodiments, the light beam is substantially without high flux regions or "hot spots" in the beam intensity profile in which the local flux, averaged over a 3 millimeter by 3 millimeter area, is more than 10% larger than the average flux. Certain embodiments of the apparatus 10 advantageously generate a light beam substantially without hot spots, thereby avoiding large temperature gradients at the patient's skin which would otherwise cause discomfort to the patient.

Divergence

In certain embodiments, the beam divergence emitted from the emission surface 22 is significantly less than the scattering angle of light inside the body tissue being irradiated, which is typically several degrees. In certain embodiments, the light beam has a divergence angle greater than zero and less than 35 degrees.

As the distance between a light source and an observer increases, the diameter of the source becomes less relevant to considerations of the beam divergence. For example, an end of the optical fiber 40 providing the light has a diameter of about 1 millimeter. At a close distance, observing from a specific location, light rays from the edges of the optical fiber end can arrive at the observation point with significantly different angles. However, as the observation point moves away from the light source, this angular discrepancy is reduced and the source appears more like a point source.

In certain embodiments, with the output optical assembly 20 mounted onto the apparatus 10, the optical distance between the emission surface 22 and the end of the optical fiber 40 is about 82.7 millimeters. The beam divergence dictated by the numerical aperture of the optical fiber 40 and the exit aperture of the optical element 23 is about 23 degrees. In certain embodiments, with the output optical assembly 20 not mounted onto the apparatus 10, the optical distance between the window 70 and the end of the optical fiber is about 57.5 millimeters, and the beam divergence dictated by the numerical aperture of the optical fiber 40 and the exit aperture of the window 70 is about 16 degrees. With a source diameter of about 1 millimeter, the angular ambiguity in the beam divergence is about ±0.35 degree. Thus, the angular ambiguity is much less than the beam divergence angle regardless of whether the output optical assembly 20 is mounted or not onto the apparatus 10, so the optical fiber 40 can be treated as a point source. In certain such embodiments, the beam divergence or radiant intensity (e.g., measured in Watts/steradian) can be calculated directly from the beam profile or from the irradiance.

Treatment Time

In certain embodiments, the treatment per treatment site proceeds continuously for a period of about 10 seconds to about 2 hours, for a period of about 1 to about 10 minutes, or for a period of about 1 to 5 minutes. For example, the treatment time per treatment site in certain embodiments is about two minutes. In other embodiments, the light energy is delivered for at least one treatment period of at least about five minutes, or for at least one treatment period of at least ten minutes. The minimum treatment time of certain embodiments is limited by the biological response time (which is on the order of microseconds). The maximum treatment time of certain embodiments is limited by heating and by practical treatment times (e.g., completing treatment within about 24 hours of stroke onset). The light energy can be pulsed during the treatment period or the light energy can be continuously applied during the treatment period. If the light is pulsed, the pulses can be 2 milliseconds long and occur at a frequency of 100 Hz, although longer pulselengths and lower frequencies can be used, or at least about 10 nanosecond long and occur at a frequency of up to about 100 kHz.

In certain embodiments, the treatment may be terminated after one treatment period, while in other embodiments, the treatment may be repeated for at least two treatment periods. The time between subsequent treatment periods can be at least about five minutes, at least two in a 24-hour period, at least about 1 to 2 days, or at least about one week. The length of treatment time and frequency of treatment periods can depend on several factors, including the functional recovery of the patient and the results of imaging analysis of the injury (e.g., infarct). In certain embodiments, one or more treatment parameters can be adjusted in response to a feedback signal from a device (e.g., magnetic resonance imaging) monitoring the patient.

Cooling Parameters

In certain embodiments, the apparatus 10 comprises an output optical element 23 in optical communication with a source of light. The output optical element 23 comprises an emission surface 22 configured to emit a light beam in accordance with the light parameters disclosed above. In certain embodiments the apparatus 10 further comprises a thermally conductive portion configured to be placed in thermal communication with the irradiated portion of the patient's scalp or skull and to remove heat from the irradiated portion of the patient's scalp or skull. In certain embodiments, the thermally conductive portion comprises the output optical element 23. The thermally conductive portion of certain embodiments is releasably coupled to the output optical element 23.

In certain embodiments, the thermally conductive portion removes heat from the irradiated portion of the patient's scalp or skull. This cooling of the scalp or skull can to improve the comfort of the patient, by controlling, inhibiting, preventing, minimizing, or reducing temperature increases at the scalp or skull due to the irradiation. Thus, by virtue of the cooling of the portion of the patient's scalp or skull being irradiated, the temperature of the irradiated portion of the patient's scalp or skull is lower than it would otherwise be if the irradiated portion of the scalp or skull were not cooled. For example, by cooling the irradiated portion of the patient's scalp or skull, the temperature of the irradiated portion of the patient's scalp or skull can be higher than the temperature of the portion of the patient's scalp or skull if it were not irradiated, but lower than the temperature of the portion of the patient's scalp or skull if it were irradiated but not cooled. In addition, this cooling of the scalp or skull can be to perform double-blind studies of the efficacy of the phototherapy treatment by masking any heating of the scalp or skull due to the irradiation. (See, e.g., B. Catanzaro et al., "Managing Tissue Heating in Laser Therapy to Enable Double-Blind Clinical Study," Mechanisms for Low-Light Therapy, Proc. of the SPIE, Vol. 6140, pp. 199-208 (2006).)

In certain embodiments, heat is removed from the irradiated portion of the patient's scalp or skull by the thermally conductive portion at a rate in a range of about 0.1 Watt to about 5 Watts or in a range of about 1 Watt to about 3 Watts. In certain embodiments, the thermally conductive portion is configured to maintain the temperature of the irradiated portion of the patient's scalp or skull to be less than 42 degrees Celsius. The thermally conductive portion of certain embodiments is in thermal communication with the emission surface 22 and is configured to maintain the temperature of the emission surface to be in a range of 18 degrees Celsius to 25 degrees Celsius under a heat load of 2 Watts. For a general description of cooling of the scalp, see, e.g., F. E. M. Janssen et al., "Modeling of temperature and perfusion during scalp cooling," Phys. Med. Biol., Vol. 50, pp. 4065-4073 (2005). In certain embodiments in which pulsed light is used, the rate of heat removal can be less, or cooling may not be utilized for certain ranges of pulsed dosimetries and timing.

Pressure Parameters

In certain embodiments, the apparatus 10 is configured to have the thermally conductive portion move relative to a second portion of the apparatus 10 upon a pressure being applied to the thermally conductive portion above a predetermined threshold pressure in a direction of movement of the thermally conductive portion relative to the second portion of the apparatus 10. The predetermined threshold pressure is sufficient to have the thermally conductive portion in thermal communication with the portion of the patient's scalp or skull. In certain such embodiments, the apparatus 10 comprises a sensor configured to be responsive to the movement of the thermally conductive portion relative to the second portion by generating a signal (e.g., binary, analog, or digital) indicative of the movement.

In certain such embodiments, the sensor 130 in conjunction with the trigger force spring 140 and the trigger force adjustment mechanism 142 provides a mechanism for detecting whether the apparatus 10 is being applied to the patient's scalp or skull with a pressure above the predetermined threshold pressure. In certain such embodiments, the sensor 130 detects movement between the first portion of the apparatus 10 and the second portion of the apparatus 10 upon placing the emission surface 22 in thermal communication with the patient's scalp or skull with sufficient pressure to overcome the restoring force of the trigger force spring 140. Upon applying the threshold pressure to the emission surface 22 move the first and second portions relative to one another, the sensor 130 detects the movement and generates a corresponding signal. In certain embodiments, the apparatus 10 further comprises a controller operatively coupled to the light source and to the sensor 130. The controller is configured to receive the signal from the sensor 130 and to turn on the light source in response to the signal being indicative of the pressure being above the predetermined threshold pressure.

In certain embodiments, the threshold pressure is set to be a pressure which results in blanching of the portion of the patient's scalp to be irradiated. In certain embodiments, the threshold pressure is 0.1 pound per square inch, while in certain other embodiments, the threshold pressure is one pound per square inch or about two pounds per square inch.

In certain embodiments in which pulsed light is used, the amount of blanching can be less, or blanching may not be utilized for certain ranges of pulsed dosimetries and timing. For example, in certain embodiments, the patient may have a heightened sensitivity to pressure applied to the scalp or skull (e.g., a TBI patient). Thus, in certain embodiments, the apparatus 10 does not apply sufficient pressure to the scalp of the patient (e.g., applies no pressure to the patient's scalp) to blanch the irradiated portion of the scalp during the irradiation. In certain other embodiments in which some amount of blanching of the irradiated portion of the scalp is desired, the maximum pressure used to blanch the irradiated portion of the scalp is limited by patient comfort levels and tissue damage levels. For example, the cranium or skull of a TBI patient may have cracks or breaks such that the brain would be adversely affected if pressure were applied to the scalp. The amount of pressure used, if any, is determined at least in part, on the amount of pressure that the patient can withstand without additional damage being done by the application of pressure.

Irradiating Multiple Portions of the Scalp or Skull

Figure 22A:
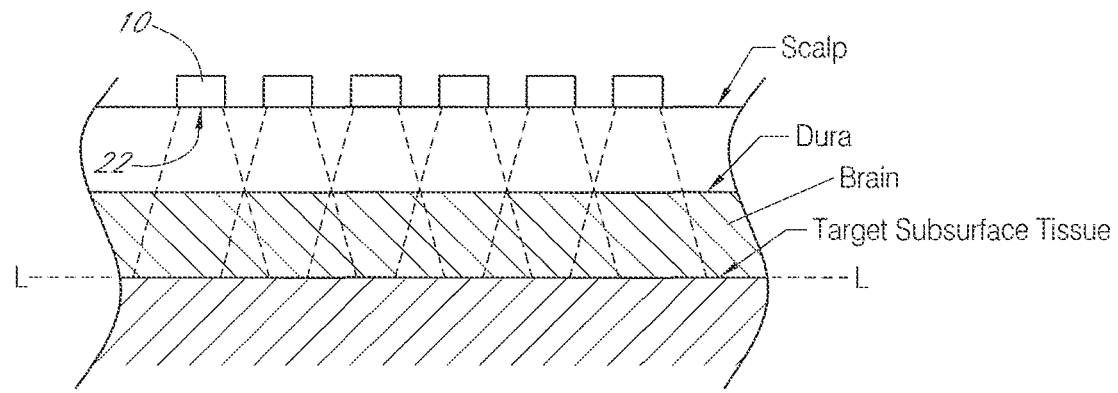
FIGS. 22A-22C schematically illustrate an embodiment in which the apparatus is placed in thermal communication sequentially with a plurality of treatment sites corresponding to portions of the patient's scalp.
Figure 22B:
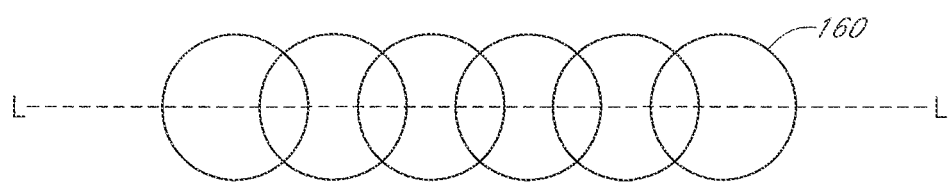
Figure 22C:
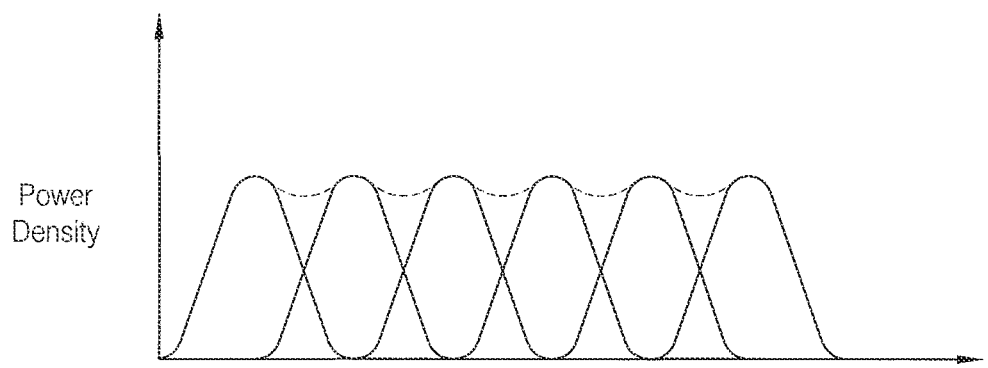

FIGS. 22A-22C schematically illustrate an embodiment in which the apparatus 10 is placed in thermal communication sequentially with a plurality of treatment sites corresponding to portions of the patient's scalp. In certain such embodiments, the light emitted from the emission surface 22 propagates through the scalp to the brain and disperses in a direction generally parallel to the scalp, as shown in FIG. 22A. In certain embodiments in which the patient is suffering from a TBI, one or more of the treatment sites has a portion of the skull is exposed and at least a portion of the light is applied to the exposed portion of the skull without propagating through scalp tissue. In certain embodiments, the treatment sites of the patient's scalp do not overlap one another. The treatment sites (e.g., twenty treatment sites) are preferably spaced sufficiently far apart from one another such that the light emitted from the emission surface 22 to irradiate a treatment site of the patient's scalp is transmitted through intervening tissue to irradiate an area of the patient's brain which overlaps one or more areas of the target tissue of the patient's brain irradiated by the light emitted from the emission surface 22 when a neighboring treatment site of the patient's scalp is irradiated. FIG. 22B schematically illustrates this overlap as the overlap of circular spots 160 across the target tissue at a reference depth at or below the surface of the brain. FIG. 22C schematically illustrates this overlap as a graph of the irradiance at the reference depth of the brain along the line L-L of FIGS. 22A and 22B. Summing the irradiances from the neighboring treatment sites (shown as a dashed line in FIG. 22C) serves to provide a more uniform light distribution at the target tissue to be treated. In such embodiments, the summed irradiance is preferably less than a damage threshold of the brain and above an efficacy threshold. In certain embodiments, portions of the brain irradiated by irradiating the treatment sites at the scalp do not overlap one another. In certain such embodiments, the treatment sites at the scalp are positioned so as to irradiate as much of the cortex as possible.

Example Wearable Apparatus

Figure 23:
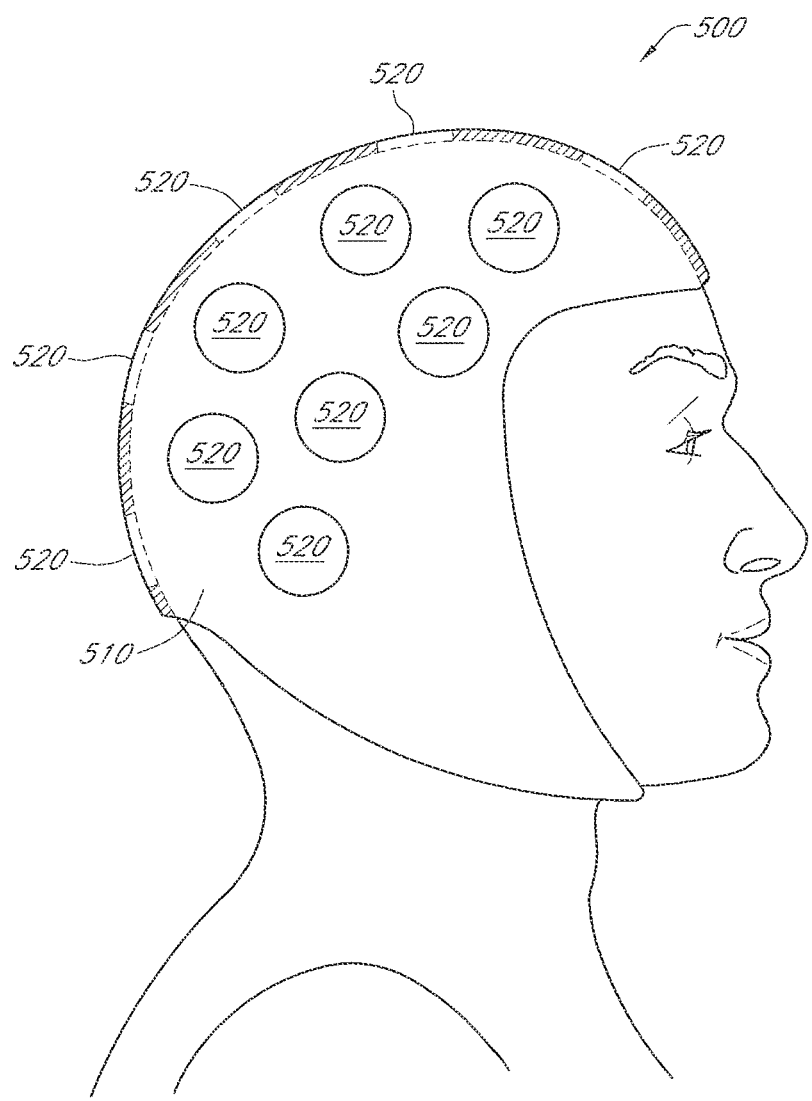
FIG. 23 schematically illustrates an example apparatus which is wearable by a patient for treating the patient's brain.

FIG. 23 schematically illustrates an example apparatus 500 which is wearable by a patient for treating the patient's brain. The apparatus 500 comprises a body 510 and a plurality of indicators 520. The body 510 is adapted to be worn over at least a portion of the patient's scalp when the apparatus 500 is worn by the patient. The plurality of indicators 520 correspond to a plurality of treatment site location at the patient's scalp where light is to be applied to irradiate at least a portion of the patient's brain. At least one indicator 520 comprises a portion of the body which is substantially transmissive (e.g., substantially transparent or substantially translucent) to light emitted from the emission surface 22 to irradiate at least a portion of the patient's brain.

In certain embodiments, at least one of the indicators 520 denotes a position within an area of the patient's scalp corresponding to a treatment site location. In certain such embodiments, the position is the center of the area of the patient's scalp. The adjacent treatment sites of certain embodiments have areas which do not overlap one another or have perimeters which are spaced from one another. In certain such embodiments, the perimeters are spaced from one another by at least 10 millimeters or at least 25 millimeters.

In certain embodiments, each indicator 520 comprises an opening or aperture through the body 510 at which the beam delivery apparatus 10 can be placed to irradiate the portion of the patient's scalp exposed by the hole or aperture. In certain embodiments, the aperture has a substantially circular perimeter and a diameter in a range between 20 millimeters and 50 millimeters or in a range between 25 millimeters and 35 millimeters. In certain embodiments, the aperture has a substantially elliptical perimeter with a minor axis greater than 20 millimeters and a major axis less than 50 millimeters. Other shapes of the aperture are also compatible with certain embodiments described herein.

In certain embodiments, the plurality of indicators 520 comprises at least about 10 indicators 520 distributed across the patient's scalp, while in certain other embodiments, the plurality of indicators 520 comprises 20 indicators 520. In certain other embodiments, the plurality of indicators 520 comprises between 15 and 25 indicators 520. In certain embodiments, the optically transmissive portion of each indicator 520 has an area of at least 1 cm$^2$, in a range between 1 cm$^2$ and 20 cm$^2$, or in a range between 5 cm$^2$ and 10 cm$^2$.

In certain embodiments, the body 510 comprises a hood, while in other embodiments, the body 510 comprises a cap or has another configuration which is wearable on the patient's head and serves as a support for orienting the indicators 520 on the patient's head. In certain embodiments, the body 510 comprises a stretchable or pliant material which generally conforms to the patient's scalp. In certain embodiments, the body 510 comprises nylon-backed polychloroprene or Tyvek®. In certain embodiments, the body 510 is available in different sizes (e.g., small, medium, large) to accommodate different sizes of heads. In certain embodiments, the body 510 is disposable after a single use to advantageously avoid spreading infection or disease between subsequent patients.

The indicators 520 of certain embodiments are configured to guide an operator to irradiate the patient's scalp at the corresponding treatment site locations sequentially one at a time in a predetermined order. In certain embodiments, the wearable apparatus 500 further comprises a plurality of labels 522 with each label in proximity to a corresponding indicator. The labels 522 advantageously provide one or more numbers, letters, or symbols (e.g., bar codes) to each of the indicators 520 to distinguish the various indicators 520 from one another. In certain such embodiments, the labels 522 are mechanically coupled to the corresponding indicators so as to be visible to users of the beam delivery apparatus 10.

Figure 24A:
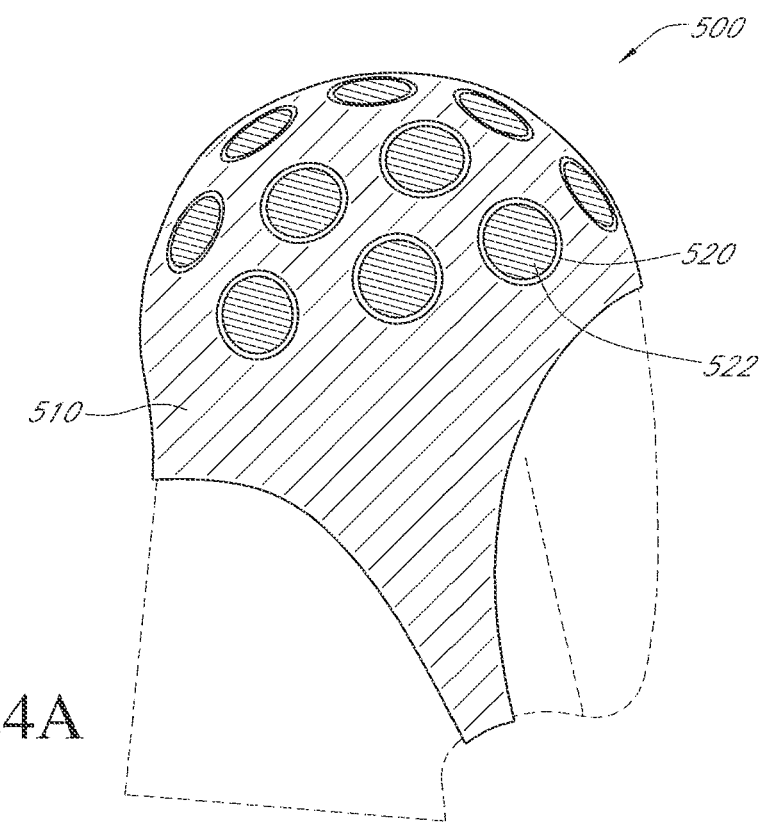
FIGS. 24A and 24B schematically illustrate the left-side and right-side of an example apparatus, respectively, with labels substantially covering the indicators corresponding to the treatment sites.
Figure 24B:
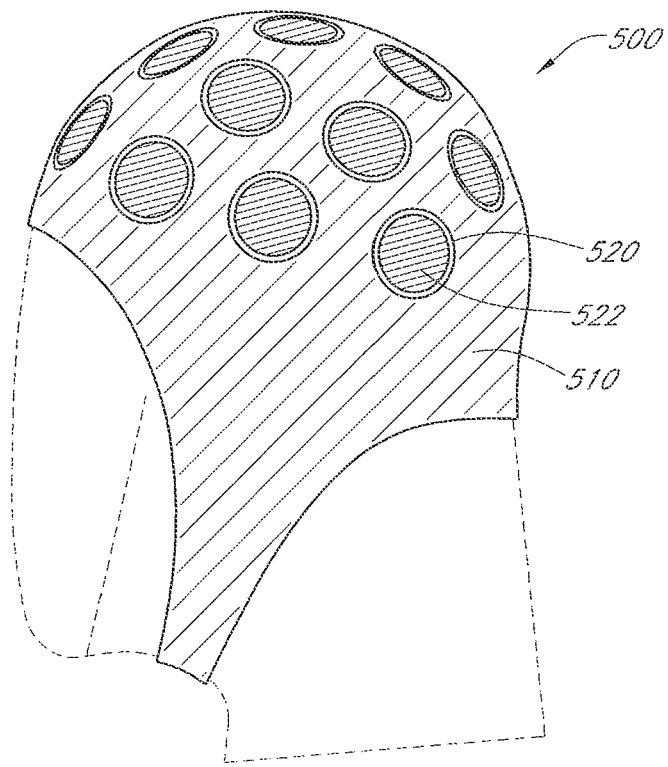

FIGS. 24A and 24B schematically illustrate the left-side and right-side of an example apparatus 500, respectively, with labels 522 substantially covering the indicators 520 corresponding to the treatment sites. In certain embodiments, the labels 522 are advantageously used to keep track of which treatment sites have been irradiated and which treatment sites are yet to be irradiated. In certain such embodiments, at least a portion of each label 522 comprises a portion of the body (e.g., a pull-off tab or flap) which is configured to be removed from the apparatus 500 when the treatment site corresponding to the indicator 520 has been irradiated. In certain embodiments, the labels 522 comprise removable portions of the body 510 which cover the corresponding indicator 520. In certain such embodiments, prior to irradiating the treatment site location corresponding to the indicator 520, the corresponding label 522 can be removed to allow access to the underlying portion of the patient's scalp.

In certain embodiments, the label 522 has a code sequence which the operator enters into the controller prior to irradiation so as to inform the controller of which treatment site is next to be irradiated. In certain other embodiments, each label 522 comprises a bar code or a radio-frequency identification device (RFID) which is readable by a sensor electrically coupled to the controller. The controller of such embodiments keeps track of which treatment sites have been irradiated, and in certain such embodiments, the controller only actuates the light source when the beam delivery apparatus 10 is in optical and thermal communication with the proper treatment site of the patient's scalp.

Figure 24C:
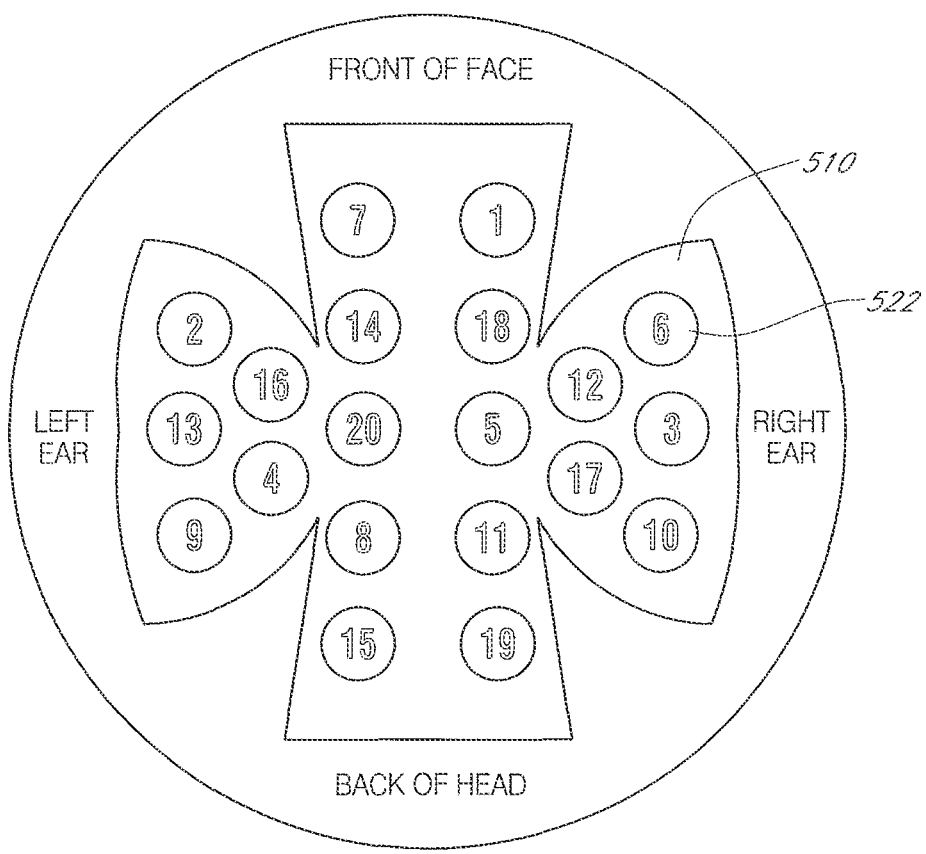
FIG. 24C schematically illustrates an example labeling configuration from above a flattened view of the apparatus of FIGS. 24A and 24B.

FIG. 24C schematically illustrates an example labeling configuration from above a flattened view of the apparatus 500 of FIGS. 24A and 24B. The labeling convention of FIG. 24C is compatible with irradiation of both halves or hemispheres of the patient's brain. Other labeling conventions are also compatible with embodiments described herein.

In certain embodiments, the labels 522 are advantageously used to guide an operator to irradiate the patient's brain at the various treatment sites sequentially at each of the treatment sites one at a time through the indicators 520 in a predetermined order by optically and thermally coupling the beam delivery apparatus 10 to sequential treatment sites corresponding to the indicators 520. For example, for the labeling configuration of FIG. 24C, the operator can first irradiate treatment site "1," followed by treatment sites "2," "3," "4," etc. to sequentially irradiate each of the twenty treatment sites one at a time. In certain such embodiments, the predetermined order of the treatment sites is selected to advantageously reduce temperature increases which would result from sequentially irradiating treatment sites in proximity to one another.

In certain embodiments, the predetermined order comprises irradiation of a first treatment site location on a first side of the patient's scalp (e.g., site "2" of FIG. 24C), then irradiation of a second treatment site location on a second side of the patient's scalp (e.g., site "3" of FIG. 24C), then irradiation of a third treatment site location on the first side of the patient's scalp (e.g., site "4" of FIG. 24C). In certain such embodiments, the predetermined order further comprises irradiation of a fourth treatment site location on the second side of the patient's scalp after irradiation of the third treatment site location. In certain embodiments, two sequentially irradiated treatment site locations are separated from one another by at least 25 millimeters.

For example, in certain embodiments, the predetermined order comprises at least a portion of the following sequence of treatment sites:
1. Right anterior frontal
2. Left lateral frontal
3. Right anteroinferior parietal
4. Left posterior mid-parietal
5. Right superior parietal
6. Right lateral frontal
7. Left anterior frontal
8. Left posterior superior parietal
9. Left posteroinferiorparietal
10. Right posteroinferior parietal
11. Right posterior superior parietal
12. Right anterior mid-parietal
13. Left anteroinferior parietal
14. Left anterosuperior frontal
15. Left superior occipital 16. Left anterior mid-parietal
17. Right posterior mid-parietal
18. Right anterosuperiorfrontal
19. Right superior occipital
20. Left superior parietal For example, the predetermined order of certain embodiments comprises two, three, four, or more of these treatment sites in the relative order listed above. The sequence of treatment sites of certain embodiments comprises two, three, four, or more of these treatment sites in a relative order which is the reverse of the sequence listed above. While certain embodiments utilize at least a portion the relative order listed above without irradiation at an additional treatment site between two sequentially listed treatment sites, certain other embodiments utilize at least a portion of the relative order listed above with one or more additional treatment sites between two of the sequentially listed treatment sites. In certain embodiments, the exact anatomic locations of each treatment site may be adjusted from those listed above to account for variations among the sizes of the heads of the patients (e.g., very large or very small). Thus, in certain embodiments, there is some variability regarding the locations of the treatment sites for any given individual.

In certain embodiments, the apparatus 500 serves as a template for marking the patient's scalp to indicate the treatment site locations. The apertures of the apparatus 500 can be used to guide a user place marks on the patient's scalp, and the apparatus 500 can then be removed from the patient's scalp before the beam delivery apparatus 10 is applied to the scalp for irradiating the patient's brain. The marks remain on the patient's scalp to guide the operator while the patient's brain is irradiated.

Methods of Light Delivery

FIGS. 25-28 are flow diagrams of example methods for irradiating a surface with light. As described more fully below, the methods are described by referring to the beam delivery apparatus 10 and components thereof, as described herein. Other configurations of a beam delivery apparatus are also compatible with the methods in accordance with embodiments described herein.

Figure 25:
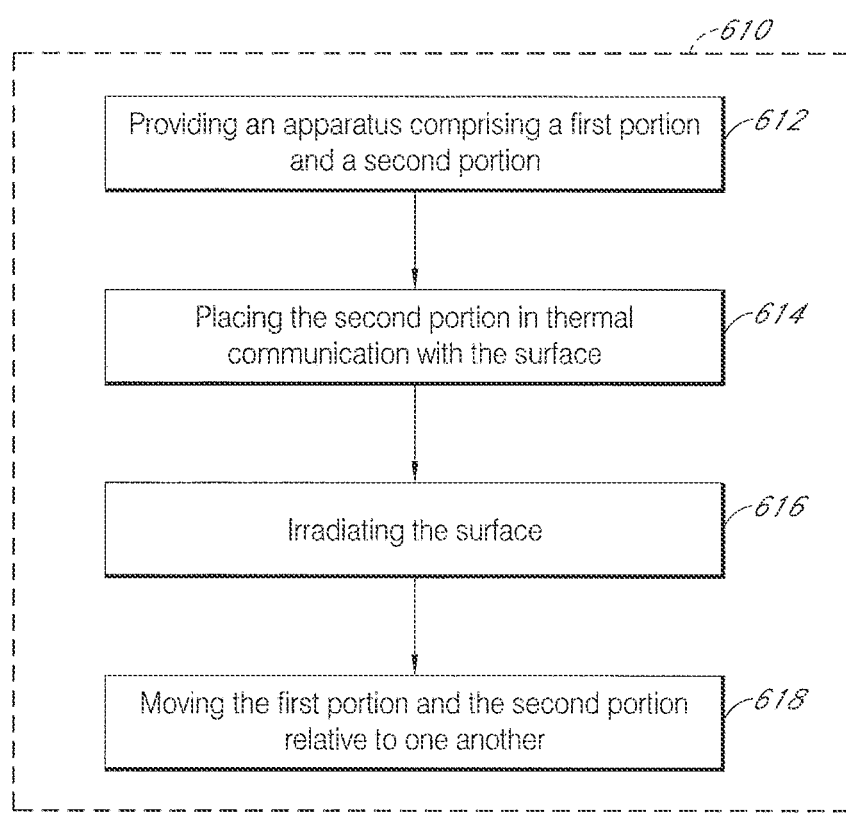
FIGS. 25-28 are flow diagrams of example methods for irradiating a surface with light.

The method 610 of FIG. 25 comprises providing a beam delivery apparatus 10 in an operational block 612. The beam delivery apparatus 10 comprises a first portion and a second portion mechanically coupled to the first portion and in optical communication with the first portion, wherein the first portion and the second portion are configured to move relative to one another, as described more fully above. The method 610 further comprises placing the second portion in thermal communication with the surface in an operational block 614 (e.g., releasably operatively coupling the second portion to the surface). The method 610 further comprises irradiating the surface such that the light from the first portion propagates through the second portion in an operational block 616. The method 610 further comprises moving the first portion and the second portion relative to one another in response to the second portion being placed in thermal communication with the surface in an operational block 618.

Figure 26:
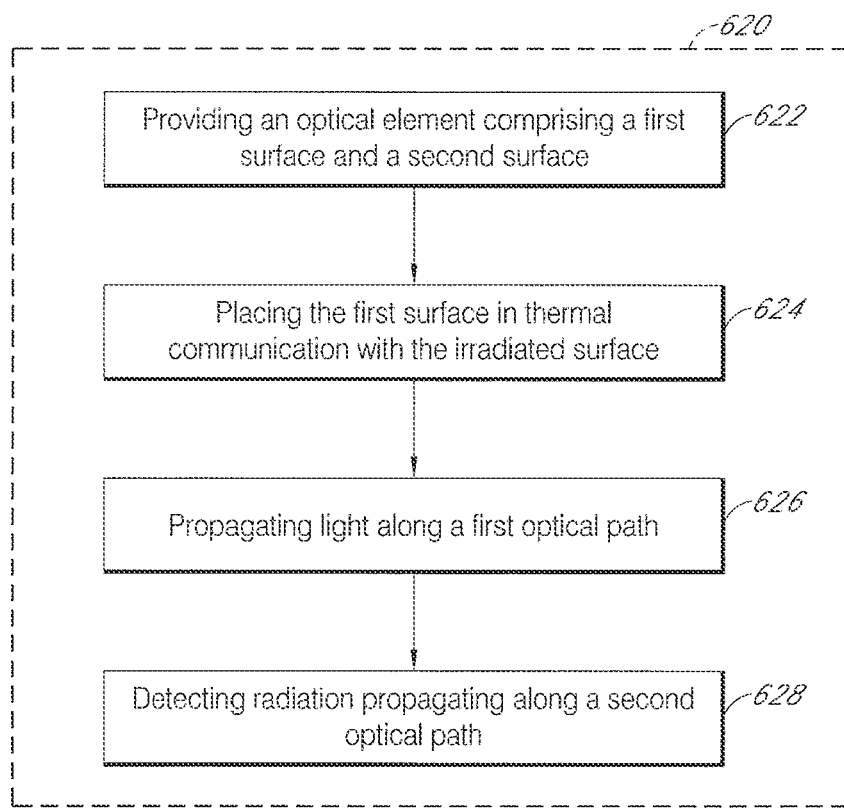

The method 620 of FIG. 26 comprises providing an optical element 23 in an operational block 622. The optical element 23 comprises a substantially optically transmissive and substantially thermally conductive material, and the optical element 23 has a first surface 22 and a second surface 24, as described more fully above. The method 620 further comprises placing the first surface 22 in thermal communication with the irradiated surface in an operational block 624 (e.g., releasably operatively coupling the first surface 22 to the irradiated surface). The method 620 further comprises propagating the light along a first optical path 32 through the second surface 24 and through the first surface 22 to the irradiated surface in an operational block 626. The method 620 further comprises detecting radiation propagating along a second optical path 82 from at least a portion of the second surface 24, wherein the first optical path 32 and the second optical path 82 have a non-zero angle therebetween in an operational block 628. In certain embodiments, the first surface 22 and the second surface 24 face in generally opposite directions, and the first surface 22 is not along the second optical path 82.

Figure 27:
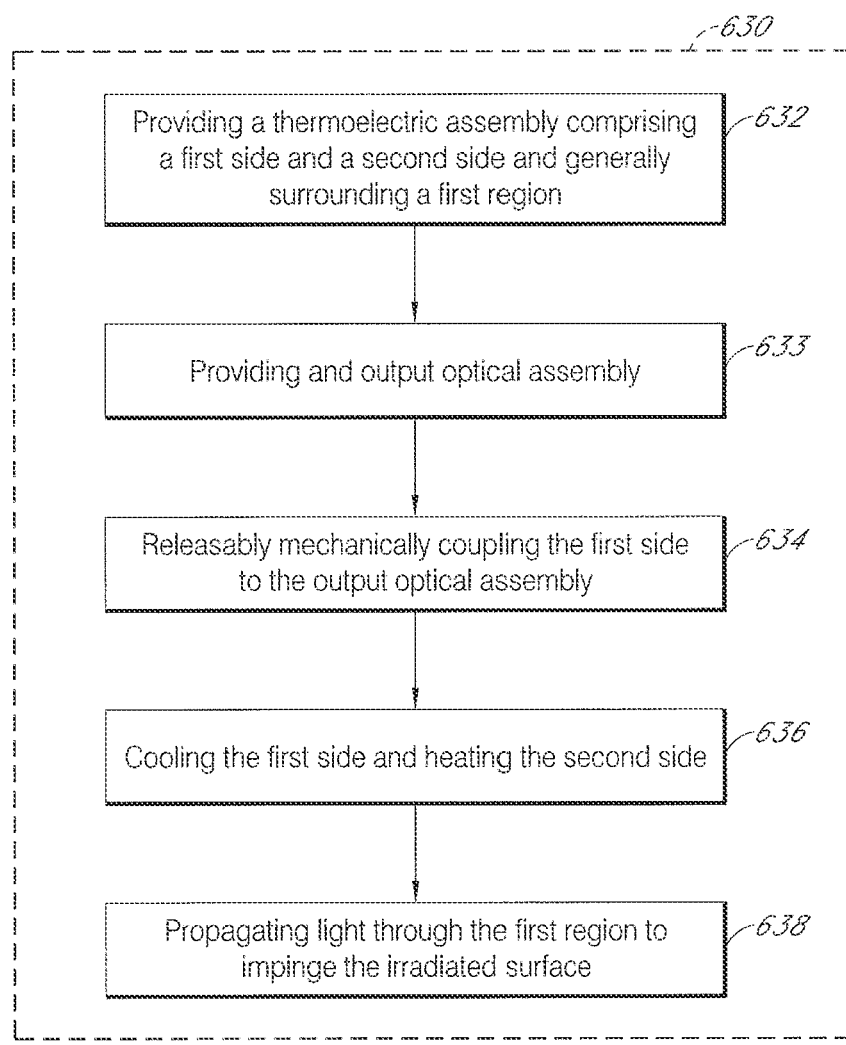

The method 630 of FIG. 27 comprises providing a thermoelectric assembly 90 in an operational block 632. The thermoelectric assembly 90 comprises a first surface 93 and a second surface 94, and the thermoelectric assembly 90 generally surrounds a first region 97, as described more fully above. The method 630 further comprises providing an output optical assembly 20 in an operational block 633. The method 630 further comprises releasably mechanically coupling the first surface 93 of the thermoelectric assembly 90 to the output optical assembly 20 so that the first surface 93 is in thermal communication with the output optical assembly 20 in an operational block 634. The method 630 further comprises cooling the first surface 93 and heating the second surface 94 in an operational block 636. The method 630 further comprises propagating light through the first region 97 to impinge the irradiated surface in an operational block 638. In certain embodiments, the first surface 22 and the second surface 24 face in generally opposite directions, and the first surface 22 is not along the second optical path 82.

In certain embodiments, the output optical assembly 20 comprises an optical element 23 and a thermally conductive portion 25 generally surrounding a second region 28. The thermally conductive portion 25 is in thermal communication with the optical element 23. In certain such embodiments, releasably mechanically coupling the first surface 93 to the output optical assembly 20 comprises releasably mechanically coupling the first surface 93 to the thermally conductive portion 25. In certain such embodiments, the method 630 further comprises placing the optical element 23 in thermal communication with the irradiated surface and propagating the light comprises transmitting the light through the first region 97, the second region 28, and the optical element 23 to impinge the irradiated surface. In certain embodiments, the method 630 further comprises providing a heat sink 100 in thermal communication with the second surface 94 of the thermoelectric assembly 90. The heat sink 100 generally surrounds a third region 107, and propagating the light comprises transmitting the light through the third region 107, the first region 97, the second region 28, and the optical element 23.

Figure 28:
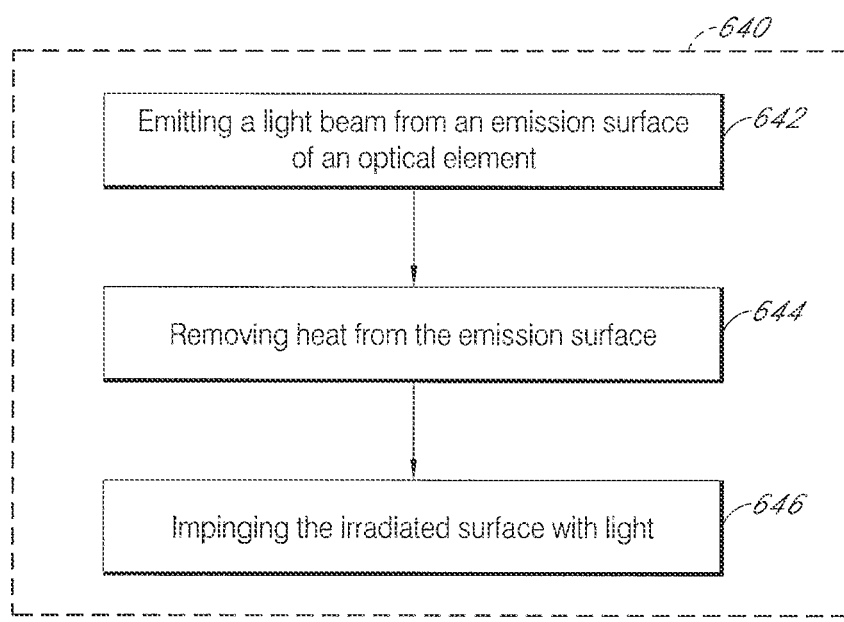

The method 640 of FIG. 28 comprises emitting a light beam from an emission surface 22 of an optical element 23 in an operational block 642. The light beam at the emission surface 22 has one or more wavelengths in a range of about 630 nanometers to about 1064 nanometers, a cross-sectional area greater than about 2 cm$^2$ and a time-averaged irradiance in a range of about 10 mW/cm$^2$ to about 10 W/cm$^2$ across the cross-sectional area, as described more fully above. The method 640 further comprises removing heat from the emission surface 22 at a rate in a range of about 0.1 Watt to about 5 Watts in an operational block 644. The method 640 further comprises impinging the irradiated surface with the light beam in an operational block 646.

The method 640 of certain embodiments further comprises placing the emission surface 22 in thermal communication with the irradiated surface (e.g., using the emission surface 22 to apply pressure to the irradiated surface by applying a force to the emission surface 22 in a direction generally towards the irradiated surface, the pressure greater than about 0.1 pound per square inch or about equal to 2 pounds per square inch).

In certain embodiments, impinging the irradiated surface with the light beam is performed for a time period of 10 seconds to two hours, for a time period of 60 seconds to 600 seconds, or for a time period of about 120 seconds. In certain embodiments, the steps of the operational blocks 642, 644, and 646 are performed concurrently. The method 640 of certain embodiments further comprises moving the emission surface 22 from a first position at which a first portion of the irradiated surface is impinged by the light beam to a second position, and repeating the steps of the operational blocks 642, 644, and 646 so as to impinge a second portion of the irradiated surface by light emitted from the emission surface 22. The first portion and the second portion do not overlap one another in certain embodiments. This method can be repeated so as to impinge twenty portions of the irradiated surface by light emitted from the emission surface 22. In certain such embodiments, the twenty portions of the irradiated surface do not overlap one another. However, the portions of the patient's brain irradiated by impinging these twenty portions of the patient's scalp do overlap one another in certain embodiments.

The irradiated surface of certain embodiments of the methods described above in reference to FIGS. 25-28 comprises a portion of the patient's scalp or skull. In certain other embodiments, the surface irradiated by the light comprises a portion of a light-detection system configured to measure one or more parameters of light irradiating the surface (e.g., irradiance, total power, beam size, beam profile, beam uniformity). In certain such embodiments, the method further comprises measuring the one or more parameters of the light from the apparatus 10 impinging the surface. For example, the light-detection system can comprise a portion of the apparatus 10 configured to test the light beam emitted from the emission surface 22 immediately prior to treatment of the patient. In this way, the light-detection system can be used to ensure that the light beam applied to the patient's scalp or skull has the desired treatment parameters.

In certain embodiments, a patient is treated by identifying a plurality of treatment sites (e.g., at least about 10) on the patient's scalp or skull, directing a light beam to each of the treatment sites, and irradiating each treatment site with the light beam. As described more fully below, in certain embodiments, the treatment sites are identified using an apparatus comprising a plurality of indicators, each of which corresponds to a treatment site location. In certain such embodiments, the treatment sites are sequentially irradiated by a light beam from the emission surface. In certain other embodiments, the treatment sites are instead identified by other indicia. For example, each of the treatment sites can be identified by markings made on the scalp, or by structures placed in proximity to the scalp or skull. Each of the treatment sites can then be irradiated. In certain embodiments, each of the treatment sites is irradiated by a light beam from the emission surface while the emission surface is in contact with the scalp or skull or in contact with an intervening optically transmissive element which contacts the scalp or skull. In certain other embodiments, the scalp or skull is not contacted by either the emission surface or an intervening element. In certain embodiments, each of the treatment sites is irradiated using a single beam delivery apparatus which is sequentially moved from one treatment site to another. In certain other embodiments, a plurality of beam delivery apparatuses are used to irradiate multiple treatment sites concurrently. In certain such embodiments, the number of beam delivery apparatuses is fewer than the number of treatments sites, and the plurality of beam delivery apparatuses are sequentially moved to sequentially irradiate the treatment sites.

Figure 29:
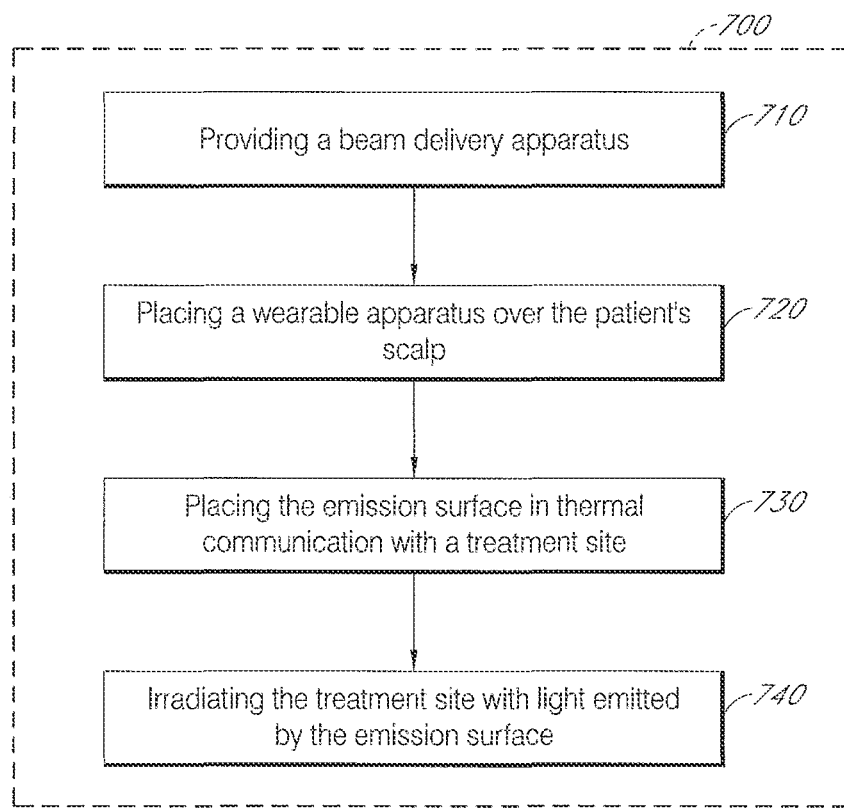
FIG. 29 is a flow diagram of an example method for controllably exposing at least one predetermined area of a patient's scalp to laser light to irradiate the patient's brain.

FIG. 29 is a flow diagram of an example method 700 for controllably exposing at least one predetermined area of a patient's scalp or skull to laser light to irradiate the patient's brain. As described more fully below, the method 700 is described by referring to the wearable apparatus 500 and the beam delivery apparatus 10 described herein. Other configurations of a wearable apparatus 500 and a beam delivery apparatus 10 are also compatible with the method 700 in accordance with embodiments described herein.

The method 700 comprises providing a beam delivery apparatus 10 in an operational block 710. In certain embodiments, the beam delivery apparatus 10 comprises an emission surface 22 configured to emit a light beam. Other configurations of the beam delivery apparatus 10 besides those described above are also compatible with certain embodiments described herein.

The method 700 further comprises placing a wearable apparatus 500 over the patient's scalp in an operational block 720. The apparatus 500 comprises a body 510 and a plurality of indicators 520. In certain embodiments, each indicator 520 is substantially transmissive to the light beam emitted from the emission surface 22. Other configurations of the wearable apparatus 500 besides those described above are also compatible with certain embodiments described herein.

The method 700 further comprising placing the emission surface 22 in thermal communication with a treatment site of the patient's scalp or skull to be irradiated in an operational block 730. The method 700 further comprises irradiating the treatment site with light emitted by the emission surface 22 in an operational block 740. In certain embodiments, the light beam is transmitted through the indicator 520.

In certain embodiments, providing the light emitting apparatus 600 in the operational block 710 comprises preparing the beam delivery apparatus 10 for use to treat the patient. In certain embodiments, preparing the beam delivery apparatus 10 comprises cleaning the portion of the beam delivery apparatus 10 through which laser light is outputted. In certain embodiments, preparing the beam delivery apparatus 10 comprises verifying a power calibration of laser light outputted from the beam delivery apparatus 10. Such verification can comprise measuring the light intensity output from the beam delivery apparatus 10 and comparing the measured intensity to an expected intensity level.

In certain embodiments, placing the wearable apparatus 500 over the patient's scalp in the operational block 720 comprises preparing the patient's scalp for treatment. For example, in certain embodiments, preparing the patient's scalp for treatment comprises removing hair from the predetermined areas of the patient's scalp to be irradiated. Removing the hair (e.g., by shaving) advantageously reduces heating of the patient's scalp by hair which absorbs laser light from the beam delivery apparatus 10. In certain embodiments, placing the wearable apparatus 500 over the patient's scalp in the operational block 720 comprises positioning the wearable apparatus 500 so that each indicator 520 is in position to indicate a corresponding portion of the patient's scalp or skull to be irradiated.

In certain embodiments, placing the emission surface 22 in thermal communication with the treatment site in the operational block 730 comprises pressing the emission surface 22 to the treatment site. In certain embodiments, by pressing the emission surface 22 against the treatment site in this way, pressure is applied to the portion of the patient's scalp of the treatment site so as to advantageously blanch the portion of the patient's scalp to be irradiated.

In certain embodiments, irradiating the treatment site of the patient's scalp or skull in the operational block 740 comprises triggering the emission of light from the emission surface 22 by pressing the emission surface 22 against the treatment site with a predetermined level of pressure. In certain embodiments, the emission of light from the emission surface 22 continues only if a predetermined level of pressure is maintained by pressing the emission surface 22 against the treatment site. In certain embodiments, light is emitted from the emission surface 22 to the treatment site for a predetermined period of time.

In certain embodiments, the method further comprises irradiating additional treatment sites of the patient's scalp or skull during a treatment process. For example, after irradiating a first treatment site corresponding to a first indicator, as described above, the emission surface 22 can be placed in contact with a second indicator corresponding to a second treatment site and irradiating the second treatment site with light emitted by the emission surface 22. The various treatment sites of the patient's scalp or skull can be irradiated sequentially to one another in a predetermined sequence. In certain embodiments, the predetermined sequence is represented by the indicators of the wearable apparatus 500. In certain such embodiments, the beam delivery apparatus 10 comprises an interlock system which interfaces with the indicators of the wearable apparatus 500 to prevent the various treatment sites from being irradiated out of the predetermined sequence.

Figure 30:
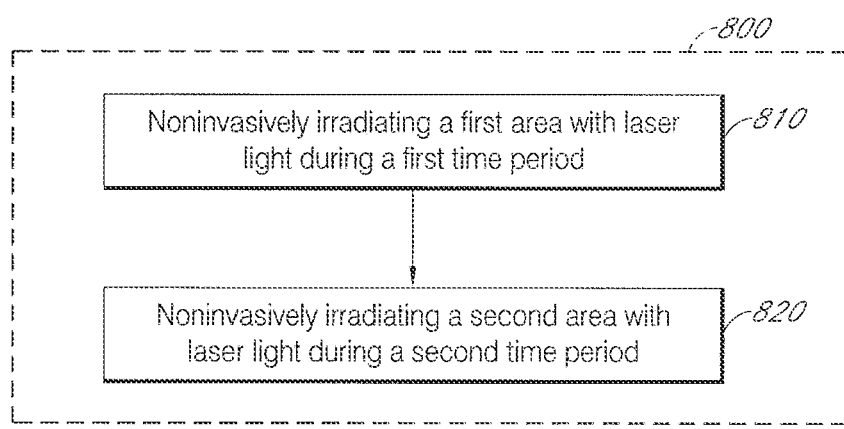
FIG. 30 is a flow diagram of another example method for treating a patient's brain.

FIG. 30 is a flow diagram of another example method 800 for treating a patient's brain. The method 800 is described below by referring to the wearable apparatus 500 and the beam delivery apparatus 10 described herein. Other configurations of a wearable apparatus 500 and a beam delivery apparatus 10 are also compatible with the method 700 in accordance with embodiments described herein.

The method 800 comprises noninvasively irradiating a first area of at least 1 cm$^2$ of the patient's scalp or skull with laser light during a first time period in an operational block 810. The method 800 further comprises noninvasively irradiating a second area of at least 1 cm$^2$ of the patient's scalp or skull with laser light during a second time period in an operational block 820. The first area and the second area do not overlap one another, and the first time period and the second time period do not overlap one another. In certain embodiments, the first area and the second area are spaced from one another by at least 10 millimeters. In certain embodiments, the first area is over a first hemisphere of the brain, and the second area is over a second hemisphere of the brain.

In certain embodiments, the method 800 further comprises identifying the first area and the second area by placing a template over the patient's scalp. The template comprises a first indicator of the first area and a second indicator of the second area. For example, the first indicator can comprise a first opening in the template and the second indicator can comprise a second opening in the template. In certain embodiments, the method 800 further comprises placing a laser light source at a first position to noninvasively irradiate the first area and moving the laser light source to a second position to noninvasively irradiate the second area.

In certain embodiments, the method 800 further comprises increasing the transmissivity of the first area to the laser light and increasing the transmissivity of the second area to the laser light. Increasing the transmissivity of the first area can comprise applying pressure to the first area to at least partially blanch the first area, removing hair from the first area prior to noninvasively irradiating the first area, applying an index-matching material to the first area, or a combination of two or more of these measures. Increasing the transmissivity of the second area can comprise applying pressure to the second area to at least partially blanch the second area, removing hair from the second area prior to noninvasively irradiating the second area, applying an index-matching material to the second area, or a combination of two or more of these measures.

Figure 38:
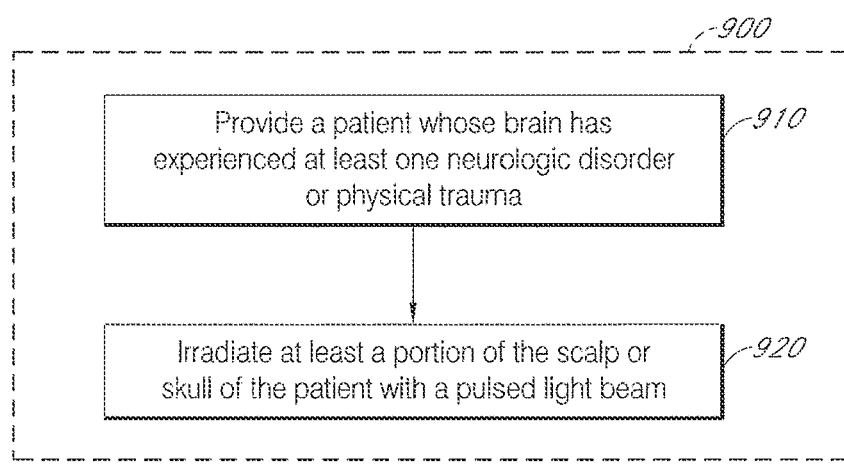
FIG. 38 is a flow diagram of an example method of treating brain tissue in accordance with certain embodiments described herein.

FIG. 38 is a flow diagram of an example method 900 for treating a patient's brain in accordance with certain embodiments described herein. The method 900 comprises providing a patient in an operational block 910 whose brain has experienced at least one neurologic disorder (e.g., Alzheimer's Disease, Parkinson's Disease, depression) or physical trauma (e.g., an ischemic stroke or a traumatic brain injury) resulting in a blood flow reduction to at least some brain cells of the patient. The method 900 further comprises irradiating at least a portion of the patient's scalp or skull with a pulsed light beam comprising a plurality of pulses transmitted through the patient's skull in an operational block 920. The pulsed light beam has a temporal profile which supports one or more intercellular or intracellular biological processes involved in the survival or regeneration of brain cells. For example, the pulsed light beam of certain embodiments comprises an average irradiance per pulse and a temporal profile comprising a temporal pulse width and a duty cycle sufficient to penetrate the skull to modulate membrane potentials, thereby enhancing cell survival (e.g., to cause increased neuron survival), cell function, or both of the irradiated brain cells.

In certain embodiments, providing the patient comprises identifying a patient whose brain has experienced at least one neurologic disorder or physical trauma. In certain such embodiments, identifying the patient comprises communicating with the patient, or with another person with knowledge regarding the patient's health or experiences, and determining whether the patient has experienced a neurologic disorder or a physical trauma to the brain. In certain other embodiments, identifying the patient comprises examining the patient's body (e.g., head or skull) for evidence of the patient having experienced a physical trauma to the brain. This examination in certain embodiments includes use of invasive or non-invasive medical devices, techniques, or probes (e.g., a magnetic resonance imaging device). In certain other embodiments, identifying the patient comprises administering a test of the patient's mental faculties (e.g., to determine the patient's abilities on a neurologic function scale) for evidence indicating that the patient has experienced a neurologic disorder or a physical trauma to the brain. Persons skilled in the art are able to identify the patient in accordance with various embodiments described herein. In certain embodiments, providing the patient comprises receiving information regarding the results of a previous identification (e.g., communication, examination, or test administration) of the patient as one who has experienced at least one neurologic disorder or physical trauma.

In certain embodiments, irradiating at least a portion of the patient's scalp or skull with a pulsed light beam comprises generating the pulsed light beam and directing the pulsed light beam to irradiate at least a portion of the patient's scalp or skull. The pulsed light beam of certain embodiments has a wavelength, time-averaged irradiance, beam size, beam profile, divergence, temporal pulse width, duty cycle, repetition rate, and peak irradiance per pulse, as described herein. Various light delivery apparatuses can be used to generate the pulsed light beam and to direct the pulsed light beam towards the patient's scalp or skull, including but not limited to, the apparatus disclosed herein or by U.S. Pat. Nos. 7,303,578, 6,214,035, 6,267,780, 6,273,905, and 6,290,714, and U.S. Patent Appl. Publ. Nos. 2007/0179570 A1, 2007/0179571 A1, and 2005/0107851 A1, each of which is incorporated in its entirety by reference herein.

In certain embodiments, irradiating at least a portion of the patient's scalp or skull comprises identifying one or more treatment sites (e.g., at least 10, between 2 and 100, or between 15 and 25) and sequentially irradiating the treatment sites with the pulsed light beam. In certain embodiments, the one or more treatment sites are identified as described herein (e.g., by an apparatus worn by the patient and comprising one or more apertures, by markings made on the scalp, or by structures placed in proximity to the scalp or skull). In certain embodiments, each treatment site is irradiated by an apparatus in contact with the scalp or skull or not in contact with the scalp or skull as described herein. In certain such embodiments, the irradiated portion of the scalp is blanched during the irradiation, is not blanched during the irradiation, is cooled during the irradiation, or is not cooled during the irradiation.

In certain embodiments, the patient's scalp is prepared for treatment prior to irradiation. For example, in certain embodiments, preparing the patient's scalp for treatment comprises removing at least a portion of the hair or substantially all the hair from the predetermined areas of the patient's scalp to be irradiated. Removing the hair (e.g., by shaving so that the irradiated portion of the scalp is substantially free of hair) advantageously reduces heating of the patient's scalp by hair which absorbs the light from the light emitting apparatus. In certain other embodiments, the hair is not shaved or otherwise removed prior to irradiation. For example, irradiating the patient's scalp can be performed using pulsed light with wavelengths, temporal pulse widths, and duty cycles which avoid adverse heating of the patient's scalp due to absorption of light by the hair.

In certain embodiments, the parameters of the pulsed light beam used to irradiate the patient's scalp or skull are selected to perform one or more of the following: (i) to cause increased neuron survival of the brain cells following at least one physical trauma, (ii) to support one or more intercellular or intracellular biological processes involved in the survival or regeneration of brain cells, or (iii) to modulate membrane potentials in order to enhance, restore, or promote cell survival, cell function, or both of the irradiated brain cells following a traumatic brain injury. In one example such embodiment, the pulsed light beam at the emission surface of the apparatus has a beam diameter in a range between 10 millimeters and 40 millimeters, an average irradiance per pulse in a range between 10 mW/cm$^2$ and 10 W/cm$^2$ one or more wavelengths in a range between 780 nanometers and 840 nanometers, and a temporal pulsewidth in a range between 0.1 millisecond and 150 seconds or between 0.1 millisecond and 300 milliseconds. The duty cycle of certain embodiments can be in a range between 10% and 30%. Other ranges of these parameters of the pulsed light beam can be selected in accordance with various other embodiments described herein.

Neurologic Function Scales

Neurologic function scales can be used to quantify or otherwise characterize the efficacy of various embodiments described herein. Neurologic function scales generally use a number of levels or points, each point corresponding to an aspect of the patient's condition. The number of points for a patient can be used to quantify the patient's condition, and improvements in the patient's condition can be expressed by changes of the number of points. One example neurologic function scale is the National Institute of Health Stroke Scale (NIHSS) which can be used for short-term measurements of efficacy (e.g., at 24 hours). The NIHSS is a comprehensive and objective scale which utilizes a seven-minute physical exam, a 13 item scale, and 42 points. Zero points corresponds to a normal exam, 42 points (the maximum) corresponds to basically comatose, and over 15-20 points indicates that the effects of the stroke are particularly severe. The NIHSS has previously been used for tPA trials in the treatment of ischemic stroke, with a 4-point change over 24 hours and an overall score of 0 or 1 at three months indicative of a favorable outcome. Other neurologic function scales include, but are not limited to, modified Rankin Scale (mRS), Barthel Index (BI), Glasgow Outcome, Glasgow Coma Scale, Canadian Neurologic Scale, and stroke impact scales such as SIS-3 and SIS-16. In some scales, an improvement in the patient's condition is indicated by a reduction in the number of points. For example, the mRS has six points total, with zero corresponding to normal functioning, and six corresponding to death. In other scales, an improvement in the patient's condition is indicated by an increase in the number of points. For example, in the Glasgow Outcome which has five points, zero corresponds to death and five corresponds to full recovery. In certain embodiments, two or more of the neurologic function scales can be used in combination with one another, and can provide longer-term measurements of efficacy (e.g., at three months).

For stroke, the U.S. Food and Drug Administration (FDA) and the neurologic community have expressed interest in clinical patient outcomes at 90 days post stroke. Two of the most common and accepted instruments for measuring efficacy are the NIHSS and mRS. The FDA is flexible in the way that neurologic function scales can be used. For example, it is acceptable to use the mRS (i) in dichotomized fashion with success at score of 0-1 or (ii) it can be analyzed looking at shifts in the scale showing improvement of patients along the five-point scale.

In certain embodiments described herein, a patient exhibiting symptoms of an ischemic stroke is treated by irradiating a plurality of treatment sites on the patient's scalp. The irradiation is performed utilizing irradiation parameters (e.g., wavelength, irradiance, time period of irradiation, etc.) which, when applied to members of a treated group of patients, produce at least a 2% average difference between the treated group and a placebo group on at least one neurologic function scale analyzed in dichotomized or any other fashion and selected from the group consisting of: NIHSS, mRS, BI, Glasgow Outcome, Glasgow Coma Scale, Canadian Neurologic Scale, SIS-3, and SIS-16. Certain other embodiments produce at least a 4% average difference, at least a 6% average difference, or at least a 10% average difference between treated and placebo groups on at least one of the neurologic function scales analyzed in dichotomized or any other fashion and selected from the group consisting of: NIHSS, mRS, BI, Glasgow Outcome, Glasgow Coma Scale, Canadian Neurologic Scale, SIS-3, and SIS-16. In certain embodiments, the irradiation of the patient's scalp produces a change in the patient's condition. In certain such embodiments, the change in the patient's condition corresponds to a change in the number of points indicative of the patient's condition. In certain such embodiments, the irradiation produces a change of one point, a change of two points, a change of three points, or a change of more than three points on a neurologic function scale.

Transmission in Human Brain

Power density (PD) measurements have been made to determine the transmission of laser light having a wavelength of approximately 808 nanometers through successive layers of human brain tissue. Laser light having a wavelength of (808±5) nanometers with a maximum output of approximately 35 Watts was applied to the surface of the cortex using a beam delivery system which approximated the beam profile after the laser light passes through the human skull. Peak power density measurements were taken through sections of human brain tissue using an Ocean Optics spectrophotometer Model USB 2000, Serial No. G1965 and beam diameter after scattering was approximated using a Sony Model DCR-IP220, Serial No. 132289.

A fresh human brain and spinal cord specimen (obtained within six hours after death) was collected and placed in physiologic Dakins solution. The pia layer, arachnoid layer, and vasculature were intact. The brain was sectioned in the midline sagittaly and the section was placed in a container and measurements taken at thicknesses of 4.0 centimeters (±0.5 centimeter), 2.5 centimeters (±0.3 centimeter), and 1.5 centimeters (±0.2 centimeter). The PD measurements are shown in Table 1:

TABLE 1

| Thickness | PD at Cortex | Average PD at thickness |
|---|---|---|
| 4.0 cm | 20 mW/cm$^2$ | 4.9 µW/cm$^2$ |
| 2.5 cm | 20 mW/cm$^2$ | 20 µW/cm$^2$ |
| 1.5 cm | 20 mW/cm$^2$ | 148 µW/cm$^2$ |

Figure 31:
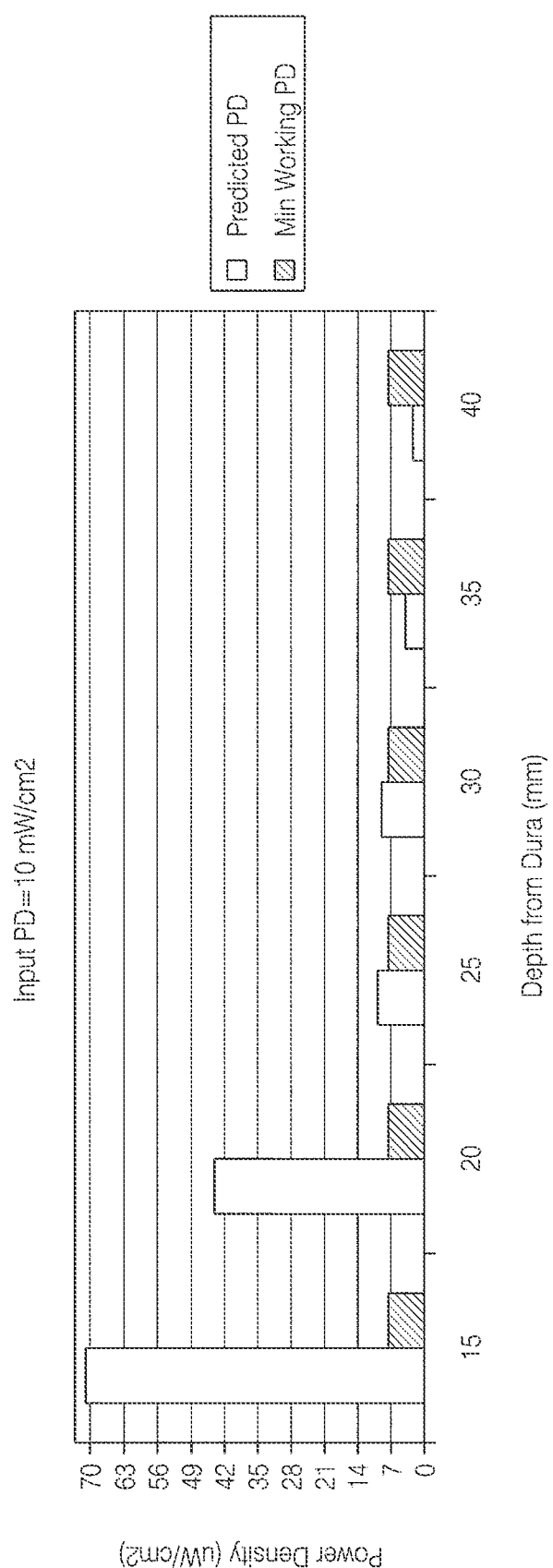
FIG. 31 is a graph of the power density versus the depth from the dura for an input power density of 10 mW/cm$^2$ with the light bars corresponding to predicted values of the power density and dark bars corresponding to an estimated minimum working PD of is 7.5 μW/cm² as described below.

FIG. 31 is a graph of the PD versus the depth from the dura for an input PD of 10 mW/cm$^2$ with the light bars corresponding to predicted values of the PD and dark bars corresponding to an estimated minimum working PD of is 7.5 µW/cm$^2$ as described below.

Based upon prior animal experimentation, a conservative estimation of the minimum known PD within the tissue of the brain which is able to show efficacy in stroke animal models is 7.5 µW/cm$^2$. This estimated minimum working PD is drawn from an experiment in which 10 mW was applied to the rat brain surface, and 7.5 µW/cm$^2$ PD was directly measured 1.8 centimeters from the surface. This stroke model consistently produced significant efficacy, including for strokes 1.8 centimeters from the laser probe. Note that this 7.5 µW/cm$^2$ is a conservative estimate; the same irradiance or power density at the brain surface also consistently produces significant efficacy in a 3-centimeter rabbit clot shower model. Note also that the power density measurements in the human brain experiment do not factor in the effect from the CNS-filled sulci, through which the laser energy should be readily transmitted. However, even conservatively assuming 7.5 µW/cm$^2$ as the minimum power density hurdle and ignoring expected transmission benefits from the sulci, the experiment described above confirms that approximately 10-15 mW/cm$^2$ transmitted upon the cortex (as per an example dosimetry in man) will be effective to at least 3.0 centimeters from the surface of the brain.

In Vivo Thermal Measurements

In vivo thermal measurements) were made to determine the heating effect in living tissue of laser light having a wavelength of approximately 808 nanometers. A GaAlAs laser source of 808-nanometer light was placed in direct contact with the skin of the heads of live rabbits and rats. The laser source had an approximately Gaussian beam profile with a beam diameter of 2.5-4.0 millimeters (1/e$^2$). Thermocouple probes (Model Bat-12 from Physitemp Instruments Inc. of Clifton, N.J.) were placed in the subcutaneous tissue and below the dura and measurements were recorded at various irradiances or power densities. The results of these measurements are shown in Table 2:

TABLE 2

| Animal | Probe location | Dose | Exposure time | Temperature increase |
|---|---|---|---|---|
| Rat | Subcutaneous | 15 mW/cm$^2$ | 4 minutes | approximately 3° C. |
| Rat | Subdural | 15 mW/cm$^2$ | 4 minutes | approximately 1° C. |
| Rat | Subcutaneous | 75 mW/cm$^2$ | 4 minutes | approximately 7° C. |
| Rat | Subdural | 75 mW/cm$^2$ | 4 minutes | approximately 7° C. |
| Rabbit | Subcutaneous | 7.5 mW/cm$^2$ | 5 minutes | less than 0.5° C. |
| Rabbit | Subdural | 7.5 mW/cm$^2$ | 5 minutes | less than 0.5° C. |
| Rabbit | Subcutaneous | 37.5 mW/cm$^2$ | 5 minutes | approximately 5.5° C. |
| Rabbit | Subdural | 37.5 mW/cm$^2$ | 5 minutes | less than 0.5° C. |

There is minimal heating (e.g., less than 0.5° C.) in the subdural region at four times the therapeutic energy density. The "heat sink" effect of living tissue that minimizes possible heating in the cortex is significantly larger in humans than in rats or rabbits, due to the larger heat sink and blood flow volume, which further limits the undesirable effects of heating in the region of stroke. Therefore, in certain embodiments described herein, a therapeutic dosage of energy is delivered to the area of a stroke without undesirable heating of the dura.

Phototherapy Example 1

One example of phototherapy (Lampl Y, Zivin J A, Fisher M, Lew R. Welin L, Dahlof B, Borenstein P, Andersson B, Perez 1, Caparo C, Ilic S, Oron U. Infrared laser therapy for ischemic stroke: a new treatment strategy: Results of the NeuroThera Effectiveness and Safety Trial-I (NEST-I). *Stroke.* 2007; 38:1843-1849, incorporated in its entirety by reference herein, suggested the safety and efficacy of transcranial light therapy (TLT) for treatment of humans 40 to 85 years of age with ischemic stroke within 24 hours of stroke onset in a small randomized, controlled trial. The NeuroThera Laser System therapeutic approach involves use of infrared laser technology and has shown significant and sustained beneficial effects in animal models of ischemic stroke.

The NeuroThera Laser System (NTS) used in this NEST-I study utilized an infrared laser technology that involves photobiostimulation. A large and growing body of scientific literature is available documenting the photobiostimulation effects of infrared laser therapy both in vitro and in vivo. The biological effects of infrared laser therapy are wavelength-specific and are not attributable to thermal effects. Energy in this region of the electromagnetic spectrum is nonionizing and, therefore, poses none of the hazards associated with UV light. It has been demonstrated that irradiation of specific infrared wavelengths is able to penetrate deeply into the brain. This form of therapy is distinguished from photodynamic therapy, which involves using light energy to penetrate the body and to activate a photosensitive drug.

Photobiostimulation involves increased adenosine triphosphate (ATP) formation after energy absorption inside mitochondria. A compound that absorbs energy in the spectral region of interest is known as a chromophore. There is evidence that suggests that a primary mitochondrial chromophore for photobiostimulation is cytochrome c oxidase. This enzyme complex contains 2 copper centers, CUA and CUB. The primary chromophore for the NTS wavelength is in the CUA center which has a broad absorption peak around 830 nm in its oxidized form. The NTS delivers energy at 808 nm, which is within this absorption peak, and is able to penetrate into the brain noninvasively. Cytochrome c oxidase is a terminal enzyme in the cellular respiratory chain and is located in the inner mitochondrial membrane. It plays a central role in the bioenergetics of eukaryotic cells by delivering protons across the inner membrane, and thereby driving the formation of ATP by oxidative phosphorylation. In addition to leading to increased ATP formation, photobiostimulation may also initiate secondary cell-signaling pathways. The overall result is improved energy metabolism, enhanced cell viability, and may also involve prevention of apoptosis in the ischemic penumbra and enhancement of neurorecovery mechanisms.

In vivo studies have suggested that infrared laser therapy could be beneficial for the treatment of acute myocardial infarction, acute ischemic stroke, injured peripheral nerves and spinal cord injury. Previous studies have shown in 2 different animal models a positive impact of infrared laser therapy on the experimental, ischemic stroke treatment outcomes in New Zealand rabbits (rabbit small clot embolic stroke model [RSCEM]) and Sprague-Dawley rats (permanent middle cerebral artery occlusion). Lapchak has shown that laser treatment at 6 hours poststroke onset in RSCEM improved behavioral performance and produced a durable effect that was measurable 21 days after embolization. De Taboada and Oron have also shown that laser treatment upto 24 hours poststroke onset in permanent middle cerebral artery occlusion showed significant improvement in neurological deficits which was evident at 14, 21 and 28 days poststroke when compared with the sham control group. Currently, the putative mechanism for infrared laser therapy in stroke involves the stimulation of mitochondria, which then leads to preservation of tissue in the ischemic penumbra and enhanced neurorecovery. The exact mechanistic pathways remain to be elucidated.

Study Design

NEST-1 was a prospective, multicenter, international, double-blind, randomized, sham (placebo) controlled trial conducted at 6 medical centers in 3 countries: Israel, Peru, and Sweden. The study examined initial safety and effectiveness of infrared wavelength laser therapy for treatment of patients within 24 hours of ischemic stroke onset.

This study was conducted in accordance with the FDA/ICH Good Clinical Practice guidelines and applicable local regulatory requirements. Investigators were required to ensure that this study was conducted in full conformity with the 1983 revision of the Declaration of Helsinki or with the laws and current regulations in biomedical research involving human patients of the country in which the study was conducted, whichever afforded greater protection to the patients. The protocol and information for patients and healthcare providers was approved by each center's ethics committee or Institutional Review Board. Country-specific independent data monitoring committees conducted safety reviews throughout the study.

Eligible patients were required to be between 40 to 85 years of age, have a clinical diagnosis (within 24 hours of stroke onset) of ischemic stroke causing a measurable neurological deficit (total NIHSS score ranging from 7 to 22 at admittance to the medical center), and to have NTS treatment initiated within 24 hours from stroke onset. The patient or parent legal representative gave written informed consent before enrollment into the study.

Ineligibility Criteria

Patients were excluded if: there was evidence on a CT scan of an intracranial, subdural or subarachnoid hemorrhage, or clinical presentation suggestive of subarachnoid hemorrhage, even if the initial CT scan was normal; the patient was a candidate for intravenous or intra-arterial administration of tissue-type plasminogen activator or other thrombolytic therapy for treatment of the acute ischemic stroke, and tissue plasminogen activator or other thrombolytic therapy was administered; the patient had a seizure at stroke onset; serum blood glucose was >400 mg/dL (22 mmol/L) or <40 mg/dL (2.2 mmol/L); the patient had sustained hypertension (defined during the baseline period by 2 readings occurring 30 minutes apart with systolic blood pressure >185 mmHg or diastolic blood pressure >110 mmHg) at time of treatment or need for aggressive treatment for blood pressure reduction; there was sustained hypotension (defined as systolic blood pressure <80 mmHg, or diastolic blood pressure <50 mmHg); there was presumed septic embolus; the patient had known hereditary or acquired hemorrhagic diathesis, e.g., activated partial thromboplastin time or prothrombin time greater than normal, unsupported coagulation factor deficiency, or oral anticoagulant therapy with the prothrombin time greater than normal; the patient had a skin condition (i.e., hemangioma, scleroderma, psoriasis, rash, or open wound) at the site chosen for infrared energy application; the patient was previously enrolled in or had participated in another investigational drug or device trial within the preceding 4 weeks; if a new medication was started within 14 days before the screening visit; the participant had severe mental deficit, severe neurological deficit or disorder (dementia, multi-infarct dementia, advanced multiple sclerosis) which would interfere with the assessment of the patient's ability for independent functioning; there was evidence of any disorder other than stroke that, in the opinion of the investigator, could be considered serious or life threatening such as active serious infections, pneumonia, pulmonary emboli, or gastrointestinal bleeding; the patient had unstable cardiac arrhythmias or other cardiac illness that, in the opinion of the investigator, was life threatening; the patient was of child bearing potential; the patient was comatose or moribund level of consciousness; or the patient was otherwise determined by the investigator to be medically unsuitable for participation in this study.

Study Groups, Evaluation Measures, and Baseline Factors

All patients received standard medical management therapy for acute ischemic stroke. In addition, they all underwent an identical NTS procedure. A randomization code that was preprogrammed within the NeuroThera Laser System determined whether the treatment was active or sham (placebo). Both patients and clinicians were blinded regarding treatment arm. The National Institutes of Health Stroke Scale (NIHSS) was assessed at the time of screening for entry into the study and again immediately before randomization to treatment group. Outcome measures (NIHSS, modified Rankin Scale [mRS], Barthel Index, and Glasgow Outcome Scale) were determined at 30, 60, and 90 days. Neurological scores and clinical data were collected on standard case report forms at each visit by trained investigators.

Baseline factors including patient demographics, time to treatment, medical history, vital signs, and routine laboratory values were collected. Factors also included age, sex, time from stroke onset to arrival at hospital, time from stroke onset to treatment, and a complete medical history.

After completion of the NTS procedure, patients entered the study follow-up phase until one of the following occurred: the patient decided to stop participation in the study; the sponsor or ethics committee/applicable regulatory body terminated the study; the investigator decided to discontinue the patient or site participation in the study; or the patient had participated in the study for 90±10 days.

The NTS Treatment Device

The NTS used in the NEST-I study was an investigational device intended to provide noninvasive, transcranial laser treatment to patients diagnosed with acute ischemic stroke. The laser wavelength of 808 nm is in the near-infrared portion of the electromagnetic spectrum, and is invisible to the naked eye. Energy in the near-infrared spectrum is nonionizing and is not associated with the risks of ionizing radiation. The NTS device used in the NEST-1 study included a class IV laser system and delivers energy via a fiber optic cable to a handheld probe that is placed on the shaved head of the patient by a trained operator. The device is portable and is similar in size to portable ultrasound equipment.

The NTS is manufactured by PhotoThera, Inc. A complete treatment regimen as defined for the NEST-1 study included removing hair from the patient's scalp, followed by NTS application (active treatment or sham/control treatment) on 20 predetermined locations on the scalp for 2 minutes at each site. The predetermined sites are identified by a cap which is placed on the patients head. The system is designed to deliver about 1 Joule/cm$^2$ of energy over the entire surface of the cortex regardless of stroke location. The sham procedure is identical to the active procedure with the exception that no laser energy is delivered to the patient from the device.

Based on current knowledge of the technology and risk assessment analysis, the most significant known hazard with NTS treatment ispotential retinal damage if the beam enters through the lens of the eye and onto the retina. Other potential hazards include skin burns and cuts to the scalp from shaving the head. Skin burns could occur if the device is not used as intended (eg, repeated treatments at the same location).

Statistical Methods

Effectiveness outcomes were reported on an intention-to-treat basis and include all 120 patients randomized to both arms. Safety outcomes were based on the same 120 patients, who also comprised all patients who received any treatment.

Patients were evaluated at baseline, 30, 60, and 90 days after baseline. Analysis focused largely on the 90-day evaluations. The NIHSS was the prospectively identified primary outcome, and the mRS, Glasgow Outcome Scale and Barthel Index scores were secondary outcomes.

Categories of baseline values of the NIHSS score and of time from stroke onset to treatment were entered into the analyses as strata or covariates. The three NIHSS strata were 7 to 10, 11 to 15, and 16 to 22. The categories for time from stroke onset to treatment were "less than 12 hours" and "12 to 24 hours." The NIHSS scale is not an interval scale. Therefore, categories of the NIHSS score were used to reduce potential heterogeneity.

NIHSS outcome was collapsed into a binary outcome, bNIH, where 'success' could occur in either of 2 ways: as a 90-day NIHSS score 0 to 1 or as a decrease in score (change) of 9 or more points from baseline to 90 days.

The mRS 90-day outcome took 2 forms. The 7-category ordinal variable form, analyzed across the whole distribution of scores on the 0 to 6 mRS scale (full mRS), and a binary mRS that makes scores of 0 to 2 as positive (success) and scores of 3 to 6 as negative (failure).

The full mRS ("shift in Rankin"), binary mRS and bNIH outcomes were tested using a stratified Cochran-Mantel-Haentzel (CMH) test: namely, the van Elteren test. The test uses the modified ridit score and thereby is a direct extension of the 2-sample Wilcoxon test. For the bNIH and the binary mRS outcomes, logistic regression analyses were used to explore the effects of covariates and the random effect of site: in particular, to assess how adding these factors altered the estimate of treatment effect.

The analyses were carried out in SAS version 9 using PROC FREQ to obtain the results for the van Elteren CMH test, and using PROC GENMOD and PROC LOGISIC to obtain results for logistic regression analyses with and without medical center as a random effect. Prevalence odds ratios were obtained from PROC GENMOD.

This study was an exploratory trial rather than a confirmatory trial, in the sense of FDA/ICH E8 Guidance on General Considerations for Clinical Trials and FDA/ICH E9 Guidance on Statistical Principles for Clinical Trials. Primary safety and effectiveness outcome measures and their analysis were identified prospectively. Multiple secondary and exploratory analyses were defined in the protocol or were designed and performed after study completion and unblinding. No corrections were made for multiple comparisons.

Figure 32:
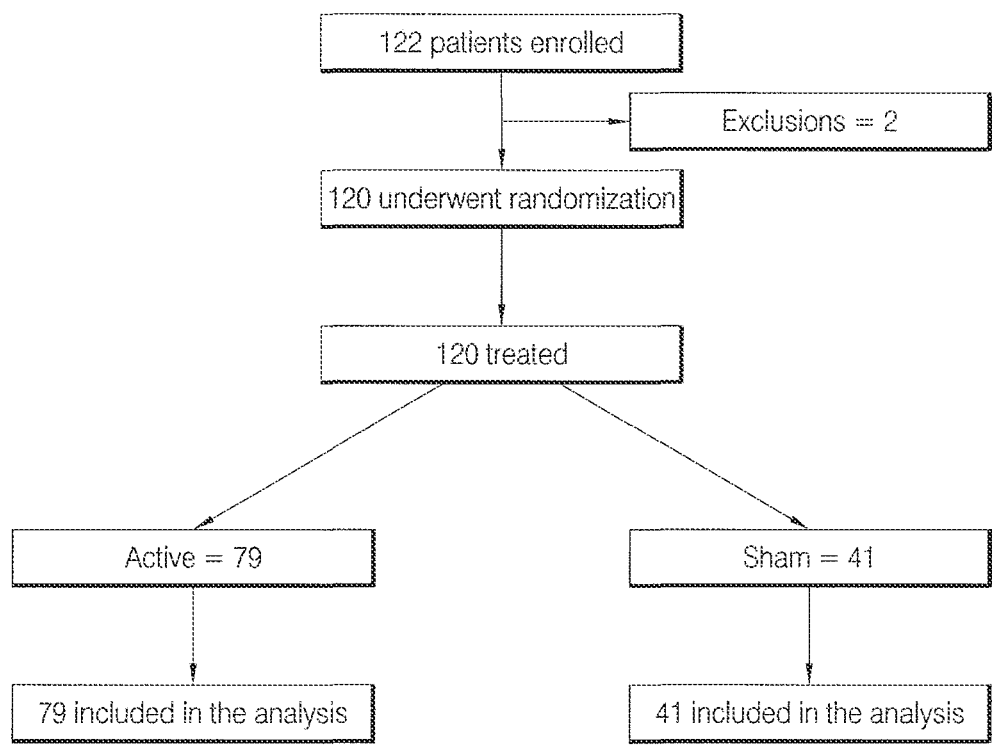
FIG. 32 shows the disposition of patients in the NEST-I study.

The study enrolled 122 eligible adult patients, between ages 40 and 85 of any ethnic background diagnosed with acute ischemic stroke within 24 hours of onset who provided their written informed consent. Two patients withdrew before randomization and are not included in any analyses, leaving 120 patients in the effectiveness analysis. Of the 120 patients, 79 were randomized to the active treatment group and 41 were randomized to the sham control group. FIG. 32 shows the disposition of patients in the study. There was only 1 patient lost to follow-up (0.8%). No significant differences in baseline characteristics were observed (see Table 3; baseline demographics and other baseline characteristics). Study data were reviewed by independent data monitoring committees in each country; there were no serious device-related adverse effects reported.

TABLE 3

| Characteristic | Active Treatment (NTS), n = 79 | Placebo (sham control), n = 41 |
|---|---|---|
| Mean age, y | 70.2 | 68.5 |
| Female, No. (%) | 36 (45.6%) | 15 (36.6%) |
| Ethnicity, No. (%) | | |
| White | 29 (36.7%) | 17 (41.5%) |
| Black | 2 (2.5%) | 0 (0.0%) |
| Hispanic | 4 (5.1%) | 2 (4.9%0 |
| Other (largely Mestizo and Native American Indians) | 44 (55.7%) | 22 (53.7%) |
| Median time to treatment, h | 18 | 17 |
| Mean time to treatment, hr:min | 16:56 | 16:20 |
| Mimimum, hr:min | 02:00 | 04:05 |
| Maximum, hr:min | 23:56 | 23:22 |
| Median NIHSS score at entry | 11 | 10 |
| First quartile | 9 | 9 |
| Third quartile | 15 | 14 |
| History, No. (%) | | |
| Hypertension | 44 (55.7%) | 20 (48.8%) |
| Previous stroke | 17 (21.5%) | 12 (29.3%) |
| Diabetes mellitus | 20 (25.3%) | 9 (22.0%) |

Effectiveness Analysis

The proportion of patients who received active treatment and had a positive bNIH outcome was 70%, which is greater than the proportion who received sham control treatment with a positive bNIH outcome (51%; CMH test P=0.035 stratified by severity and time from stroke onset to treatment; P=0.048 stratified only by severity). The treatment effect remained significant with other choices of strata for the CMH analysis. Logistic regression analyses confirmed that the results held controlling for both fixed covariates (eg, age, sex, time-to-treatment, baseline severity, previous stroke) and the random effects of medical site. Controlling only for baseline severity the logistic regression gave a prevalence odds ratio favoring treatment of 1.40 (95% CI, 1.01 to 1.93). Among the 79 treated patients, 38% achieved both a final NIHSS score of 0 to 1 and improved by ≥9 points, 20% had only a >9-point improvement, 11% obtained a final score of 0 to 1 without improving by >9, and 30% achieved neither end point. Among the 41 control patients the corresponding proportions were 29%, 7%, 15%, and 49%.

Figure 33:
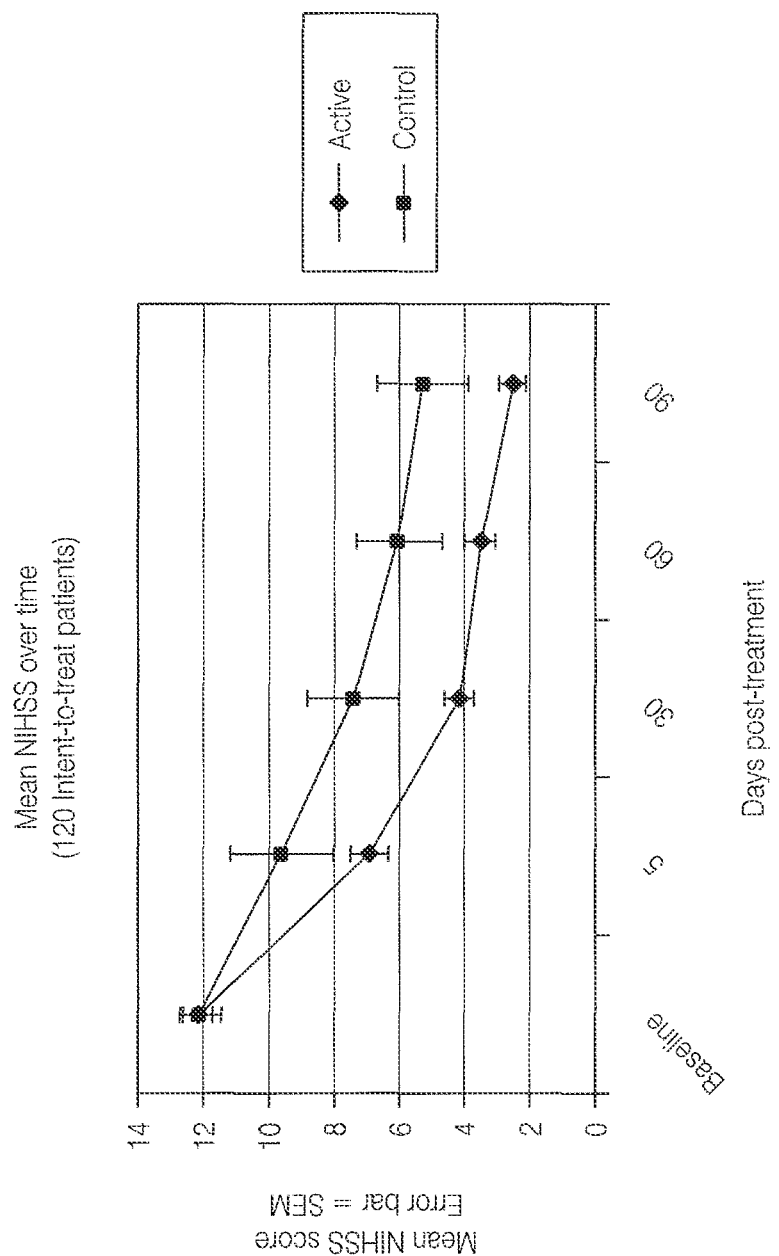
FIG. 33 shows the mean NIHSS over time for each treatment group of the NEST-I study.

Differences in mean NIHSS scores between the treatment groups appeared soon after treatment and were apparent throughout the 90-day study period. FIG. 33 shows the mean NIHSS over time for each treatment group. Patients in the active treatment group showed greater improvement in the change in NIHSS scores from baseline to day 90, as compared with the sham control group (P=0.021, CMH test stratified by time to treatment).

For the binary mRS outcome (0 to 2 versus 3 to 6), a similar pattern of significance held. The proportion of patients who received active treatment and had a positive binary mRS outcome was 60%, which is greater than the proportion who received sham control treatment with a positive binary mRS outcome (44%; CMH test P=0.034 stratified by severity and time to treatment; P=0.043 stratified only by severity). Only the CMH test without strata was not significant (P<0.11 $\chi^2$ test). The rate of positive results markedly varies across the baseline severity strata. Controlling only for baseline severity, logistic regression gave prevalence odds ratios favoring treatment of 1.38 (95% CI, 1.03 to 1.83) for the binary mRS outcome.

The effect of the NTS when compared with sham treatments with respect to the score on the full mRS at 90 days or the last rating, analyzed across the whole distribution of scores on the 0 to 6 mRS scale was significant, with the use of the Cochran-Mantel-Haentzel nonparametric rank test, stratified by categories of (1) baseline NIHSS score and time to treatment (P=0.020) and (2) baseline NIHSS score only (P=0.026; see Table 4).

TABLE 4

| | mRS | | | | | | | |
|---|---|---|---|---|---|---|---|---|
| | 0 | 1 | 2 | 3 | 4 | 5 | 6 | Total |
| Control | 5 | 10 | 3 | 8 | 6 | 5 | 4 | 41 |
| % | 12.20 | 24.39 | 7.32 | 19.51 | 14.63 | 12.20 | 9.75 | |
| Active | 12 | 25 | 10 | 11 | 12 | 2 | 7 | 79 |
| % | 15.19 | 31.65 | 12.66 | 13.92 | 15.19 | 2.53 | 8.86 | |
| Total | 17 | 35 | 13 | 19 | 18 | 7 | 11 | 120 |

Figure 34:
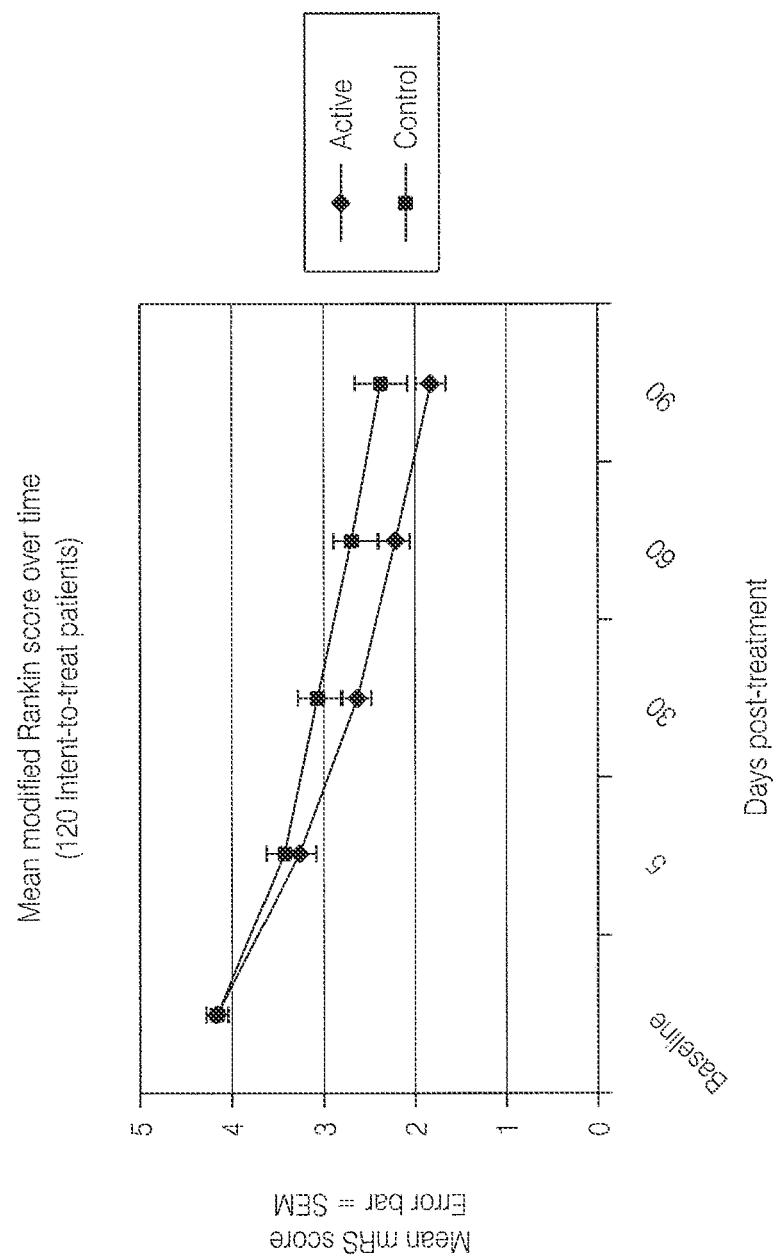
FIG. 34 shows the mean mRS over time for each treatment group of the NEST-I study.

FIG. 34 shows the mean nRS over time for each treatment group. Stratification by baseline severity gave similar results for the 3 outcomes (bNIH, binary mRS, and full mRS); all 3 outcomes had significance levels <0.05 (see Table 5; 2-sided significance levels for the van Elteren CMH test). When also controlled for time-to-treatment (0 to 12 hours versus 12 to 24 hours) little significance is gained. However, in a trial with a larger sample size, time-to-treatment would be expected to have a stronger association with outcome.

TABLE 5

| Outcome | Stratified by Severity Only | Stratified by Severity and Time-to-Treatment |
|---|---|---|
| Binary_NIH | 0.048 | 0.035 |
| Binary_mRS | 0.043 | 0.034 |
| Full mRS | 0.026 | 0.020 |

Results of analyses using the Glasgow Outcome Scale and Barthel Index are similar to those for the NIHSS and the mRS. Patients who received active treatment had better outcomes than patients who received sham control treatment as measured on the Glasgow Outcome Scale (CMH test P=0.056), and the Barthel Index scale (CMH test P=0.035), stratified by baseline NIHSS score and time to treatment.

The logistic regression analyses indicated the negligible effects of covariate adjustment on the logistic regression coefficient for treatment. The results in Table 6 indicate that treatment effect is stable across 2 binary outcomes and across 3 different nested sets of covariates. In fact, the treatment effect tends to increase as covariates are added. Furthermore, treating hospital site as a repeated measures effect virtually does not alter the logistic regression coefficient for treatment. The 95% Cis are not shown to focus on the consistency of the regression coefficients. In all but one model the probability value for treatment is <5%. In the models with the bNIH outcome, the covariate 'severity' is not significant and time-to-treatment is significant only once with P=0.0496. However with the binary mRS outcome, the covariate 'severity' is significant with P<0.001 in all 3 models. This indicates that the 9-point decrease in the NIHSS score captures the variation of treatment effect across the baseline severity categories. We explored many sets of additional covariates and found that after including the covariates 'gender', 'age', and 'prior stroke' all other covariates had negligible predictive value. Gender was significant in the binary mRS model with P<0.01. Otherwise, these factors did not achieve statistical significance. See Table 6 which shows the results for two sets of nested multivariate models, I set of models with outcome bNIH and 1 set of models with outcome binary mRS (time-to-tx indicates time from onset to treatment). The first P value is for simple logistic regression and the second P value is for logistic regression with the factor 'site' included as a repeated measures effect.

TABLE 6

| Covariates in Model | Outcome bNIH TX Coefficient and (P values)* | Outcome Binary mRS TX Coefficient and (P values)* |
|---|---|---|
| Severity | 0.82 (0.046) | 0.92 (0.044) |
|  | 0.82 (0.007) | 0.92 (0.095) |
| Severity and time-to-tx | 0.89 (0.034) | 1.03 (0.027) |
|  | 0.89 (0.009) | 1.03 (0.032) |
| Severity, time-to-tx, gender, age, prior stroke | 0.99 (0.027) | 1.43 (0.009) |
|  | 0.99 (0.010) | 1.44 (0.020) |

Safety Analysis

Table 7 (mortality rates and SAEs) shows the mortality rates and SAEs by treatment group and totals. No significant difference in mortality between the active treatment group and the sham control group is evident. Table_7 shows the number of patients with serious adverse events, worsening of underlying disease, cardiovascular SAEs, infection, or central nervous system SAEs, in total and by treatment group. These data indicate that there were no significant differences between the treatment groups with respect to these measures. Where there was a trend toward differences between the treatment groups, such as in rates of infection or rates of central nervous system SAEs, the patients receiving active treatment appear to have had better outcomes than patients receiving sham control treatment.

TABLE 7

| No. of Patients with: | Total n = 120 | Percent | Active, n = 79 | Percent | Sham, n = 41 | Percent | Fisher Exact, p Value |
|---|---|---|---|---|---|---|---|
| Mortality (all sites) | 11 | 9.2% | 7 | 8.9% | 4 | 9.8 | 0.87 |
| SAEs | 35 | 29.2% | 20 | 25.3% | 15 | 36.6 | 0.211 |
| Worsening of underlying disease | 8 | 6.7% | 3 | 3.8% | 5 | 12.2 | 0.120 |
| CVS | 8 | 6.7% | 5 | 6.3% | 3 | 7.3 | 1.000 |
| Infection | 13 | 10.8% | 5 | 6.3% | 8 | 19.5 | 0.059 |
| CNS | 14 | 11.7% | 6 | 7.6% | 8 | 19.5 | 0.072 |

Discussion

The NEST-1 trial provides initial evidence on the safety and effectiveness of infrared laser therapy for the treatment of ischemic stroke in humans within 24 hours of stroke onset. The outcome variable scales used in the NEST-1 study had excellent correlation: R=0.79 to 0.92. The correlation coefficients for the NEST-I trial are essentially the same as those reported in the article by Lyden and colleagues reviewing tissue plasminogen activator data. That is, the outcome variables have correlation coefficients with each other of about 0.8 (absolute value) or higher. This concordance with prior studies is evidence that the outcomes are being measured appropriately and consistently.

The results suggest that infrared laser therapy may benefit a broad spectrum of stroke patients without increasing the rate of adverse events. Furthermore, the relatively large magnitude of the effect implies that a phase III trial should not require a substantial number of subjects.

Patients receiving active treatment had a higher proportion of positive NIHSS outcomes than did patients receiving sham control treatment. Results were similar using the other neurological outcome scales. No significant differences between the treatment groups were observed in rates of mortality or SAEs, but the sample size (n=120) gives low power to detect small differences. Where there is a trend toward differences between the treatment groups, patients receiving active treatment appeared to have had fewer SAEs than did patients receiving sham control treatment. The safety profile of the NTS treatment as demonstrated in this study was clear. There were no adverse outcomes that can be attributed to the laser therapeutic procedure.

The bNIH outcome with the 9-point change incorporates variation in baseline severity (from NIHSS score 7 to 22) and suggests a global potential benefit. In contrast, the binary mRS outcome does not account for change from baseline. Thus, once the analysis controlled for baseline severity, the results based on the 2 binary outcomes closely agreed. Controlling for baseline severity, the analyses by the CMH test and by logistic regression gave prevalence odds ratios favoring treatment exceeding I 0.40 for the bNIH outcome and exceeding 1.38 for the binary mRS outcome.

This global potential benefit is also demonstrated through the full mRS, analyzed across the entire distribution of Rankin scores, from 0 to 6. The mRS is a simple and reliable outcome measure when consistently implemented by trained clinicians. The full mRS analysis takes into consideration the entire spectrum of the patient outcomes. As a result, the full mRS is increasingly considered as a primary outcome measure for ischemic stroke trials involving neuroprotective technologies.

This exploratory study had a prespecified analytic plan with a primary outcome of bNIH, the binary form of NIHSS that regards a final score of 0 to 1 or a 9-point decrease as a success. But our presentation of several analytic approaches raises the concern of type 1 error. We described several approaches to the same hypothesis: some having an mRS outcome, some having an NIHSS outcome, and some using logistic regression to confirm the nonparametric results. These results showed the substantial concordance among these outcomes and methods. Also, they showed that after control for NIHSS baseline severity, other factors had little or no effect on the magnitude of the treatment effect. Hence, we did not present a multiple comparisons correction such as the Bonferroni correction because, in particular, the Bonferroni correction assumes that the hypotheses are independent of one another. Another reason for the various analyses was to associate an effect size with the results of the primary analysis by the nonparametric CMH test. Simple estimates of effect size were obtained from the other tests and both the simple proportions of success for the binary outcomes and prevalence odds ratios obtained from logistic regression were reported.

An extended treatment window of up to 24 hours after stroke onset will have a number of implications. Thrombolytics have a proven treatment window of 3 hours, although it may be that effectiveness for this form of therapy extends out somewhat further. The first neuroprotective trial to show efficacy was the study of NXY-059. That study had a 6-hour treatment window, but a majority of patients were treated within 4 hours. It is a reasonable contention that the reason the NXY-059 study was successful, whereas all the previous neuroprotective therapies were not, was that the average time to treatment was kept so low. NEST-I had a 24-hour treatment window and a much longer time to treatment (median 18 hours) than nearly all other clinical trials to date for the treatment of acute ischemic stroke. A major problem for treatment of strokes has been that large numbers of patients present after 6 hours. Therefore, an expanded treatment window of 24 hours would make it possible to treat many more ischemic stroke victims.

Although the mechanism of action of infrared laser therapy for stroke is not completely understood, a number of effects of this type of irradiation have been documented. Infrared laser therapy is a physical process that can produce biochemical changes at the tissue level. The putative mechanism for NTS treatment involves stimulation of ATP formation by mitochondria and may also involve prevention of apoptosis in the ischemic penumbra and enhancement of neurorecovery mechanisms. An example of another physical process that reduces neurological damage is hypothermia. In animal model studies, there are few, if any therapies that have been shown as consistently to reduce stroke-related damage as hypothermia. What is clear is that infrared irradiation is probably delivering its effect independent of restoration of blood flow and the mechanism is probably related to an improved energy metabolism and enhanced cell viability.

Other advantages of this form of therapy are that treatment can be started rapidly, without any need for preliminary laboratory testing, invasive procedures, or extensive training of the clinicians who administer the treatment. Furthermore, it is not necessary to know the location of the vascular occlusion to administer the NTS treatment. Thus, this form of therapy is likely to require much less infrastructure than virtually all other types of devices and medical therapies available to date for acute stroke treatment or clot removal.

Although the NEST-I study results are encouraging, and may indicate that infrared laser therapy has potential to become a treatment of ischemic stroke in humans when initiated within 24 hours of stroke onset, a larger confirmatory trial to demonstrate safety and effectiveness is warranted.

Phototherapy Example 2

Another example of phototherapy (NeuroThera Effectiveness and Safety Trial-2 (NEST-2) was nearly identical to the trial study discussed above, but was larger and included patients 40 to 90 years of age. NEST-2 was a double blind, placebo (sham) controlled trial in which 660 patients were enrolled at 57 centers in 4 countries. Patients were eligible for inclusion in the study if they were 40 to 90 years of age, had a baseline NIHSS score between 7 to 22, had a clinical diagnosis of ischemic stroke, no evidence of hemorrhagic infarct by CT scan or Mill, and had not received tPA Initiation of treatment had to occur within 24 hours after stroke onset. The inclusion and exclusion criteria are summarized in Table 8.

TABLE 8

Major Inclusion and Exclusion Criteria

Inclusion 40-90 years of age
Diagnosis of acute ischemic stroke within 24 hours of onset
NIHSS ≥ 7-≤ 22
Informed consent
Exclusion Evidence of intracranial, subdural, or subarachnoid hemorrhage
Prestroke ≥3 mRS
Clinical diagnosis of a brain stem or cerebellar stroke
Seizure at onset
Blood glucose >400 or <60
Sustained systolic BP >220 mmHg, <80 mmHg or diastolic >140 mmHg, <50 mmHg
Suspected septic embolus
CNS tumor (except asymptomatic meningioma)
Dermatologic conditions (eg., psoriasis) of the scalp
Thrombolytic stroke therapy
Head implant (eg, clipped aneurysm, Hakim valve)
Photodynamic therapy within 14 days (eg, Visudyne)
Pregnancy
Sever comorbidities
CNS indicates central nervous system.

Randomization and Treatment

Patients were randomly assigned in a 1:1 ratio to receive either TLT or sham. All patients underwent the identical TLT procedure that involves removal of the patient's scalp hair followed by application of a laser probe to the patient's head. The total procedure time was approximately 2 hours. After consent, an interactive voice randomization system was used, with dynamic randomization at centers to ensure balanced distribution of treatment assignments. All patients received standard of care medical management throughout the course of trial.

Study Management

This study was conducted in accordance with the FDA/ICH Good Clinical Practice (GCP) guidelines and applicable local regulatory requirements. The trial was also conducted in full conformity with the 1983 revision of the Declaration of Helsinki or with the laws and current regulations in biomedical research involving human patients of the country in which the study was conducted, whichever afforded greater protection to the patients. The study was designed and overseen by the steering committee. Each center's ethics committee or Institutional Review Board and an independent data monitoring committee (DMC) conducted safety reviews. The DMC periodically reviewed serious adverse event data between the groups. The patient or legal representative gave written informed consent before enrollment into the study. Data management and statistical analysis was conducted by an independent contract research organization (Parexel, Waltham, Mass.), as well as by the study sponsor (PhotoThera, Carlsbad, Calif.). After database lock and independent review by the DMC, the steering committee had complete access to the trial data and assumed responsibility for the analysis and interpretation of the results.

Treatment

The NeuroThera Laser System (NTS) included an apparatus with a hand-held housing to apply the light to selected portions of the patient's scalp. The NTS uses energy at a wavelength of 808 nm which is near-infrared, nonionizing, and is invisible to the naked eye. Experiments using cadavers indicated that optimal amounts of laser energy are able to penetrate the brain to a depth of approximately 2 cm. The dosimetry of wavelength and irradiance levels was based on transmission experiments with fresh human cadavers without fixation. Monte Carlo simulations, in vitro experiments, review of the literature using infrared therapy for other indications and the results of preclinical studies in validated stroke animal models. A complete treatment regimen as defined for the NEST-2 study included applying the handheld probe on 20 predetermined locations on the shaved scalp for 2 minutes at each site. The predetermined sites, which are irrespective of stroke location, are identified by a cap which is placed on the patient's head. The sham procedure is identical to the TLT procedure with the exception that no laser energy is delivered to the patient from the device.

Based on current knowledge of the technology and risk assessment analysis, the most significant known hazard with TLT is potential retinal damage if the beam enters the eye and is focused onto the retina which could result in permanent eye injury. Because of this potential ocular hazard, the procedure must be conducted in a laser safe environment by a trained user.

Clinical Assessments

Patients were assessed by examiners who were unaware of the treatment group. All examiners were trained on the NIHSS and certified on the mRS. The NIHSS is a neurological function scale that ranges from 0 to 42: scores between 7 and 22 are considered to represent moderate to severe neurological impairment. The mRS is a disability index ranging from 0 (no symptoms) to 6 (death). Outcome measures (mRS and NIHSS) were assessed, in addition to baseline, at 5, 30, 60, and 90 days. Baseline data were collected including age, sex, patient demographics, time from stroke onset to arrival at hospital, time to treatment, prestrike mRS, vital signs, and a complete medical history.

Safety Assessments

Vital signs, neurological scores, concomitant medications, adverse events, and serious adverse events were recorded from study entry to day 90. Unresolved serious adverse events were followed for an additional 30 days.

The Data Monitoring Committee examined rates of death, adverse events, and serious adverse events, as well as anticipated and unanticipated device effects during the study. After evaluating the safety data for the first 100 and 400 patients, they did not stop further recruitment into the trial. Because of rapid enrollment, there was no efficacy interim analysis. Neuroimaging assessments were completed at baseline and at 5-day follow-up ±2 days.

Statistical Analysis

All analyses are intention-to-treat. Outcomes were obtained from two 90-day scores, the mRS and the NIHSS score. Patients without a day-90 visit had their last observation carried forward. The mRS outcomes were: (1) the entire ordinal scale 0 to 6; and (2) a dichotomous outcome with a favorable outcome (success) defined as a 0 to 2 score and an unfavorable outcome (failure) defined as a 3 to 6 score. The NIHSS outcomes were: (1) the change in score from baseline to 90 days using the entire ordinal scale 0 to 42 (with death scored as 42); and (2) a dichotomous outcome for which success could be achieved in 2 ways, either as a 90-day score of 0 to 1 or as a beneficial change from baseline to 90 days of 9 or more points.

The primary efficacy outcome measure was the dichotomous mRS 90-day end point with success (mRS 0 to 2) and failure (mRS 3 to 6). The null hypothesis that the proportion of successes did not differ by treatment, was tested using multiple logistic regression with 2 prespecified covariates: (1) stroke severity at baseline; and (2) time from stroke onset to time of randomization (TFSO). Baseline stroke severity had 3 levels: NIHSS score 7 to 10 (moderate), 11 to 15 (moderately severe), and 16 to 22 (severe). TFSO had 2 levels: 0 to 12 hours and 12 to 24 hours. The randomization procedure was balanced on (but not stratified by) these factors.

Secondary analyses determined the sensitivity of results to the choice of covariates, of test procedure, and of analytic outcome. The logistic model was run on the primary outcome measure with additional covariates: age, sex, history of CAD, history of diabetes, and history of stroke. To vary the test procedure of logistic regression with a dichotomous outcome, we used the nonparametric 'shift' test with the same dichotomous outcome. Explicitly, the shift test is the Cochran-Mantel-Haenszel (CMH) test with ridit scores to rank outcomes (the van Elteren test, Stokes M E, Davis C S, Koch G C. *Categorical Data Analysis Using the SAS System II* Cary, N.C.: SAS Institute, Inc; 2000). In the stroke literature, the shift test has often only been applied to the full range of the mRS scale, but we applied it to all dichotomous and ordinal outcomes. Logistic regression as run using only dichotomous outcomes. All tests were adjusted for baseline severity and TFSO. Odds ratios were calculated only for tests with dichotomous outcomes.

The safety end points included mortality and all adverse events including procedure and device related adverse events. Safety end points were summarized with descriptive statistics and tables. The analyses were carried out in SAS version 9.1.

Results

Baseline Characteristics

Figure 35:
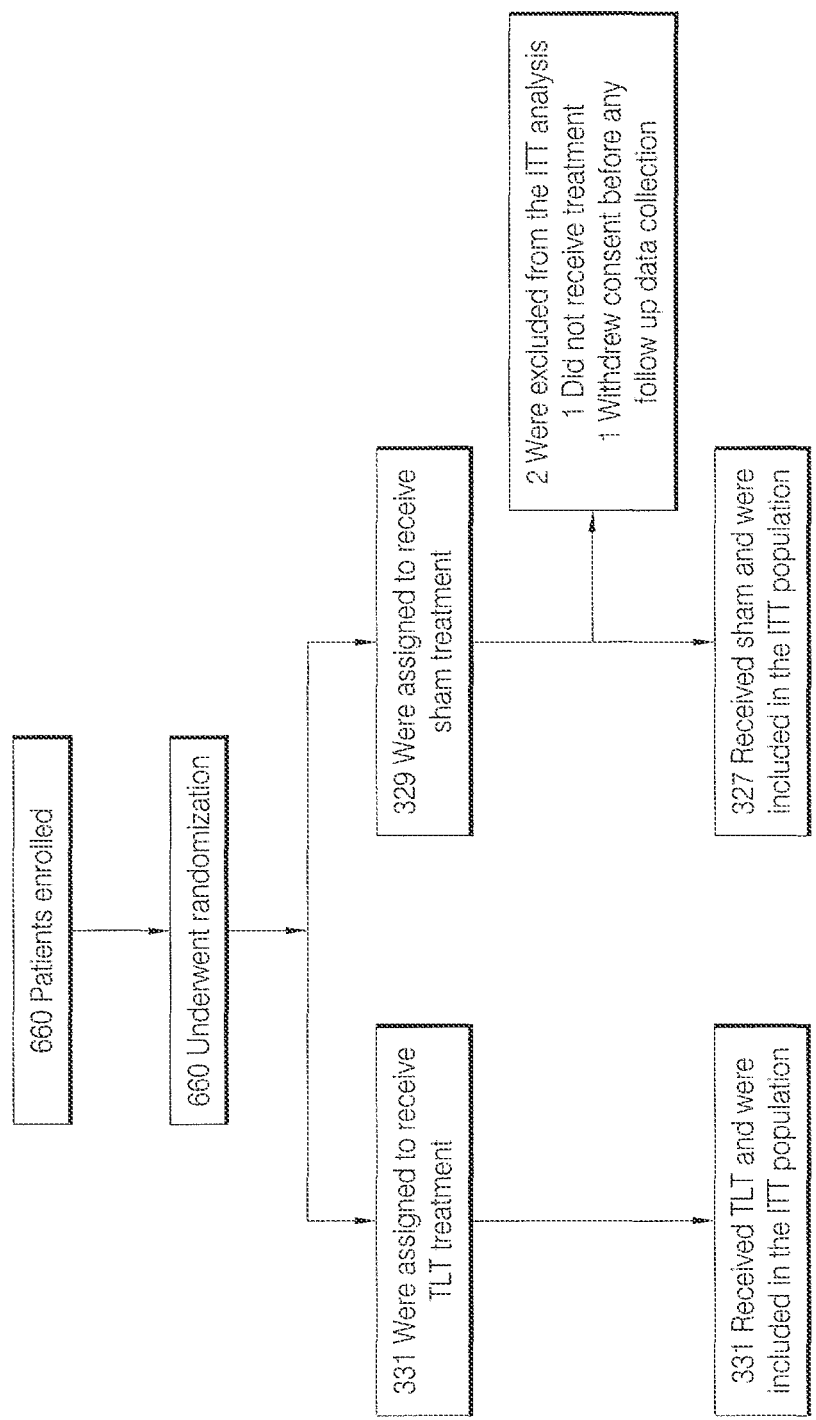
FIG. 35 shows the disposition of patients for the NEST-2 study.

The patients were enrolled between January 2007 and April 2008. A total 660 patients were randomized (331 TLT and 327 sham), as shown in FIG. 35. There were 7 (1.1%) patients lost to follow-up. The groups were balanced with respect to baseline characteristics (see Table 9). Mean time from stroke onset was 14.6±5.9 hours (range 2.7 to 23.9) for the TLT group and 14.7±6.1 hours (range 2.5 to 23.9) for the shame group; median times were 15 hours and 16 hours for the TLT group and sham group, respectively. Baseline NIHSS means scores were 13.1 (range 7 to 22) for TLT and 13.2 (range 7 to 23) for shame. Median NIHSS scores were 12 for TLT and 13 for sham.

TABLE 9

Demographic and Baseline Characteristics

| | TLT (n = 331) | Sham (n = 327) |
|---|---|---|
| Age (v) | 70.4 ± 12.6 | 70.0 ± 11.9 |
| Male (%) | 55.3 | 57.8 |
| Ethnicity (No., %) | | |
| White | 256 (77%) | 254 (77%) |
| Black | 37 (11%) | 38 (12%) |
| Hispanic | 7 (2%) | 8 (2%) |
| Other (Largely Mestizo and Native American Indians) | 31 (10%) | 29 (9%) |
| Time | | |
| Median time to treatment (h) | 15 | 16 |
| Mean time to treatment (h:min) | 14.38 ± 5:55 | 14:43 ± 6:12 |
| Min (h:min) | 2:42 | 2:30 |
| Max (h:min) | 23:54 | 23:54 |
| Range (h) | 3-24 | 3-24 |

TABLE 9-continued

Demographic and Baseline Characteristics

| | TLT (n = 331) | Sham (n = 327) |
|---|---|---|
| Time to treatment strata (%) | | |
| <12 h | 35.6 | 35.6 |
| 12-24 h | 64.4 | 64.4 |
| NIHSS score | | |
| Mean | 13.1 ± 4.7 | 13.2 ± 4.6 |
| NIHSS score strata (%) | | |
| Median | 12 | 13 |
| Mean 7-10 | 39.0 | 38.9 |
| 11-15 | 26.6 | 27.1 |
| 16-22 | 34.4 | 34 |
| History (%) | | |
| Diabetes | 31.4 | 33.4 |
| Hypertension | 82.2 | 83.9 |
| Atrial fibrillation | 38.7 | 35.6 |
| Current smoker | 20.2 | 19.1 |

Clinical Outcomes

Figure 36:
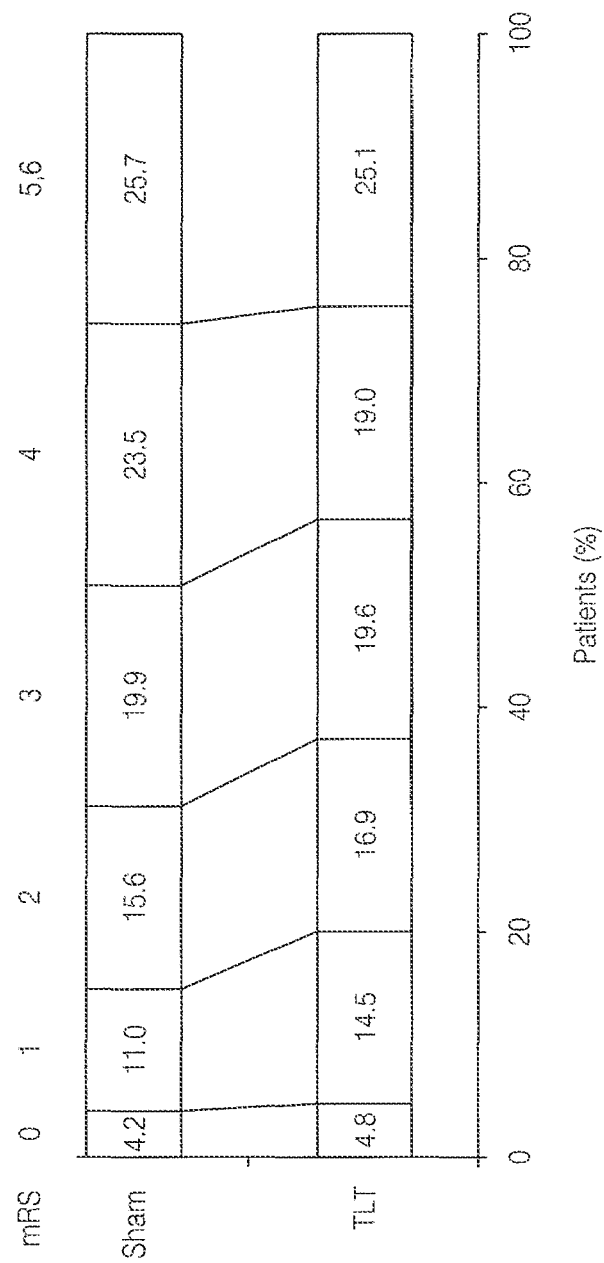
FIG. 36 shows the distribution of scores on the mRS for the NEST-2 study.

Of the 660 patients: 331 received TLT and 327 received sham; 120 (36.3%) in the TLT group achieved successful outcome versus 101 (30.9%), in the sham group (P=0.094). OR 1.38 (95% CI, 0.95 to 2.00) as shown in FIG. 36, which shows the distribution of scores on the mRS. The scores on the mRS indicate the following: 0, no symptoms at all; 1, no significant disability despite symptoms; 2, slight; 3, moderate; 4, moderately severe; 5, severe disability; 6, death.

Figure 37:
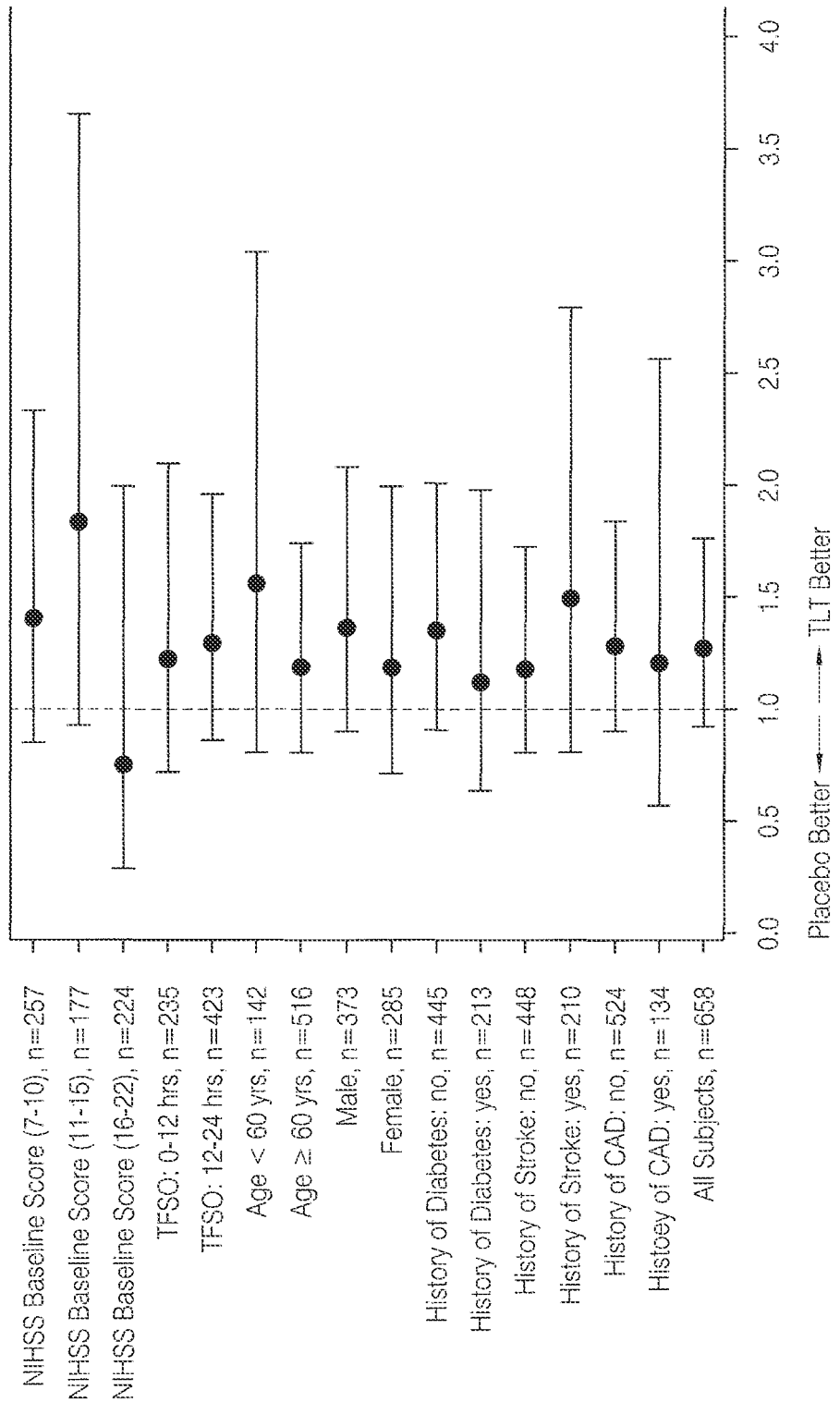
FIG. 37 shows the effects of TLT on the primary end point, on subsets of the data defined by categories of selected baseline characteristics for the NEST-2 study.

The results of secondary analyses on the prespecified outcomes were consistent with those of the primary analysis. The logistic regression analysis of the primary outcome measure with additional covariates yielded a treatment OR-1.34 (95% CI, 0.94 to 2.03). All covariates except sex and history of stroke were significant. With success defined as a mRS score of 0 to 2, the shift test, stratified for the baseline severity and TFSO, showed a nonsignficiant trend toward better outcomes with TLT having a probability value of 0.091 and had an OR 1.38 (95% CI, 0.95 to 2.01). For the ordinal mRS, scores 0 to 6, the shift test trended in favor of TLT with a probability value of 0.113. The odds ratios for all subsets on the primary outcome measure showed a nonsignificant trend favoring TLT treatment except for those patients with severe strokes at baseline. FIG. 37 shows the effects of TLT on the primary end point, on subsets of the data defined by categories of selected baseline characteristics. The simple unadjusted odds ratios for TLT as compared to sham for the 90-day outcome of success defined as mRS score 0 to 2. The horizontal lines indicate 95% CIs. Also shown are the probability values for the test of an interaction between the primary end point and the categories within each subgroup. CAD indicates coronary artery disease; TFSO, time from stroke onset to randomization.

For the dichotomous NIHSS score outcome for which success had 2 components, the shift test trended in favor of TLT with an OR of 1.23 (95% CI, 0.88 to 1.73) and a probability value of 0.23. Logistic regression analysis results for the dichotomous NIHSS outcome were very similar. An extension of the logistic regression analysis separated the 2 components of success, a 90-day NIHSS score of 0 to 1 and change from baseline >9 points, and treated them as correlated outcomes: the OR was 1.30 (95% CI, 0.96 to 1.75) in favor of TLT with a probability value of 0.086. For the ordinal outcome of change in NIHSS score from baseline to 90 days, controlling for baseline severity and TFSO, the shift test indicated the TLT group and had a probability value of 0.65. In patients with deep infarcts, there was no difference in response between the active and sham groups.

Safety Analysis

Mortality rates, serious adverse event (SAE) rates, and adverse event (AE) rates were virtually the same. The TLT and sham groups, respectively, had 58 (17.5%) and 57 (17.4%) deaths, 125 (37.8%) and 137 (41.8%) SAEs; and 92.7% and 93.6% of subjects, respectively, had at least 1 adverse event. No SAEs were directly attributable to TLT. The proportion of patients in the TLT group showing hemorrhagic transformation at day 5 was 49 (14.8%) in the TLT group and 56 (17.1%) in the sham group. There was no difference in the safety outcomes between the 2 groups.

Discussion

The NEST-2 trial results presented here provide evidence of the safety of TLT. The effective size of TLT for the treatment of ischemic stroke in humans within 24 hours of stroke onset was inadequate to meet conventional levels of statistical significance for efficacy, even when the corrections were made for the baseline imbalances in stroke severity and time to treatment, but showed a consistent signal toward better outcomes associated with TLT.

Baseline severity was prespecified into 3 categories: NIHSS=7 to 10, 11 to 15, and 16 to 22. Patients with baseline NIHSS 16 to 22 had a combined dichotomous mRS success rate of 8% (n=224; TLT 7.0%, sham 9.1%). When restricted to the 434 patients with moderate and moderately severe stroke (baseline NIHSS score 7 to 15), a post hoc analysis found a significant beneficial effect (P=0.044). For these 434 patients, the dichotomous mRS success rate of TLT showed an absolute improvement rate of 9.7% (TLT 51.6%, sham 41.9%). A similar beneficial effect was also found in the NEST-1 trial on the dichotomous mRS.

The failure to initially find the optimal treatment population is reminiscent of the tPA development program. When tPA therapy was administered between 0 and 6 hours, the treated groups improved compared to the placebo ones on all measures, but the final results did not achieve statistical significance. Again, there was a strong signal of efficacy, but it was not until several trials were completed and the proper inclusion and exclusion criteria were established that the clinical benefit of tPA was unequivocally established. TLT may take additional trial(s) to find the treatment groups that are indisputably helped by the therapy. In contrast to tPA, however, TLT has no untoward side effects, so the barrier to treatment should be much lower.

There are potential weaknesses in the study that should be noted. There was insufficient previous human experience with TLT to be able to correctly power the study. The trial could have excluded patients with severe strokes at baseline and a prestroke mRS ≥2. Also, it is possible that TLT does not have nay effect on stroke recovery. However, substantial preclinical studies, the NEST-1 study, and the trends in the current trial argue against this unfavorable interpretation.

A new feature of this form of therapy is that that electromagnetic energy, in the past, has been used almost exclusively for its destructive actions, such as burning out parts of solid tumors with a gamma knife, various types of radiation therapy, and both skin lesion removal and assorted ophthalmologic uses. Preclinical studies have demonstrated that infrared energy produces potential beneficial action by alteration of biochemical pathways, and that these changes are not due to thermal effects. Based on preclinical studies, it is thought that when administering TLT, the temperature of the brain is insignificantly elevated, and the energy is producing its beneficial actions by alteration of some biochemical reactions. It is known that infrared energy can stimulate mitochondria, increase ATP formation, mitigate apoptosis, and possibly enhance neurorecovery mechanisms. The precise nature and balance of these reactions in the ischemic human brain are not fully understood; therefore, the exact mechanism of action of TLT remains unknown. Nevertheless, this docs open up a whole new range of potential photobiology therapies for a variety of disorders. Brain trauma and hemorrhagic stroke are obvious extensions; it is also possible that TLT will be useful for a range of neurodegenerative diseases that may involve mitochondrial dysfunction.

Conclusion

The NEST-2 included a very broad range of stroke patients with respect to baseline severity, prestrike disability, and time to treatment. In this overall population, TLT was safe but did not significantly improve patient outcomes as measured by both mRS and NIHSS; however, both outcome measures showed positive trends in that direction. Post hoc analyses suggest a meaningful beneficial effect in patients with moderate to moderately severe ischemic stroke within 24 hours of onset. Further clinical studies in this redefined population should be considered.

Phototherapy Example 3

Another example examined the efficacy of low-level laser therapy (LLLT) for TBI using the mouse closed-head injury (CHI) model by studying the neurobehavioral and histological outcome of the traumatized mice (A. Oron et al., "Low-Level Laser Therapy Applied Transcranially to Mice following Traumatic Brain Injury Significantly Reduces Long-Term Neurological Deficits," Journal of Neurotrauma, Volume 24, Number 4, 2007 which is incorporated in its entirety by reference herein.)

A total of 24 male Sabra mice (Hebrew University strain) weighing 25-35 g were studied. The mice were housed in groups of six per cage, under a 12 h/12 h, light/dark, reversed light cycle. Food and water were provided ad libitum. The study was performed according to the guidelines of the Institutional Animal Care Committee in The Hebrew University, Jerusalem, Israel. CHI trauma was induced to the heads of the mice under ether anesthesia using a weight-drop device. Following sagittal scalp incision, mice were manually immobilized, and a tipped Teflon cone was placed 3 mm lateral to the midline and 1 mm caudal to the left coronal suture. Following this, a metal rod (94 g) was allowed a free fall on the cone from a precalibrated height.

Motor function and reflexes of the traumatized mice were evaluated at different time intervals after CHI using a neurological severity score (NSS), which was modified to emphasize the motor functions. The neurological tests were based on the ability of the mice to perform 10 different tasks (listed in Table 10) that evaluate the motor ability, balancing, and alertness of the mouse. One point is given for failing to perform each of the tasks: thus, a normal, uninjured mouse scores zero. The severity of injury is defined by the initial NSS, evaluated one hour post-CHI and referred to as NSSI, and is a reliable predictor of the late outcome. Thus, fatal or near-fatal injury is defined in mice as having a NSSI of 9-10; severe injury in mice with an NSSI of 7-8; moderate injury with NSSI of 5-6, and mild injury in mice with an NSS I of less than 4.

TABLE 10

| Task | NSS |
| --- | --- |
| Presence of mono- or hemiparesis | 1 |
| Inability to walk on a 3-cm-wide beam | 1 |
| Inability to walk on a 2-cm-wide beam | 1 |
| Inability to walk on a 1-cm-wide beam | 1 |
| Inability to balance on a 1-cm-wide beam | 1 |
| Inability to balance on a round stick (0.5 cm wide | 1 |
| Failure to exit a 30-cm-diameter circle (for 2 min) | 1 |
| Inability to walk straight | 1 |
| Loss of startle behavior | 1 |
| Loss of seeking behavior | 1 |
| Maximum total | 10 |

All mice were subjected to CHI and assigned to control or laser-treated groups as described below. Assessment of neurological score (NSS) was performed one hour post-injury. The NSS scores of the mice ranged from 4 to 6, indicating a mild-moderate trauma. The mice were then divided into three groups of eight mice per group, so that the means NSS in each group were similar, to ensure similar average severity of injury in all groups. Two groups of mice received low level light therapy at two different doses (10 and 20 mW/cm$^2$) while the third group, serving as a sham-operated control, underwent the same procedures as the laser-treated group, but did not receive actual laser irradiation.

Laser treatment was performed four hours post-CHI using an experimental laser 808-nm wavelength and maximal power output of 200 mW equipped with metal-backed glass fiber optic (3 mm diameter). Laser light was applied by placing the distal tip of the fiber optics in full contact with a point in the midline of the skull (sagittal suture) located 4 mm caudal to the coronal suture of the skull after skin had been removed in that region by a small longitudinal incision. In preliminary experiments, the entire cortical part of a fresh skull was excised from a mouse four hours post-TBI. The distal tip of the fiber optic of the laser was placed on the same location of the skull as described above. The power density of the laser post-transmission through the skull was measured by placing the probe of the laser power meter (Ophir Inc., Jerusalem, Israel) under the dura. Based upon prior measurements, this location was chosen as being sufficient to illuminate the entire brain (1.2-cm beam diameter measured by an infrared viewer) due to dispersion of the laser beam by the skull. The laser irradiation power density at the tip of the fiber optic was set to deliver a power density of 10 and 20 mW/cm$^2$ to the brain. The duration of laser irradiation was two minutes (energy densities of 1.2-2.4 J/cm$^2$). The power and energy densities of the laser were chosen based on preliminary experiments with various parameters of the laser applied in the CHI mouse model. Similar laser parameters were used in previous rat and rabbit stroke models where beneficial effects were evident.

Cortical tissue loss was evaluated in the traumatized cross-section of the brain. At the end of the four-week follow-up period, mice were anesthetized, and their brains were perfused with 4% paraformaldehyde solution and fixed in the same formaldehyde solution for three days. Two-mm-thick cross-sections were taken from the trauma region of the brain. This region was located in the parietal part of the brain by means of a small blood clot that served as a good marker of the spot where the skull was hit during the induction of the trauma. The 2-mm-thick brain slices were processed in an automated tissue processor and embedded in paraffin. Eight-micron-thick coronal sections were prepared from each 2-mm-thick brain slice block. Three random sections from each brain slice were stained with hematoxylin and eosin, and processed for quantitative measurements of the lesion area in each section. The brain area was calculated in each hemisphere [ipsilateral (traumatized) and contralateral] separately in each histological section. The brain hemisphere volume was then calculated by multiplying average area of the three sections by 2-mm thickness of the slice. Lesion volume (in percentage) was expressed as contralateral (nontraumatized hemisphere) volume minus ipsilateral hemisphere volume divided by the contralateral hemisphere volume.

Data were analyzed using one-way analysis of variance (ANOVA) followed by Student Neuman Keuls test (using Sigma Stat software from Sigma of St. Louis, Mo.). Data from this study discussed below are presented as mean±standard deviation. A value of p less than 0.05 was regarded as statistically significant.

The severity of injury as reflected by the NSS at one hour was similar in both groups of mice: 4.8±0.7 and 4.8±0.8 in the control (n=8) and laser-treated (n=16) mice, respectively. Since during the whole follow-up period there was no statistical difference between the mice that received 10 and 20 mW/cm$^2$, the results were pooled together to one laser-treated group of mice.

Figure 39:
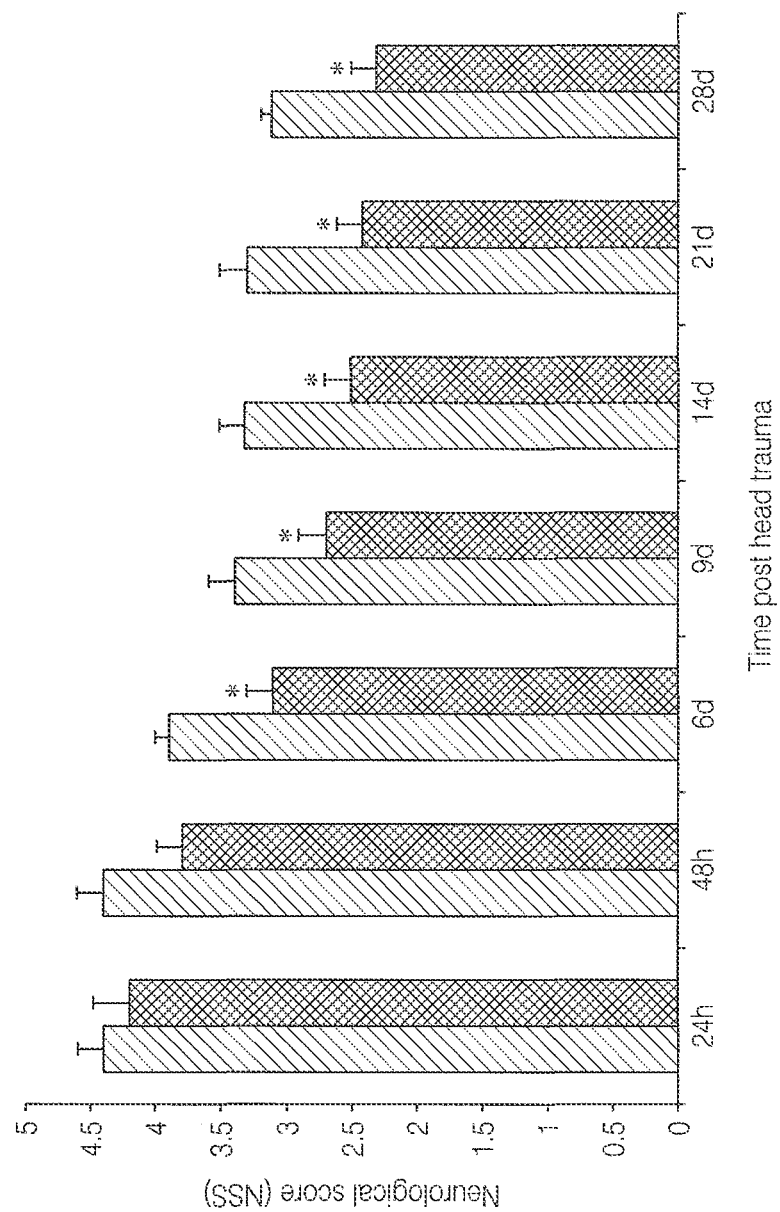
FIG. 39 is a plot of the neurologic score (NSS) of control/non-laser-treated (light columns) and laser-irradiated (dark columns) mice at different time intervals after induction of brain trauma.

FIG. 39 is a plot of the neurologic score (NSS) of control/non-laser-treated (light columns) and laser-irradiated (dark columns) mice at different time intervals after induction of brain trauma. At 24 hours post-CHI, no significant differences between sham-laser, control, traumatized mice, and those that had received active laser treatment four hours post-trauma were observed. Yet, from 48 hours on, there was a significant improvement in the NSS in the laser-treated mice as compared to control non-treated mice (p=0.05 at 48 hours and p<0.05 at later times). The significant differences between the laser-treated and control mice were sustained thereafter up to 28 days post-TBI, where the neurobehavioral scores were 26-27% lower in the laser-treated versus control mice.

Figure 41:
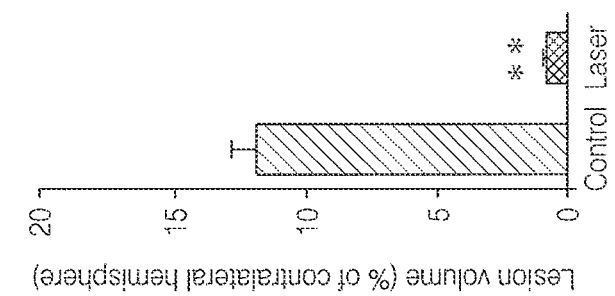
FIG. 41 is a plot of lesion volume of control (light column) and laser-treated (dark column) traumatized brains 28 days after induction of head trauma.
Figure 40:
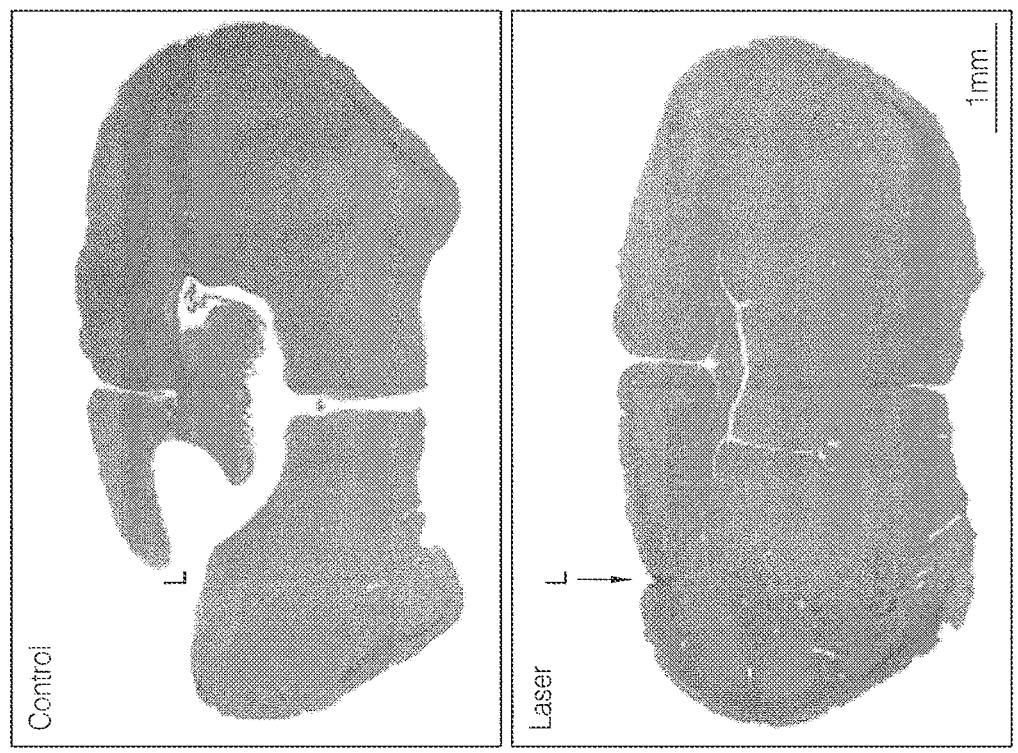
FIG. 40 shows representative micrographs of cross-sections of control non-laser-treated and laser-treated mice brains.

FIG. 40 shows representative micrographs of cross-sections of control non-laser-treated and laser-treated mice brains. Note lesion (L) in the control micrograph as compared to minimal lesion (arrow) in the laser-treated brain. FIG. 41 is a plot of lesion volume of control (light column) and laser-treated (dark column) traumatized brains 28 days after induction of head trauma (scale bar=5 mm; **p<0.01). At 28 days post-TBI, the sham control mice showed a significantly higher (p<0.001) loss (12.1±1.3%) of cortical tissue at the injured site compared to the laser-treated mice (1.4±0.1%).

The results of the study demonstrate for the first time that low level laser therapy given at four hours post-TBI improves short- and long-term (28 days) neurobehavioral function and reduces brain tissue loss. The results corroborate previous findings in rat and rabbit models that low-level light therapy applied transcranially improves functional outcome after stroke. This result is consistent with the hypothesis that pathophysiologies and secondary mechanisms of damage of cerebral ischemia and head trauma are quite similar, with a common involvement of both harmful and protective mechanisms. In recent studies on the effect of low-level light therapy on stroked rats, however, it was shown that the beneficial effect on neurological function was evident only 2-3 weeks after laser application, whereas in the study described herein, the marked improvement in overall neurological function of the laser-treated mice over sham control mice was significant already at five days post-trauma. This phenomenon can be partially explained based on rapid elevation of ATP content after laser irradiation in the ischemic heart. Furthermore, increase in total antioxidants, angiogenesis, heat shock proteins content, and antiapoptotic activity following low-level laser therapy were found previously for the ischemic heart and skeletal muscles and can be suggested as possible processes that are attenuated by the low-level laser therapy also in the ischemic/traumatic brain. The modulation of the above processes by low-level laser therapy could contribute in concert to the better neurological outcome and the significant reduction in lesion size of the laser-treated mice as compared to controls as found in this study. Another mechanism that may contribute to the long-term improvement of neurological function in the laser-irradiated mice post-TBI include neurogenesis that is induced by low-level laser therapy as found recently in laser-treated stroked rats. Neurogenesis may also partially account for the significant reduction in lesion size in the laser-treated mice compared to control as demonstrated in this study.

The results of this study may also have clinical relevance. The laser treatment was given four hours post-trauma, which is a reasonable time for a patient to arrive at the hospital emergency room. In a prior safety study in rats, no alterations in functional neurological outcome or brain histopathology that had been treated with low-level laser therapy at different intensities or frequencies over both short- and long-term time intervals were shown.

Phototherapy Example 4

Photobiostimulation effects of near-infrared light therapy (NILT) have been documented for both in vitro and in vivo models (see, e.g., L. DeTaboada et al., "*Transcranial application of low-energy laser irradiation improves neurological deficits in rats following acute stroke,*" Lasers Surg. Med. 38:70-73 (2006)). Energy in the infrared region of the electromagnetic spectrum is non-ionizing and poses none of the hazards associated with ultraviolet light. Irradiation of brain tissue with specific infrared wavelengths (e.g., 808-810 nanometers) can penetrate the brain (see, e.g., S. Ilic et al., "*Effects of power densities, continuous and pulse frequencies, and number of sessions of low-level laser therapy on intact rat brain,*" Photomed. Laser Surg. 24:458-466 (2006)) and can stimulate adenosine triphiosphate (ATP) formation by mitochondria (see, e.g., A. P. Sommer et al., "*Stressed cells survive better with light,*" J. Proteome. Res. 1:475 (2002)). A primary mitochondrial chromophore responsible for photobiostimulation is the enzyme cytochrome c oxidase, a terminal enzyme in the cellular respiratory chain located in the inner mitochondrial membrane. Cytochrome c oxidase (COX) plays a central role in the bioenergetics of cells by delivering protons across the inner membrane, thereby driving the formation of ATP by oxidative phosphorylation. The overall result of NILT is improved energy metabolism and potentially, enhanced cell viability (both neuronal and non-neuronal).

NILT or photon energy delivered using a gallium-arsenic diode near-infrared laser may be useful to treat the behavioral function deficits associated with embolic stroke (see, e.g., P. A. Lapchak et al., "*Transcranial infrared laser therapy improves clinical rating scores after embolic strokes in rabbits,*" Stroke 35:1985-1988 (2004)). These rabbit small clot embolic stroke model (RSCEM) studies showed that NILT used in administered within 6 hours of an embolic stroke using a continuous wave (CW) of light at high power densities (25 mW/cm$^2$) and long treatment durations (10 min.) significantly improved behavioral function. Lower energies and shorter treatment durations improve behavior when applied early on following embolization. However, there were also documented unwanted side-effects related to using high power densities, such as an increase in both skin and brain temperature directly under the laser probe. Studies by Michael Chopp and colleagues (see, e.g., A. Oron et al., "Low-level laser therapy applied transcranially to rats after induction of stroke significantly reduces long-term neurological deficits," Stroke 37:2620-2624 (2006)) using the rat middle cerebral artery occusion (MCAO) model have also shown that laser therapy can significantly improve behavioral deficits using a rodent stroke model. In contrast to the RSCEM study cited above in which laser light therapy was neuroprotective when applied within 6 hours postembolization in the MCAO model, laser treatment was only effective when applied 24 hours, but not 4 hours after stroke onset. Laser light therapy in the MCAO model also attenuated neurological deficits without a corresponding reduction in stroke lesion volume. Since there was no apparent statistically significant difference in the infarct area of control and laser-irradiated rats with ischemic strokes, the authors hypothesized that noninvasive laser light therapy intervention may improve function by inducing neurogenesis. This was demonstrated using immunocytochemistry for double-cortin, a marker of migrating cells and bromodeoxyuridine, a marker of proliferating cells. Nevertheless, in both models, laser light therapy using CW energy delivery resulted in behavioral improvement.

CW NILT delivery and pulse wave (PW) frequency settings have been examined to determine the most efficacious treatment regimen using the RSCEM, which is produced by injection of blood clots into the cerebral vasculature. The RSCEM, which is a model of multiple infarct ischemia, results in ischemia-induced behavioral deficits that can be measured quantitatively with a dichotomous clinical rating scale. The use of clinical rating scores (a behavioral endpoint) in rabbits parallels the use of the National Institutes of Health Stroke Scale (NIHSS) in stroke patients, the primary behavioral endpoint for all clinical trials of new treatment for acute ischemic stroke. For the study described below, three different treatment regimens were used: 1) CW power density of 7.5 mW/cm$^2$; 2) pulse mode 1 (P1) using a frequency of 300 µs pulse at 1 kHz; or 3) pulse mode 2 (P2) using a frequency of 2 ms pulse at 100 Hz. The lower power density settings and pulse mode frequencies have been shown to be safer methods of irradiation because they produce little heating or no tissue damage.

Experimental Procedures

Surgery

The Department of Veterans Affairs approved the surgical and treatment procedures used in this study. Surgery was done in a sterile controlled environment with a room temperature between 22.8-23.2° C. Using the RSCEM, male New Zealand White rabbits weighing 2.2-2.5 kg were anesthetized with halothane/O$_2$ and a catheter was inserted into the common carotid artery (CCA) through which microdots were injected. Briefly, the bifurcation of one CCA was exposed and the external carotid was ligated just distal to the bifurcation. A catheter was inserted into the CCA and secured with ligatures. The incision was closed around the catheter so that the distal end was accessible outside the animal's neck. The catheter line was then filled with heparinized saline and plugged with an injection cap. Rabbits were allowed to recover from anesthesia until they were fully awake and behaving normally. Once rabbits had recovered from anesthesia, they were self-maintaining and have a normal core body temperature (see, e.g., P. A Lapchak et al., "Neuroprotective effects of the spin trap agent disodium-[(tert-butylimino)methyl]benzene-1,3-disulfonate N-oxide (generic NXY-059) in a rabbit small clot embolic stroke model: combination studies with the thrombolytic tissue plasminogen activator," Stroke 33:1411-1415 (2002)).

Rabbit Embolic Strokes

For the RSCEM, blood was drawn from one or more donor rabbits and allowed to clot for 3 hours at 37° C. The large blood clots were then suspended in phosphate-buffered saline (PBS) containing 0.1% bovine serum albumin (BSA) and Polytron-generated fragments were sequentially passed through metal screens and nylon filters. The resulting small clot suspension was then labeled with "cobalt containing NEN-Trac microspheres, so that the quantity of clots that becomes lodged in the brain following embolization could be calculated. For embolization, rabbits were placed in Plexiglas restrainers, the catheter injection cap was removed and the heparinized saline was cleared from the carotid catheter system. Then, the clot particle suspension was rapidly injected through the catheter into the brain, which was then flushed with sterile saline. Rabbits were fully awake during the embolization procedure and they were self-maintaining (i.e., they did not require artificial respiration or other external support). The use of awake non-anesthetized rabbits allows for immediate observation of the effects of embolization on behavior at the time of clot injection and thereafter.

Clinical Rating Score Behavioral and Quanta! Dose-Response Analysis

The use of clinical rating scores and quantal analysis is a sophisticated method to determine how a large population of stroke "patients" in this case, rabbits, will respond to a treatment and is an appropriate primary endpoint to use when a treatment is being developed to support a clinical trial. To evaluate the quantitative relationship between clot dose and behavioral deficits, logistic sigmoidal quantal analysis curves were fitted to the dose. A wide range of clot doses was used to produce behaviorally normal or abnormal animals. In the absence of a neuroprotective treatment regimen, small number of microdots causes no grossly apparent neurologic dysfunction. However, when large numbers of microdots are injected, they invariably caused encephalopathy and sometimes death. Abnormal rabbits with encephalopathy include those with one or more of the following symptoms: ataxia, leaning, circling, lethargy, nystagmus, loss of balance, loss of limb/facial sensation and occasionally, paraplegia. Using a simple dichotomous rating system, with a reproducible composite result and low inter-rater variability (<5%), each animal was rated as either behaviorally normal or abnormal by a naïve observer. Using quantal analysis, behavioral changes was detected following pharmacological intervention. With this simple rating system, the composite result for a group of animals is quite reproducible. A separate curve was generated for each treatment condition and a statistically significant increase in the value or the amount of microdots that produce neurologic dysfunction in 50% of a group of animals compared with control is indicative of a behavioral improvement.

Power and Statistical Analysis

Power analysis of the quantal dose-response curves indicates that, assuming a=0.05 and β=0.90, a coefficient of variation of 15% and a difference between means of 20%, a sample size of 14 animals is required per group. However, previous experience shows that approximately 20 animals per group are needed due to premature losses caused by preparation difficulties or death after ischemia, but before treatment can be fully administered. The behavioral data are presented as $P_{50}$ (mean±S.E.M.) in mg clots for the number of rabbits in each group (n). $P_{50}$ values are analyzed using the t-test, which included the Bonferroni correction where appropriate. In the study, a full sham-treated control group was run parallel to the treatment groups and all groups are rated using the same behavioral analysis scale described above to remove any experimental or investigator bias. NILT-treated groups are directly compared with control groups. For all animals in this study, prior to carotid catheter placement, the fur on the scalp covering the skull of all rabbits used in this study was shaved to reveal pink skin. All shaved rabbits were randomly allocated into treatment groups before the embolization procedure, with concealment of the randomization until all postmortem analyses were complete.

Near Infrared Light Therapy

Rabbits were placed in a Plexiglas restrainer for the duration of the treatment. The probe was placed in direct contact with the skin, since the fur over the head region was shaved prior to juxtaposing the laser probe to the skin. An Acculaser low energy laser fitted with a fiberoptic cable and laser probe (OZ Optics Ltd., Berkeley, Calif.) measuring 2 centimeters in diameter was used (wavelength of 808±5 nanometers). Instrument design studies showed that these specifications would allow for light penetration of the rabbit skull and brain to a depth of approximately 2.5-3 centimeters and that the light beam would encompass the majority of the brain if placed on the skin surface posterior to bregma on the midline. Using the specifications described above, the average energy delivered to the brain was 0.9-1.2 joules. Table 11 provides details for the three different treatment regimens used in the present studies: 1) CW; 2) P1 using a frequency of 300 μs pulse at 1 kHz; and 3) P2 using a frequency of 2 ms pulse at 100 Hz.

TABLE 11

NILT treatment regimens

| Treatment regimen | Power density (mW/cm²) | Pulse (Hz) | On time (ms) | Duty cycle | Treatment duration (min.) | Time post-embolization (hours) |
|---|---|---|---|---|---|---|
| CW | 7.5 | NA | NA | 100% | 2 | 6 and 12 |
| PW mode 1 | 7.5 | 1000 | 0.3 | 30% | 2 | 6 and 12 |
| PWmode2 | 7.5 | 100 | 2 | 20% | 2 | 6 |

Results

Transcranial NILT Improves Clinical Rating Scores: 6-Hour Treatment

In this study, 48 hours has been used as the time to measure the behavioral endpoint in determining the relative effectiveness of different treatment regimens. In the previous 2004 Lapchak study cited above, the improvements in behavior that were present at 48 hours were also measurable up to 21 days following treatment. In this study, a power density setting of 7.5 mW/cm² and treatment duration of 2 min. were used. In order to define effective regimens of NILT, the three different modes: CW, P1 and P2 described above were used. The main difference between the three modes is the duty cycle and the overall time for brain irradiation.

Figure 42A:
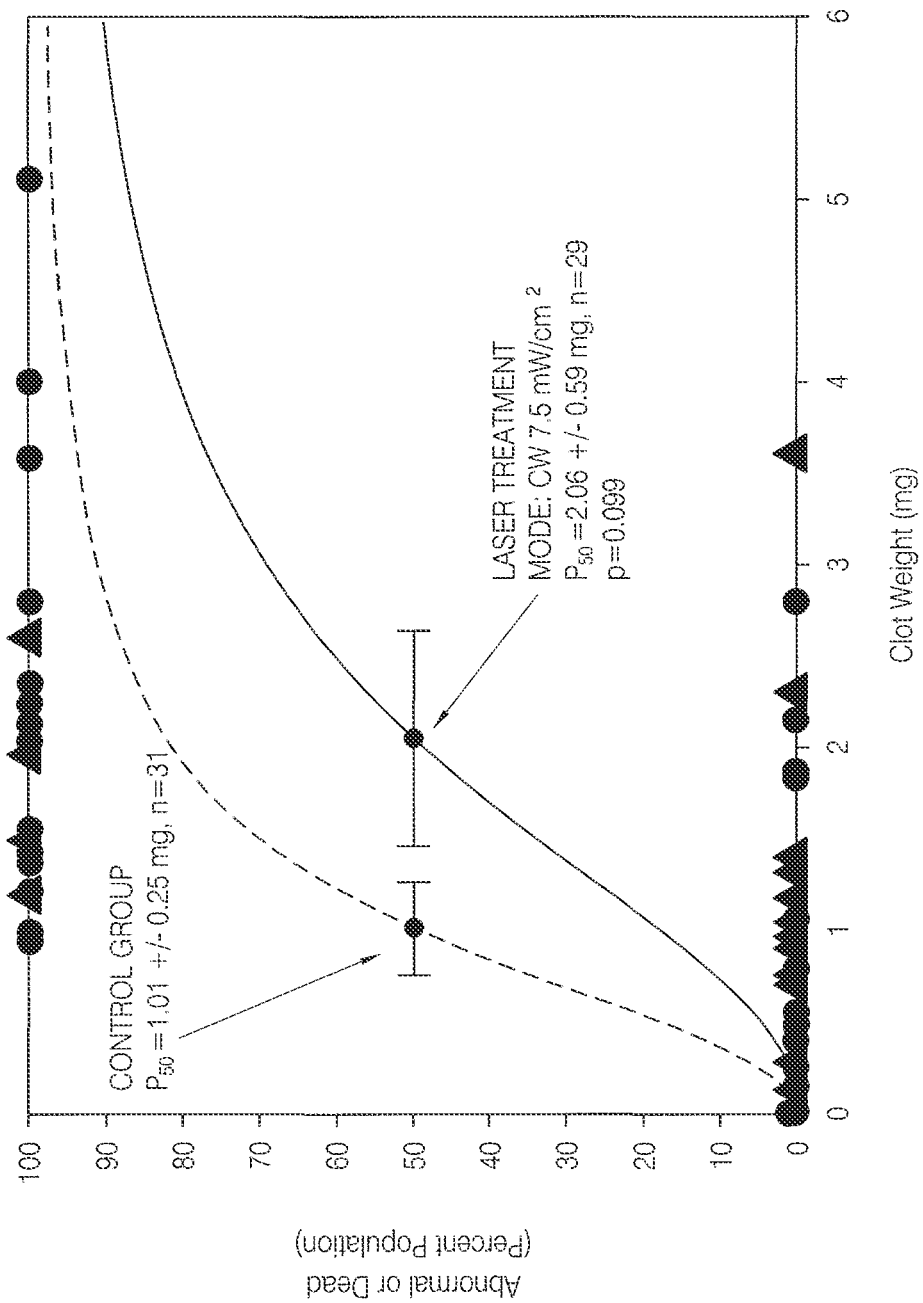
FIGS. 42A-42C show the results of a study of stroke in a rabbit model using a 6-hour post-embolization time of treatment.
Figure 42B:
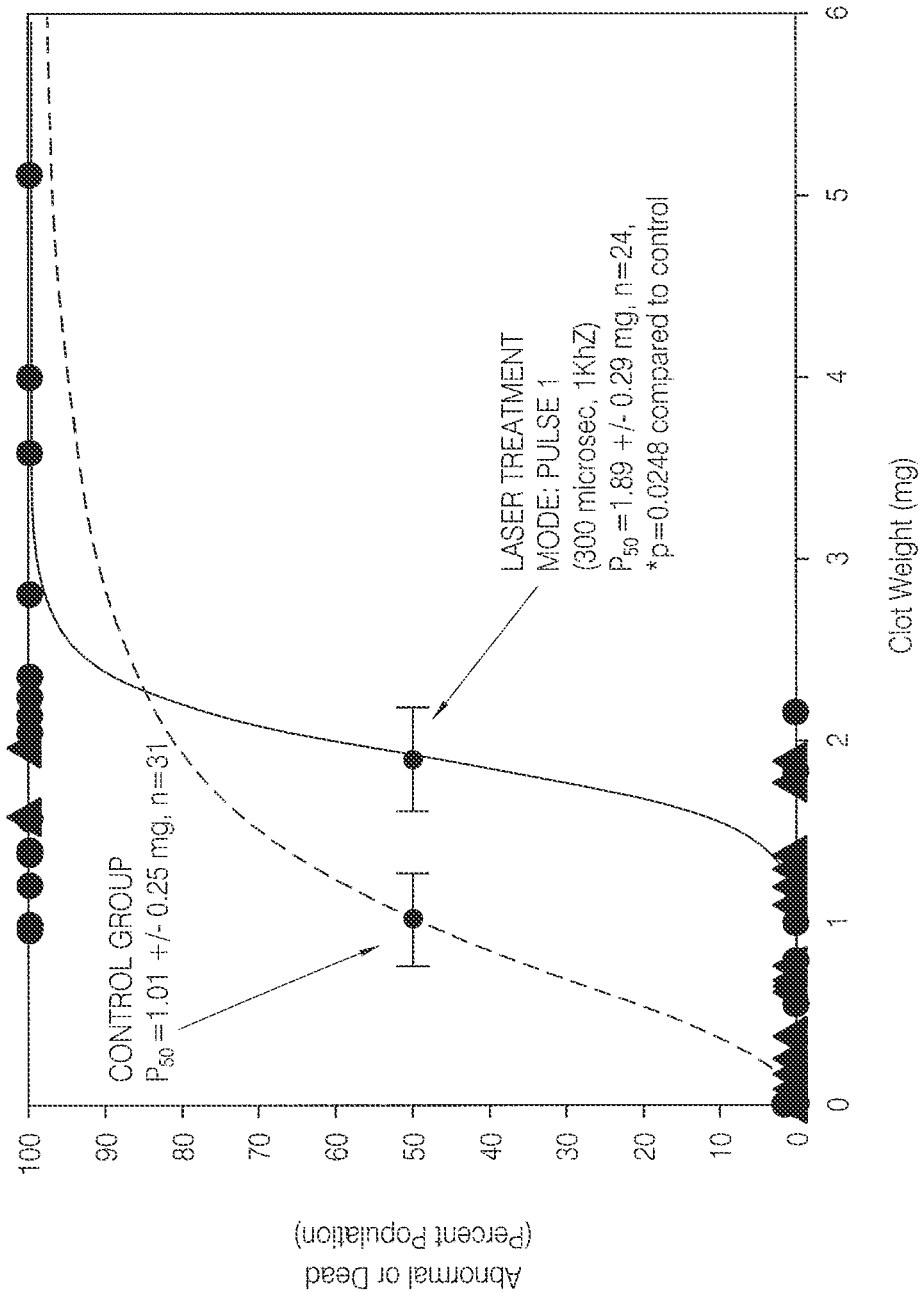
Figure 42C:
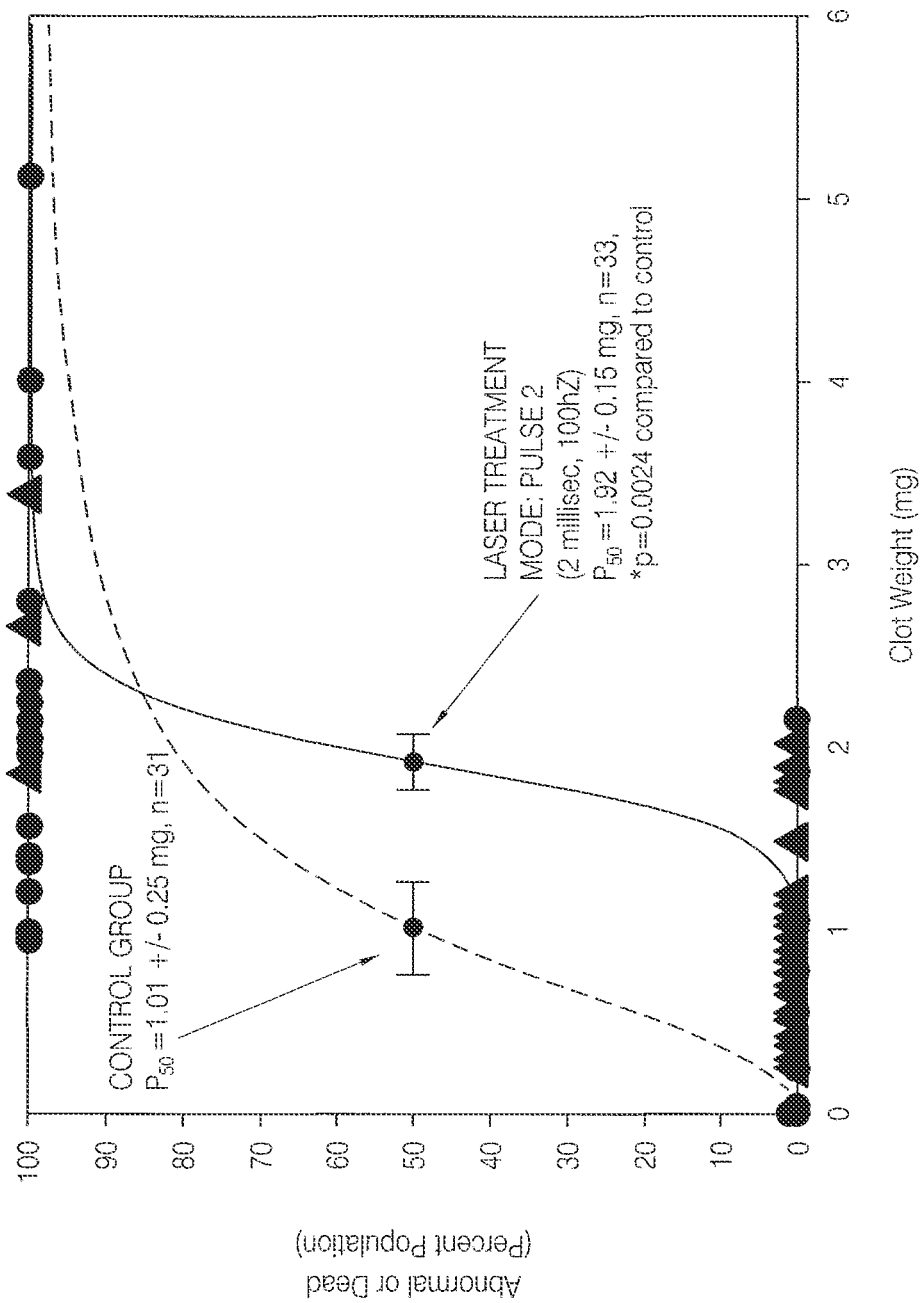

FIGS. 42A-42C show the results of the studies using a 6-hour post-embolization time of treatment. The dark circles represent the raw data for the control group and the triangles represent the raw data for the laser-treated group. A normal animal for a specific clot weight is represented by a symbol plotted at 0 on they axis, whereas an abnormal animal for a specific clot weight is represented by a symbol plotted at 100 on they axis. NILT initiated 6 hours following embolization using all three treatment regimens improved behavioral performance compared with a cumulative control group when behavior was measured 24 hours following treatment. As shown in FIG. 42A, NILT given as a CW increased the $P_{50}$ value to 2.06±0.59 mg (n=29, P=0.099) and this was not statistically different from the control group $P_{50}$ value which was 1.01±0.25 mg (n=31). However, when NILT was given either as a PW using the P1 or P2 modes, there were significant increases in behavioral function that were reflected by significantly increased $P_{50}$ values for the groups. The $P_{50}$ values were 1.89±0.29 mg (n=25, P=0.0248) and 1.92±0.15 mg (n=33, P=0.0024), respectively for the P1 and P2 groups, as shown in FIGS. 42B and 42C.

Effect of Transcranial NILT on Behavioral Function when Initiated 12 Hours Following Embolization In the previous 2004 Lapchak study cited above, laser therapy was reported to not be effective when applied to rabbits 24 hours following a stroke. Thus, it is important to determine if the therapeutic window for NILT could be extended past 6 hours using either the CW or P1 regimens. For this series of experiments, the cumulative control group described above was used, a group that had a $P_{50}$ value of 1.01±0.25 mg (n=31). This cumulative control group was used because it has been previously documented that the baseline $P_{50}$ value for embolized rabbits is quite consistent over time and between experiments. The use of a cumulative control group in this study allows the reduction of the utilization of large number of rabbits.

Figure 43A:
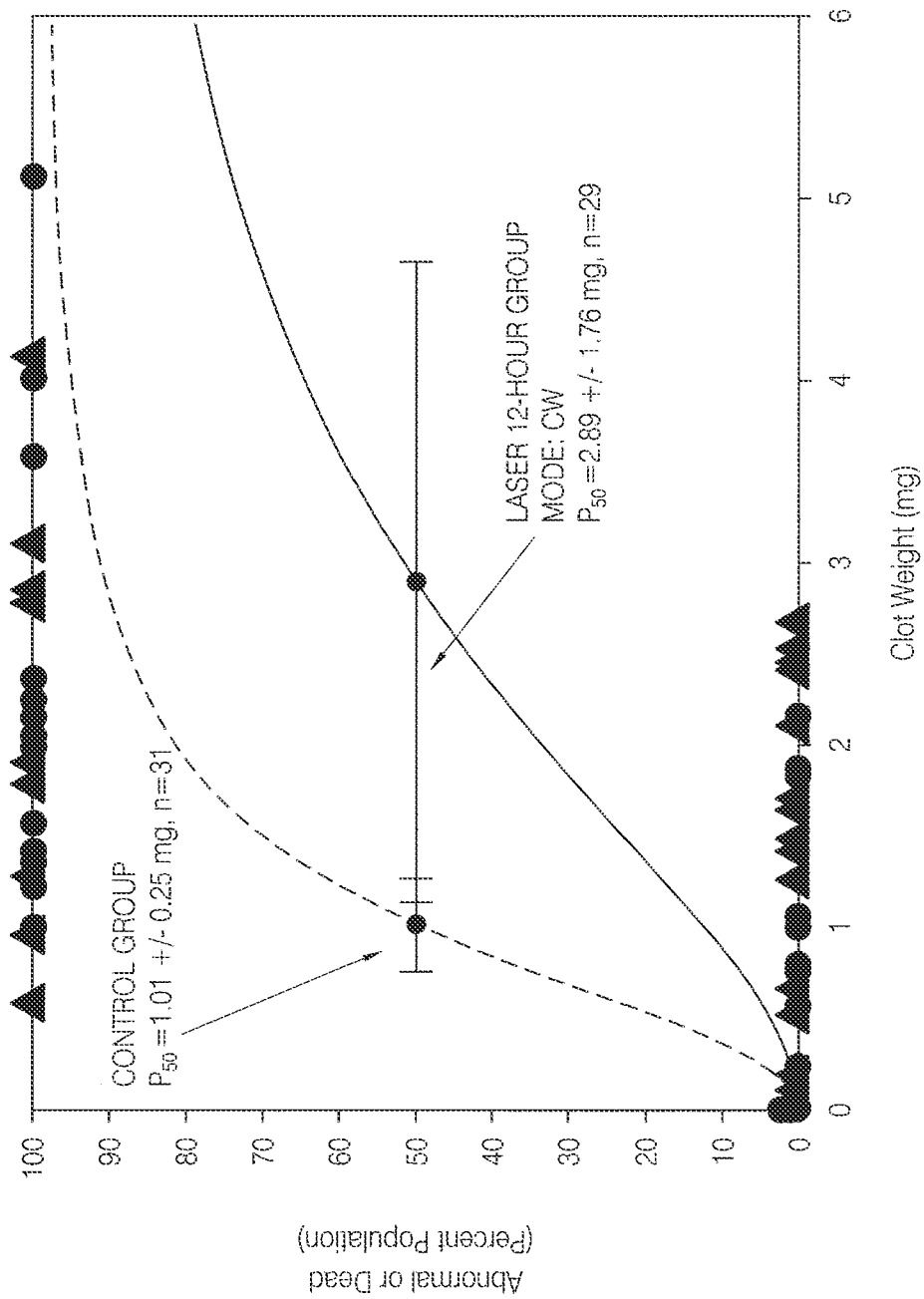
FIGS. 43A and 43B show the results of a study of stroke in a rabbit model using a 12-hour post-embolization time of treatment.
Figure 43B:
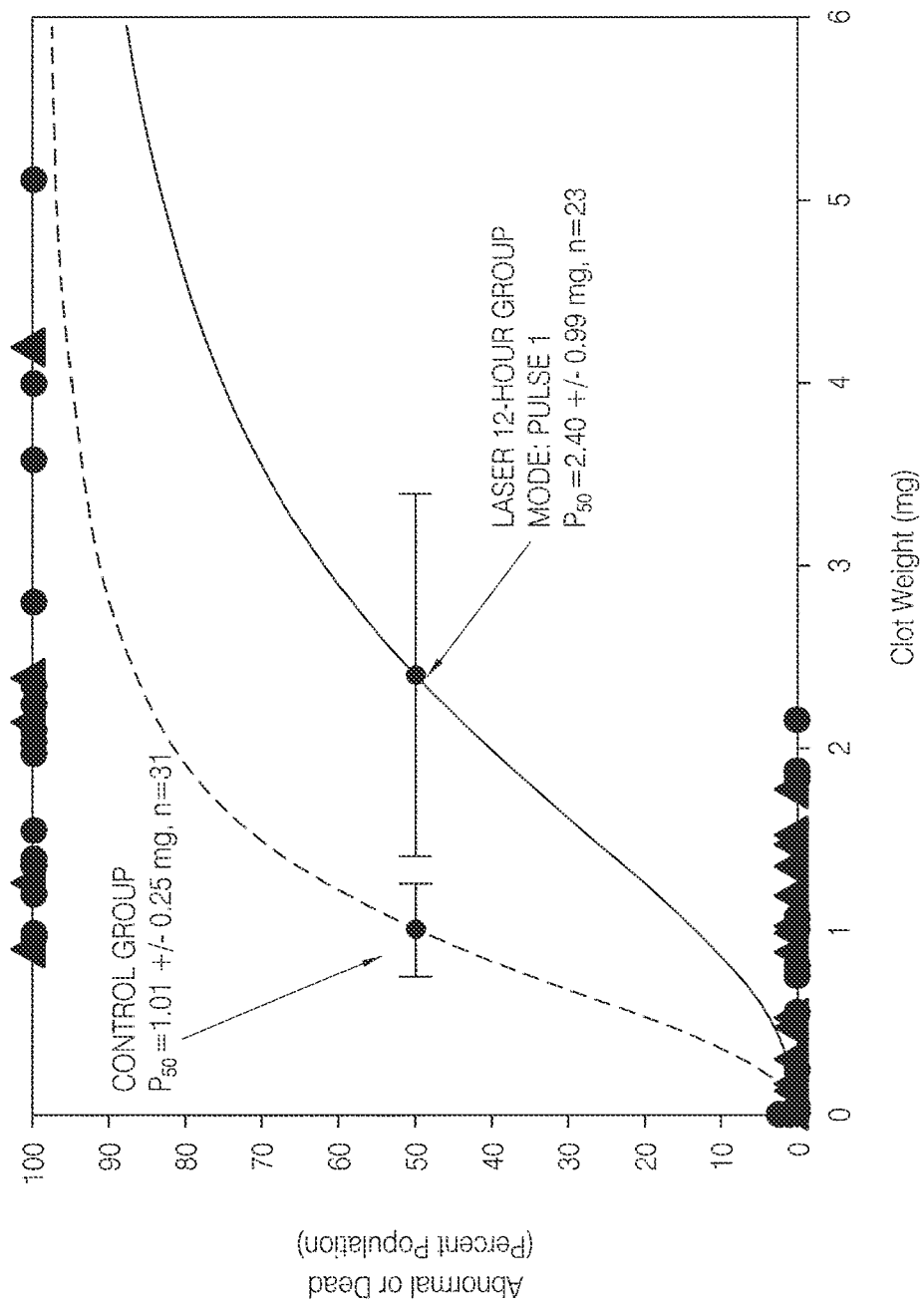

FIGS. 43A and 43B show the results of the studies using a 12-hour post-embolization time of treatment. The dark circles represent the raw data for the control group and the triangles represent the raw data for the laser-treated group. A normal animal for a specific clot weight is represented by a symbol plotted at 0 on they axis, whereas an abnormal animal for a specific clot weight is represented by a symbol plotted at 100 on they axis. NILT initiated 12 hours following embolization using either of the treatment regimens did not significantly improve behavioral performance compared with the cumulative control group when behavior was measured 24 hours following treatment. As shown in FIG. 43A, NILT given as a CW increased the $P_{50}$ value to 2.89±1.76 mg (n=29, P=0.279). In addition, as shown in FIG. 43B, when NILT was given as a PW using the P1 the $P_{50}$ value was 2.40±0.99 mg (n=24, P=0.134). Thus, although there was an increase in the mean $P_{50}$ values, inherent variability in the response of the treatment group to NILT prevented the treatment from showing statistically significant differences. Since neither the CW nor the P1 regimens were effective at significantly increasing the $P_{50}$ value, the effects of NILT using the $P_2$ regimen at the 12-hour post-embolization time point were not investigated.

Discussion

The principal aim of this study was to directly evaluate the effects of CW and PW transcranial NILT on clinical rating scores following multiple small clot embolic strokes in rabbits. To achieve this goal, the RSCEM was used which is a useful preclinical animal model to develop new stroke treatments that can be quickly translated to the clinic. In the model, the primary cause of stroke or ischemic injury is related to the administration of blood clots that lodge in cerebral vessels, the same cause of many strokes in humans responsible for the interruption of cerebral blood flow and clinical deficits. Moreover, RSCEM is a model of multiple infarct ischemia that uses a scale of clinical rating scores as the primary endpoint which is based upon motor function components of the NIHSS for stroke in humans.

In the present) study that used the RSCEM, transcranial NILT applied to embolized rabbits 6 hours following an embolic stroke improved behavioral rating scores, specifically motor function. There are three important aspects of these findings. First, the low power density (7.5 mW/cm$^2$) with an estimated brain penetration of 2.5-3 cm as used in the study was effective at improving clinical rating scores (e.g., motor function). Second, a 2 minute application of near infrared light promoted recovery of function when NILT is applied transcranially to embolized rabbits. Third, the studies were designed to determine if there were differential effects of CW therapy compared with pulse therapy. Interestingly, although the CW regimen increased the $P_{50}$ value of group, the resulting increase was not statistically significant from control. However, both pulse treatment regimens significantly increased the $P_{50}$ value of group compared with control.

In the previous 2004 Lapchak study, laser therapy at a high power density (25 mW/cm$^2$) was tested using a CW regimen for a 10 minute duration to show that laser therapy could improve behavioral function following embolic strokes in rabbits. The present study shows that the power density of 7.5 mW/cm$^2$ and treatment time of 2 minutes can produce beneficial effects at the extended 6 hour post-embolization treatment time. However, in this study, CW therapy did not result in "statistically" significant behavioral improvements. But pulse therapy, whether using the P1 or P2 regimen, did result in a statistically significant increase in behavior. These results with low power density NILT can be compared with those previously reported using a rodent stroke model which had some significant differences with the present study. Using a rodent filament model to produce permanent cerebral ischemia, the rat MCAO study cited above was unable to show a benefit to early laser treatment (i.e., 4 hours following filament placement). However, this study found that laser treatment was effective when applied 24 hours following the stroke and that the beneficial effect was observable up to 21 days following the stroke. The durability of the laser therapy effects is comparable to that previously published. However, even though the previous 2004 Lapchak study indicated that NILT attenuates stroke-induced behavioral deficits in rabbits when applied up to 6 hours following the stroke, it did not show any "statistically" significant behavioral improvement when NILT was started 12 hours following the stroke.

There appears to be an important difference between the results published for the rodent filament permanent occlusion model cited above and the rabbit embolic stroke model 2004 study of Lapchak cited above. The difference may simply be associated with the cause of stroke in the two models. The placement of a plastic filament into the middle cerebral artery of a rodent that is being maintained on 1-2% halothane, 70% $N_2O$ and 30% $O_2$ and being monitored for blood glucose, pH, $pO_2$ and $pCO_2$ and rectal temperature (all levels were undefined in the publication) may represent an extreme artificial model of cerebral stroke. The rabbit embolic stroke model as described within used rabbits 3 hours following the placement of a carotid catheter to ensure that the rabbits were self-maintaining and free of anesthetic when they were embolized. Moreover, fresh blood clots prepared from donor rabbits were used for the embolization procedure on the day that the blood was drawn and allowed to clot free of additives. Thus, during the embolization procedure, rabbits were awake and behaving normally. With such differences between the two models, differential effects of NILT are not too surprising. The different findings resulting from the use of two diverse animal models of ischemic stroke may shed some light on the mechanism(s) of action of NILT in the ischemic brain. In the rat model study, it was proposed that laser therapy may be inducing neurogenesis in the brain primarily because the effect of laser was only evident when applied 24 hours following ischemia and that there was coincident elevation of neurogenesis-associated markers in the brain. Moreover, the physiological effects of laser therapy were not observed immediately, but required a delay of between 2 and 4 weeks post-treatment. The authors suggested that laser therapy induces the formation of new neurons and neuron-supporting cells in the brain and that the behavioral improvement following laser therapy requires the new neuronal pathways. Unfortunately, this idea was not supported by measures of hematoxylin and eosin (H&E) staining for lesion volume in the laser-treated and control ischemic brains as there was no statistically significant difference in lesion volume between the two groups, suggesting that there was little or no neurogenesis in brain.

In contrast to the delayed effects of laser therapy in the rat model, in the rabbit model, NILT is effective when applied 5 minutes to 6 hours following embolization and the behavioral effects of NILT are measurable within 24-48 hours of embolization. The results described herein suggest that NILT is inducing a rapid response element (RRE) in brain following embolization that results in behavioral improvement, an effect that appears to be independent of neurogenesis or long-term remodeling. Moreover, in stroke patients entered in the NeuroThera Effectiveness and Safety Trial (NEST-1), a significant reduction in NUBS score was evident by day 5 after laser treatment, which continued to improve up to 90 days after treatment (see, Y. Lampl et al., "*Infrared laser therapy for ischemic stroke: a new treatment strategy: results of the NeuroThera Effectiveness and Safety Trial-I (NEST-I)*," Stroke 38(6): 1843-1849 (2007)). This finding is in agreement with the results of the rabbit embolic stroke model studies, which show that laser therapy induces rapid recovery of function following an ischemic stroke.

Taken together, results from experimental stroke studies suggest that NILT may be useful in patients if applied between 6 and 24 hours of a stroke. Based upon correlative preclinical and clinical acute ischemic stroke studies, the 6 hour therapeutic window observed in the RSCEM may be equivalent to approximately 18 hours in a stroke patient because of the following. In the RSCEM, tPA effectively improves behavior when given 1-1.5 hours following embolization and in patients the therapeutic window for tPA is along the order of 3-6 hours after stroke onset. Thus, there appears to be a two- to threefold differential between the observed times for effectiveness of tPA in the rabbit model compared with patients. Consistent with this hypothesis, in the RSCEM, NILT was effective up to 6 hours following a stroke and as predicted by the model, the NEST-1 clinical trial cited above found that laser therapy improved clinical rating scores if patients were treated within 24 hours following a stroke. Thus, because of the time differential discussed above, it would appear that NILT may be useful in patients if they present at a clinic within 24 hours of a stroke.

The NEST-1 study cited above has provided some indication that transcranial laser therapy may be a useful approach to treating motor function deficits resulting from ischemic strokes when laser therapy is initiated 2-24 hours following the stroke. The first trial of the NEST-I study used a CW mode with a power density of 10 mW/cm$^2$ at 20 pre-determined locations on the scalp for 2 minutes of irradiation at each site. The preliminary results from the NEST-1 trial of 120 Acute ischemic stroke patients (biased design of 1:2) with a treatment time between 2 and 24 hours (median time 18 hours) showed that more patients in the laser-treated group had successful outcomes from baseline to 90 days, measured by a mean change in the NIHSS and mRS scores, than did controls (P=0.035, stratified by severity and time to treatment; P=0.048, stratified by severity alone). The positive results documented for NILT in animal models of stroke prompted the initiation of the NEST-II trial, a prospective, intent-to-treat, multi-center, international, double-blinded trial sponsored by the manufacturers of the transcranial laser device, PhotoThera Inc.

NILT effectively improves behavioral deficits when applied to the rabbit brain using PWs of light energy. While the data do support the use of NILT therapy in a clinical setting, the differential results obtained using CW and PW treatment suggest that the use of a PW mode of NILT will be most beneficial to patients to improve motor function and overall well-being.

Phototherapy Example 5

In another example study performed under contract with Neurological Testing Service, Inc. (Charleston, S.C.), Infrared Transcranial Laser Therapy (TLT) was tested for efficacy in an amyloid precursor peptide (APP) transgenic mouse model of Alzheimer's Disease (AD). Laser light therapy was administered three times per week at various doses for 26 weeks, starting at 3 months of age, and the results were compared to no laser (control group). Animals were examined for amyloid load, inflammatory markers, brain Aβ levels, plasma Aβ levels, CSF Aβ levels, sAPP levels, and NS behavioral changes. The number of AP plaques was significantly reduced in the brain with administration of laser therapy in a dose dependent fashion. Administration of laser therapy demonstrated a dose dependent reduction in amyloid load. All therapies were effective in the reduction in amyloid deposition. All laser treatments reduced the behavioral effects seen with advanced amyloid deposition. Overall, laser therapy was effective at limiting the extent of Aβ amyloid in the brain and reversing the effect of deposition of Aβ peptide and behavioral deficits in the mouse. In addition, the laser therapies were able to reduce the expression of inflammatory markers in the APP transgenic mice. Aβ peptide levels were significantly changed in the brains of the APP transgenic mice, and there was no detectable difference in plasma Aβ peptide levels. Studies showed an increase in sAPPβ and a decrease in sAPPβ levels consistent with inhibition of the -secretase activity. These studies suggest that laser light therapy is a potential candidate for therapeutic treatment of AD.

As used herein, the following abbreviations have the following definitions:

| Abbreviations | Definition |
|---|---|
| Aβ | Abeta |
| APP | Amyloid Precursor Protein |
| Aβ peptide | Abeta peptide |
| AD | Alzheimer's Disease |
| 4G8 | Abeta peptide antibody |
| PTI | PhotoThera, Inc. |
| NTS | Neurological Testing Service, Inc. |
| BACE | Beta secretase |
| IL-1 | Interleukin-1 |
| TNF-α | Tumor necrosis factor-α |
| TGF-β | Transforming growth factor-β |

Aβ containing senile plaques are one of the neuropathological hallmarks of Alzheimer's Disease (AD) and a considerable effort has been expended in understanding the relationship of Aβ and Aβ-containing senile plaques to AD. Much of this work has focused on the biosynthesis of Aβ and factors that influence its deposition. The A peptides are primarily two peptides of either 40 or 42 amino acids generated via internal proteolysis of its precursor, the amyloid precursor protein (APP). In addition to Aβ-containing senile plaques, a variety of neuronal cytoskeletal alterations are prominent features of AD neuropathology. These include phospho-tau containing neurofibrillary tangles, free-lying dystrophic neurites and those present in neuritic senile plaques, and synapse loss. Whether these abnormal features are the result of or cause of neuronal loss is still controversial. Regardless of the precise mechanism, this neuronal and synaptic loss leads to cognitive decline. Early onset autosomal dominant AD is directly linked to mutations in one of several genes: APP, presenilin 1 (PS 1), or presenilin 2 (PS2). In addition several risk factor genes, most notably the APOE4 allele, alter risk for later onset AD, and it is clear that mutations or polymorphisms in several other genes can lead to similar AD phenotypes.

The A peptide is derived from APP, which is cleaved by the sequential action of the γ and γ-secretases. The β-site APP cleavage enzyme (BACE) is a member of the membrane bound aspartyl proteases which results in the cleavage of APP on the extracellular side of the membrane releasing the soluble APP-β (sAPP) fragment. In addition, the γ-secretase enzyme (a complex of PS-1 and PS-2) cleaves the transmembrane domain to release the Aβ peptide and carboxyl terminus. The α-secretase enzyme is the predominant APP activity that cleaves in the middle of the Aβ peptide and prevents the generation of the Aβ peptide. Altered functions of these enzymes can lead to the enhanced production of Aβ peptide, which may contribute to AD pathogenesis. A number of studies have shown that mutations in the APP gene or in presenilins result in the increase in.—secretase cleavage and the production of both Aβ1-40 and Aβ1-42. In addition, a depletion of cholesterol using cholesterol lowering-agents produced a decrease in Aβ peptide synthesis and sAPP-α. Therefore, understanding the mechanisms associated with altered Aβ processing and the role of β-secretase in the process will help in the design of selective inhibitors of β-secretase and eventually therapeutic treatment of AD.

Methods and Materials

The amyloid precursor protein (APP) transgenic model of mouse Aβ peptide amyloidosis was used. APP transgenic mice were administered no laser or laser therapy as outlined below 3x/week for 26 weeks starting at 3 months of age. At the end of the experiment, animals were subject to behavioral analysis, were sacrificed and the brains were divided in half and prepared as follows: ½ brain was examined for Aβ plaque burden in the brain (i.e., plaque number), and inflammatory markers and the second ½ of the brain was homogenized for brain Aβ peptide level and sAPP levels. Animals were treated daily at 1 pm and were tested on days 176-179 for the behavioral studies and the final trials were performed on the 26$^{th}$ week (four hours after the treatment). Animals were sacrificed immediately after training and plasma, CSF and brain were collected for analysis.

A control APP group was used to determine the baseline of amyloid deposits (treatment was simulated with the laser disabled, no laser energy). The group started as 3 month old mice and maintained in the study for 26 weeks to reach 9 months of age. In addition, at the end of the study, the animals were subjected to behavioral (Morris water maze) analysis. NTS was not blinded to the study parameters. The laser was prepared by PTI and shipped to NTS. The animals were subjected to behavioral studies, amyloid load, Aβ peptide analysis, inflammatory markers, sAPP levels, brain and plasma for Aβ analysis. The animals in each of the groups were allowed to complete the study and all protocols were carried out after 26 weeks. Endpoints were as follows:

Amyloid load in brain (left hemisphere)
Inflammatory markers in brain (IL-I, TNF-alpha, TGF-β)
Aβ 1-40, 1-42 in brain (½ from animals/plasma from all animals)
Plasma Aβ levels (13 and 26 weeks: 4 hrs post dose).
sAPPα and levels from brain. Brain collection (week 26 only) for brain/plasma/CSP Aβ peptide levels.
Gross necropsy examination
Behavior analysis—MWM performed during the last week of treatment, animals to be sacrificed after last administration. Test includes tracking of swimming distance and time to reach platform.

Male APP transgenic mice (NTS, Inc.) weighing approximately 35-40 grams each were given free access to food and water before and during the experiment. The animals were administered laser therapy. The laser was prepared by PTI and delivered to NTS. The APP mice (male) used in this experiment were designed by microinjection of the human APP gene (with the Swedish and London mutations) into mouse eggs under the control of the platelet-derived growth factor B (PDGF-B) chain gene promoter. The mice were generated on a C57BL/6 background and were developed by MTI. Animals were housed in the Medical University of South Carolina Animal Facility under a 12:12 light:dark cycle. Animals were housed in standard non-sterile rodent microisolator cage, with filtered cage top and housed 4 to a cage. Animals were fed ad libitum and maintained by brother sister mating. Transgenic animals were identified by PCR analysis. The mice generated from this construct, develop amyloid deposits starting at 6 months of age. Animals were aged for 3 months and then maintained for 26 weeks and sacrificed for amyloid quantification.

For histological examination, the animals were anesthetized with an intraperitoneal injection of sodium pentobarbital (50 mg/kg). The animals were transcardially perfused with 4° C., phosphate-buffered saline (PBS) followed by 4% paraformaldehyde. The brains were removed and placed in 4% paraformaldehyde over night. The brains were processed to paraffin and embedded. Ten serial 30-μm thick sections through the brain were obtained. Tissue sections were deparaffinized and washed in Tris buffered saline (TB S) pH and blocked in the appropriate serum (mouse). Sections were blocked overnight at 4° C. and then subjected to primary antibody overnight at 4° C. (Aβ peptide antibody, 4G8, Signet) in order to detect the amyloid deposits in the brain of the transgenic animals. Sections were washed in TBS and secondary antibody (Vector Laboratories) was added and incubated for 1 hour at room temperature. After washing the sections were incubated as instructed in the Vector ABC Elite kit (Vector Laboratories) and stained with diaminobenzoic acid (DAB). The reactions were stopped in water and cover slipped after treatment to xylene. The amyloid area in each section was determined with a computer-assisted image analysis system, consisting of a Power Macintosh computer equipped with a Quick Capture frame grabber card, Hitachi CCD camera mounted on an Olympus microscope and camera stand. NIH Image Analysis Software, v. 1.55 was used. The images were captured and the total area of amyloid was determined over the ten sections. A single operator blinded to treatment status performed all measurements. Summing the amyloid volumes of the sections and dividing by the total number of sections calculated the amyloid volume per animal.

For quantitative analysis, we used an enzyme-linked immunosorbent assay (ELISA) to measure the levels of human $A\beta_{1-40}$ and $A\beta_{1-42}$ in the brains of APP transgenic mice (IBL, 27718 for 1-40 and 27711 for 1-42). $A\beta_{1-40}$ and $A\beta_{1-42}$ were extracted from mouse brains as described below:

1. Weighed frozen hemi-brains.
2. Prepared Tissue Homogenization Buffer (THB-see following recipe) by adding Protease Inhibitor Cocktail (PIC, Sigma) 1:1000 dilution immediately before use.
3. Homogenized hemi-brains in 1 mL of THB+PIC per each 100 mg of tissue (e.g. 2.2 mL of buffer was used to homogenize a hemi-brain weighing 220 mg).
4. Homogenized brains (using polytron) and samples were aliquoted and snap frozen in liquid nitrogen.

Tissue Homogenization Buffer (THB):
(250 mM sucrose, 20 mM tris base, 1 mM EDTA, 1 mM EGTA)

| 5 mL | 1M Tris base (pH 7.4) |
|---|---|
| 21.4 g | sucrose |
| 0.5 mL | 0.5M EDTA |
| 1.0 mL | 0.25 EGTA |

Added ddH$_2$O to 250 mL.
Sterile filtered and handled aseptically.
Stored at 4° C.
ELISA assays were performed as described by the manufacturer (IBL):

1) The wells for reagent blank were determined. 100₄, each of "4, EIA buffer" was put into the wells.
2) Wells for test sample blank, test sample and diluted standard were determined. Then, 100₄, each of test sample blank, test sample and dilutions of standard were placed into the appropriate wells.
3) The precoated plate for were incubated overnight at 4° C. after covering it with plate lid.
4) Each well of the precoated plate was washed vigorously with wash buffer using washing bottle (3 times). Then, each well was filled with wash buffer and place the precoated plate for 15-30 seconds. Wash buffer was removed completely from the precoated plate by snapping. This procedure was repeated more than 7 times. Then, the remaining liquid was removed from all wells completely by snapping the precoated plate onto paper towel.

5) 100 µL of labeled antibody solution was pipetted into the wells of test samples, diluted standard and test sample blank.
6) The precoated plate was incubated for 1 hour at 4° C. after covering it with plate lid.
7) The precoated plate was washed 9 times in the same manner above (4).
8) The required quantity of "6, Chromogen" was pipetted into a disposable test tube. And then, 100 µL was pipetted from the test tube into the wells.
9) The precoated plate was incubated for 30 minutes at room temperature in the dark.
10) 100 µL of "7, Stop solution" was pipetted into the wells. The liquid was mixed by tapping the side of precoated plate.
11) The plate reader was run and measurement conducted at 450 nm. The measurement shall be done within 30 minutes after the addition of "7, stop solution".

For quantitative analysis of Aβ peptide levels in the plasma and CSF, an enzyme-linked immunosorbent assay (ELISA) was used to measure the levels of human $A\beta_{1-40}$ and $A\beta_{1-42}$ in the plasma and CSF of APP transgenic mice (IBL, 27718 for 1-40 and 27711 for 1-42). $A\beta_{1-40}$ and $A\beta_{1-42}$ ELISAs were performed as above. Blood was collect by saphenous vein collection or cardiac puncture (terminal bleed) in lithium:heparin and plasma was prepared by centrifugation. CSF was collected an analyzed.

For sAPP assays in the hemibrain, Western blot analysis, extracts containing 20-50 µg of total protein were mixed with Tris/glycine reducing buffer, denaturing loading buffer, loaded, and electrophoresed on 8% Tris/glycine gels (Invitrogen). Gels were transferred to nitrocellulose membranes, incubated with the respective primary antibodies followed by secondary antibodies conjugated to horseradish peroxidase and processed for visualization by enhanced chemiluminescence ECL Plus™ (Amersham Biosciences). The 6E10 monoclonal Ab (Signet, Dedham, Mass.) recognizes the first 17 amino acids of the Aβ peptide. 6E10 Ab was used for Western blotting to detect soluble APPα. Rabbit 869 antibody was used to detect sAPPβ by Western blotting. Secondary antibodies conjugated to horseradish peroxidase were from Jackson ImmunoResearch (West Grove, Pa.).

For immunohistochemical analysis for cytokine evaluation in the hemibrain, tissue sections were deparaffinized and washed in Tris buffered saline (TBS) pH 7.4 and blocked in the appropriate serum (goat). Sections were blocked overnight at 4° C. and then subjected to primary antibody overnight at 4° C. Sections were washed in TBS and secondary antibody was added and incubated for 1 hour at room temperature. After washing the sections were incubated as instructed in the Vector ABC Elite kit and stained with diaminobenzoic acid (DAB). The reactions were stopped in water and cover slipped after treatment to xylene.

Morris water-maze testing was used for behavioral analysis. All mice were tested once in the Morris water maze test at the end of the experiment. Mice were trained in a 1.2 m open field water maze. The pool was filled to a depth of 30 cm with water and maintained at 25° C. The escape platform (10 cm square) was placed 1 cm below the surface of the water. During the trials, the platform was removed from the pool. The cued test was carried out in the pool surrounded with white curtains to hide any extra-maze cues. All animals underwent non-spatial pretraining (NSP) for three consecutive days. These trials are to prepare the animals for the final behavioral test to determine the retention of memory to find the platform. These trials were not recorded (for training purposes only). For the training and learning studies, the curtains were removed to extra maze cues (this allowed for identification of animals with swimming impairments). On day 1, the mice were placed on the hidden platform for 20 seconds (trial 1), for trials 2-3 animals were released in the water at a distance of 10 cm from the cued-platform or hidden platform (trial 4) and allowed to swim to the platform. On the second day of trials, the hidden platform was moved randomly between the center of the pool or the center of each quadrant. The animals were released into the pool, randomly facing the wall and were allowed 60 seconds to reach the platform (3 trials). In the third trial, animals were given three trials, two with a hidden platform and one with a cued platform. Two days following the NSP, animals were subjected to final behavioral trials (Morris water maze test). For these trials (3 per animal), the platform was placed in the center of one quadrant of the pool and the animals released facing the wall in a random fashion. The animal was allowed to find the platform or swim for 60 seconds (latency period, the time it takes to find the platform). All animals were tested within 4-6 hours of dosing and were randomly selected for testing by an operator blinded to the test group. Animals were tested on days 176-179 for the non-spatial pretraining and the final trials were performed on day 180.

The results are expressed as the mean±standard error of mean (SEM). The significance of differences in the amyloid and behavioral studies were analyzed using a t-test. Comparisons were made between the 9-month-old APP control group (baseline group —started at 3 months of age) and the 9-month old treated mice. Differences below 0.05 were considered significant. Percent changes in amyloid and behavior were determined by taking the summation of the data in each group and dividing by the comparison (i.e., treated/9 month control=% change). Animals that developed severe complications following administration of laser were excluded from the study.

Animals (100 mice) were subjected to administration of no laser or laser for two minutes 3x/week beginning at 3 months of age and continued for 6 months. Animals were male and were randomly assigned to the different treatment groups per Table 12 and Table 13.

TABLE 12

| Treatment Mode[1] | Temporal Format | Radiant Power at the Skin[2] | Beam diameter at the Skin | Irradiance at the Skin[3] | Regime (Treatment Frequency) |
|---|---|---|---|---|---|
| Regime Control (20) | OFF | 0 mW | N/A | 0 W/cm² | 3 x Week |
| CW (20) | Continuous | 40 mW | 3 mm | 1.3 W/cm² | 3 x Week |
| Pulsed I (20) | ON = 2 mSec; @, 100 Hz | 40 mW | 3 mm | 1.3 W/cm² | 3 x Week |

TABLE 12-continued

| Treatment Mode[1] | Temporal Format | Radiant Power at the Skin[2] | Beam diameter at the Skin | Irradiance at the Skin[3] | Regime (Treatment Frequency) |
|---|---|---|---|---|---|
| Pulsed II (20) | ON = 2 mSec; @, 100 Hz | 200 mW | 3 mm | 6.4 W/cm$^2$ | 3 x Week |
| Pulsed III (20) | ON = 2 mSec; @, 100 Hz | 400 mW | 3 mm | 12.7 W/cm$^2$ | 3 x Week |

[1]Total Number of Animals = 100
[2]These values are based on tissue transmission and scattering measurements done on mice at earlier TLT studies (Ischemic Stroke and TBI), and updated based on measurements of scalp/skull transmission and scatter on two APP mice. The measured data was used to calculate the Radiant Power at the skin -- Table 13, needed to deliver the irradiances listed to the animals Dura.
[3]These are calculated values showing average Irradiances for Continuous TLT and Peak Irradiances for Pulsed TLT. Irradiance at the Skin = Radiant Power/Area of beam = Radiant Power/($\pi$ * (0.1 cm)$^2$) = Radiant Power/0.0314 cm$^2$

TABLE 13

| Treatment Mode | Group Name for Tables and Figures | Temporal Format | Radiant Power at the Skin | Irradiance at the Dura[1] |
|---|---|---|---|---|
| Regime Control | A | OFF | 0 mW | 0 mW/cm$^2$ |
| CW | B | Continuous | 40 mW | 10 mW/cm$^2$ |
| Pulsed I | C | ON = 2 mSec; @, 100 Hz | 40 mW | 10 mW/cm$^2$ |
| Pulsed II | D | ON = 2 mSec; @, 100 Hz | 200 mW | 50 mW/cm$^2$ |
| Pulsed III | E | ON = 2 mSec; @, 100 Hz | 400 mW | 100 mW/cm$^2$ |

[1]These are calculated values showing average Irradiances for Continuous TLT and Peak Irradiances for Pulsed TTL.

Results

Figure 44:
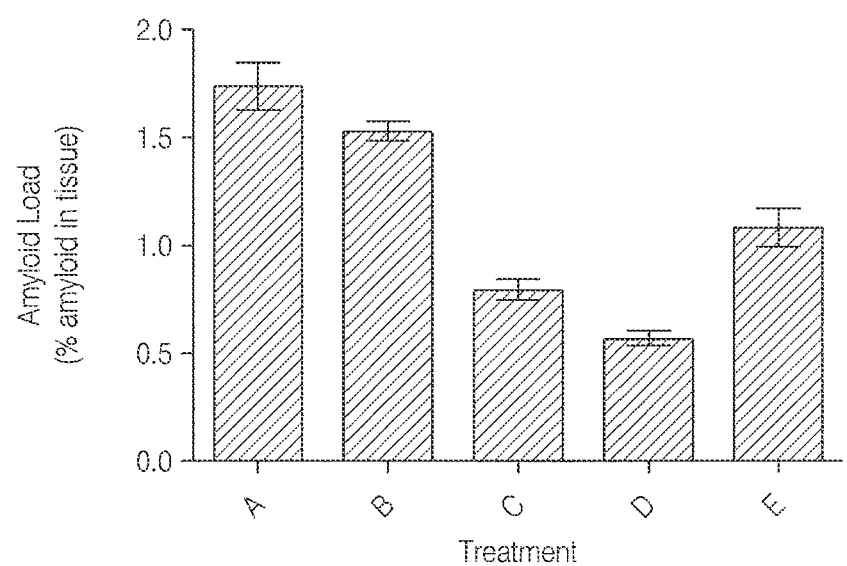
FIG. 44 shows the effect of LLT on Aβ amyloid deposition in the mouse with mean±SEM for each group. APP transgenic animals were treated with TLT and no laser, treatments were administered starting on day 0 (3 months of age) and continued for 26 weeks (3×/week treatment). Animals were sacrificed on the 26th week and processed to determine the amyloid burden.

The laser was provided as a powder to NTS. Amyloid load was determined in the animals treated with laser therapy and no laser. Table 14 and FIG. 44 illustrate the results. The no laser group demonstrated a ~2% amyloid burden which is the standard level of amyloid in this particular model at ~9 months of age (previous studies). The laser therapy demonstrated a dose dependent attenuation of the amyloid load when compared to the vehicle group. At all doses except CW, the amount of amyloid actually was lower than in the 9 month control group indicating that the laser therapy not only stopped amyloid deposition, but may have even reversed the level of amyloid. This suggests that the laser therapy was capable of attenuating the amyloid in these mice. There were no deaths in this study. Animals were examined for gross abnormalities following sacrifice. No gross pathological features were detected in the animals.

TABLE 14

Percent decrease in amyloid in the brain

| Treatment | Percent change in A amyloid* | A amyloid Burden % +/- SEM | P-value** |
|---|---|---|---|
| No laser | NA | 1.741 ± 0.1120 | NA |
| CW | -11.8% | 1.535 ± 0.04399 | 0.0951 |
| Pulse I | -54% | 0.8015 ± 0.05021 | <0.0001 |
| Pulse II | -67% | 0.5740 ± 0.03374 | <0.0001 |
| Pulse III | -37.3% | 1.091 ± 0.09192 | <0.0001 |

*Percent changes are compared to no laser
**P value compared to no laser

Figure 45A:
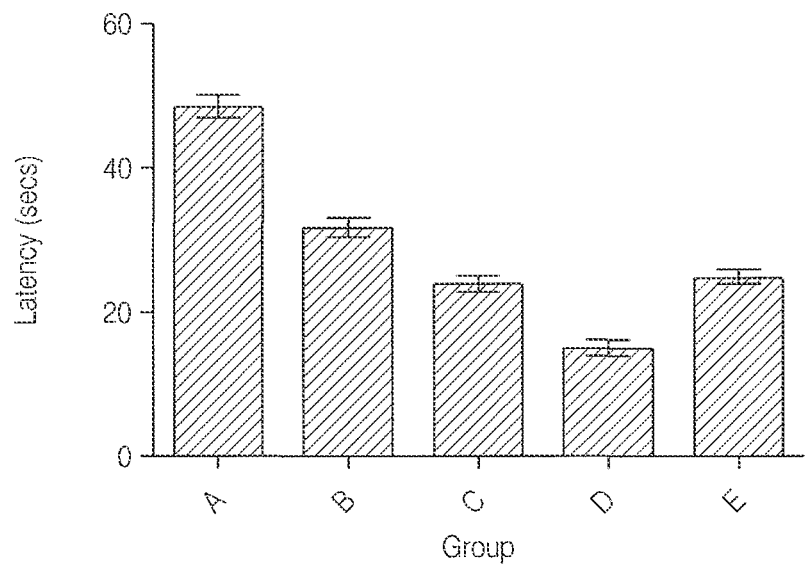
FIG. 45A shows the effects of LLT on latency time to find hidden platform (Morris water maze) with mean±SEM for each group. APP transgenic animals were treated with TLT and no laser, treatments were administered starting on day 0 (3 months of age) and continued until day 180 (3×/week treatment), and were subjected to water maze and the time to reach the platform was recorded. Animals were analyzed for day 180 and processed to determine the latency time.

The behavioral effects (behavior and distance) of treatment with laser therapy were determined in the APP transgenic mice at the termination of the experiment. Mice were subjected to the Morris water maze task and the latency period and distance were determined. Table 15 and FIG. 45A illustrate the results. The no laser control demonstrated a latency time of 48.58 seconds, which is the standard in this particular model at ~9 months of age (previous studies). All the laser treated animals demonstrated a significant difference in latency when compared to the control. This suggests that laser therapy was capable of attenuating the latency time in these mice.

TABLE 15

Behavioral changes in APP transgenic mice treated with LLT.

| Treatment | % Change in Latency Period* | Latency time (sec) | P value** |
|---|---|---|---|
| No laser | NA | 48.58 ± 1.421 | NA |
| CW | -34.5% | 31.82 ± 1.382 | <0.0001 |
| Pulse I | -50.5% | 24.05 ± 1.060 | <0.0001 |
| Pulse II | -68.8% | 15.15 ± 1.082 | <0.0001 |
| Pulse III | -48.6% | 24.99 ± 0.9763 | <0.0001 |

*Percent changes are compared to no laser
**P value compared to no laser

Figure 45B:
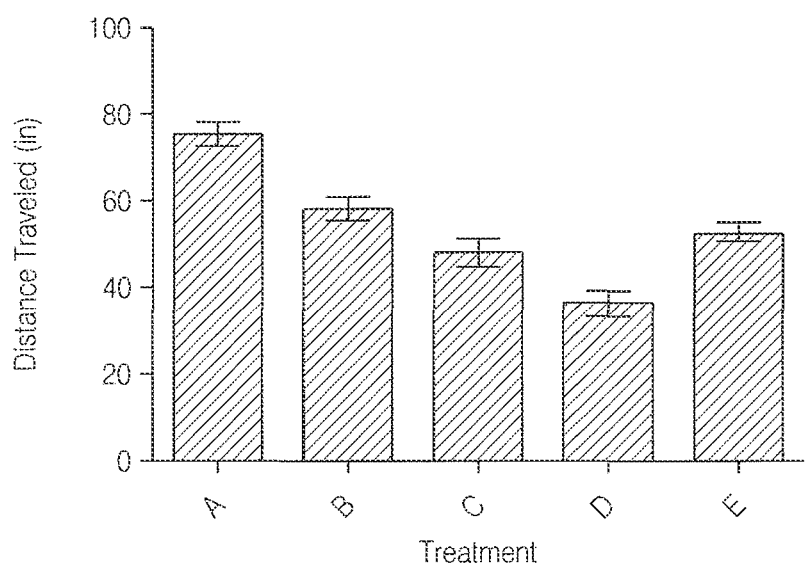
FIG. 45B shows the effects of LLT on distance to find hidden platform (Morris water maze) with mean±SEM for each group. APP transgenic animals were treated with TLT and no laser, treatments were administered starting on day 0 (3 months of age) and continued for 26 weeks (3×/week treatment), and were subjected to water maze and the distance to reach the platform was recorded. Animals were analyzed and processed to determine the distance.

Table 16 and FIG. 45B illustrates the results comparing distance traveled in the water maze. The vehicle control demonstrated a distance of 75.53 in, which is the standard in this particular model at ~9 months of age (previous studies). All the animals demonstrated a significant difference in distance when compared to the control group. This suggests that laser therapy was capable of attenuating the behavioral effects in these mice.

TABLE 16

Behavioral changes in APP transgenic mice treated with LLT.

| Treatment | % Change in Distance* | Distance (in) | P value** |
|---|---|---|---|
| No laser | NA | 75.53 ± 2.746 | NA |
| CW | -22.9% | 58.27 ± 2.710 | <0.0001 |

TABLE 16-continued

Behavioral changes in APP transgenic mice treated with LLT.

| Treatment | % Change in Distance* | Distance (in) | P value** |
|---|---|---|---|
| Pulse I | −36.1% | 48.24 ± 3.184 | <0.0001 |
| Pulse II | −51.5% | 36.60 ± 2.737 | <0.0001 |
| Pulse III | −29.6% | 53.15 ± 2.206 | <0.0001 |

*Percent changes are compared to no laser
**P value compared to no laser

Figure 46A:
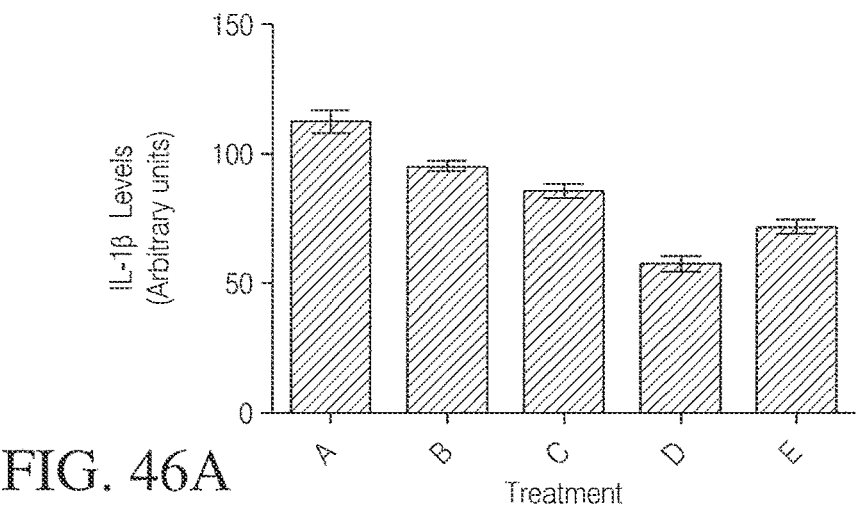
FIGS. 46A-46C show the effects of LLT on inflammatory mediators in the brain of APP transgenic mice with mean±SEM for each group. APP transgenic animals were treated with TLT and no laser, treatments were administered starting on day 0 (3 months of age) and continued for 26 weeks (3×/week treatment). Animals were sacrificed on the 26th week and processed to determine the inflammatory markers, interleukin-I (IL-I), tumor necrosis factor-α (TNF) and transforming growth factor-β (TGF-β). Animals were analyzed and processed to determine the inflammatory markers via immunohistochemical and image analysis.
Figure 46B:
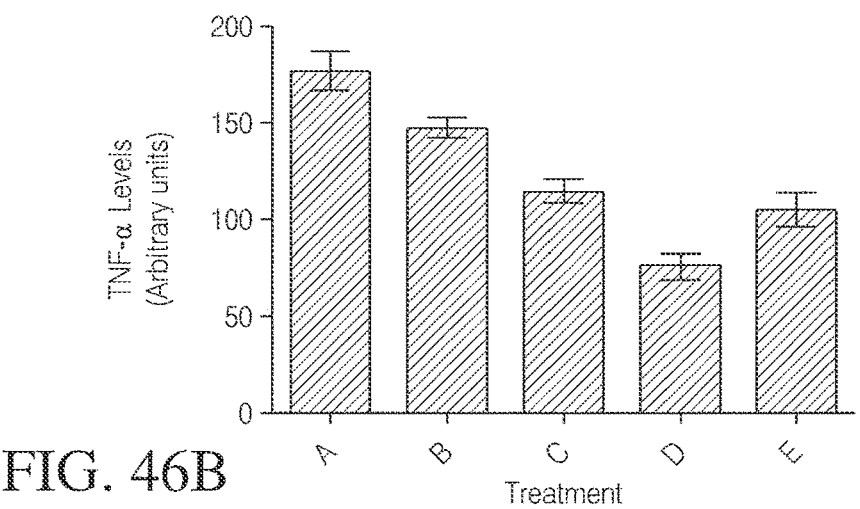
Figure 46C:
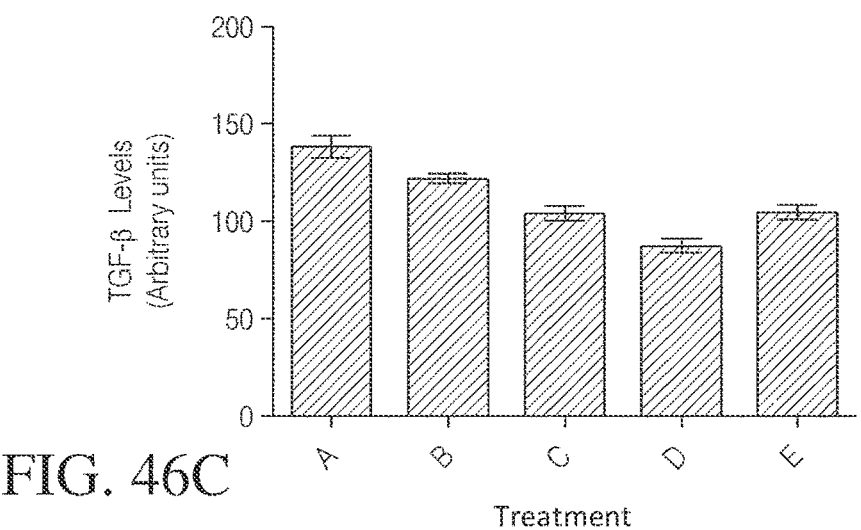

The effect of laser therapy was determined on the expression of inflammatory markers (IFMs) in the brain of APP transgenic mice (FIGS. 46A-46C and Table 17). Table 17 and FIGS. 46A-46C illustrate the results of the animals terminated at 26 weeks after the start of treatment. The no laser control demonstrated specific staining for inflammatory markers (IL-I, TNF and TGF-β) as indicated in Table 17, which are the standard in this particular model at ~9 months of age (previous studies). Laser therapy at all the doses demonstrated a significant difference from the control animals. This suggests that laser therapy was capable of attenuating the IFMs in these mice.

TABLE 17

Changes in inflammatory markers in APP transgenic mice treated with LLT*.

| Treatment | % Change in IL-I intensity units +/− SEM) | % Change in TNF intensity units +/− SEM) | % Change in TGF- intensity units +/− SEM) |
|---|---|---|---|
| No laser | 0% (112.6 ± 4.305) | 0% (178.0 ± 10.26) | 0% (137.6 ± 5.428) |
| CW | −15.3% (95.35 ± 2.164) <br> p = 0.010 | −16.9% (148.0 ± 5.494) <br> p = 0.0139 | −11.9% (121.2 ± 2.597) <br> p = 0.0096 |
| Pulse I | −23.6% (85.80 ± 2.448) <br> p = >0.0001 | −35.3% (115.2 ± 6.161) <br> p = >0.0001 | −24.6% (103.7 ± 3.373) <br> p < 0.0001 |
| Pulse II | −48.9% (57.50 ± 2.948) <br> p = >0.0001 | −57.5% (75.68 ± 6.875) <br> p = >0.0001 | −36.8% (86.99 ± 3.660) <br> p < 0.0001 |
| Pulse III | −36.1% (71.92 ± 2.512) <br> p = >0.0001 | −40.8% (105.3 ± 9.080) <br> p = >0.0001 | −24.4% (104.0 ± 3.836) <br> p < 0.0001 |

*Percent changes are compared to no laser

Figure 47A:
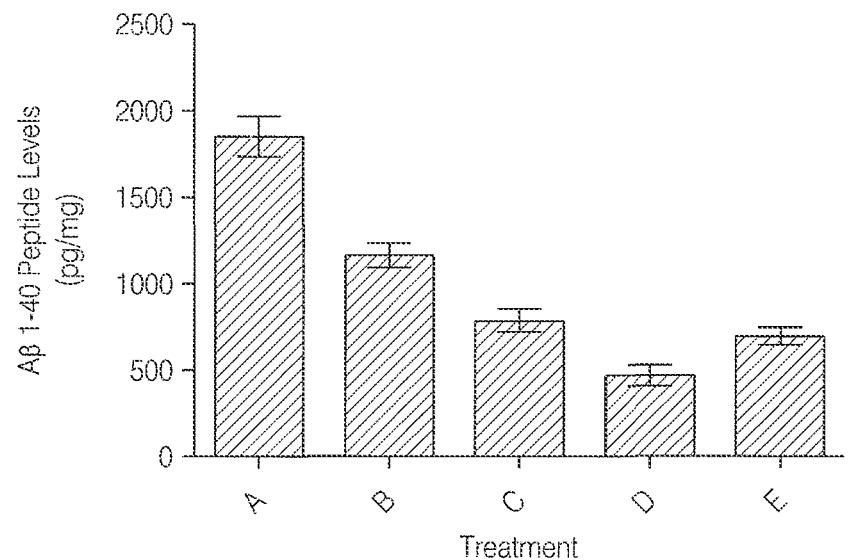
FIGS. 47A and 47B show the effects of LLT on Aβ peptide levels in the brain of APP transgenic mice with mean±SEM for each group. APP transgenic animals were treated with TLT and no laser, treatments were administered starting on day 0 (3 months of age) and continued for 26 weeks (3×/week treatment). Animals were sacrificed on the 26th week, and the brains were subjected to Aβ peptide analysis and compared to no laser control. Animals were analyzed and processed to determine the brain AP peptide levels.
Figure 47B:
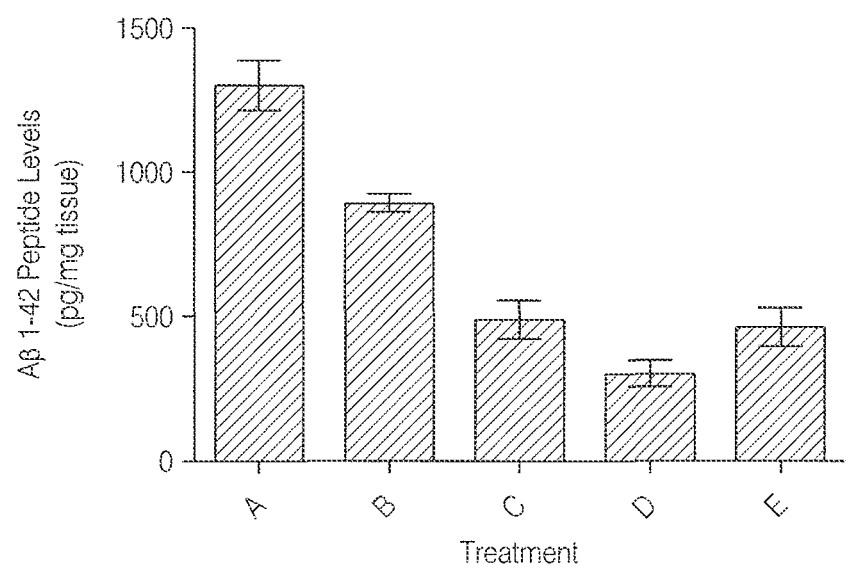

The effect of laser therapy was determined on the changes in A peptide in the brain of APP transgenic mice (FIGS. 47A and 47B and Tables 18 and 19). Measurement of Aβ 1-40 and Aβ 1-42 peptide (guanidine extractable) in the brain showed an increase as the APP transgenic mice aged from 3 to 9 months. Table 18 and FIG. 47A illustrates the results of the animals terminated at 26 weeks after the start of treatment. The control demonstrated the levels of Aβ 1-40 in the brain as indicated in Table 18, which is the standard in this particular model at ~9 months of age (previous studies). Laser therapy at all doses demonstrated a decrease in Aβ 1-40 when compared to the control and they were significant. This suggests that laser therapy was capable of attenuating the A 1-40 increase in these mice.

TABLE 18

Changes in A peptide levels in the brain of APP transgenic mice

| Treatment | % Change in A 1-40 peptide levels (pg/mg tissue +/− SEM)* | P value** |
|---|---|---|
| No laser | NA (1849 ± 117.4) | NA |
| CW | −37% (1165 ± 68.12) | <0.0001 |
| Pulse I | −57.1% (792.6 ± 68.39) | <0.0001 |

TABLE 18-continued

Changes in A peptide levels in the brain of APP transgenic mice

| Treatment | % Change in A 1-40 peptide levels (pg/mg tissue +/− SEM)* | P value** |
|---|---|---|
| Pulse II | −74.3% (476.2 ± 59.75) | <0.0001 |
| Pulse III | −62% (702.2 ± 50.10) | <0.0001 |

*Percent changes are compared to no laser
**P value compared to no laser

Table 19 and FIG. 47B illustrates the results of the animals terminated on the 26$^{th}$ week after the start of treatment for Aβ 1-42 peptide levels. The control demonstrated the levels of Aβ 1-42 in the brain as indicated in Table 19, which is the standard in this particular model at ~9 months of age (previous studies). Laser therapy at all doses demonstrated a significant decrease in Aβ 1-42 when compared to control. This suggests that laser therapy was capable of attenuating the Aβ 1-42 peptide levels in these mice.1

TABLE 19

Changes in Aβ peptide levels in the brain of APP transgenic mice

| Treatment | % Change in Aβ 1-42 peptide levels (pg/mg tissue +/− SEM) | P value** |
|---|---|---|
| No laser | NA (1306 ± 86.60) | NA |
| CW | −31.4% (896.4 ± 31.95) | <0.0001 |
| Pulse I | −62% (495.7 ± 67.13) | <0.0001 |
| Pulse II | −76.4% (308.2 ± 44.68) | <0.0001 |
| Pulse III | −63.9% (471.3 ± 64.11) | <0.0001 |

*Percent changes are compared to no laser
**P value compared to no laser

Figure 48A:
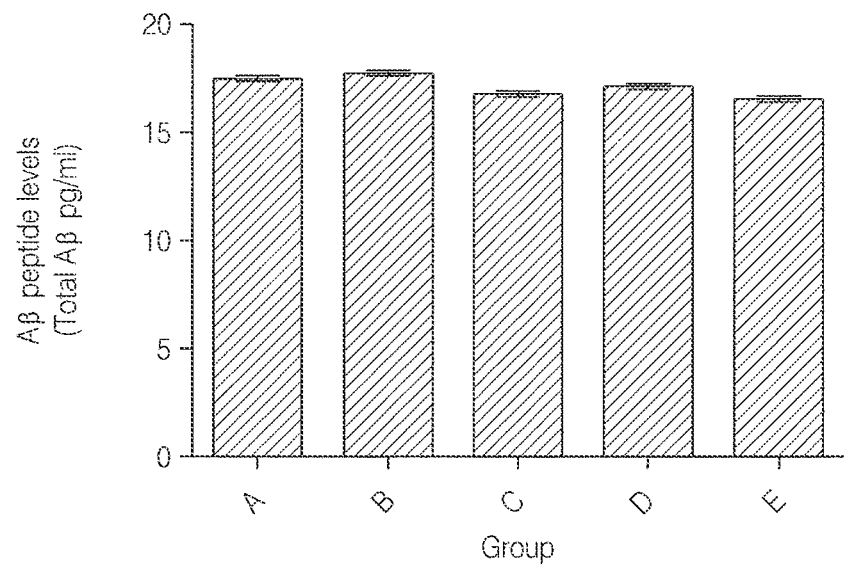
FIGS. 48A and 48B show the effects of LLT on Aβ peptide levels in the plasma of APP transgenic mice at 13 and 26 weeks, respectively, with mean±SEM for each group. APP transgenic animals were treated with TLT and no laser, treatments were administered starting on day 0 (3 months of age) and continued for 26 weeks (3×/week treatment), and the plasma was subjected to Aβ peptide analysis and compared to no laser control. Blood was collected from APP transgenic animals on the 13th and 26th week and processed to determine the plasma Aβ peptide levels.
Figure 48B:
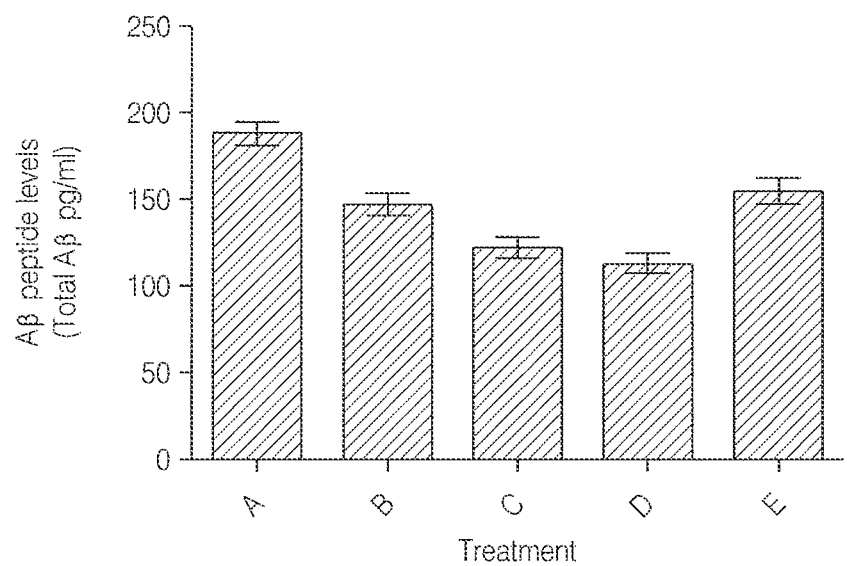

The effect of laser therapy was determined on the changes in Aβ peptide levels in the plasma of APP transgenic mice (FIGS. 48A and 48B and Tables 20 and 21). Measurement of total Aβ peptide in the plasma was performed on weeks 13 and 26 in the APP transgenic mice treated from 3 to 9 months. As seen in the Tables 20 and 21 and FIGS. 48A and 48B, the total plasma Aβ peptide levels were similar in all groups for the 90 day time period. As the study progressed and the animals were treated with laser therapy, there was a significant change in the apparent plasma total Aβ peptide profile. This suggests that laser therapy was capable of lowering the plasma Aβ peptide levels, while brain Aβ peptide levels also changed.

TABLE 20

Changes in plasma total Aβ peptide levels in the APP transgenic mice treated with LLT. Week 13.

| Treatment | % Change in total Aβ peptide levels (pg/ml plasma +/− SEM) | P value** |
|---|---|---|
| No laser | NA (17.52 ± 0.08758) | NA |
| CW | +101.5% (17.78 ± 0.1051) | 0.0580 |
| Pulse I | −3.8% (16.86 ± 0.09818) | <0.0001 |
| Pulse II | −1.7% (17.23 ± 0.1104) | 0.0469 |
| Pulse III | −4.9% (16.67 ± 0.1206) | <0.0001 |

*Percent changes are compared to no laser
**P value compared to no laser

TABLE 21

Changes in plasma total Aβ peptide levels in the βtransgenic mice treated with LLT. Week 26.

| Treatment | % Change in total Aβ peptide levels (pg/ml plasma +/− SEM) | P value** |
|---|---|---|
| No laser | NA (187.8 ± 7.337) | NA |
| CW | −21.7% (147.0 ± 6.521) | <0.0001 |
| Pulse I | −35.3% (121.6 ± 6.325) | <0.0001 |
| Pulse II | −39.8% (113.0 ± 5.840) | <0.0001 |
| Pulse III | −17.7% (154.5 ± 7.647) | <0.0001 |

*Percent changes are compared to no laser
**P value compared to no laser

Figure 49A:
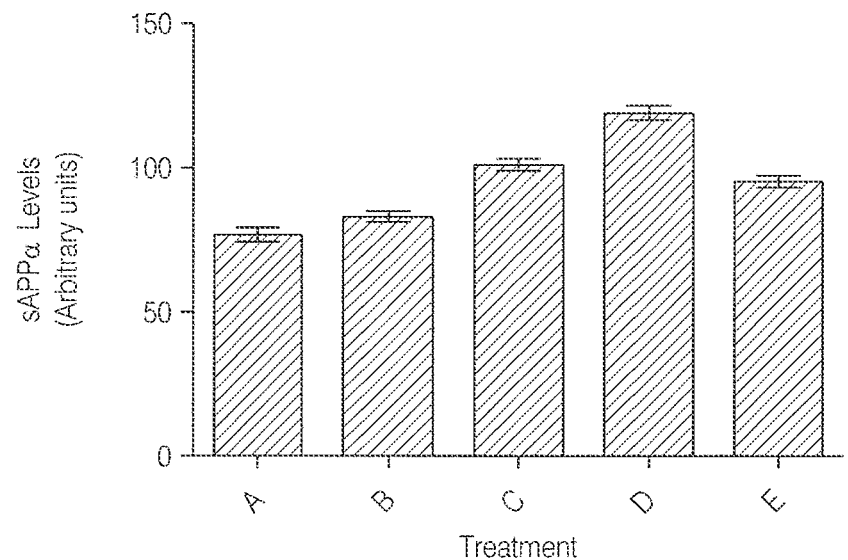
FIGS. 49A and 49B show the effects of LLT on sAPPα and CTF levels, respectively, in the brain of APP transgenic mice with mean±SEM for each group. APP transgenic animals were treated with TLT and no laser, treatments were administered starting on day 0 (3 months of age) and continued for 26 weeks (3×/week treatment) Animals were sacrificed on the 26th week, and the brain was subjected to sAPPα and CTFβ protein analysis by western blot and compared to no laser control. Animals were analyzed and processed to determine the brain protein levels.
Figure 49B:
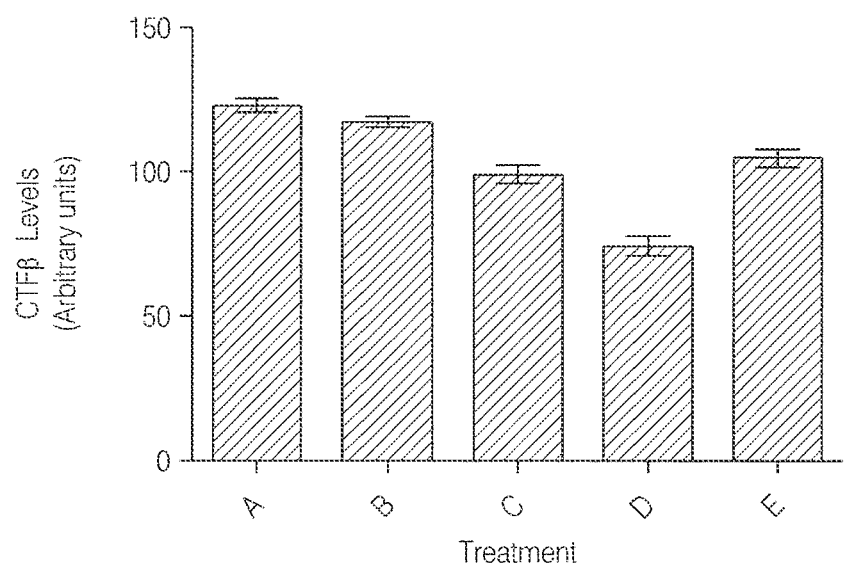

The effects of treatment with TTP-5854 laser therapy on sAPPα and CTFβ levels in the brain were determined in the APP transgenic mice at the termination of the experiment. Brain tissue was subjected to extraction and Western blot analysis for sAPPα and CTFβ levels following treatment. Tables 22 and 23 illustrate the results of the animals terminated at 26 weeks after the start of treatment. The control demonstrated a given level of sAPPα and CTFβ in the brain, which is the standard in this particular model at ~9 months of age (previous studies). Laser therapy demonstrated a significant difference in both sAPPα and CTFβ levels when compared to the control. For sAPPα, laser therapy at all doses demonstrated significant differences from the control (Table 22 and FIG. 49A). For CTFβ, again all doses of laser therapy demonstrated a significant difference from the control (Table 23 and FIG. 49B). This suggests that laser therapy was capable of increasing the sAPPα and decreasing CTFβ in these mice suggesting a shift from-to a-secretase activity.

TABLE 22

Changes in sAPPα levels in the brain of APP transgenic mice

| Treatment | % Change in sAPPα levels*(band intensity arbitrary units) +/− SEM?) | P value** |
|---|---|---|
| No laser | NA (76.74 ± 2.301) | NA |
| CW | +108.2% (83.05 ± 2.104) | 0.0463 |
| Pulse I | +131.2% (100.7 ± 1.994) | <0.0001 |
| Pulse II | +154.7% (118.7 ± 2.475) | <0.0001 |
| Pulse III | +123.5% (94.80 ± 2.018) | <0.0001 |

*Percent changes are compared to no laser
**P value compared to no laser

TABLE 23

Changes in CTFβ levels in the brain of APP transgenic mice

| Treatment | % Change in CTFβ levels* (band intensity arbitrary units +/− SEM) | P value** |
|---|---|---|
| No laser | NA (123.4 ± 2.261) | NA |
| CW | −4.8% (117.5 ± 2.142) | 0.0645 |
| Pulse I | −19.5% (99.31 ± 3.245) | <0.0001 |
| Pulse II | −39.7% (74.45 ± 3.492) | <0.0001 |
| Pulse III | −15% (104.9 ± 3.147) | <0.0001 |

*Percent changes are compared to no laser
**P value compared to no laser

Figure 50:
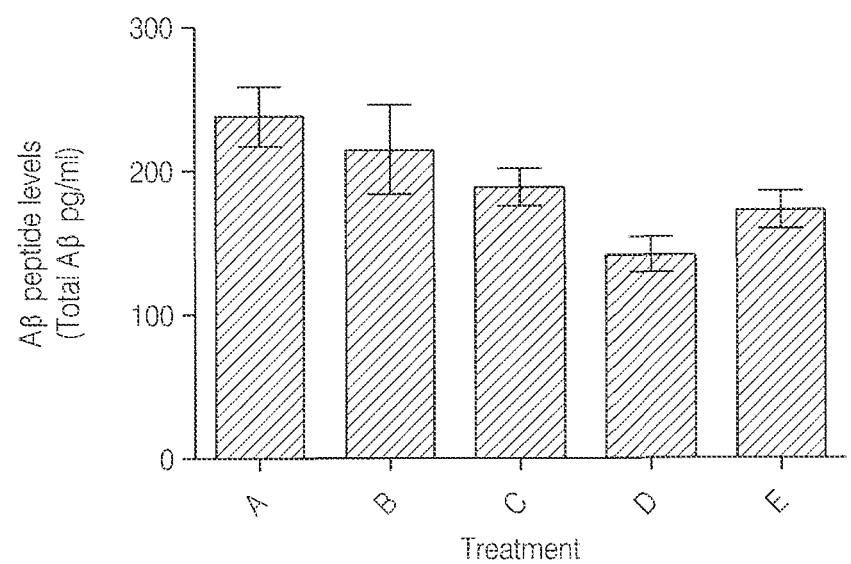
FIG. 50 shows the effect of LLT on CSF Aβ peptide levels in APP transgenic mice with mean±SEM for each group. APP transgenic animals were treated with TLT and no laser, treatments were administered starting on day 0 (3 months of age) and continued for 26 weeks (3×/week treatment). Animals were sacrificed on the 26th week, and the CSF was subjected to total Aβ peptide analysis by ELISA and compared to no laser control. Animals were analyzed and processed to determine the CSF Aβ peptide levels.

The treatment with laser therapy on CSF Aβ peptide levels was determined in the APP transgenic mice at the termination of the experiment (FIG. 50 and Table 24). Mice were subjected to ELISA for total Aβ peptide levels were determined because of the small amount of CSF obtained. Table 24 illustrates the results of the animals terminated at 26 weeks after the start of treatment. The control demonstrated Aβ peptide levels shown in Table 24, which is the standard in this particular model at −9 months of age (previous studies). CW and Pulse I demonstrated no significant difference in CSF when compared to the control. However, laser therapy at Pulse II and Pulse III demonstrated significant differences from the control (Table 24 and FIG. 50). This suggests that laser therapy was capable of attenuating the A peptide levels in the brain in these mice at specific doses.

TABLE 24

Changes in A peptide levels in the CSF of APP transgenic mice

| Treatment | % Change in CSF total Aβ peptide levels* (CSF total Aβ peptide levels and units +/− SEM) | P value** |
|---|---|---|
| No laser | NA (237.8 ± 20.70) | NA |
| CW | −9.8% (214.8 ± 30.64)1' | 0.5407 |
| Pulse I | −20.7% (188.7 ± 12.99) | 0.0598 |
| Pulse II | −39.6% (141.6 ± 12.40) | 0.0009 |
| Pulse III | −27.5% (172.4 ± 13.15) | 0.0157 |

*Percent changes are compared to no laser
**P value compared to no laser

Statistical analysis was performed on the samples as described by GraphPad Prism (Version 4.00). The changes in the different parameters were significant to the 0.05 level or greater. This is due not only to the number of animals in each group, but also to the number of samples taken for each measurement from each animal (20). Therefore, there is confidence in the numbers. The numbers fall within the range of acceptable results.

Animals were examined for gross abnormalities following sacrifice. No gross pathological features were detected in most of the animals except for Group E (Pulse III). Animals showed some lesioning in the brain following treatment. Animals after a few weeks began to develop lesions on the skin. They were switched to a regime of I minute treat, ice, I minute treat without further injury.

Discussion

Transgenic mice expressing the mutant form of the human APP gene begin to deposit amyloid fibrils by 6 months of age. This process is associated with increased Aβ peptide in the deposits in the brain. Recent studies have shown that administration of laser light therapy can be protective against various neuronal injuries. In this study, LLT was tested in the APP model to determine the efficacy on amyloid load, inflammatory markers, brain Aβ levels, plasma and CSF Aβ levels, and behavioral changes. The number of Aβ plaques was significantly reduced in the brain with administration of LLT in a dose dependent fashion. Administration of LLT demonstrated variable effects and with increasing doses showing the greatest effect of reduction of amyloid deposition.

NTS was not blinded to the study as outlined by PTI. Overall, laser light therapy was effective at limiting the extent of Aβ amyloid in the brain and altering the amount of deposition of Aβ peptide and behavioral deficits in the mouse.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

What is claimed is:

1. A method of irradiating a portion of a patient's scalp or skull with light, the method comprising:
   delivering a pulsed light beam to the patient's scalp or skull from an emission surface of an output optical element in communication with a source of light;
   providing a thermal conduit in thermal communication with the output optical element and with a cooling mechanism; and
   cooling the output optical element using the cooling mechanism via the thermal conduit,
   wherein the pulsed light beam comprises a plurality of pulses having a temporal pulsewidth in a range between 0.1 millisecond and 150 seconds, the pulsed light beam having a cross-sectional area greater than 2 cm$^2$ at the emission surface of the output optical element, and having a temporal profile comprising a time-averaged irradiance in a range of 10 mW/cm$^2$ to 10 W/cm$^2$ across the cross-sectional area, and
   wherein the temporal profile does not optimize a thermal relaxation of an irradiated brain tissue.

2. The method of claim 1, further comprising selecting the patient, wherein the patient is selected at least partly because the patient has experienced one or more conditions selected from the group consisting of a primary destructive event, Parkinson's disease, and depression.

3. The method of claim 1, wherein the pulsed light beam has a fluence at a cortical surface of a brain of the patient between 12.5 μJ/cm$^2$ to 1 J/cm$^2$.

4. The method of claim 1, wherein the pulsed light beam at the emission surface has a beam diameter in a range between 10 millimeters and 40 millimeters, an average irradiance per pulse in a range between 10 mW/cm$^2$ and 10 W/cm$^2$, one or more wavelengths in a range between 600 nanometers and 1064 nanometers.

5. The method of claim 1, wherein the source of light comprises a laser light source.

6. The method of claim 1, wherein the output optical element comprises sapphire.

7. The method of claim 1, wherein the output optical element comprises diamond, calcium fluoride, or zinc selenide.

8. The method of claim 1, wherein the output optical element comprises a rigid, optically transmissive, and thermally conductive material.

9. The method of claim 1, wherein the output optical element comprises a flexible optically transmissive, and thermally conductive material.

10. The method of claim 1, wherein the output optical element has a thermal conductivity of at least 10 watts/meter-K.

11. The method of claim 1, wherein the emission surface is concave to conform to a curvature of the patient's scalp or skull, thereby reducing or preventing air gaps from forming between the emission surface and the patient's scalp or skull.

12. The method of claim 1, wherein the emission surface comprises one or more optical coatings, films, layers, or membranes configured to reduce back reflections.

13. The method of claim 1, wherein the emission surface comprises one or more diffusers.

14. The method of claim 1, wherein the temporal pulsewidth is in a range between 0.1 millisecond and 300 milliseconds.

15. The method of claim 1, wherein the cross-sectional area is in a range of 2 cm$^2$ to 20 cm$^2$ at the emission surface of the output optical element.

16. The method of claim 1, wherein the output optical element has an aperture diameter of less than 33 millimeters.

17. The method of claim 1, wherein the pulsed light beam comprises one or more wavelengths in a range between 600 nanometers and 1064 nanometers.

18. The method of claim 1, wherein the time-averaged irradiance at the scalp or skull provides a time-averaged irradiance greater than 0.01 mW/cm$^2$ to a target subsurface tissue of a brain of the patient below a dura of the patient.

19. The method of claim 1, wherein the time-averaged irradiance at the emission surface averaged over one second is in a range between 100 mW/cm$^2$ and 10 W/cm$^2$ and a peak irradiance at the scalp is in a range between 10 mW/cm$^2$ and 10 W/cm$^2$.

20. The method of claim 19, wherein the pulsed light beam has one or more wavelengths in a range between 600 nanometers and 1064 nanometers.

21. The method of claim 19, wherein the temporal profile further comprises a temporal pulsewidth in a range between 0.1 millisecond and 300 milliseconds.

22. The method of claim 1, wherein the pulsed light beam has a duty cycle in a range between 10% and 30%.

23. The method of claim 1, wherein a timing of the temporal profile corresponds to a timing of a biomolecular process involved in an absorption of one or more photons in the irradiated brain tissue.

* * * * *